United States Patent
Appel et al.

(10) Patent No.: US 11,945,892 B2
(45) Date of Patent: Apr. 2, 2024

(54) POLYMER EXCIPIENTS FOR BIOPHARMACEUTICAL FORMULATIONS

(71) Applicant: The Board of Trustees of the Leland Stanford Junior University, Palo Alto, CA (US)

(72) Inventors: Eric A. Appel, Palo Alto, CA (US); Caitlin Maikawa, Boston, MA (US); Joseph L. Mann, Mountain View, CA (US)

(73) Assignee: The Board of Trustees of the Leland Stanford Junior Univeristy, Stanford, CA (US)

(*) Notice: Subject to any disclaimer, the term of this patent is extended or adjusted under 35 U.S.C. 154(b) by 0 days.

(21) Appl. No.: 17/962,252

(22) Filed: Oct. 7, 2022

(65) Prior Publication Data
US 2023/0108947 A1    Apr. 6, 2023

Related U.S. Application Data

(63) Continuation of application No. PCT/US2021/027693, filed on Apr. 16, 2021.

(60) Provisional application No. 63/159,306, filed on Mar. 10, 2021, provisional application No. 63/011,928, filed on Apr. 17, 2020.

(51) Int. Cl.
*C08F 220/36* (2006.01)
*A61K 9/127* (2006.01)
*A61K 9/51* (2006.01)

(52) U.S. Cl.
CPC .......... *C08F 220/36* (2013.01); *A61K 9/1272* (2013.01); *A61K 9/5146* (2013.01)

(58) Field of Classification Search
None
See application file for complete search history.

(56) References Cited

U.S. PATENT DOCUMENTS

| 5,415,864 A | 5/1995 | Kopecek et al. |
| 7,160,970 B2 | 1/2007 | Creamer et al. |

(Continued)

FOREIGN PATENT DOCUMENTS

| CN | 107629767 A | 1/2018 |
| JP | H11503616 | 3/1999 |

(Continued)

OTHER PUBLICATIONS

Chan et al. Combinatorial Polyacrylamide Hydrogels for Preventing Biofouling on Implantable Biosensors. bioRxiv; 2020. (Year: 2020).*

(Continued)

*Primary Examiner* — Sanza L. McClendon
(74) *Attorney, Agent, or Firm* — Rudy J. Ng; Bozicevic, Field & Francis LLP

(57) ABSTRACT

A polyacrylamide-based copolymer reduces or prevents aggregation of biologic molecules including proteins, peptides, and nucleic acids, and lipid-based vehicles such as liposomes, lipid nanoparticles, polymerosomes, and micelles, in aqueous formulations at hydrophobic interfaces, thereby increasing the thermal stability of the molecules in the formulation. Methods and compositions comprising the copolymer and a protein or the copolymer and insulin can be used for treating conditions including diabetes.

23 Claims, 34 Drawing Sheets

(56) References Cited

U.S. PATENT DOCUMENTS

| | | | |
|---|---|---|---|
| 7,309,593 B2* | 12/2007 | Ofstead | C07H 21/00 435/7.1 |
| 7,462,363 B2 | 12/2008 | Braun et al. | |
| 7,829,317 B2* | 11/2010 | Ofstead | G01N 33/54353 435/7.1 |
| 7,989,401 B2 | 8/2011 | Kurian et al. | |
| 8,048,258 B2* | 11/2011 | Kurimura | A61K 45/06 525/218 |
| 8,129,159 B2* | 3/2012 | Ofstead | C07H 21/00 435/7.1 |
| 9,526,687 B2 | 12/2016 | Klug et al. | |
| 9,790,381 B2 | 10/2017 | Arita et al. | |
| 10,717,799 B2 | 7/2020 | Tale et al. | |
| 11,021,620 B2 | 6/2021 | Herlihy | |
| 11,021,622 B2 | 6/2021 | Kim et al. | |
| 2005/0277739 A1 | 12/2005 | Yang et al. | |
| 2009/0124707 A1 | 5/2009 | Tamori et al. | |
| 2010/0204424 A1 | 8/2010 | Tamori et al. | |
| 2014/0328918 A1 | 11/2014 | Fetzer | |
| 2015/0159009 A1 | 6/2015 | Lau | |
| 2017/0038500 A1 | 2/2017 | Benz et al. | |
| 2018/0066091 A1 | 3/2018 | Tale et al. | |
| 2018/0296680 A1 | 10/2018 | Webber et al. | |
| 2019/0358341 A1 | 11/2019 | Adams et al. | |
| 2020/0113816 A1 | 4/2020 | Bellan | |
| 2022/0125886 A1 | 4/2022 | Appel et al. | |

FOREIGN PATENT DOCUMENTS

| | | |
|---|---|---|
| JP | 2014227384 A | 12/2014 |
| WO | WO1997023614 | 12/1996 |
| WO | 2000046262 A1 | 8/2000 |
| WO | 2001005578 A1 | 1/2001 |
| WO | 2003066791 A1 | 8/2003 |
| WO | 2013024800 A1 | 2/2013 |
| WO | 2018112313 A1 | 6/2018 |
| WO | 2018112551 A1 | 6/2018 |
| WO | 2021119607 A1 | 6/2021 |
| WO | 2021142391 A1 | 7/2021 |

OTHER PUBLICATIONS

Tang et al. Temperature-Responsive Polymer Modified Surface for Cell Sheet Engineering. Polymers 2012, 4, 1478-1498. (Year: 2012).*

Kye et al. Tunable Temperature Response of a Thermochromic Photonic Gel Sensor Containing N-Isopropylacrylamide and 4-Acryloyilmorpholine. Sensors (Basel). Jun. 15, 2017;17(6):1398 (Year: 2017).*

Akimoto et al. (2018), Controlled aggregation behavior of thermoresponsive polymeric micelles by introducing hydrophilic segments as corona components. J. Polym. Sci. Part A: Polym. Chem., 56: 1695-1704 (Year: 2018).*

Gu et al. Combinatorial synthesis with high throughput discovery of protein-resistant membrane surfaces. Biomaterial, vol. 34, Issue 26, 2013, pp. 6133-6138. (Year: 2013).*

Chiklis, C. et al. Swelling of Thin Films. I. Acrylamide-N-Isopropylacrylamide Copolymers in Water, Journal of Polymer Science, pp. 1617-1626, 1970.

Mann, J. et al. An Ultrafast Insulin Formulation Enabled by High-Throughput Screening of Engineered Polymeric Excipients, Science Translational Medicine, 12 pages, Jul. 2020 vol 12.

PCT/US2021/027693 International Search Report and Written Opinion, dated Oct. 14, 2021, 15 pages.

Tuncel, A. et al., A Novel Approach for Albumin Determination in Aqueous Media by Using Temperature- and pH-Sensitive N-Isopropylacrylamide-co-N-[3-(dimethylamino)-propyl] methacrylamide Random Copolymers, Chemical Engineering Department, Hacettepe University, May 17, 2021, pp. 2060-2071.

Webber, M.J., et al., Supramolecular PEGylation of biopharmaceuticals, Proc. Nat. Acad. Sci., Dec. 13, 2016, vol. 113, No. 50, 14189-14194.

Maikawa, C.L., et al., Engineering biopharmaceutical formulations to improve diabetes management, Science Translational Medicine, vol. 13, 11 pages, Jan. 27, 2021.

Li, Xueting, Preparation, Self Assembly of N-Substituted Acrylamide Nanogel for Photonic Crystal and its Application, 2018, pp. 73-76.

CN 202180034611.6 First Office Action, dated Sep. 21, 2023, 21 pages.

* cited by examiner

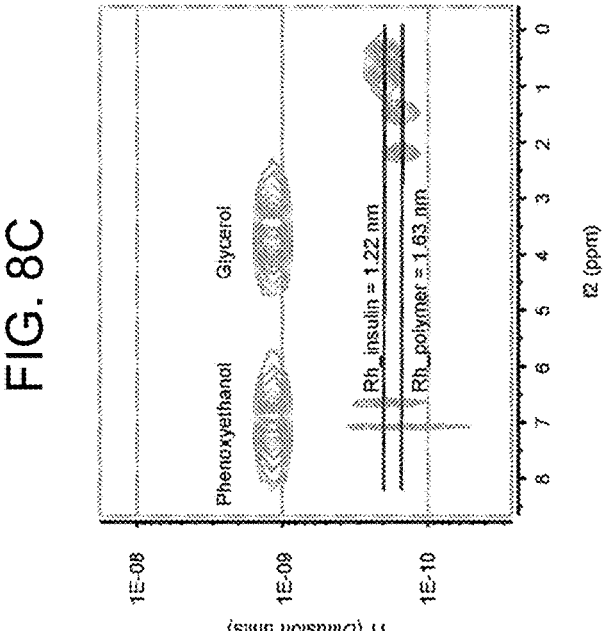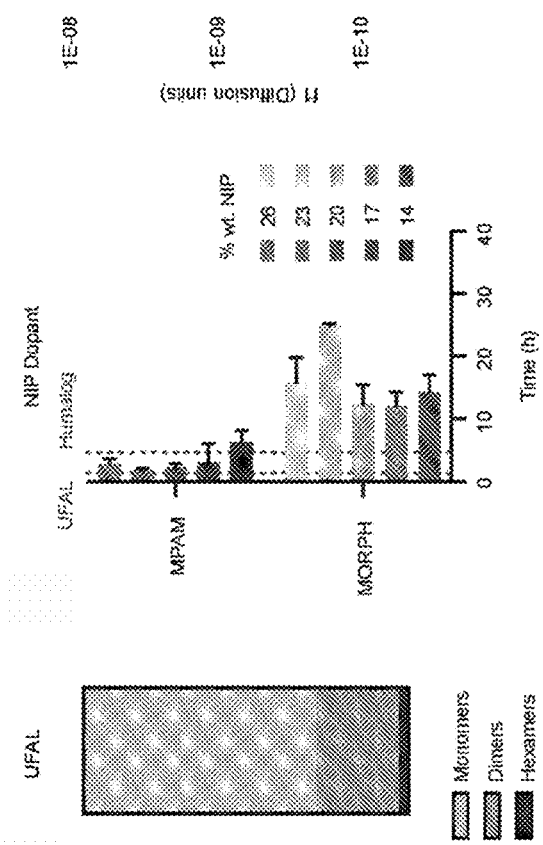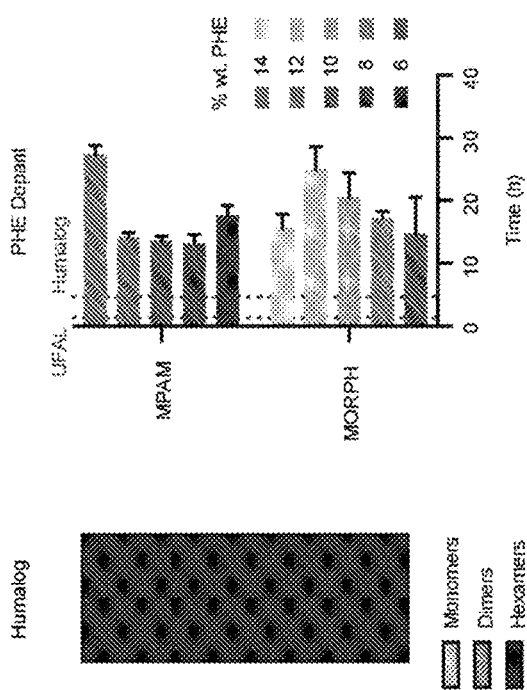
FIG. 8A  FIG. 8B  FIG. 8C  FIG. 8D

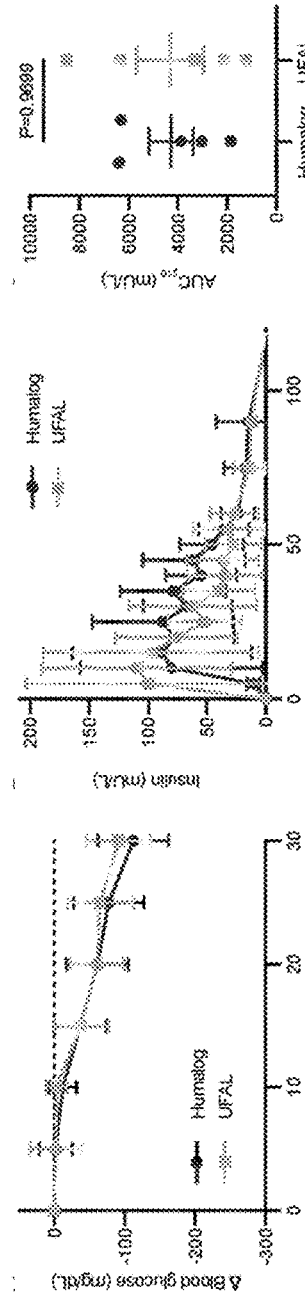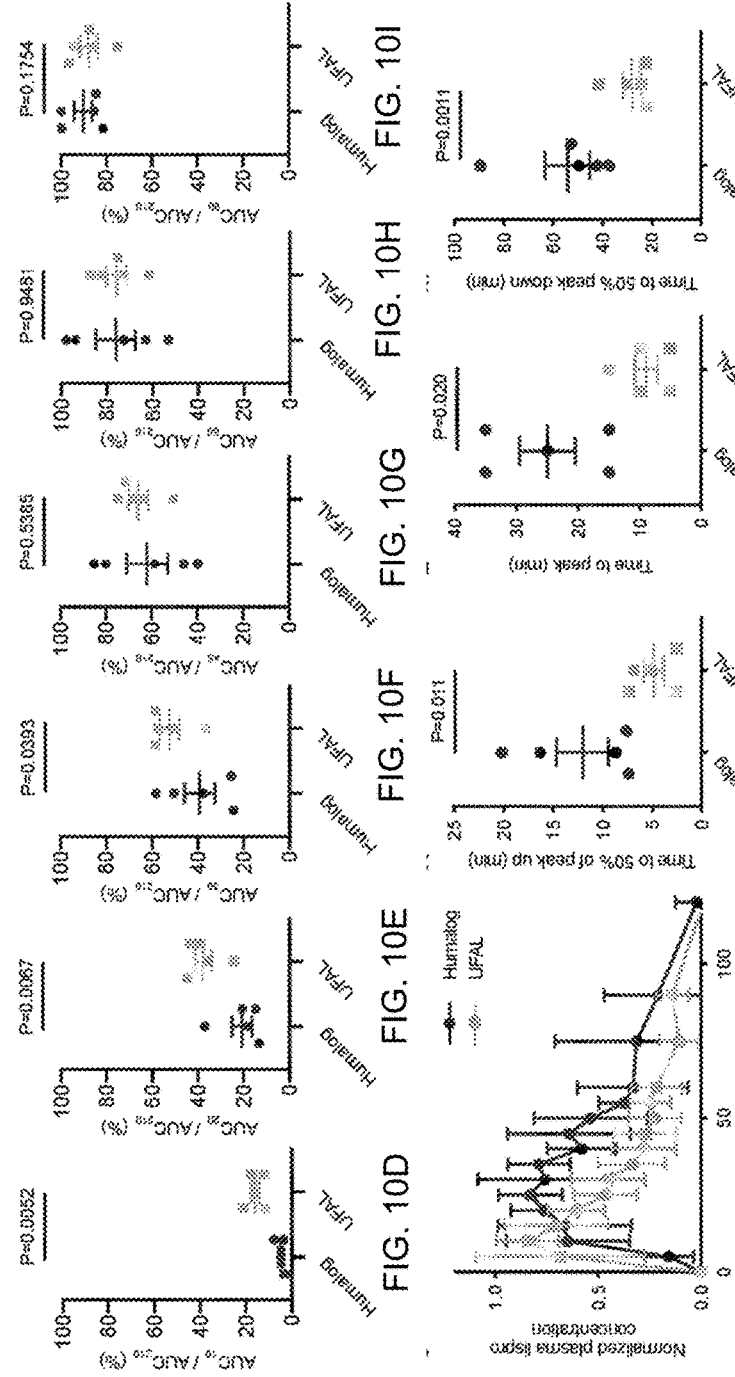
FIG. 10A FIG. 10B FIG. 10C FIG. 10D FIG. 10E FIG. 10F FIG. 10G FIG. 10H FIG. 10I FIG. 10J FIG. 10K FIG. 10L FIG. 10M

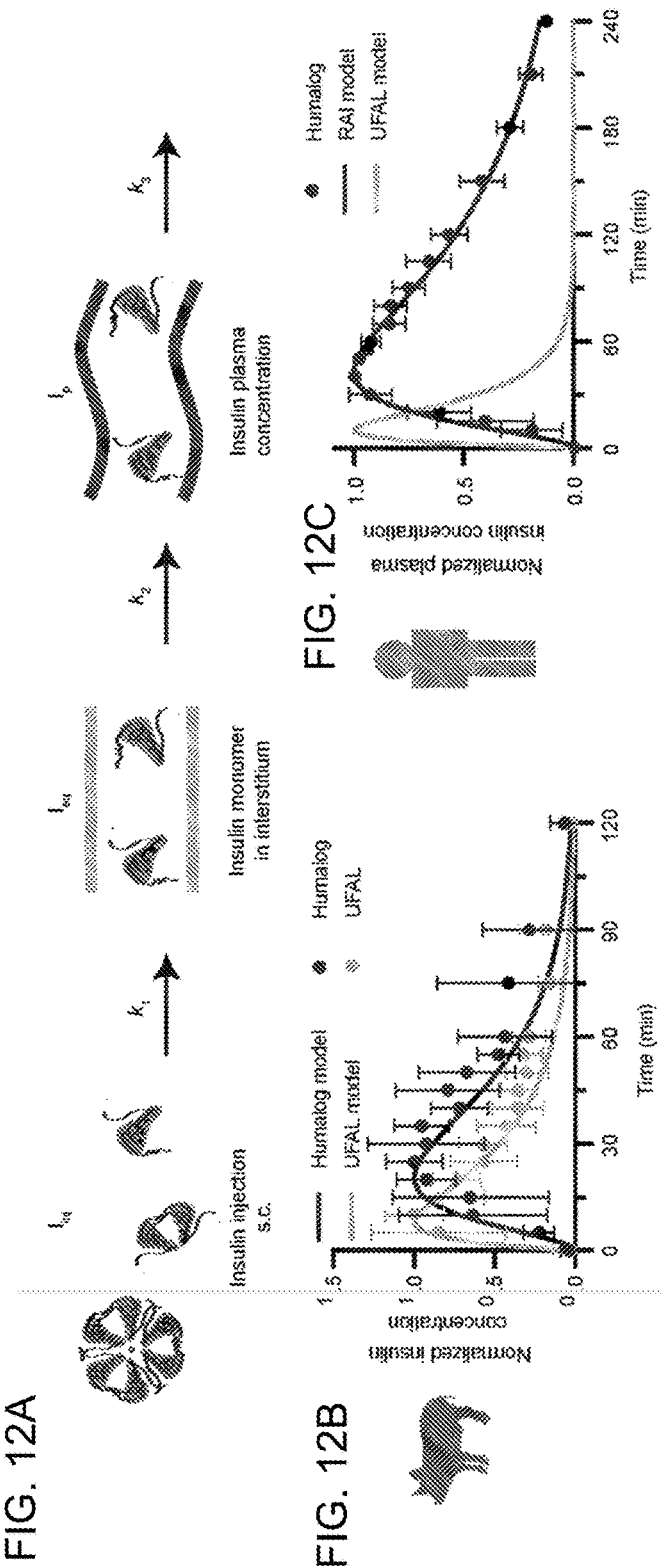
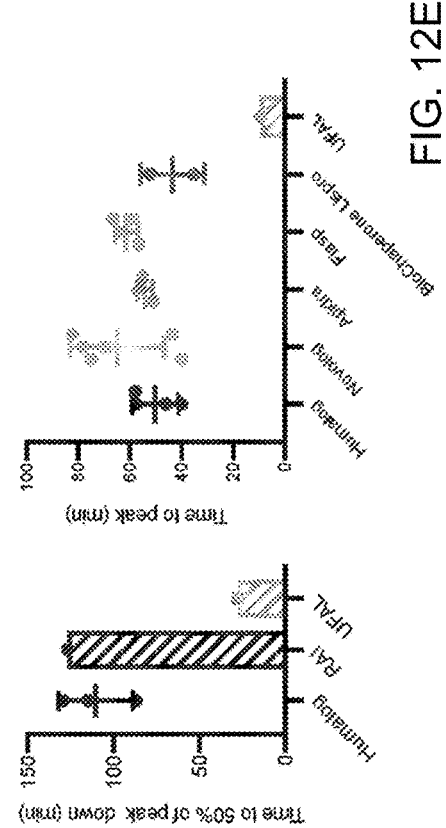
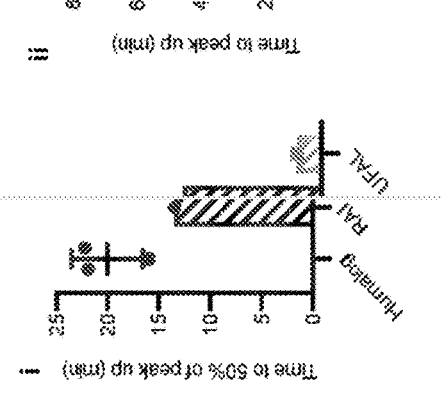
FIG. 12A
FIG. 12B
FIG. 12C
FIG. 12D
FIG. 12E

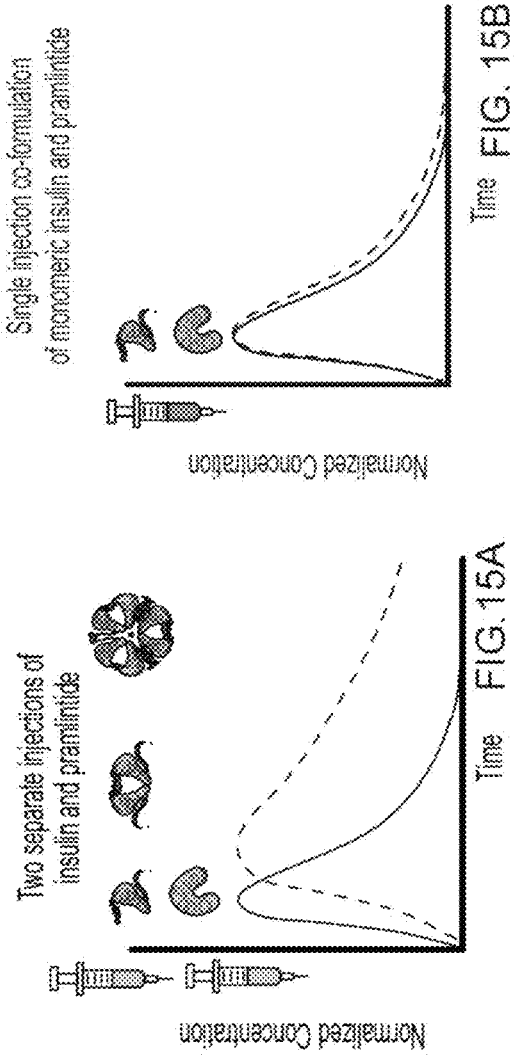
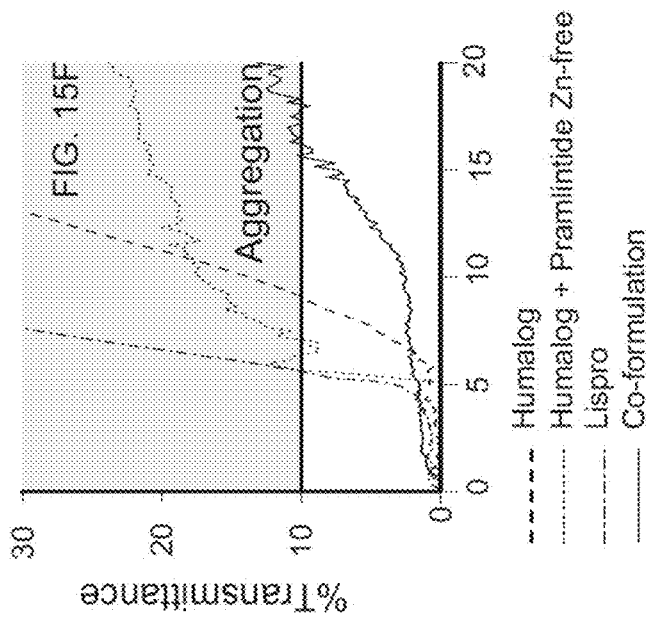
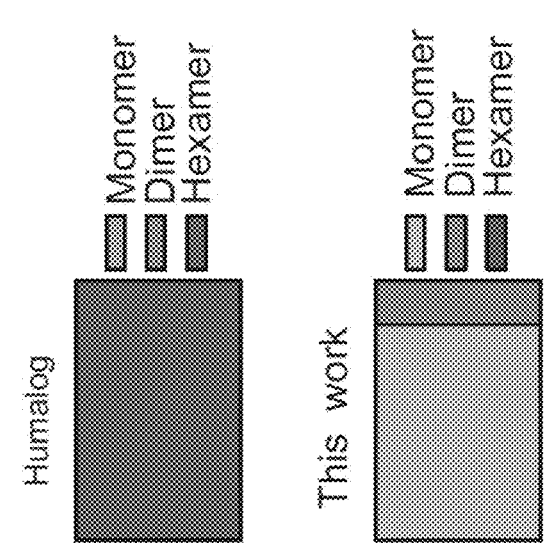
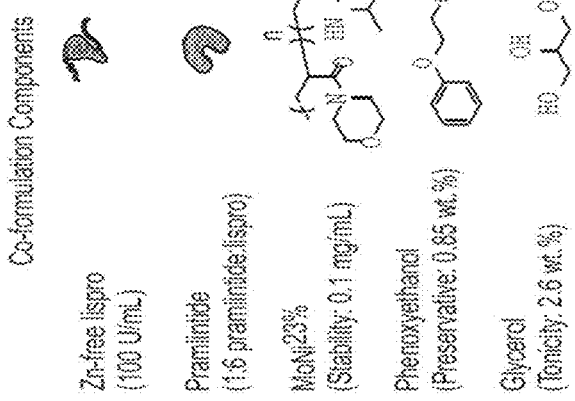

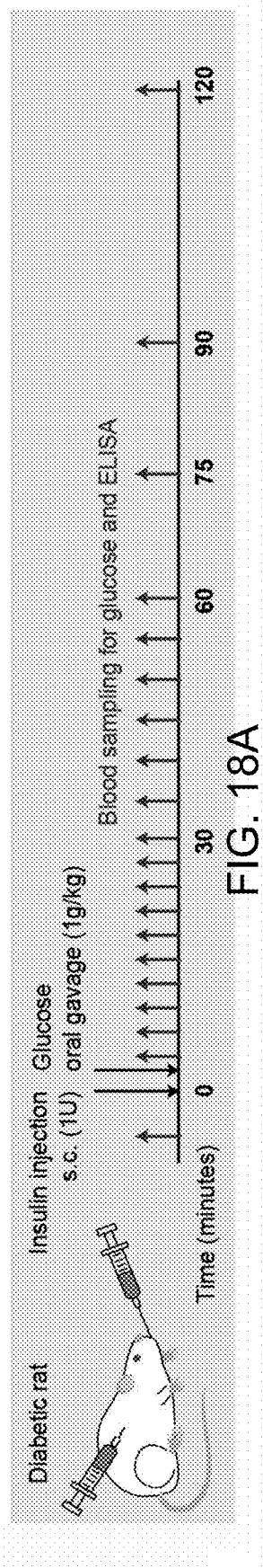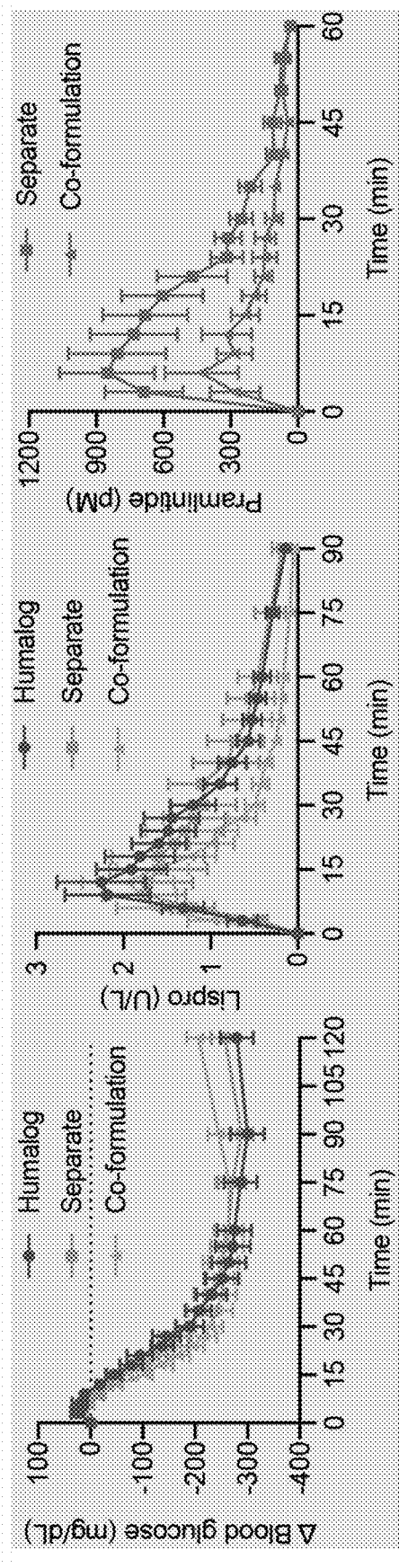
FIG. 18A
FIG. 18B
FIG. 18C
FIG. 18D

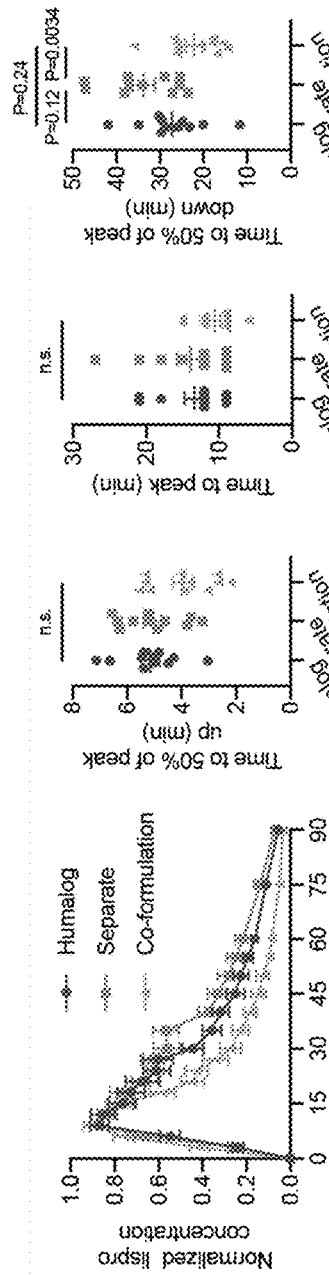
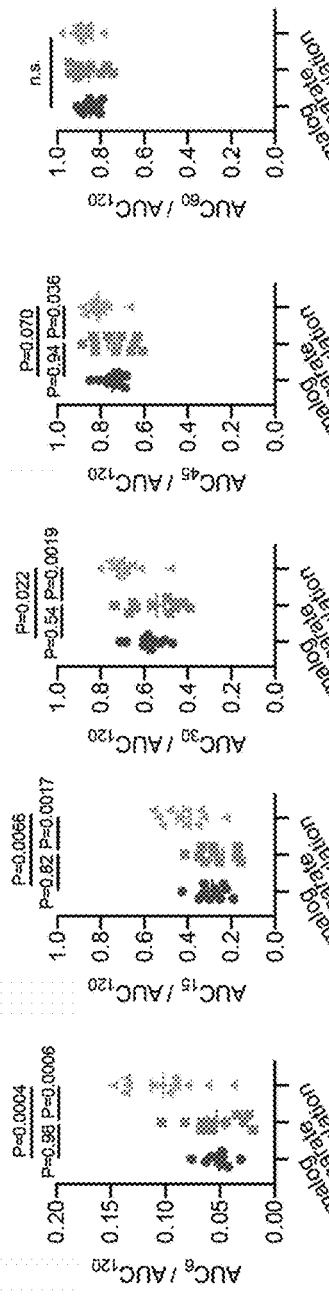
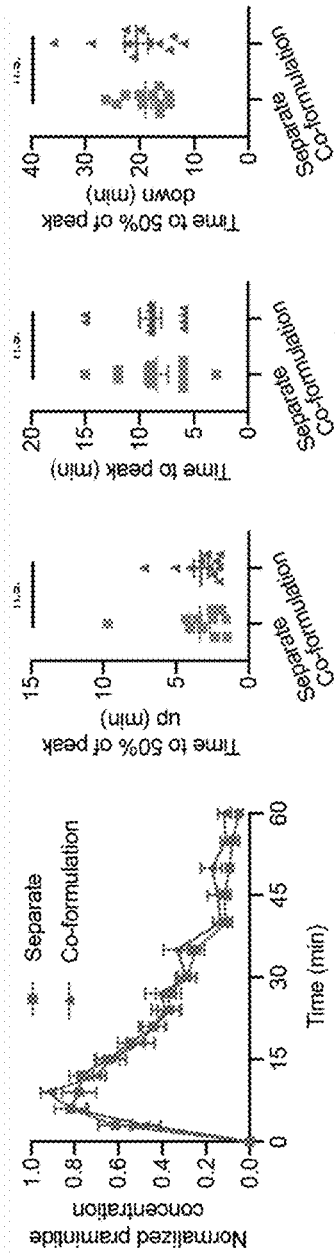

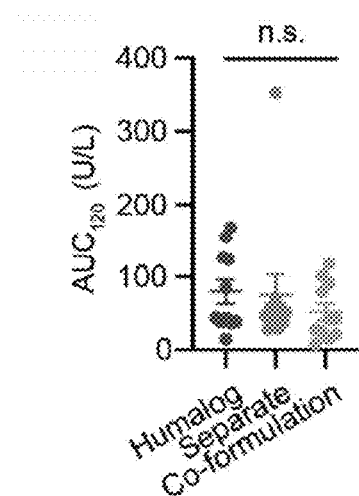 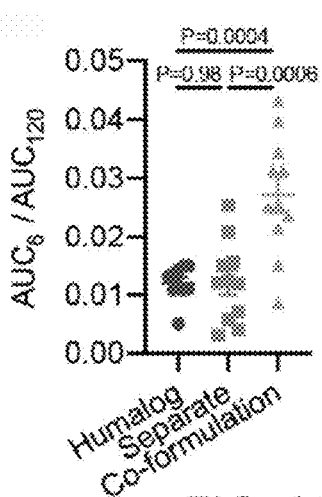 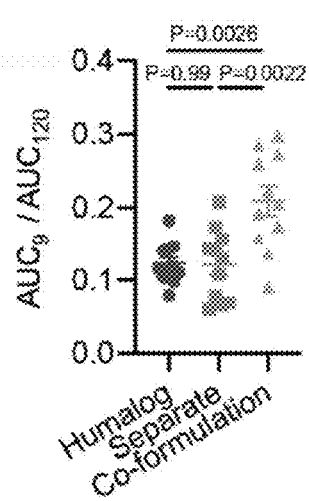
FIG. 20A  FIG. 20B  FIG. 20C
FIG. 21B  FIG. 21C  FIG. 21D
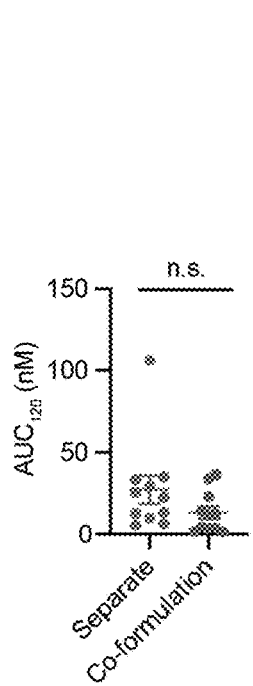 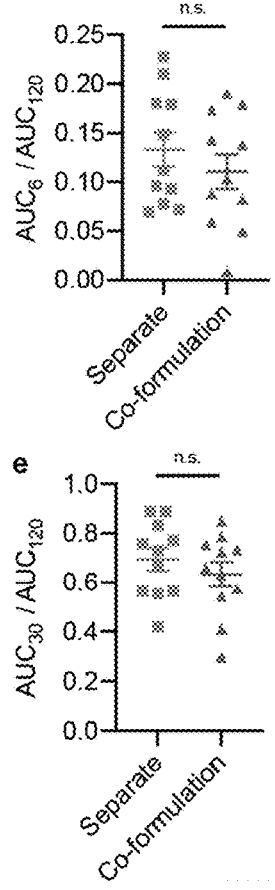 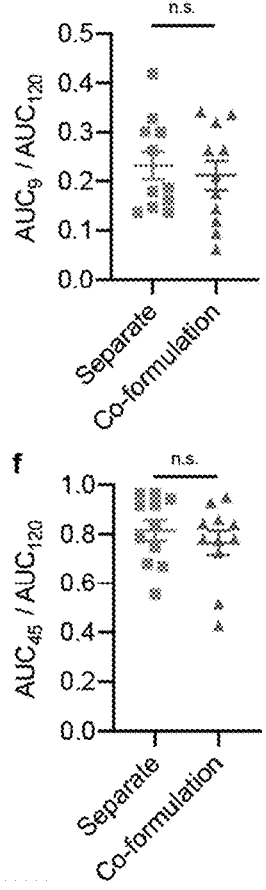 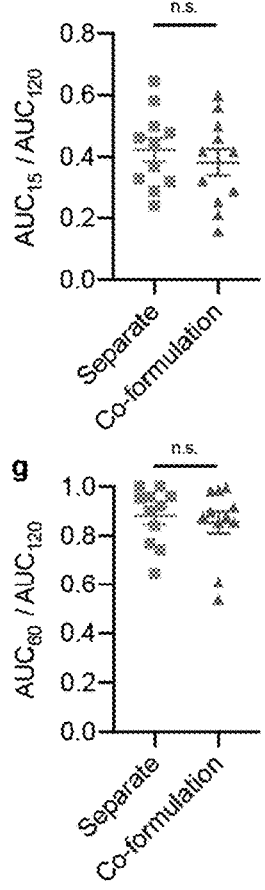
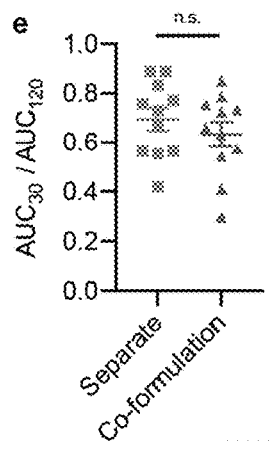 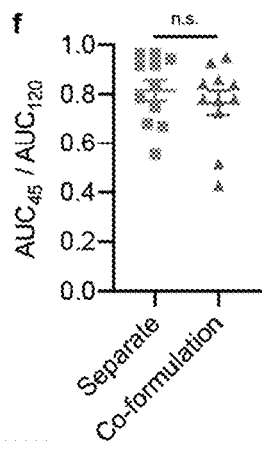 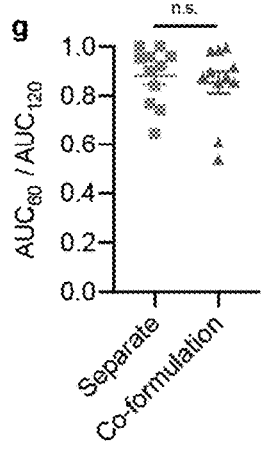
FIG. 21A  FIG. 21E  FIG. 21F  FIG. 21G

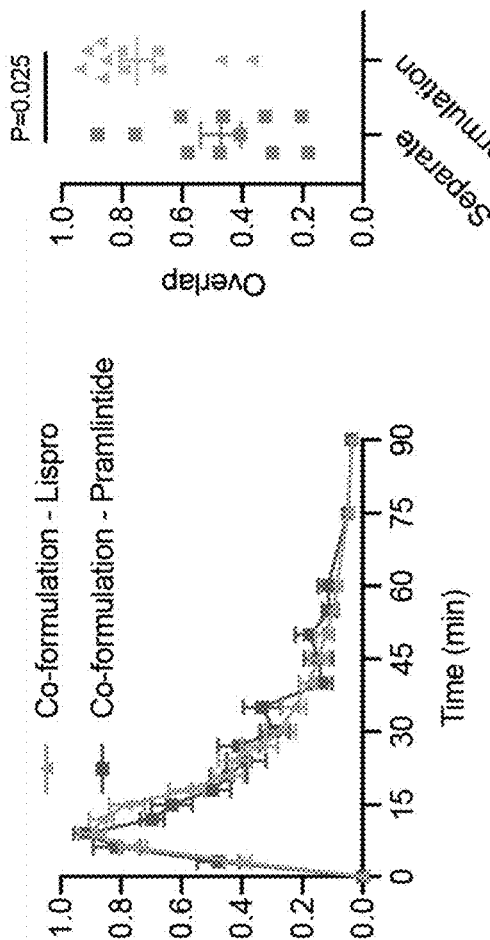
FIG. 22A
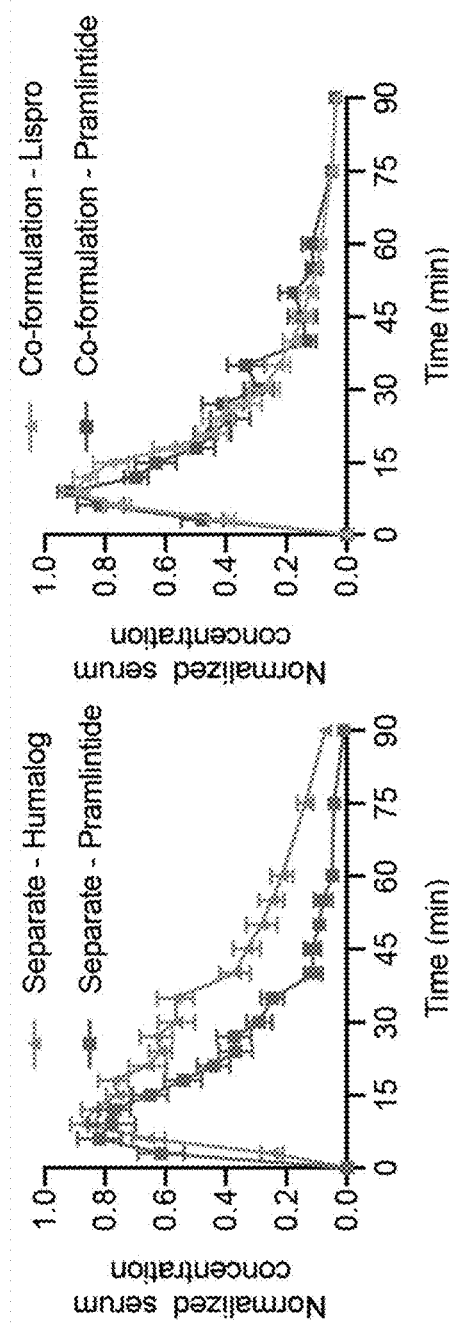
FIG. 22B
FIG. 22C
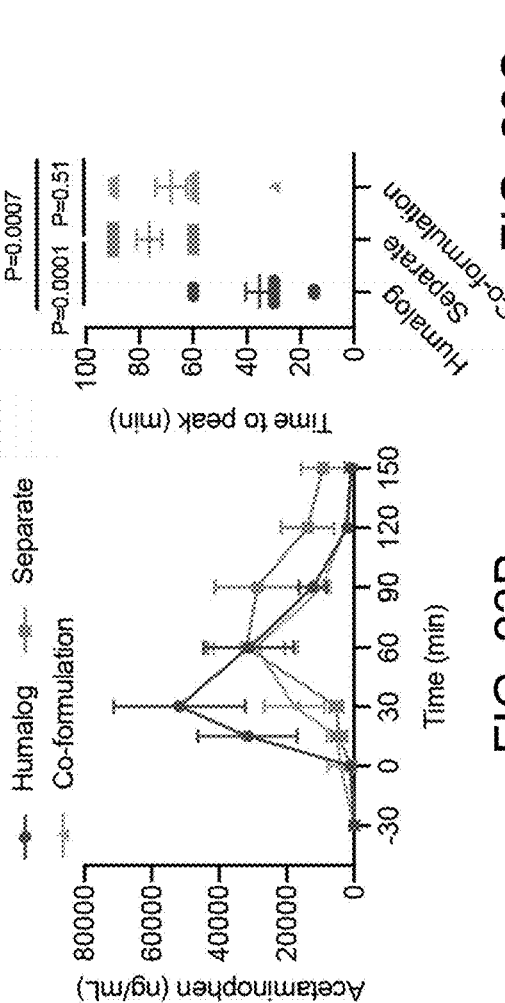
FIG. 23B
FIG. 23C
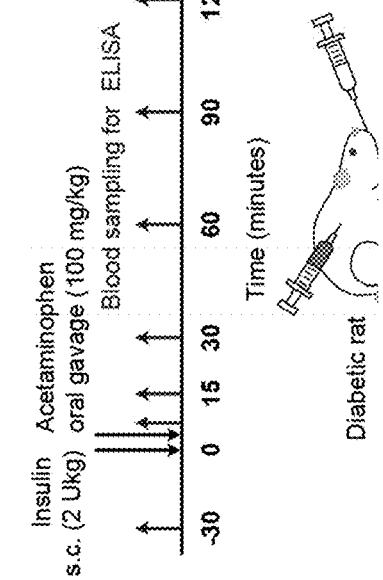
FIG. 23A

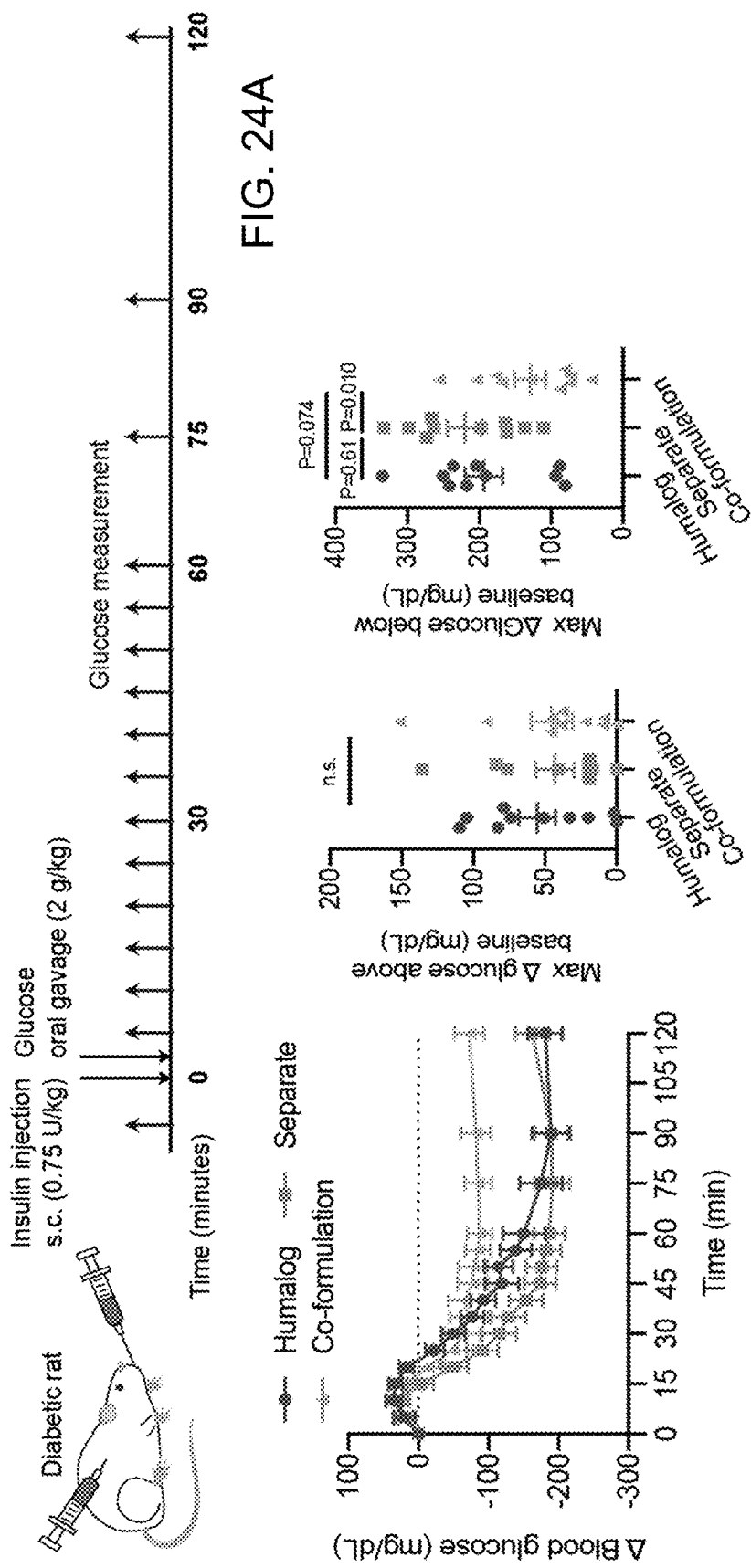

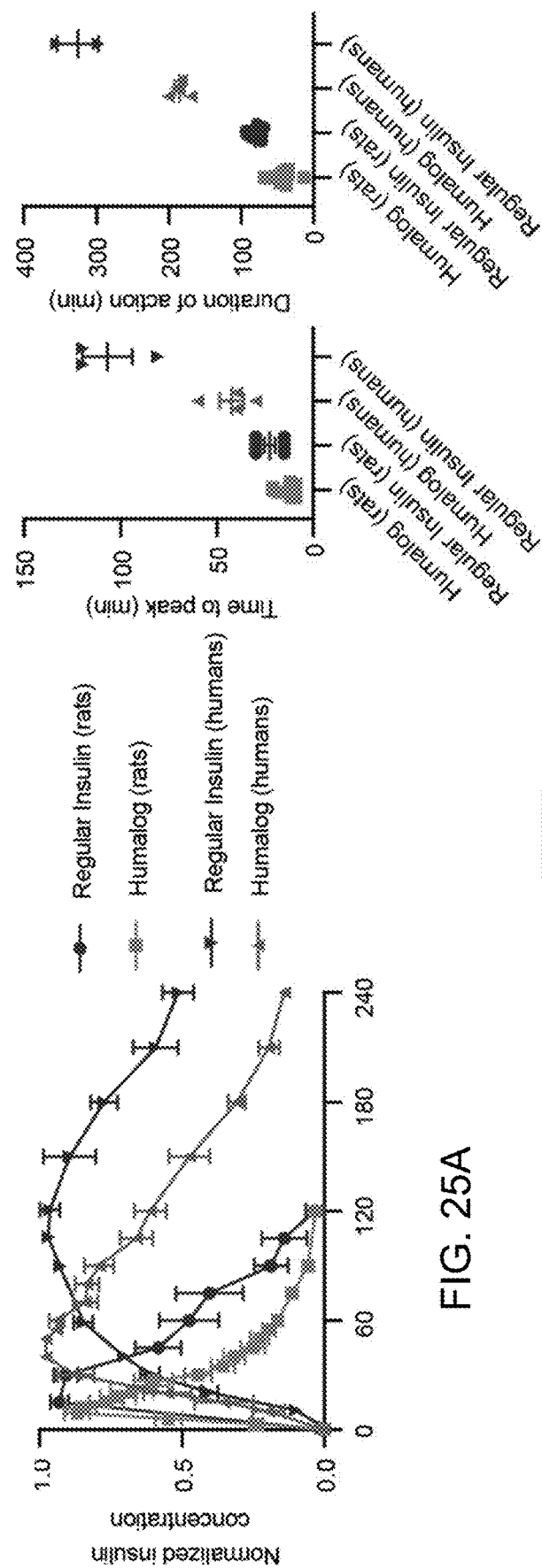

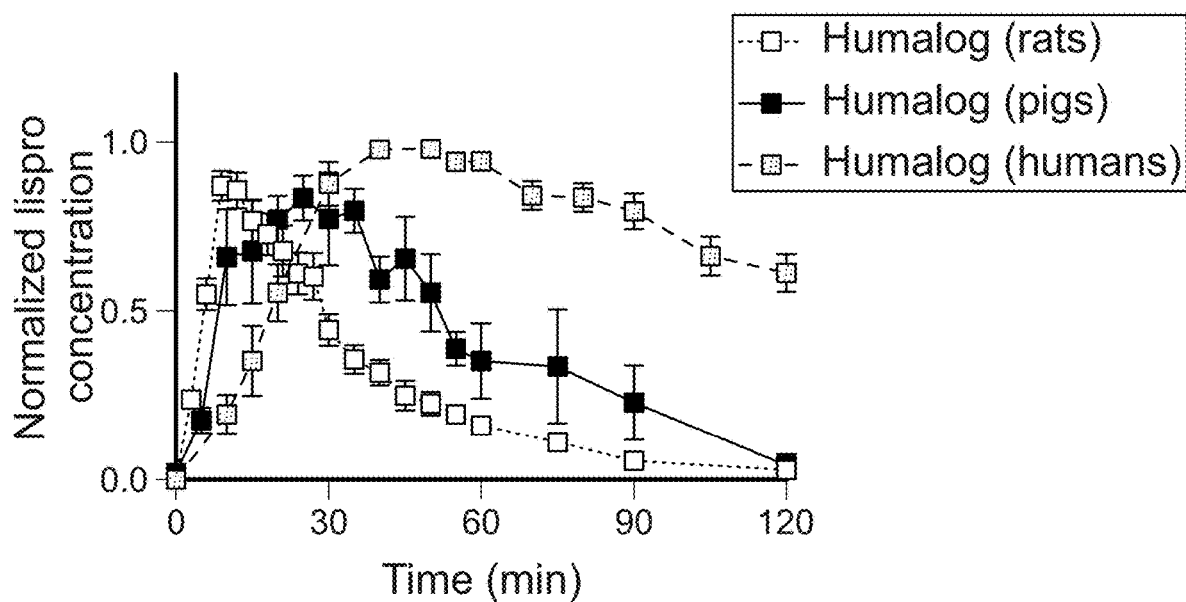
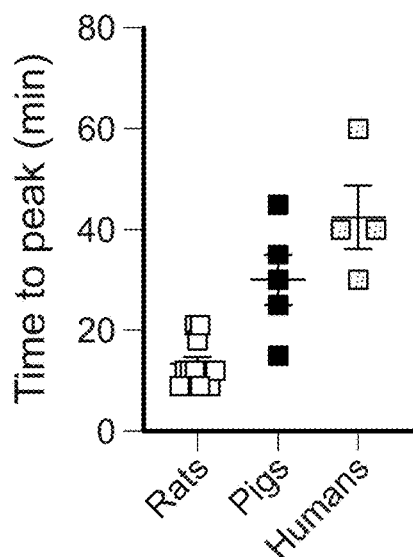
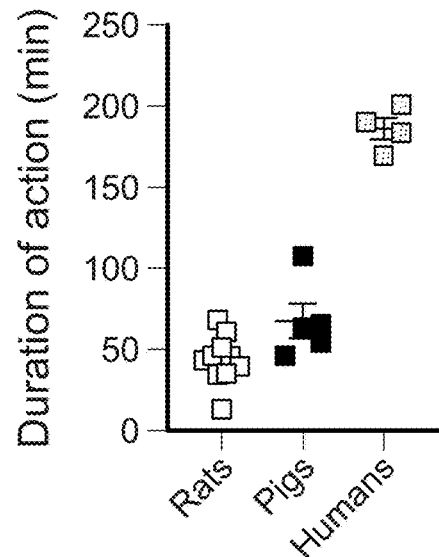
FIG. 26A

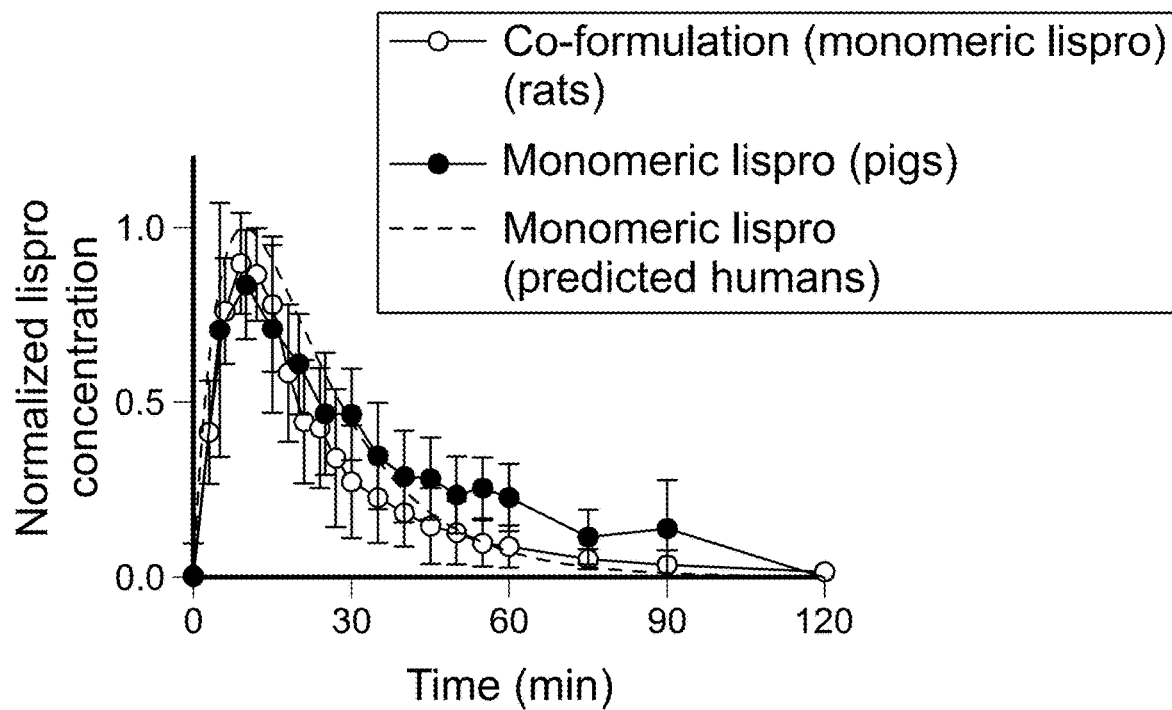
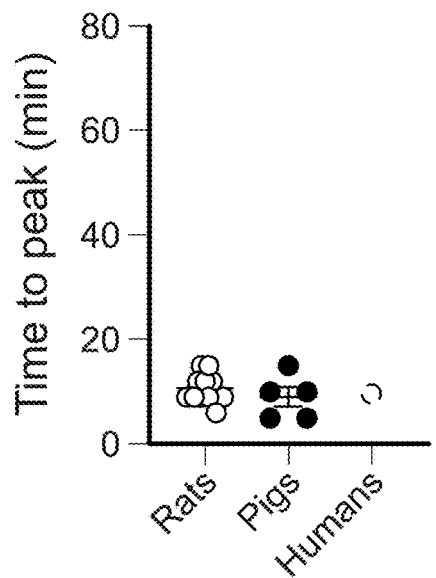
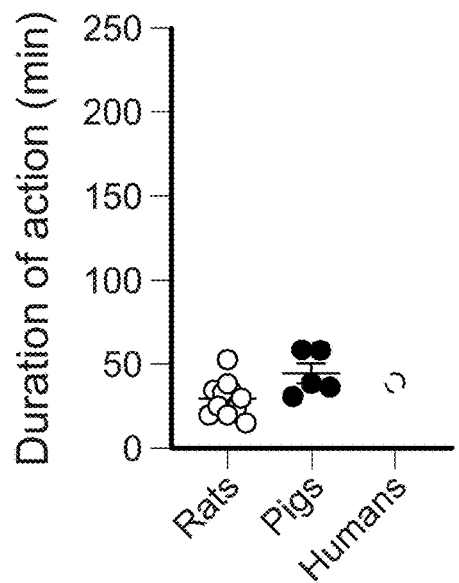
FIG. 26B

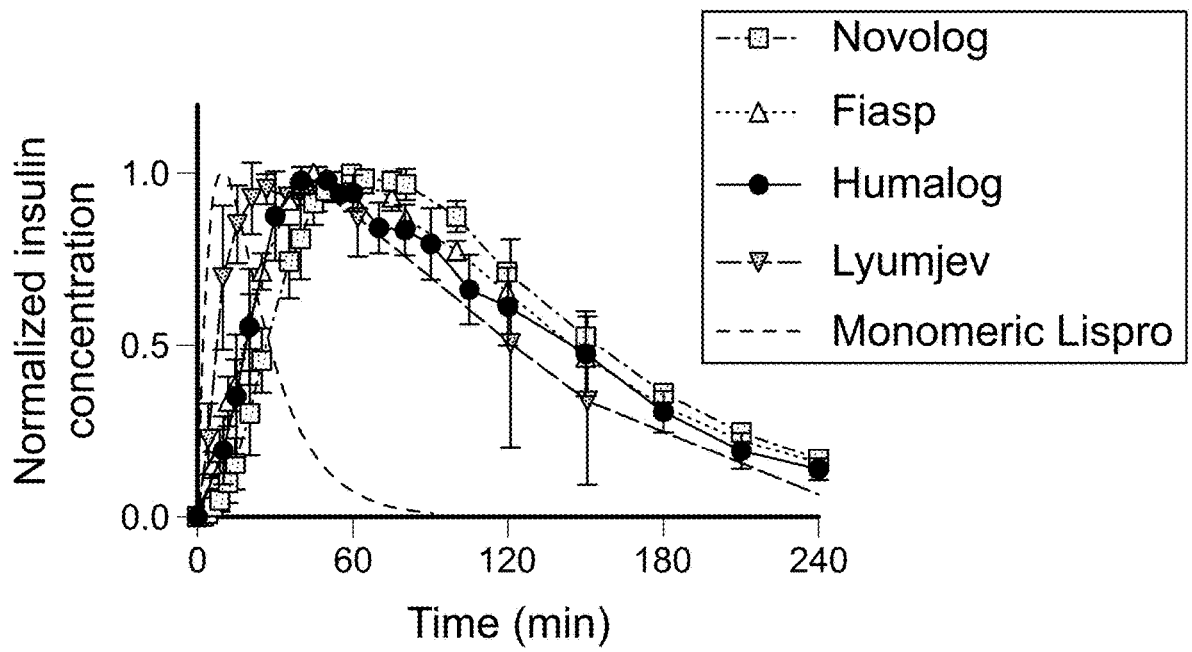
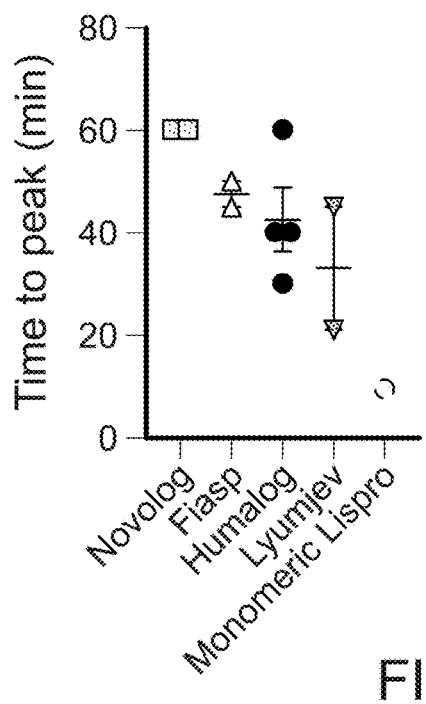
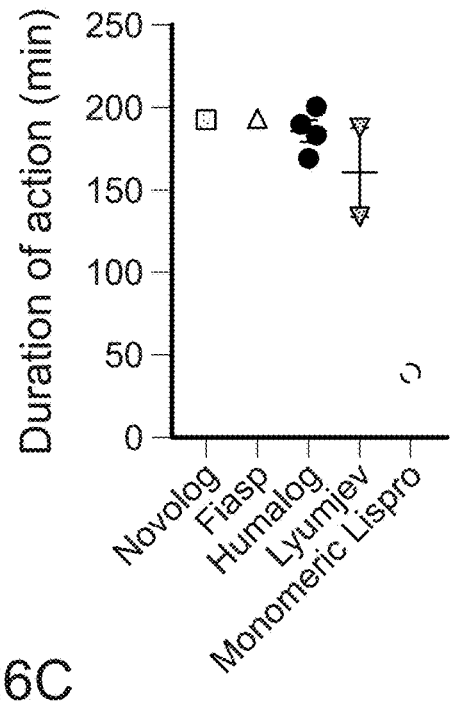
FIG. 26C

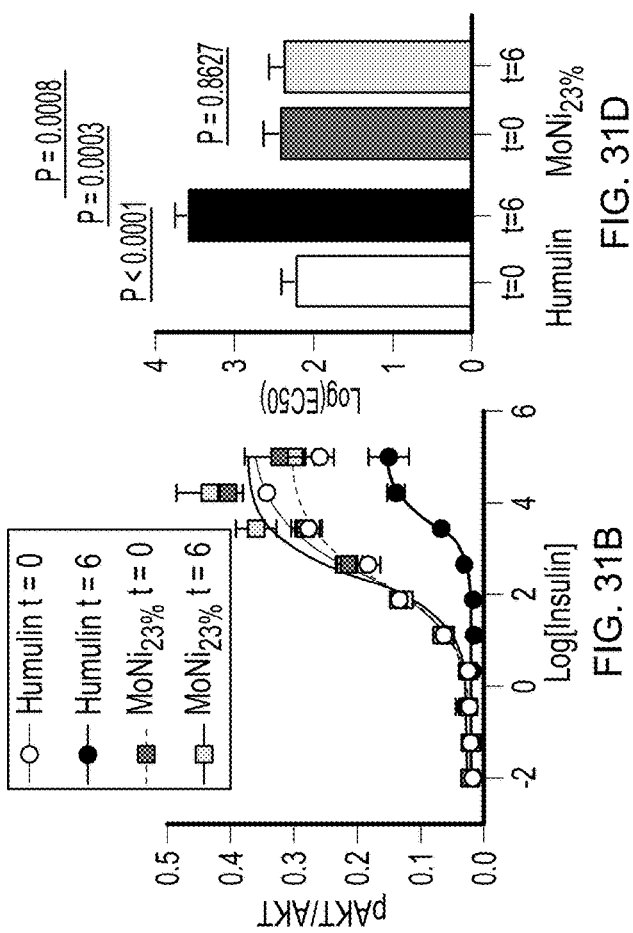
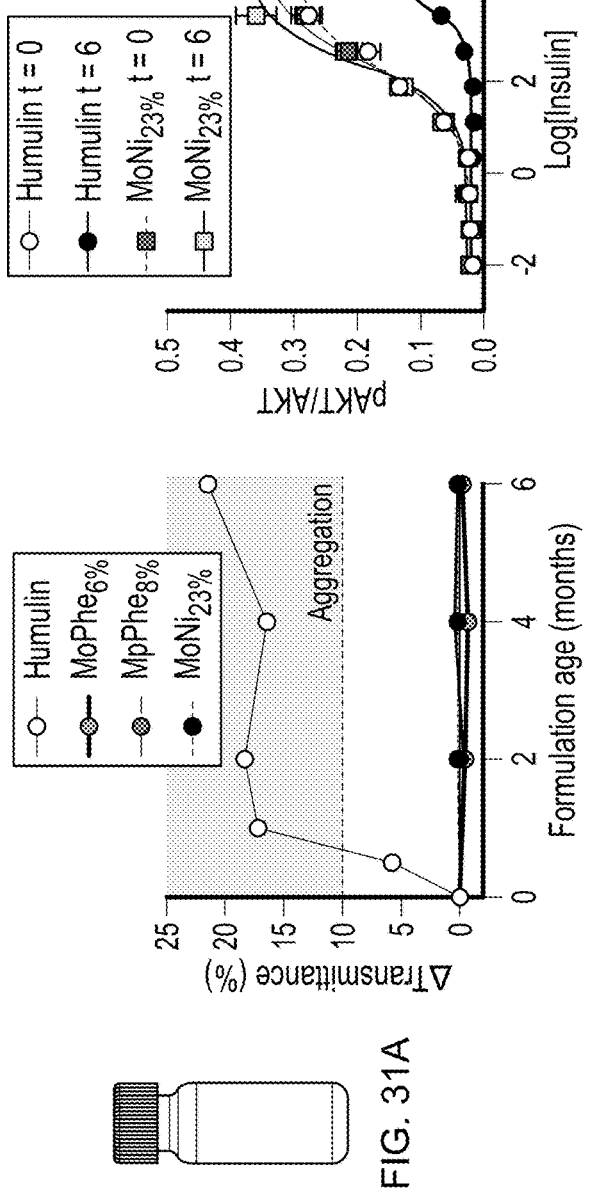
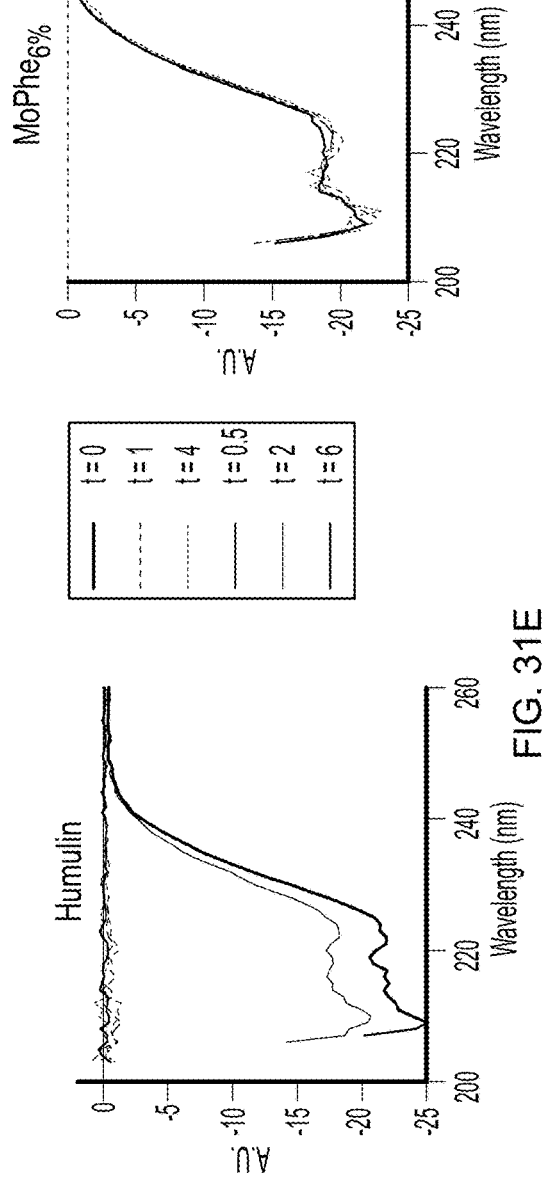
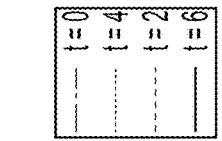
FIG. 31A
FIG. 31B
FIG. 31D
FIG. 31E
FIG. 31F

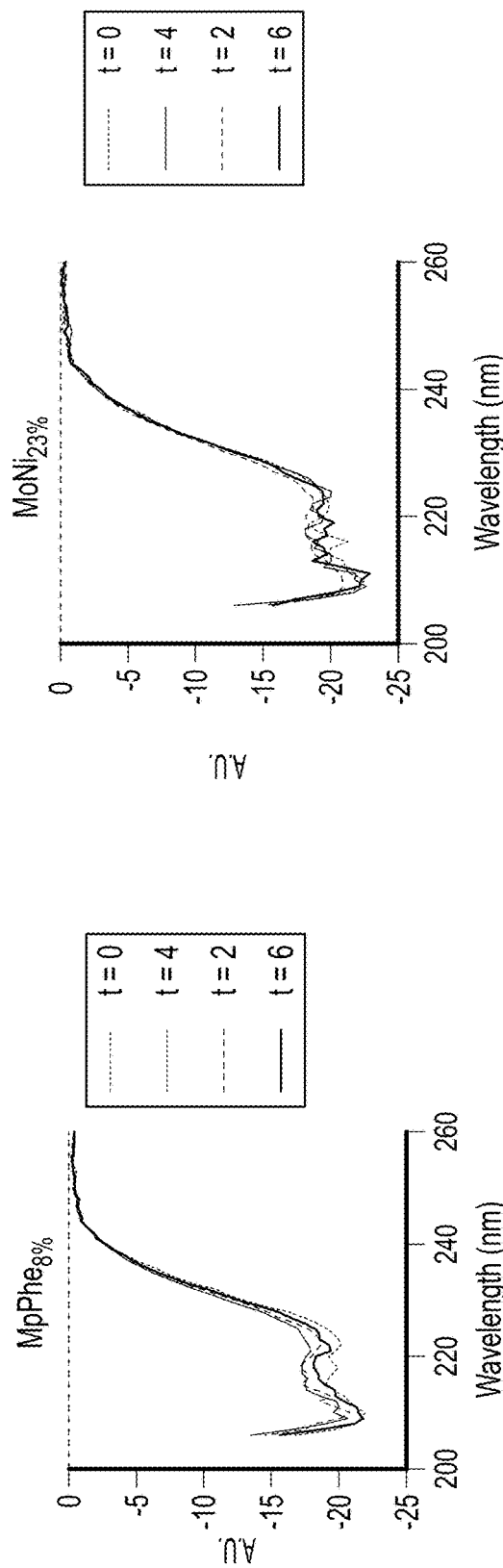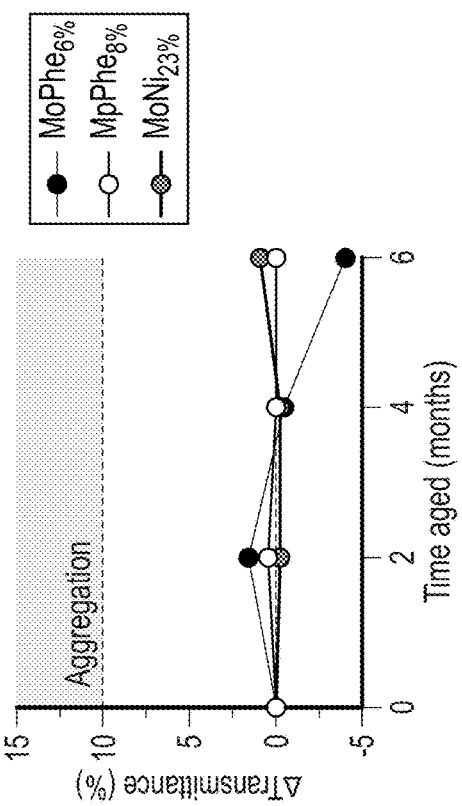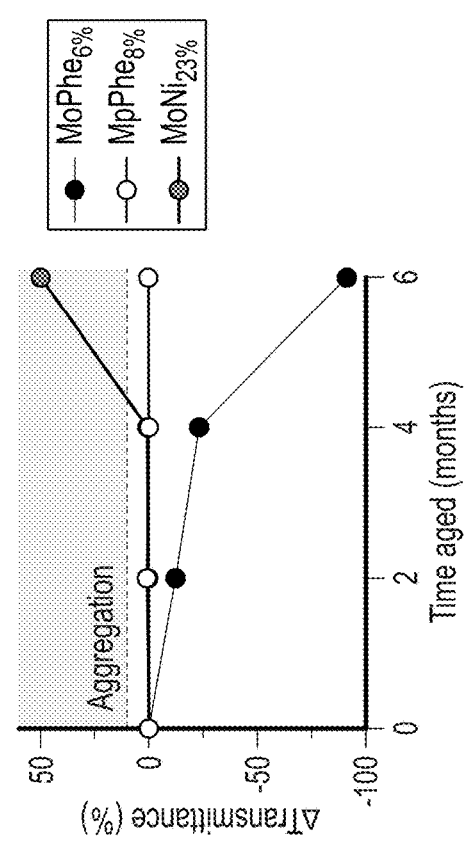

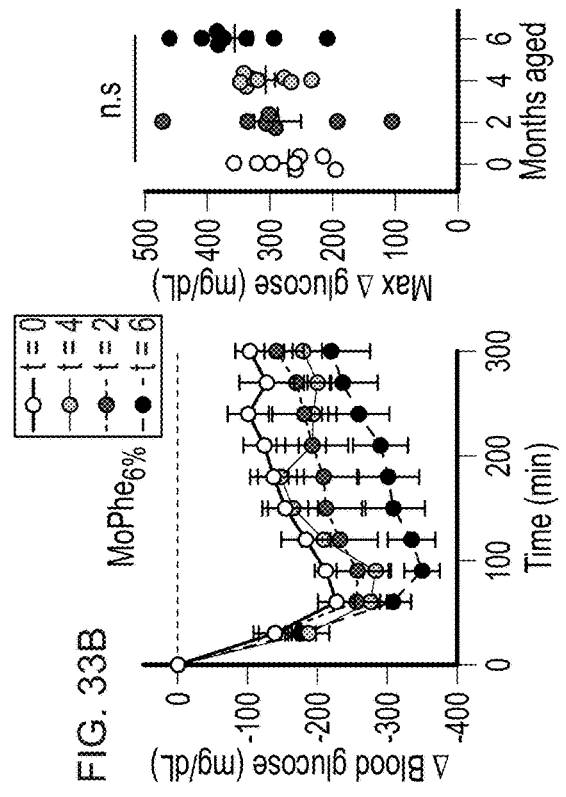
FIG. 33A
FIG. 33B
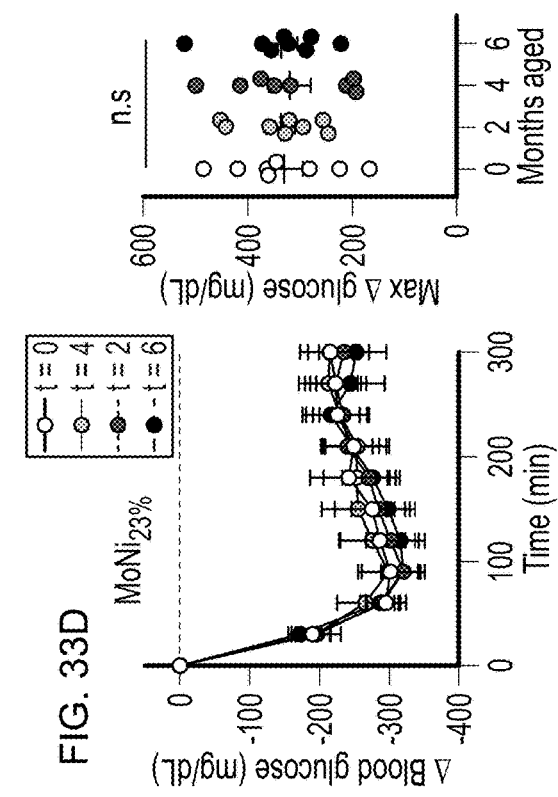
FIG. 33C
FIG. 33D
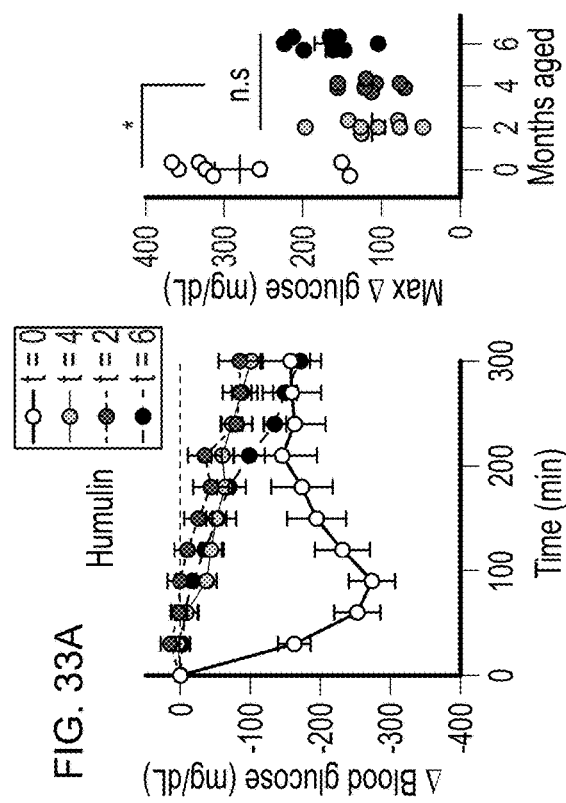
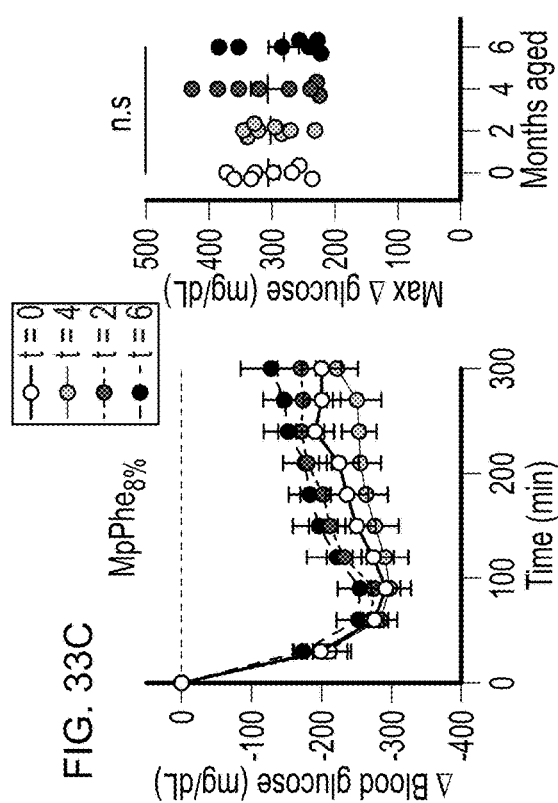

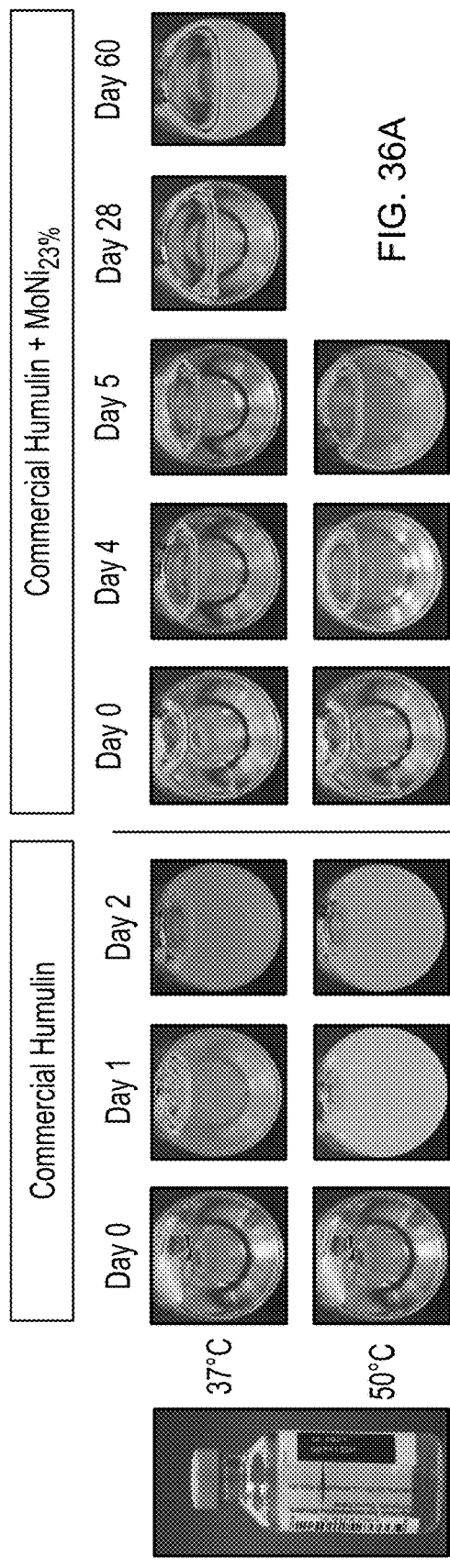
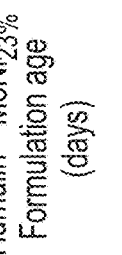
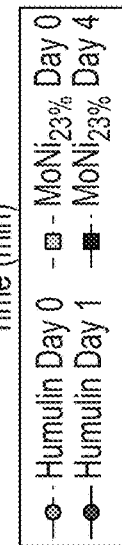
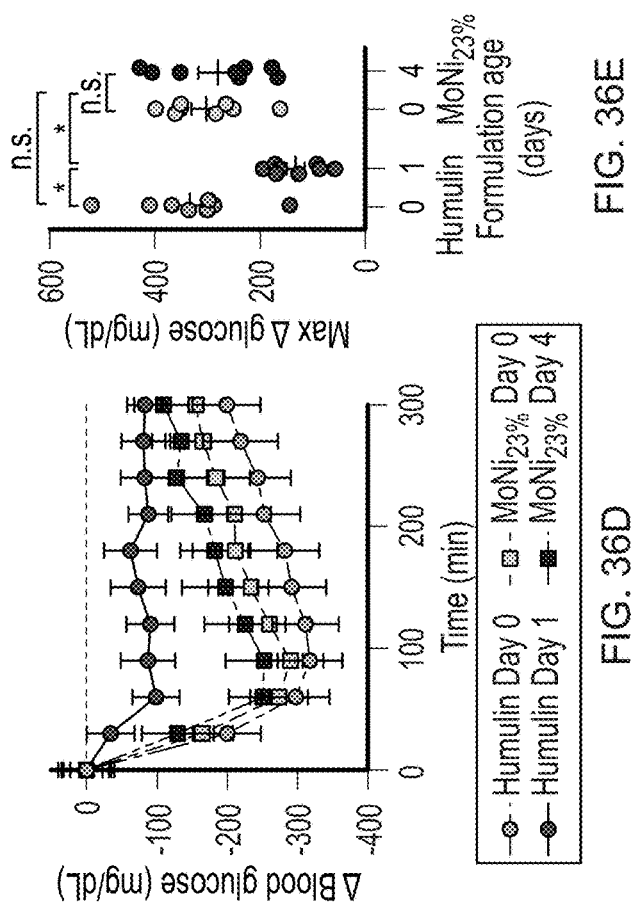
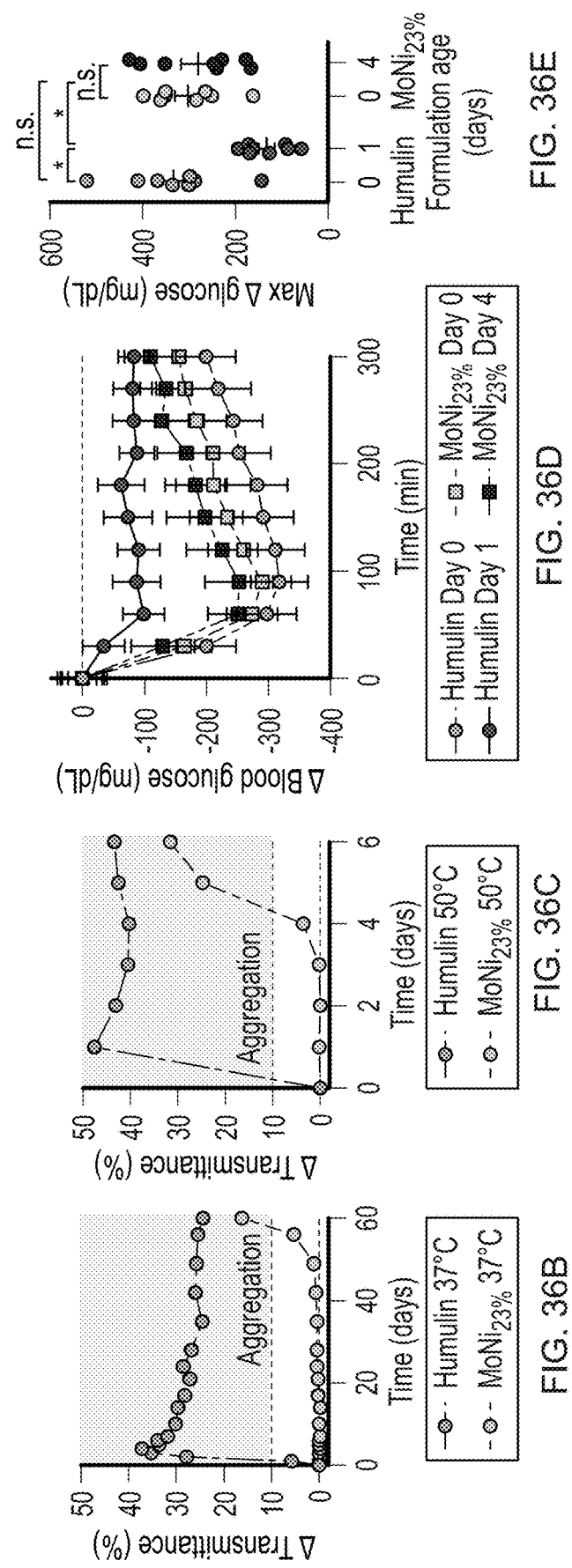
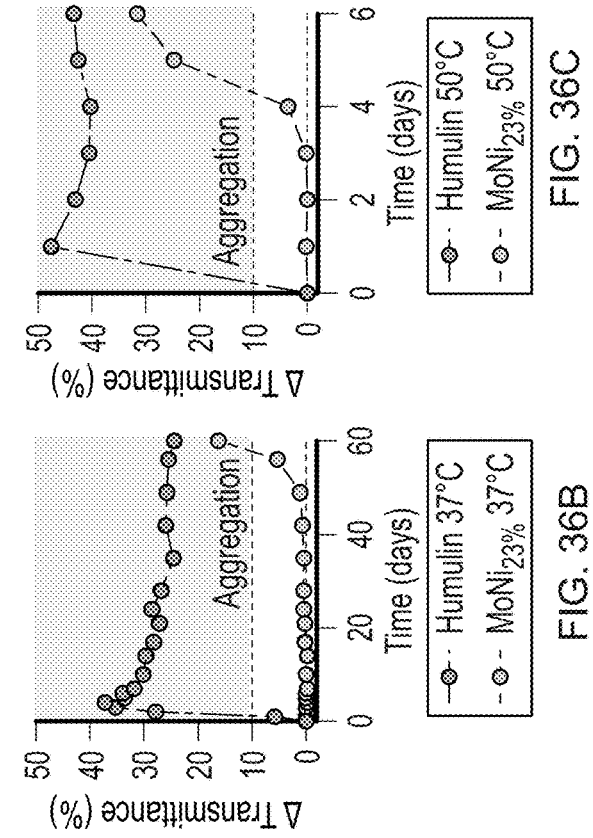
FIG. 36A
FIG. 36B
FIG. 36C
FIG. 36D
FIG. 36E

POLYMER EXCIPIENTS FOR BIOPHARMACEUTICAL FORMULATIONS

RELATED APPLICATIONS

This is a continuation under 35 U.S.C. §§ 120 and 365(c) of International Application No. PCT/US2021/027693, filed Apr. 16, 2021, which claims the benefit of the priority of U.S. Applications No. 63/159,306, filed Mar. 10, 2021, and No. 63/011,928, filed Apr. 17, 2020, the disclosures which are incorporated herein by reference in their entireties.

GOVERNMENT RIGHTS

This invention was made with government support under Grant DK119254 awarded by the National Institutes of Health (NIH). The government has certain rights in the invention.

FIELD OF THE INVENTION

The present disclosure relates to amphiphilic polyacrylamide-based copolymer excipients that can be used to reduce or prevent aggregation of biologic molecules, such as proteins and peptides, and lipid-based vehicles in aqueous formulations at hydrophobic interfaces, thereby increasing the thermal stability of the molecules in the formulation. The present disclosure also relates to formulations of a monomeric insulin, and co-formulations of insulin and other proteins. The formulations containing the copolymer excipient exhibit increased stability as compared to current rapid acting mealtime insulin.

BACKGROUND

Over 40 million patients live with diabetes worldwide and rely on insulin replacement therapy through daily subcutaneous insulin injections or insulin infusion pumps. These patients are unable to produce sufficient insulin required to promote cellular glucose uptake for basic metabolic function and therefore must deliver calculated insulin doses to manage glycemic excursions. Unfortunately, the pharmacokinetics of current insulin formulations do not mimic endogenous insulin secretion, which can reach peak concentrations in 30 minutes in a non-diabetic individual. Even current "rapid-acting" insulin analogues, designed for mealtime boluses, exhibit delayed onset of action of 20-30 minutes, peak action at 60-90 minutes, and a total duration of action of 3-4 hours. These kinetics are an outcome of the mixed association states of the insulin molecules in formulation. Commercial insulin formulations typically contain a mixture of insulin hexamers, dimers, and monomers. While monomers are rapidly absorbed into the bloodstream after injection, dimers and hexamers are absorbed more slowly on account of their size and must dissociate into monomers to become active (FIG. 1). Further, the extended duration of insulin action can make controlling post-prandial glycemic excursions difficult and increases the risk of hypoglycemia, as insulin may remain on board even after the mealtime glucose load passes.

An insulin formulation that is absorbed rapidly from the subcutaneous space to more closely mimic endogenous post-prandial insulin secretion is needed to better control mealtime blood glucose. A monomeric insulin formulation would enable both faster onset and shortened duration of action, thus reducing the risk of post-prandial hypoglycemia by eliminating the subcutaneous depot of insulin hexamers (FIG. 1A and FIG. 1B). However, monomeric insulin is unstable in formulation and rapidly aggregates into amyloid fibrils, which are both inactive and immunogenic. Presently, zinc and phenolic preservatives are commonly used as excipients in insulin formulations because their propensity to promote insulin hexamer formation enables them to act as stabilizing agents. It is critical to develop a new class of excipients that are capable of improving insulin stability in the monomeric state to enable a viable ultra-fast acting insulin formulation.

Insulin aggregation typically is initiated at hydrophobic interfaces, such as the air-liquid interface, where monomers undergo partial unfolding upon adsorption and can nucleate amyloid fibril formation (FIG. 1C). The monomeric state is most susceptible to aggregation because hydrophobic moieties typically shielded in the dimeric and hexameric association states are responsible for aggregation. Current zinc-free methods for monomeric insulin stabilization have relied on shielding hydrophobic interactions by covalently or non-covalently attaching hydrophilic polymers such as poly(ethylene glycol) (PEG) or trehalose glycol-polymers directly to insulin. While these methods have proven effective at stabilizing insulin in formulation, they lead to increased circulation time in vivo, which is undesirable for an ultra-fast acting insulin formulation. Further, while poly(ethylene glycol) polymers have been traditionally used in drug delivery because of their water solubility and biocompatibility, recent concerns around immunogenicity are beginning to limit their use.

An alternative approach to insulin stabilization exploits the propensity of amphiphilic polymers to occupy the interface, preventing insulin-interface interactions (FIG. 1C). Poloxamers are an example of polymer surfactants that have been used to improve the stability of commercial insulin formulations (INSUMAN® U400, Sanofi-Aventis). Yet, these poloxamer excipients comprise a limited chemical space, exhibit a propensity to form micro-structures such as micelles in solution, and are susceptible to transitioning into gels at high concentrations, and as such, a stable ultra-fast monomeric insulin formulation is still evasive.

Insulin has been used to treat diabetes for almost 100 years, yet existing rapid-acting insulin formulations do not have fast enough pharmacokinetics to maintain tight glycemic control during times of rapid glucose fluctuation such as at mealtimes. Dissociation of the insulin hexamer, the primary association state of insulin in rapid-acting formulations, is the rate limiting step that leads to delayed onset and extended duration of action. A formulation of insulin monomers would more closely mimic endogenous post prandial insulin secretion, but using known formulation strategies, monomeric insulin is unstable in solution and rapidly aggregates into amyloid fibrils.

Patients with certain types of diabetes lack sufficient pancreatic beta cell mass and/or function to produce both endogenous insulin and amylin. In non-diabetic individuals, insulin and amylin work synergistically to control post-prandial glucose; amylin delays gastric emptying and suppresses glucagon action, while insulin promotes cellular glucose uptake. Studies have shown that dual-hormone replacement therapy with insulin and amylin results in improved glycemic outcomes for patients with diabetes, including a 0.3% reduction in HbA1c compared to treatment with insulin alone. However, treatment of type 1 diabetes over the last 100 years has primarily focused on insulin replacement. While a commercially available amylin analog (pramlintide) exists, only 1.5% of patients who would benefit from amylin replacement therapy had adopted it by 2012. This is primarily due to formulation challenges that result in the need for a burdensome separate injection of amylin in addition to insulin at mealtimes.

Amylin is highly unstable and rapidly aggregates to form inactive and immunogenic amyloid fibrils. Pramlintide, an amylin analog, has three amino acid modifications to reduce its propensity to aggregate into amyloid fibrils, thus improving its shelf-life, but is formulated at pH=4 making it incompatible to be mixed with insulin formulations (typically pH~7). Further, in typical clinical administrations insulin and pramlintide have disparate pharmacokinetics, which is in contrast to endogenous co-secretion of the two hormones from the beta-cells following the same diurnal patterns. The difference in absorption kinetics when delivered exogenously results from the different association states of insulin and pramlintide in formulation (FIG. 15A). Pramlintide only exists as a monomer, while insulin formulations contain a mixture of hexamers, dimers, and monomers. The mixture of insulin association states results in delayed absorption and prolonged duration of insulin action.

SUMMARY

Provided in the present disclosure are polyacrylamide-based copolymer excipients that contain a water-soluble carrier monomer with an acrylamide reactive moiety and a functional dopant monomer with an acrylamide reactive moiety. The copolymers have been found to reduce or prevent aggregation of biologic molecules and lipid-based vehicles in aqueous formulations at hydrophobic interfaces. Thus, the biologic molecules and lipid-based vehicles in the formulations containing the polyacrylamide-based copolymers exhibit increased stability, such as increased thermal stability, as compared to the same formulations that do not contain the polyacrylamide-based copolymers. The polyacrylamide-based copolymers can be used with any biologic molecule or lipid-based vehicle that is susceptible to aggregation in an aqueous medium, including, but not limited to, proteins, such as antibodies and fragments thereof, cytokines, chemokines, hormones, vaccine antigens, cancer antigens, adjuvants, and combinations thereof. In some embodiments, the protein is a monoclonal antibody. In some embodiments, the polyacrylamide-based copolymers reduce or prevent aggregation of a protein susceptible to aggregation in an aqueous medium. The polyacrylamide-based copolymers can also be used with lipid-based vehicles that are susceptible to aggregation in an aqueous medium, including, but not limited to, liposomes, lipid nanoparticles, polymerosomes, and micelles, to prevent or reduce aggregation.

In some embodiments, the protein is insulin. In some embodiments, the polyacrylamide-based copolymer is used in the development of an ultra-fast absorbing insulin lispro (UFAL) formulation, which remains stable under stressed aging conditions for 25±1 hours, compared to 5±2 hours for commercial fast-acting insulin lispro formulations (HUMALOG®). In a swine model of insulin-deficient diabetes, UFAL exhibited peak action at 9±4 minutes while commercial HUMALOG® exhibited peak action at 25±10 minutes. These ultra-fast kinetics make UFAL a promising candidate for improving glucose control and reducing burden for patients with diabetes.

According to exemplary embodiments, the polyacrylamide-based copolymer excipients enable stable formulation of an ultra-fast acting monomeric insulin. In some embodiments, these excipients are synthetic copolymers composed of a water-soluble carrier monomer, chosen to aid polymer solubility, and a functional dopant monomer, which affords the ability to screen a wide chemical space unexplored in current surfactant excipients. The dopant monomer is hypothesized to promote polymer-interface interactions, reducing insulin-insulin interactions at the interface, and thus improving insulin stability. In some embodiments, precision high-throughput synthesis using reverse additional fragmentation transfer (RAFT) polymerization is employed to generate a library of over 100 polyacrylamide-based copolymers. In the present disclosure, it is demonstrated that the polyacrylamide-based copolymers enable the stable formulation of monomeric insulin lispro and that this ultra-fast absorbing insulin lispro (UFAL) formulation exhibits pharmacokinetics that are 2-fold faster than commercial fast-acting insulin formulations in a swine model of insulin-deficient diabetes.

In addition, in some embodiments, the polyacrylamide-based copolymers enable the stable co-formulation of monomeric insulin lispro and pramlintide with synchronized ultrafast insulin-pramlintide pharmacokinetics that result in better glycemic control in a mealtime simulation. This co-formulation has potential to improve glucose management and reduce patient burden in clinical applications using it whenever rapid acting insulin would otherwise be used. The herein described copolymer excipients can also be applied more broadly to improve the thermal stability of protein formulations, including insulin formulations, as simple "drop-in" excipients, without altering their bioactivity, pharmacokinetics or pharmacodynamics. For example, the copolymer excipients described herein can be used as a drop-in excipient in combination with other formulation approaches that are intended to alter or modulate the pharmacokinetics of the protein formulation.

Also provided in the present disclosure is a polyacrylamide-based copolymer comprising a water-soluble carrier monomer comprising an acrylamide reactive moiety; and a functional dopant monomer comprising an acrylamide reactive moiety; wherein the weight percent (wt %) of the water-soluble carrier monomer is about 70% to about 98%; the weight percent (wt %) of the functional dopant monomer is about 2% to about 30%; the average molecular weight ($M_n$) of the polyacrylamide-based copolymer is about 1,000 g/mol to about 30,000 g/mol; and the degree of polymerization is about 10 to about 250.

As disclosed herein, high throughput controlled radical polymerization techniques were implemented to generate a large library of polyacrylamide-based copolymer excipients. Non-limiting examples of polyacrylamide-based copolymers as provided herein include a polyacrylamide-based copolymer comprising a water-soluble carrier monomer selected from the group consisting of N-(3-methoxypropoyl) acrylamide (MPAM), 4-acryloylmorpholine (MORPH), N,N-dimethylacrylamide (DMA), N-hydroxyethyl acrylamide (HEAM), and acrylamide (AM); and a functional dopant monomer selected from the group consisting of N-[tris (hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE).

Provided in the present disclosure is a composition comprising about 0.005 wt % to about 0.2 wt % of a polyacrylamide-based copolymer comprising about 70% to about 95% by weight of a MORPH carrier monomer; and about 5% to about 30% by weight of a NIP dopant monomer; and about 100 U/mL insulin, or an analog thereof.

Also provided in the present disclosure is a composition comprising about 0.005 wt % to about 0.2 wt % of a polyacrylamide-based copolymer comprising about 70% to about 95% by weight of a MORPH carrier monomer; and about 5% to about 30% by weight of a NIP dopant monomer; about 100 U/mL insulin, or an analog thereof; and about 0.01 mg/mL to about 0.1 mg/mL pramlintide.

Also provided is a method of treating diabetes in a subject in need thereof, comprising administering to the subject a therapeutically effective amount of a composition comprising a polyacrylamide-based copolymer of the present disclosure.

Also provided is a method of managing the blood glucose level in a subject in need thereof, comprising administering to the subject a therapeutically effective amount of a composition comprising a polyacrylamide-based copolymer of the present disclosure.

Also provided is a method for increasing stability of a formulation containing a biologic molecule, comprising adding about 0.005 wt % to about 5 wt % of a polyacrylamide-based copolymer of the present disclosure to the formulation.

Also provided is a method for increasing stability of a protein formulation, comprising adding about 0.005 wt % to about 5 wt % of a polyacrylamide-based copolymer of the present disclosure to the protein formulation.

Also provided is a method for increasing stability of a formulation containing a lipid-based vehicle, comprising adding about 0.005 wt % to about 5 wt % of a polyacrylamide-based copolymer of the present disclosure to the formulation.

Also provided is a method for reducing the rate of aggregation of a biologic molecule in an aqueous composition, comprising adding about 0.005 wt % to about 5 wt % of a polyacrylamide-based copolymer of the present disclosure to the formulation.

Also provided is a method for reducing the rate of aggregation of a protein in an aqueous composition, comprising adding about 0.005 wt % to about 5 wt % of a polyacrylamide-based copolymer of the present disclosure to the protein formulation.

Also provided is a method for reducing the rate of aggregation of a lipid-based vehicle in an aqueous composition, comprising adding about 0.005 wt % to about 5 wt % of a polyacrylamide-based copolymer of the present disclosure to the formulation.

DESCRIPTION OF THE DRAWINGS

FIG. 1A: Commercial "rapid-acting" insulin formulations contain a mixture of insulin hexamers, dimers, and monomers. Only the monomeric form of insulin is active, thus, the dissociation from the hexamer to the monomer is rate limiting for therapeutic action. An ultra-fast insulin formulation would contain primarily insulin monomers and no insulin hexamers for rapid insulin absorption after subcutaneous administration. FIG. 1B illustrates the mixture of insulin hexamers, dimers, and monomers in commercial rapid-acting insulin formulations that result in extended duration of insulin action when delivered subcutaneously. Insulin monomers are absorbed in approximately 5-10 minutes, dimers are absorbed in 20-30 minutes, and hexamers can take 1-2 hours to be absorbed and result in prolonged insulin action accordingly. A primarily monomeric insulin formulation would reduce time to onset and result in shorter duration of insulin action for better management of blood glucose at mealtimes. FIG. 1C illustrates a hexamer-free ultra-fast insulin formulation that will face stability challenges due to the propensity for insulin monomers to aggregate into amyloid fibrils. At the air-water interface (shown on the left), unfolding of insulin molecules and exposure of hydrophobic domains during insulin-insulin interaction promotes amyloid fiber formation. Stabilizing polymer excipients are drawn to the air-liquid interface (shown on the right), impeding the unfolding of insulin molecules and the interfacial nucleation of insulin amyloidosis.

FIG. 5G is a heat-map of the top performing excipient for each carrier-dopant combination (the longest time to aggregation). Dotted black squares indicate the top dopant-carrier combinations, which were selected for further screening. These assays assess the aggregation of proteins in formulation over time during stressed aging (continuous agitation at 37° C. by monitoring changes in absorbance at 540 nm. Data shown are average time to aggregation (n=3; mean±s.d.) where aggregation is defined as a 10% increase in absorbance.

FIG. 7A shows MPAM copolymerized with PHE. FIG. 7B shows MPAM copolymerized with NIP. FIG. 7C shows MORPH copolymerized with PHE. FIG. 7D shows MORPH copolymerized with NIP.

FIGS. 8A-8D illustrate a stabilized ultra-fast absorbing insulin lispro (UFAL) formulation using polyacrylamide-based copolymer excipients. FIG. 8A shows insulin association states in HUMALOG® (top) and UFAL (bottom) as determined by MALS. FIG. 8B is a UFAL stability screen with a polymer excipient library. Time to aggregation of UFAL (100 U/mL) formulated with polymer excipients from the second screen (0.01 wt. %) is shown. Polyacrylamide-based copolymers excipients comprised of MPAM and MORPH carrier polymers with varied weight percent of dopants PHE (top) or NIP (bottom). FIG. 8C depicts representative absorbance traces showing UFAL stability when formulated with MORPH-NIP$_{23\%}$ compared to controls of UFAL with no polymer excipient, and HUMALOG®. These assays assess the aggregation of proteins in formulation over time during stressed aging (i.e., continuous agitation at 37° C.) by monitoring changes in transmittance at 540 nm. Data shown are average time to aggregation (n=3; mean±s.d.) where aggregation is defined as a 10% increase in absorbance. FIG. 8D shows diffusion-ordered NMR Spectroscopy (DOSY) of UFAL with polymer excipient MORPH-NIP$_{23\%}$. DOSY provides insight into the insulin association state and the insulin and polymer rates of diffusion in formulation. Diffusion characteristics demonstrate that lispro and MORPH-NIP$_{23\%}$ diffuse at different rates and are not associated, suggesting that disruption of interfacial interactions are the primary contributor to the observed stabilizing effects.

(FIG. 9A) In vitro activity was tested by assaying for phosphorylation of Ser473 on AKT. Data shown are mean±s.e.m. for n=3 experimental replicates. Results were plotted as a ratio of [pAKT]/[AKT] for each sample (n=3 cellular replicates) and an EC$_{50}$ regression [log(agonist) vs. response (three parameters)] was plotted using GraphPad Prism 8. (FIG. 9B) In vivo bioactivity was assessed in diabetic male Sprague Dawley rats. Rats fasted for 4 to 6 h received a subcutaneous injection of insulin (1.5 U/kg) and glucose measurements were taken using a handheld glucose monitor every 30 minutes for 4 hours. 16 rats were randomly assigned to two groups: (i) HUMALOG® (n=8) and (ii) UFAL (n=8). Within each group each rat received both the fresh and aged formulations on separate days. The order the formulations were given was randomized. It is hypothesized that the loss of activity for aged HUMALOG® observed in the blood glucose assay, but not the AKT assay, is a result of reversible insulin aggregation. When this aged formulation undergoes significant dilution for the in vitro AKT assay, these aggregates dissociate into active insulin, whereas the minimal dilution necessary for accurate dosing in rats is not enough for this dissociation to occur and the insulin aggregates result in the observed loss of activity. Data shown are mean±s.e.m.

FIGS. 10A-10M illustrate pharmacokinetics and pharmacodynamics of monomeric insulin in diabetic swine. Diabetic female pigs received subcutaneous administration of therapies comprising either (i) commercial HUMALOG® or (ii) UFAL formulated with polymer. Pigs were dosed with insulin according to their individual insulin sensitivities to decrease their glucose levels by approximately 200 mg/dL. FIG. 10A: Blood glucose measurements in pigs after insulin dosed subcutaneously. FIG. 10B: Pharmacokinetics of insulin lispro in mU/L following s.c. injection. FIG. 10C: Total exposure represented by area under the curve for 210 minutes. FIGS. 10D-10I: Percent exposure at various time points (AUC$_t$/AUC$_{210}$). FIG. 10J: Pharmacokinetics for each pig were individually normalized to peak concentrations and normalized values were averaged for lispro concentration for each treatment group. FIG. 10K: Time to reach 50% of peak lispro concentration (onset). FIG. 10L: Time to reach peak lispro concentration. FIG. 10M: Time for lispro depletion to 50% of peak concentration. FIGS. 10A, 10B, and 10J: Error bars indicate mean±s.d. with n=5 for all groups. FIGS. 10D-10I: Error bars indicate mean±s.e.m. with n=5 for all groups. Bonferroni post-hoc tests were performed to account for comparisons of multiple individual exposure timepoints and significance and alpha was adjusted (alpha=0.008). (FIGS. 10C, 10K-10M) Error bars indicate mean±s.e.m. with n=5 for all groups (alpha=0.05). Statistical significance was determined by restricted maximum likelihood (REML) repeated measures mixed model.

FIG. 11A: Scheme of subcutaneous injection site behind the foreleg of the pig. Pigs have tight skin and subcutaneous tissue that is very similar to humans, making them the most relevant preclinical model for studying pharmacokinetics of biopharmaceuticals following subcutaneous administration. Pigs are sufficiently large for insulin to be administered accurately using standard concentrations (100 U/mL), ensuring the observed pharmacokinetics are not skewed by dilution effects. FIG. 11B: Pigs were dosed with insulin according to their individual insulin sensitivities to decrease their blood glucose concentrations by about 200 mg/dL. Blood glucose measurements in pigs after insulin dosed subcutaneously. Error bars indicate mean±s.d. with n=5 for all groups.

FIGS. 12A-12E illustrate pharmacokinetic modelling of UFAL in humans. FIG. 12A: A model of insulin plasma concentrations after injection in human patients was adapted from Wong et al. (*J. Diabetes Sci. Technol.* (2008) 2:658-671). Rapid-acting insulin analogues are injected into the subcutaneous space (Iii), then dissociate and diffuse into the interstitium ($k_1$) where they are then absorbed into the plasma ($k_2$) and ultimately cleared ($k_3$). FIG. 12B: Normalized pharmacokinetic data for HUMALOG® and UFAL in diabetic pigs modeled using a least squares fit to determine $k_1$, $k_2$, and $k_3$ in pigs (FIG. 14 and Table 6). FIG. 12C: Human clinical HUMALOG® pharmacokinetic data compared to modeled rapid-acting insulin (RAI) analogue kinetics (using known human parameters, Table 6), and the predicted kinetics of UFAL in humans. UFAL human pharmacokinetics were predicted by first fitting the pig pharmacokinetic data for HUMALOG® and UFAL. The human UFAL pharmacokinetics was then plotted by using the estimated $k_1$ with the known $k_2$ and $k_3$ parameters. FIG. 12D: Model predicted kinetics of RAI and UFAL compared to HUMALOG® kinetics in published clinical studies, time to 50% peak up (left), time to peak (middle) and duration of action time to 50% of peak down (right). FIG. 12E: Comparison of the model predicted time to peak for UFAL in humans compared to human clinical data for commercial rapid-acting insulin formulations (see, for example: Heise et al., *Diabetes Obes. Metab.* (2017) 19:208-215; Andersen et al., *Diabetes Obes. Metab.* (2018) 20:2627-2632; Rave et al., *Diabetes Care* (2006) 29:1812-1817).

FIG. 14A: Time to 50% of peak up. FIG. 14B: Time to the peak. FIG. 14C: Time to 50% of the peak down. Stars indicate predicted pharmacokinetic timepoints from the model. Data points are the same used in FIGS. 10K-10M.

FIGS. 15A-15F illustrate the formulation kinetics and stability. FIG. 15A: Current dual-hormone replacement of insulin and pramlintide requires two separate injections at mealtimes. Not only is this additional injection burdensome, but there is a kinetic mismatch between insulin and pramlintide when delivered exogenously compared to endogenous co-secretion from the beta-cells. This results from the mixed insulin association states present in rapid-acting insulin formulations where monomers and dimers are rapidly absorbed, but the slow dissociation of the insulin hexamer causes extended duration of action. FIG. 15B: A single injection co-formulation of monomeric insulin and pramlintide would reduce patient burden, and have better pharmacokinetic overlap that more closely mimics endogenous secretion from the healthy pancreas. FIG. 15C: Amphiphilic acrylamide copolymer excipients can be used to stabilize an insulin-pramlintide co-formulation. These excipients preferentially adsorb onto the air-water interface, displacing insulin and/or pramlintide and preventing the nucleation of aggregation events that initiate amyloid fibril formation. FIG. 15D: Co-formulation components. FIG. 15E: Insulin association states in HUMALOG® (top); adapted from 57, compared to zinc-free lispro with phenoxyethanol (0.85 wt. %) and glycerol (2.6 wt. %) (bottom). FIG. 15F: Formulation stability in a stressed aging assay (continuous agitation, 37° C.) of (i) HUMALOG®, (ii) HUMALOG®+pramlintide (1:6 pramlintide:lispro), (iii) zinc-free lispro (100 U/mL lispro, 0.85 wt. % phenoxyethanol, 2.6 wt. % glycerol, 0.1 mg/mL $MoNi_{23\%}$), (iv) Co-formulation (100 U/mL lispro, 1:6 pramlintide:lispro, 0.85 wt. % phenoxyethanol, 2.6 wt. % glycerol, 0.1 mg/mL $MoNi_{23\%}$). Change in transmittance is shown from baseline transmittance. Aggregation is defined as a change in transmittance >10%.

FIGS. 18A-18D illustrate the pharmacokinetics and pharmacodynamics in diabetic rats. Fasted male diabetic rats (n=11) received subcutaneous administration of (i) HUMALOG®, (ii) separate injections of HUMALOG® and pramlintide, or (iii) insulin-pramlintide co-formulation. Insulin administration was immediately followed with oral gavage with a glucose solution (1 g/kg). Each rat received all treatment groups. Change in blood glucose levels from baseline following treatment is shown in FIG. 18A. FIGS. 18B-18C show the pharmacokinetics of insulin lispro (FIG. 18B) or pramlintide (FIG. 18C).

FIGS. 19A-19M illustrate onset and duration of action in diabetic rats. Fasted male diabetic rats (n=11) received subcutaneous administration of (i) HUMALOG®, (ii) separate injections of HUMALOG® and pramlintide, or (iii) insulin-pramlintide co-formulation. Insulin administration was immediately followed with oral gavage with a glucose solution (1 g/kg). Each rat received all treatment groups. Pharmacokinetics for each rat was individually normalized to the peak serum levels and the normalized values were averaged for insulin lispro (FIG. 19A) or pramlintide (FIG. 19J). Exposure onset defined as time to 50% of the peak up for insulin lispro (FIG. 19B) or pramlintide (FIG. 19K). Exposure peak for insulin lispro (FIG. 19C) or pramlintide (FIG. 19L). Exposure onset defined as time to 50% of the peak up for insulin lispro (FIG. 19D) or pramlintide (FIG. 19M). Fraction of lispro exposure as a ratio of $AUC_t/AUC_{120}$ at FIG. 19E, t=6; FIG. 19F, t=15; FIG. 19G, t=30; FIG. 19H, t=45; FIG. 19I, t=60. Statistical significance was determined by restricted maximum likelihood repeated measures mixed model. Tukey HSD post-hoc tests were applied to account for multiple comparisons (FIGS. 19b-19I, 19K, 19M). Bonferroni post hoc tests were performed to account for comparisons of multiple individual exposure time points, and significance and a were adjusted (α=0.01) (FIGS. 19E-19I).

FIGS. 20A-20C illustrate lispro area under the curve and exposure ratios. Total lispro exposure as area under the pharmacokinetic curve (FIG. 20A). Fraction of lispro exposure as a ratio of $AUC_t/AUC_{120}$ at FIG. 20B, t=3; FIG. 20C, t=9. Statistical significance was determined by restricted maximum likelihood repeated measures mixed model. Tukey HSD post-hoc tests were applied to account for multiple comparisons (FIGS. 20B-20C).

FIGS. 21A-21G illustrate pramlintide area under the curve and exposure ratios. Total pramlintide exposure as area under the pharmacokinetic curve (FIG. 21A). Fraction of pramlintide exposure as a ratio of $AUC_t/AUC_{120}$ at FIG. 20B, t=6; FIG. 20C, t=9; FIG. 20D, t=15; FIG. 20E, t=30; FIG. 20F, t=45; FIG. 20G, t=60. Statistical significance was determined by restricted maximum likelihood repeated measures mixed model.

FIGS. 22A-22C illustrate the pharmacokinetic overlap of formulations. Average normalized serum concentrations (for each rat, n=11/group) for insulin and pramlintide when delivered as two separate injections and when delivered together as a co-formulation are shown in FIGS. 22A and 22B, respectively. Overlap between the two curves was defined as the total time spent above 0.5 for both insulin and pramlintide curves (width at half-peak height), shown as a ratio of the overlap time to the total width of both peaks (overlap÷(lispro+pramlintide−overlap) (FIG. 22C). Statistical significance was determined by restricted maximum likelihood repeated measures mixed model.

FIGS. 23A-23C illustrate gastric emptying in diabetic rats. Fasted male diabetic rats received subcutaneous administration of (i) HUMALOG®, (ii) separate injections of HUMALOG® and pramlintide, or (iii) insulin-pramlintide co-formulation. FIG. 23A depicts a gastric emptying experiment where insulin administration (2 U/kg) was immediately followed with oral gavage with an acetaminophen slurry (100 mg/kg). Each rat (n=11) received all treatment groups. Acetaminophen serum concentration is shown in FIG. 23B. Time to peak exposure of acetaminophen serum concentration is shown in FIG. 23C. All data is shown as mean±SE. Statistical significance was determined by restricted maximum likelihood repeated measures mixed model. Tukey HSD post-hoc tests were applied to account for multiple comparisons.

FIGS. 24A-24D illustrate mealtime simulations with glucose. Fasted male diabetic rats received subcutaneous administration of (i) HUMALOG®, (ii) separate injections of HUMALOG® and pramlintide, or (iii) insulin-pramlintide co-formulation. FIG. 24A depicts oral glucose challenge where insulin administration (0.75 U/kg) was immediately followed with oral gavage with a glucose solution (2 g/kg). Each rat (n=10) received all treatment groups. Change in blood glucose after administration is shown in FIG. 24B. Max change in glucose above baseline is shown in FIG. 24C. Max change in glucose below the baseline is shown in FIG. 24D. All data is shown as mean±SE. Statistical significance was determined by restricted maximum likelihood repeated measures mixed model. Tukey HSD post-hoc tests were applied to account for multiple comparisons.

FIGS. 25A-25C illustrate interspecies pharmacokinetics for HUMALOG® and HUMULIN®. Normalized pharmacokinetics for commercial HUMALOG® and regular human insulin (ex. HUMULIN® R) delivered in rats and humans is shown in FIG. 25A. Time to peak exposure for each formulation is shown in FIG. 25B and duration of action for each formulation is shown in FIG. 25C. Differences in time to onset and time to peak in rats between rapid-acting and regular insulin formulations are minimal and difficult to detect. However, in humans, these small differences translate to distinct differences in time to onset and time to peak. This suggests that the trend for more rapid action we observe for insulin in the co-formulations of the present application compared to HUMALOG® could translate into substantial differences in humans. Duration of action is defined here as peak width at 25% peak height (time 25% down–time 25% up). Rat data for HUMALOG® is taken from this study, and rat data for regular human insulin is adapted from previous work. Human HUMALOG® data is from three external studies and has been adapted from presentation in previous work. Human regular human insulin data is from three external studies (Pettis et al., *Diabetes Technol. Ther.* (2011) 13:443-450; Andersen et al., *Diabetes Obes. Metab.* (2018) 20:2627-2632; Plank et al., *Diabetes Care* (2002) 25:2053-2057; Linnebjerg et al., *Clin. Pharmacokinet.* (2020) 59:1589-1599).

FIGS. 26A-26C illustrate interspecies pharmacokinetics for HUMALOG® and monomeric lispro formulations. FIG. 26A shows normalized pharmacokinetics for commercial HUMALOG® delivered in rats, pigs and humans (left), time to peak (middle), and duration of action (right). FIG. 26B shows normalized pharmacokinetics for monomeric insulin delivered in rats, pigs and humans (left), time to peak (middle), and duration of action (right). HUMALOG® shows increased time to onset and longer duration of action as you shift to species with more complex subcutaneous architecture (rats<pigs<humans). In contrast, monomeric lispro has very similar onset and duration of action between rats and pigs. Since the difference between rats and pigs is minimal for this formulation, it is also likely that the difference between pigs and humans will be small. Further, we observe that pramlintide—which only exists as a monomer—has very similar kinetics between pigs and humans. FIG. 26C shows normalized pharmacokinetics for commercial formulations in humans (left), time to peak exposure for each formulation (middle), and duration of action for each formulation (right). Even with the shift towards faster time to peak with next generation rapid-acting insulins like Fiasp and Lyumjev there have not been similar increases in reducing duration of action. Duration of action is defined here as peak width at 25% peak height (time 25% down–time 25% up). Rat data is taken from the study described in Example 3 (monomeric lispro in rats was delivered as part of the co-formulation). Pig data was adapted from previous work. Human HUMALOG® data is from four external studies (Pettis et al., *Diabetes Technol. Ther.* (2011) 13:443-450; Andersen et al., *Diabetes Obes. Metab.* (2018) 20:2627-2632; Plank et al., *Diabetes Care* (2002) 25:2053-2057; Linnebjerg et al., *Clin. Pharmacokinet.* (2020) 59:1589-1599). Predicted monomeric lispro in humans has been adapted from pharmacokinetic modeling from previous work in pigs. For FIG. 26C, data is adapted from clinical studies in humans for (i) regular human insulin (Rave et al., *Diabetes Care* (2006) 29:1812-1817; Lindholm et al., *Diabetes Care* (1999) 22:801-805; Heinemann et al., *Diabetic Medicine* (1996) 13:625-629), (ii) NOVOLOG® (Novo Nordisk) (Fath et al., *Pediatr. Diabetes* (2017) 18:903-910; Heise et al., *Clin. Pharmacokinet.* (2017) 56:551-559), (iii) Fiasp (Novo Nordisk) (Fath et al., *Pediatr. Diabetes* (2017) 18:903-910; Heise et al., *Clin. Pharmacokinet.* (2017) 56:551-559), (iv) HUMALOG® (Eli Lily) (Pettis et al., *Diabetes Technol. Ther.* (2011) 13:443-450; Andersen et al., *Diabetes Obes. Metab.* (2018) 20:2627-2632; Plank et al., *Diabetes Care* (2002) 25:2053-2057; Linnebj erg et al., *Clin. Pharmacokinet.* (2020) 59:1589-1599), and (v) Lyumjev (Eli Lily) (Linnebjerg et al., *Clin. Pharmacokinet.* (2020) 59:1589-1599; Shiramoto et al., *J. Diabetes Invest.* (2020) 11:672 680). Predicted monomeric lispro in humans has been adapted from pharmacokinetic modeling from previous work in pigs (Mann et al., *Sci. Transl. Med.* (2020) 12:eaba6676).

FIG. 28B shows the aggregation mechanism of commercial insulin formulations. The insulin hexamer is at equilibrium with monomers in formulation. These monomers interact at the interface, where the exposure of hydrophobic domains during insulin-insulin interaction nucleate amyloid fiber formation. FIG. 28C depicts the chemical structure of an example polyacrylamide-based copolymer excipient, poly(acryloylmorpholine$_{77\%}$-co-N-isopropylacrylamide$_{23\%}$) (MoNi$_{23\%}$). Polyacrylamide-based copolymer excipients are amphiphilic copolymers that adsorb to interfaces, reducing insulin-insulin interactions and delaying the nucleation of insulin amyloidosis (FIG. 28D).

FIG. 29A is an illustration of a proposed stabilization mechanism. In commercial HUMULIN®, monomers at the interface have associative interactions (top). Alone, MoNi$_{23\%}$ occupies the interface without the presence of insulin (middle). In combination with HUMULIN® formulations, MoNi$_{23\%}$ disrupts insulin-insulin surface interactions, providing a mechanism for inhibiting aggregation (bottom). FIG. 29B shows surface tension measurements of HUMULIN®, MoNi$_{23\%}$ (0.01 wt. %) formulated with formulation excipients, and HUMULIN® formulated with MoNi$_{23\%}$ (0.01 wt. %) (n=2). FIG. 29C shows interfacial rheology measurements of HUMULIN®. Measurements for HUMULIN® formulated with MoNi$_{23\%}$ (0.01 wt. %) fell below the resolution of the instrument, indicating that there is no protein aggregation at the interface (n=3).

FIGS. 31A-31H illustrate that formulation with polyacrylamide-based copolymers stabilizes insulin. FIG. 31A: 1 mL of Commercial HUMULIN® or HUMULIN® with the addition of polyacrylamide-based copolymer excipients (i) MoPhe$_{6\%}$, (ii) MpPhe$_{8\%}$, (iii) MoNi$_{23\%}$ were aliquoted into 2 mL glass vials and aged at 37° C. with constant agitation (150 rpm) for 0, 2, 4, and 6 months. Additional 2 week and 1 month timepoints were added for the HUMULIN® control. All formulations were at a concentration of 95 U/mL (diluted so that copolymers could be added to commercial HUMULIN®). FIG. 31B shows a transmittance assay used to assess the aggregation of proteins in formulation over time by monitoring changes in transmittance at 540 nm (n=1 per formulation timepoint). FIG. 31C shows in vitro activity by assaying for phosphorylation of Ser473 on AKT after stimulation with either HUMULIN® or MoNi$_{23\%}$ at 0 month and 6 month timepoints. Insulin concentrations are shown as Log(ng/mL). FIG. 31D shows the Log(EC$_{50}$) values for each formulation. Statistical significance was assessed using the Extra sum-of-squares F-test to determine if Log(EC$_{50}$) differed between datasets. Data sets were compared in pairs, and Bonferroni post-hoc tests were used to adjust for multiple comparisons (alpha=0.008). FIGS. 31E-31H depict circular dichroism spectra from 200-260 nm for each formulation (diluted to 0.2 mg/mL in PBS) at each time point. For FIG. 31C, results shown are mean±s.e plotted as a ratio of [pAKT]/[AKT] for each sample (n=3 cellular replicates) and an EC$_{50}$ regression (log(agonist) vs. response (three parameters)) was plotted using GraphPad Prism 8. For FIG. 31D, statistical significance was assessed using the Extra sum-of-squares F-test to determine if Log (EC$_{50}$) differed between datasets. Data sets were compared in pairs, and Bonferroni post-hoc tests were used to adjust for multiple comparisons (alpha=0.008).

FIGS. 32A-32B illustrate transmittance assays for 5 mg/mL and 1 mg/mL formulations. 1 mL of HUMULIN® with the addition of polyacrylamide-based copolymer excipients (i) MoPhe6%, (ii) MpPhe8%, (iii) MoNi$_{23\%}$ were aliquoted into 2 mL glass vials and aged at 37° C. with constant agitation (150 rpm) for 0, 2, 4, and 6 months. FIG. 32A shows 5 mg/mL polymer excipient in formulation (0.5 wt. %) and FIG. 32B shows 1 mg/mL polymer excipient in formulation (0.1 wt/%).

FIGS. 33A-33F illustrate insulin activity after aging in diabetic rats. Fasted diabetic male rats received subcutaneous administration (1.5 U/kg) of each insulin formulation HUMULIN® (FIG. 33A), HUMULIN® with MoPhe$_{6\%}$ (FIG. 33B), HUMULIN® with MpPhe$_{8\%}$ (FIG. 33C), or HUMULIN® with MoNi$_{23\%}$ (FIG. 33D) at each aging timepoint (0, 2, 4, 6 months). FIG. 33E is a comparison of each formulation at t=0 months. In these assays, 32 rats were randomly assigned to one of the four formulation groups (n=8) and each rat received one dose of the formulation at each aging timepoint in a random order. Blood glucose levels were measured every 30 minutes using a handheld glucose monitor and the change in blood glucose relative to baseline glucose measurements were plotted. The maximum difference in glucose from baseline (Δ glucose) was also plotted for each formulation as a measure of formulation potency. FIG. 33F shows the pharmacokinetics of HUMULIN® and HUMULIN® with MoNi$_{23\%}$ at t=0 and t=6 months. All data is shown as mean±s.e. Statistical significance between max Δ glucose was assessed using a REML repeated measures mixed model with rat as a random effect and the age of the formulation as a within-subject fixed effect. A post-hoc Tukey HSD test was used on HUMULIN® formulations to determine statistical significance between aging timepoints.

FIGS. 36A-36E illustrate stressed aging in commercial packaging. FIG. 36A: HUMULIN® is often sold in standardized 10 mL glass vials and packaged in cardboard boxes. The stabilizing capacity of polyacrylamide-based copolymers in commercial packaging conditions under stressed conditions was tested. 10 mL vials of U100 HUMULIN® R were diluted to 95 U/mL with the addition of 50 µL of a MoNi$_{23\%}$ stock solution (to a final concentration of 0.01 wt. % copolymer) or water (control). Dilution was necessary to add copolymer to the formulation. These vials were replaced in their original boxes and taped to a shaker plate (150 rpm) in a 37° C. (n=1 per formulation) or 50° C. (n=1 per formulation) incubator. Samples were observed and imaged daily. FIGS. 36B-36C are transmittance assays for HUMULIN® or HUMULIN® comprising MoNi$_{23\%}$ after aging at 37° C. (FIG. 36B) and 50° C. (FIG. 36C). Single samples (n=1) were tested for each transmittance curve. Blood glucose curves (FIG. 36D) and maximum change in blood glucose (Δ glucose) in fasted diabetic rats for samples aged at 50° C. (FIG. 36E) are shown. Data is shown as mean±s.e. Statistical significance between max Δ glucose was assessed using a REML repeated measures mixed model with rat as a random effect and the age of the formulation as a within-subject fixed effect. A post-hoc Tukey HSD test was used to determine statistical significance between aging timepoints and groups.

DETAILED DESCRIPTION OF EMBODIMENTS

Figures 1A, 1B, 1C:
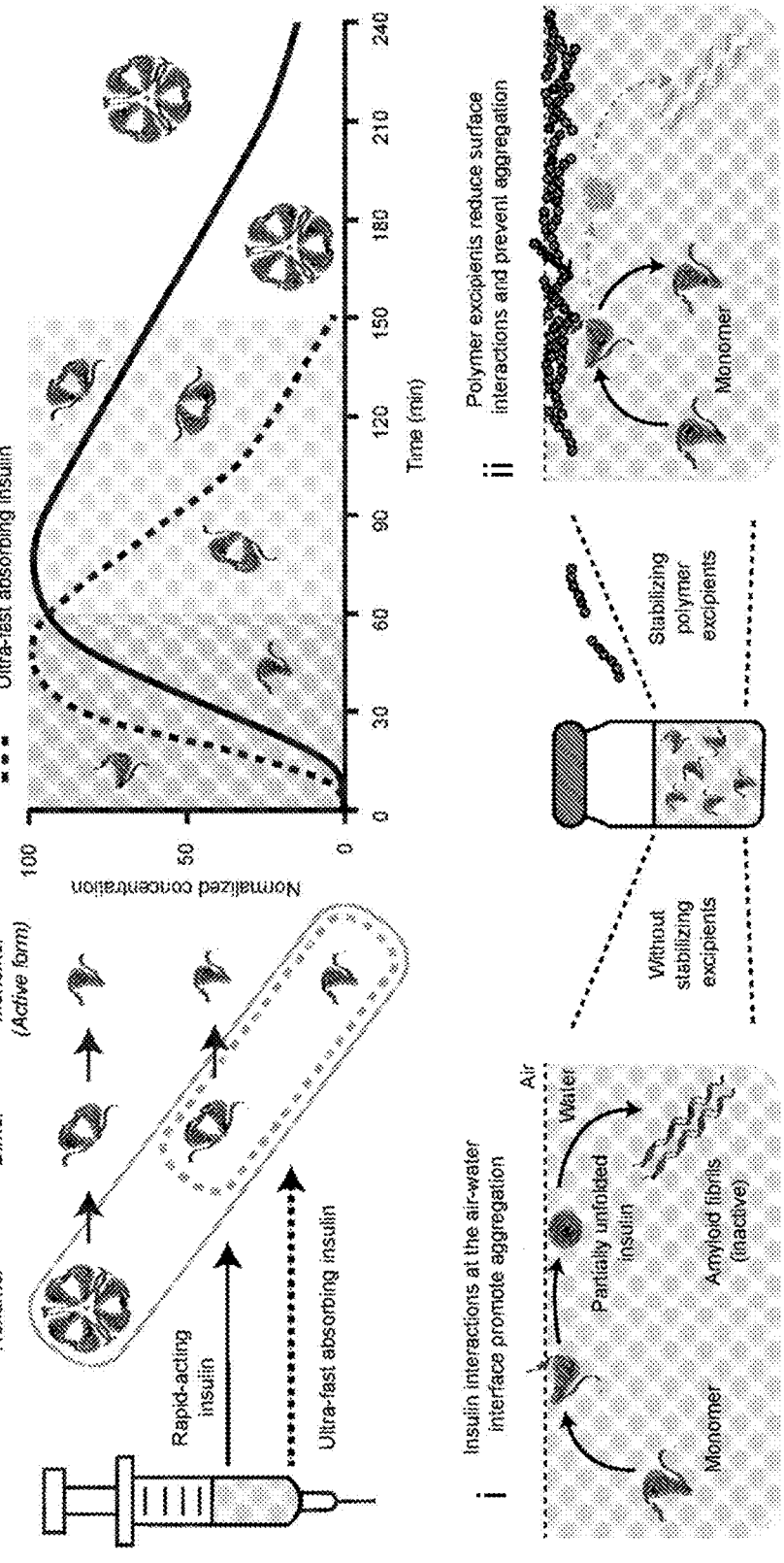
FIGS. 1A-1C illustrate a scheme of absorption kinetics of the various association states of insulin.

The present disclosure describes the synthesis and characterization of a library of copolymers comprising different water-soluble acrylamide monomers and functional dopant monomers in a variety of weight ratios, molecular weights, and degree of polymerization. The copolymers of the present disclosure are effective at reducing or preventing aggregation of biologic molecules (e.g., protein and peptides) or lipid-based vehicles in aqueous formulations at hydrophobic interfaces, particularly molecules that are susceptible to aggregation in an aqueous medium. Proteins and other biologic molecules are often used in the treatment of a wide variety of diseases and disorders; however, maintaining the stability of such formulations and preventing aggregation of the molecules is a key challenge faced by the biopharmaceutical industry. Proteins, other biologic molecules, and lipid-based vehicles, including, but not limited to, liposomes, micelles, polymerosomes, and lipid nanoparticles, can aggregate due to a variety of factors, including thermal stress, chemical degradation, or exposure to surfaces and interfaces. Non-covalent physical aggregation is mediated by forces like hydrophobic interaction, van der Waals interaction, hydrogen bonding, and electrostatic forces. Adsorption of such molecules to a variety of interfaces, particularly air-water interfaces, plays a key role in inducing aggregation. These aggregates could trigger immunogenic responses in the body and result in the production of anti-therapeutic antibodies.

The polyacrylamide-based copolymers of the present disclosure have been found to reduce or prevent aggregation of biologic molecules and lipid-based vehicles in aqueous formulations, resulting in increased stability. The polyacrylamide-based copolymers can be used with any molecule that is susceptible to aggregation in an aqueous medium, including, but not limited to, proteins such as antibodies and fragments thereof, cytokines, chemokines, hormones, vaccine antigens, cancer antigens, adjuvants, and combinations thereof. In some embodiments, the protein is insulin. In some embodiments, the protein is a monoclonal antibody. Monoclonal antibodies (mAbs) are therapeutic proteins used in the treatment of many diseases, but tend to aggregate, making their use a major challenge in formulation development. MAbs spontaneously adsorb onto air-solution interfaces and experience interfacial stresses, which is one of the major causes of aggregation. In some embodiments, the protein is a hormone. In some embodiments, the protein is a vaccine. In some embodiments, the biologic molecule is a nucleic acid. In some embodiments, the biologic molecule is a nucleic acid such as mRNA, DNA, siRNA, and miRNA.

The polyacrylamide-based copolymers can also be used with lipid-based vehicles that are susceptible to aggregation in an aqueous medium, including, but not limited to, liposomes, lipid nanoparticles, polymerosomes, and micelles, to prevent or reduce aggregation.

The polyacrylamide-based copolymers of the present disclosure prevent aggregation of proteins, other biological molecules, and lipid-based vehicles such as liposomes, lipid nanoparticles, polymerosomes, and micelles, by providing an inert barrier at the hydrophobic interface of an aqueous formulation to prevent interaction between the molecules, such as protein-protein interactions. In some embodiments, the hydrophobic interface is an air-water interface. In some embodiments, the hydrophobic interface is an enclosure-water interface, including, but not limited to, a glass-water interface, a rubber-water interface, a plastic-water interface, or a metal-water interface. In some embodiments, the hydrophobic interface is an oil-water interface.

As described in the present disclosure, copolymers were identified that can act as stabilizing agents for formulations containing biologic molecules. In some embodiments, the formulation is a protein formulation. The polyacrylamide-based copolymers can also act as stabilizing agents for formulations containing lipid-based vehicles that are susceptible to aggregation in an aqueous medium, including, but not limited to, liposomes, lipid nanoparticles, polymerosomes, and micelles. In some embodiments, the copolymers were identified using a high-throughput screen of a large library of combinatorial acrylamide-based copolymer excipients. In some embodiments, these copolymers enhance the stability of the formulation without any modifying effects on the molecules in the formulation. For example, the copolymers can enhance protein formulation stability without any protein-modifying effects. In some embodiments, copolymers comprising a water-soluble "carrier" monomer and a functional "dopant" monomer act as stabilizing excipients to reduce interactions of the biologic molecule with an interface, such as the air-liquid interface. In some embodiments, the biologic molecule is a protein. In some embodiments, copolymers comprising a water-soluble "carrier" monomer and a functional "dopant" monomer act as stabilizing excipients to reduce interactions of a lipid-based vehicle with an interface, such as the air-liquid interface.

Thus, provided in the present disclosure is a method for reducing aggregation of a biologic molecule or lipid-based vehicle comprising a polyacrylamide-based copolymer excipient as disclosed herein. In some embodiments, the biologic molecule is a protein. In some embodiments, the protein is selected from antibodies and fragments thereof, cytokines, chemokines, hormones, vaccine antigens, cancer antigens, adjuvants, and combinations thereof. In some embodiments, the biologic molecule is a nucleic acid. In some embodiments, the lipid-based vehicle is a liposome, micelle, polymerosome, or lipid nanoparticle. The polyacrylamide-based copolymer of the present disclosure comprises a water-soluble carrier monomer comprising an acrylamide reactive moiety and a functional dopant monomer comprising an acrylamide reactive moiety. In some embodiments, the copolymer comprises MPAM or MORPH carriers with NIP or PHE dopants.

Also provided are methods for increasing stability of a formulation containing a biologic molecule or a lipid-based vehicle. In some embodiments, methods for increasing thermal stability of a formulation containing a biologic molecule or a lipid-based vehicle are provided. In other embodiments, methods for reducing the rate of aggregation of a biologic molecule or a lipid-based vehicle in an aqueous composition are provided. The methods include adding the copolymer of the present disclosure to the formulation.

In some embodiments, the biologic molecule is a protein. In some embodiments, the protein is insulin. In some embodiments, concerns of reduced insulin activity or extended circulation times typically associated with covalent insulin modification (e.g., PEGylation) are reduced or eliminated.

Also provided in the present disclosure are methods of treating an elevated glucose level in a subject in need thereof, comprising administering to the subject a composition containing the polyacrylamide-based copolymer of the present disclosure and insulin. Also provided are methods of managing the blood glucose level in a subject in need thereof, comprising administering to the subject a composition containing the polyacrylamide-based copolymer of the present disclosure and insulin.

Definitions

Unless otherwise defined, all technical and scientific terms used herein have the same meaning as commonly understood by one of ordinary skill in the art to which this disclosure belongs. Methods and materials are described herein for use in the present application; other, suitable methods and materials known in the art in some aspects this disclosure are also used. The materials, methods, and examples are illustrative only and not intended to be limiting. All publications, patent applications, patents, sequences, database entries, and other references mentioned herein are incorporated by reference in their entireties. In case of conflict, the present specification, including definitions, will control. When trade names are used herein, the trade name includes the product formulation, the generic drug, and the active pharmaceutical ingredient(s) of the trade name product, unless otherwise indicated by context.

The term "polymer" refers to a substance or material consisting of repeating monomer subunits.

An "acrylamide monomer," as used herein, refers to a monomer species that possesses an acrylamide functional group

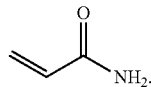

The term "acrylamide monomer" includes not only monomeric acrylamide, but derivatives of monomeric acrylamide. Examples of acrylamide monomers include, but are not limited to, acrylamide (AM), N-(3-methoxypropoyl)acrylamide (MPAM), 4-acryloylmorpholine (MORPH), N,N-dimethylacrylamide (DMA), N-hydroxyethyl acrylamide (HEAM), N-[tris(hy droxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE).

The term "polyacrylamide-based copolymer" refers to polymers that are formed from the polymerization of two or more monomer species, in which at least one of the monomer species possesses an acrylamide functional group (acrylamide monomer) and the monomers are structurally different. In some embodiments, the polyacrylamide-based copolymer is formed from the polymerization of two structurally different acrylamide monomers (two structurally different monomers that each possess an acrylamide functional group). The resulting copolymer can be an alternating copolymer wherein the monomer species are connected in an alternating fashion; a random copolymer, wherein the monomer species are connected to each other within a polymer chain without a defined pattern; a block copolymer, wherein polymeric blocks of one monomer species are connected to polymeric blocks made up of another monomer species; and graft copolymer, wherein the main polymer chain consists of one monomer species, and polymeric blocks of another monomer species are connected to the main polymer chain as side branches. In some embodiments, the polyacrylamide-based copolymers of the present disclosure are formed from the polymerization of a water-soluble carrier monomer and a functional dopant monomer. In some embodiments, the polyacrylamide-based copolymers of the present disclosure are random copolymers.

As defined herein, the term "water-soluble carrier monomer" refers to an acrylamide monomer species that is the water-soluble species within the polyacrylamide-based copolymer. In some embodiments, the water-soluble carrier monomer is the predominant species within the polyacrylamide-based copolymer. In some embodiments, the water-soluble carrier monomer imparts aqueous solubility to the copolymer. In some embodiments, the water-soluble carrier monomer within the polyacrylamide-based copolymer provides an inert barrier at the interface of an aqueous formulation to prevent protein-protein interactions. In some embodiments, the interface is an air-water interface. In some embodiments, the interface is an enclosure-water interface, including, but not limited to, a glass-water interface, a rubber-water interface, a plastic-water interface, or a metal-water interface. In some embodiments, the interface is an oil-water interface. In some embodiments, the interface is an interface between a liquid and tubing. In some embodiments, the interface is an interface between a liquid and a catheter. In some embodiments, the enclosure-water interface is in a pump system. In some embodiments, the enclosure-water interface is in a closed-loop system. In some embodiments, the water-soluble carrier monomer is non-ionic. Examples of water-soluble carrier monomers include, but are not limited to, acrylamide (AM), N-(3-methoxypropoyl)acrylamide (MPAM), 4-acryloylmorpholine (MORPH), N,N-dimethylacrylamide (DMA), and N-hydroxyethyl acrylamide (HEAM).

The term "functional dopant monomer," as used herein, refers to an acrylamide monomer species that has physicochemical properties (e.g., hydrophobicity, charge) different from those of the water-soluble carrier monomer. In some embodiments, the functional dopant monomer within the polyacrylamide-based copolymer promotes association of the polymers to an interface; such interfaces can include, but are not limited to, polymer-air-water interface interactions, polymer-protein interactions, polymer-peptide interactions, polymer-micelle interactions, polymer-liposome interactions, and polymer-lipid nanoparticle interactions. The functional dopant monomer can act as a stabilizing moiety to facilitate interactions with biomolecules, for example, proteins, peptides, antibodies, antibody-drug conjugates, nucleic acids, lipid particles, and combinations thereof (e.g., to prevent aggregation of the biomolecules). The functional dopant monomers can be further classified into hydrogen-bonding, ionic, hydrophobic, and aromatic monomers based on their chemical composition. Typically, the functional dopant monomers are copolymerized at a lower weight percentages as compared to the water-soluble carrier monomers.

The term "polymerization" refers to the process in which monomer molecules undergo a chemical reaction to form polymeric chains or three-dimensional networks. Different types of polymerization reactions are known in the art, for example, addition (chain-reaction) polymerization, condensation polymerization, ring-opening polymerization, free radical polymerization, controlled radical polymerization, atom transfer radical polymerization (ATRP), single-electron transfer living radical polymerization (SET-LRP), reversible addition-fragmentation chain transfer (RAFT) polymerization, nitroxide-mediated polymerization (NMP), and emulsion polymerization. In some embodiments, the copolymers of the present disclosure are prepared using RAFT polymerization.

The term "degree of polymerization" (DP) refers to the number of monomer units in a polymer. It is calculated by dividing the average molecular weight of a polymer sample by the molecular weight of the monomers. As defined herein, the average molecular weight of a polymer can be represented by the number-averaged molecular weight ($M_n$), the weight-average molecular weight ($M_w$), the Z-average molecular weight ($M_z$) or the molecular weight at the peak maxima of the molecular weight distribution curve ($M_p$). The average molecular weight of a polymer can be determined by a variety of analytical characterization techniques known to those skilled in the art, for example, gel permeation chromatography (GPC), static light scattering (SLS) analysis, multi-angle laser light scattering (MALLS) analysis, nuclear magnetic resonance spectroscopy (NMR), intrinsic viscometry (IV), melt flow index (MFI), and matrix-assisted laser desorption/ionization mass spectrometry (MALDI-MS), and combinations thereof. Degree of polymerization can also be determined experimentally using suitable analytical methods known in the art, such as nuclear magnetic spectroscopy (NMR), Fourier Transform infrared spectroscopy (FT-IR) and Raman spectroscopy.

The term "amphiphilic" refers to chemical substances that possess both hydrophilic (water-loving, polar) and lipophilic (fat-loving, nonpolar) properties. Examples of common amphiphilic compounds include detergents, soaps, surfactants, lipoproteins, and phospholipids. In some embodiments, the amphiphilic substance is a charged species. In some embodiments, the amphiphilic substance is a neutral species.

A "lipid-based vehicle," as used herein, refers to structures having a protective outer layer of lipids that can be used as drug delivery vehicles. For example, a lipid-based vehicle can be used to encapsulate and transport cargo (e.g., a therapeutic agent) to a biologic target. Examples of lipid-based vehicles include, but are not limited to, liposomes, micelles, polymerosomes, and lipid nanoparticles.

"Biologic molecule," as used herein, refers to molecules such as proteins, nucleic acids, polysaccharides, and lipids.

The term "protein" is defined as a class of large molecules comprising one or more long chains of amino acids. A wide variety of proteins may be considered as belonging to a family of proteins based on having similar structural features, having particular biological functions, and/or being related to specific microorganisms, particularly disease causing microorganisms. Such proteins include, for example, antibodies (immunoglobulins), cytokines, chemokines, enzymes, hormones, vaccine antigens, cancer antigens, adjuvants, nutritional markers, and tissue specific antigens.

The term "nucleic acid," as used herein, includes deoxyribonucleic acid (DNA), ribonucleic acid (RNA), messenger RNA (mRNA), small-interfering RNA (siRNA), short hairpin RNA (shRNA), and microRNA (miRNA).

The term "antibody" refers to large, Y-shaped proteins produced by the immune system to identify and neutralize foreign objects such as pathogenic bacteria and viruses. The term "antibody" includes monoclonal antibodies (for example, full length or intact monoclonal antibodies), polyclonal antibodies, multivalent antibodies, multi specific antibodies (e.g., bispecific or trispecific antibodies, so long as they exhibit the desired biological activity) and can also include certain antibody fragments. An antibody can be human, humanized and/or affinity matured. "Antibody fragments" comprise only a portion of an intact antibody, where in certain embodiments, the portion retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

The term "insulin" refers to a hormone produced by the beta cells in the pancreatic islets that regulates the amount of glucose in the blood. Many eukaryotes, including humans, primates, pigs, cows, cats, dogs, and rodents, produce insulin. Thus, "insulin," as used herein, includes insulin produced by humans, and analogs thereof, as well as insulin, and analogs thereof, produced by other eukaryotes, including, but not limited to, primates, pigs, cows, cats, dogs, and rodents, and also includes recombinant, purified or synthetic insulin or insulin analogs having similar function and structure, unless otherwise specified. The human insulin protein consists of 51 amino acids, and has a molecular weight of approximately 5.8 kilodalton (kDa). Human insulin is a heterodimer of an A-chain and a B-chain that are connected by disulfide bonds.

Insulin also includes monomeric and oligomeric forms, such as dimeric and hexameric forms. Insulin can exist as a monomer as it circulates in the plasma, and it also binds to its receptor while in a monomeric form. Insulin formulations (or insulin analog formulations) containing a predominance of protein molecules in the form of monomers and dimers ordinarily have a strong tendency to aggregate and form inactive fibrils. Insulin hexamers are too large to be absorbed, and so hexameric insulin formulations must disassemble into dimers or monomers before the insulin can be absorbed and function in the body. The active form of insulin in the blood stream is the monomeric form.

Insulin can be isolated from the pancreatic islets extracts of an animal that produces insulin, or expressed recombinantly in a suitable expression system such as E. coli, yeast, insect cells, and mammalian cells (e.g. Chinese hamster ovary (CHO) cells). Depending upon their specific pharmacokinetics and pharmacodynamics (PK/PD) properties (e.g. duration of action, maximum concentration observed ($C_{max}$), time-to-onset, area under the curve (AUC)), insulin can be further characterized as a rapid-acting insulin, a short-acting insulin, an intermediate-acting insulin, a long-acting insulin, and a pre-mixed insulin.

The term "aggregation" refers to the formation of higher molecular weight, amorphous species due to non-covalent adherence ("clumping") of smaller species. The aggregation process can be irreversible or reversible. Many biological and synthetic molecules can undergo aggregation, including proteins, peptides, lipid particles, nucleic acids, inorganic nanoparticles and organic nanoparticles (e.g., micelles, lipid nanoparticles, liposomes, polymerosomes) that may further comprise an encapsulated species.

In the case of protein aggregation, formation of protein aggregates can be due to the protein's intrinsic disordered nature, or misfolding of protein molecules, which results in the exposure of hydrophobic residues and surfaces that are normally buried within the interior of the protein three-dimensional structure. Due to the hydrophobic effect, the exposed hydrophobic portions of a misfolded protein have the tendency to interact with other misfolded protein molecules to shield the exposed hydrophobic surfaces, which can lead to protein aggregation.

Some biologic molecules are more "susceptible to aggregation" than others. For example, the amino-acid sequence and overall three-dimensional structure of a protein is relevant to its susceptibility to aggregation. For example, transmembrane proteins are more prone (or susceptible) to aggregation than non-membrane proteins, particularly when expressed recombinantly without the use of a stabilizing agent. Proteins that are subject to conditions beyond the physiological conditions (37° C., ~neutral pH, isotonic) may also be more susceptible to aggregation than when in their native environment. Stress conditions such as temperature fluctuations, light, mechanical perturbation (e.g., shaking), surfaces, ultrasonic vibration, pH changes, and changes in ionic strength can affect protein stability and induce aggregation. Protein aggregation can lead to the formation of sub-visible or visible particles (i.e., precipitation). The extent of sub-visible protein aggregation can be measured by a variety of analytical methods known in the art, for example, size-exclusion chromatography (SEC), gel electrophoresis, asymmetric field-flow fractionation (AF4), analytical ultracentrifugation (AUC), mass spectrometry (MS), optical microscopy, fluorescence microscopy, dynamic light scattering (DLS), multi-angle laser light scattering (MALLS), flow imaging, turbidity/nephelometry, and transmittance measurement.

As used herein, the term "reduced aggregation" of a biologic molecule or lipid-based vehicle includes all forms of reducing aggregation. The degree or amount of aggregation observed (e.g., in the composition) can be reduced as compared to a composition of the same biologic molecule or lipid-based vehicle in the absence of the polyacrylamide-based copolymer of the present disclosure. Thus, "reduced aggregation" includes no observable aggregation or reduced amounts of aggregation (e.g., reduced levels of aggregated protein). Thus, the amount of aggregates present in the composition can be reduced by at least about 10 mol %, about 20 mol %, about 30 mol %, about 40 mol %, about 50 mol %, about 60 mol %, about 70 mol %, about 80 mol %, about 90 mol %, or about 100 mol % as compared to the amount of aggregates of the same biologic molecule or lipid-based vehicle in the absence of the polyacrylamide-based copolymer. Aggregation can be measured by any method known in the art, including, but not limited to, size-exclusion chromatography (SEC), gel electrophoresis, asymmetric field-flow fractionation (AF4), analytical ultracentrifugation (AUC), mass spectrometry (MS), optical microscopy, fluorescence microscopy, dynamic light scattering (DLS), multi-angle laser light scattering (MALLS), flow imaging, turbidity/nephelometry, and transmittance measurement.

As used herein, the term "increased stability," when referring to a formulation containing a biologic molecule or lipid-based vehicle, refers to a measurable decrease in the amount of aggregation over a fixed period of time under testing or fixed storage conditions as compared to the amount of aggregates of the same biologic molecule or lipid-based vehicle in the absence of the polyacrylamide-based copolymer.

The terms "aggregated protein" or "protein aggregates" as used herein refer to a collection of proteins that are disordered or misfolded and grouped together. The aggregates can be soluble or insoluble. Protein aggregates include, but are not limited to, inclusion bodies, soluble and insoluble precipitates, soluble non-native oligomers, gels, fibrils, films, filaments, protofibrils, amyloid deposits, amyloid fibrils, plaques, and dispersed non-native intracellular oligomers. In some embodiments, the proteins in a protein aggregate are, prior to their aggregation, soluble precursors. Protein aggregation can be prevented in compositions containing the polyacrylamide-based copolymer of the present disclosure. Protein aggregation can also be reduced in a composition containing the polyacrylamide-based copolymer of the present disclosure as compared to a composition containing the same protein that does not contain the polyacrylamide-based copolymer of the present disclosure. Thus, the polyacrylamide-based copolymer can reduce or prevent the aggregation of a protein.

In some embodiments, the protein is insulin, or an analog thereof. The terms "aggregated insulin" or "insulin aggregates" as used herein, refer to insulin that has aggregated to form a high molecular weight polymer or aggregate particles or amyloid fibrils. Formation of insulin aggregates can be due to, for example, heat or shaking and partial unfolding of the insulin. Insulin aggregation can be prevented, i.e., insulin molecules are prevented from aggregating and forming high molecular weight polymers or amyloid fibrils, in compositions containing the polyacrylamide-based copolymer of the present disclosure. Aggregation can also be reduced in a composition containing insulin, or an analog thereof, and the polyacrylamide-based copolymer of the present disclosure as compared to a composition containing insulin, or an analog thereof, that does not contain the polyacrylamide-based copolymer of the present disclosure. Thus, the polyacrylamide-based copolymer can reduce or prevent the aggregation of insulin, or analogs thereof.

As defined herein, the term "duration of action" is defined as the length of time that injected insulin is acting to lower blood glucose levels, i.e., the timeframe over which the injected insulin continues to be active. The term "maximum concentration observed" ($C_{max}$) refers to the peak serum concentration that an active agent achieves in a specified compartment or test area of the body after administration of the first dose of the active agent and before the administration of the second dose. The term "time-to-onset" refers to the amount of time it takes an active agent to reach the minimum effective concentration after administration. The term "area under the curve" (AUC) refers to the definite integral of a curve that describes the variation of the concentration of the active agent in blood plasma as a function of time, which can be measured by analytical methods such as liquid-chromatography-mass spectrometry (LC-MS). The AUC reflects the exposure of the active agent upon administration, and is expressed in mg*h/L. The AUC of an active agent is dependent on the rate of elimination of the active agent from the body and the dose administered.

Polyacrylamide-Based Copolymers

Provided in the present disclosure are polyacrylamide-based copolymers. In some embodiments, the polyacrylamide-based copolymers contain a water-soluble carrier monomer and a functional dopant monomer. In some embodiments, the polyacrylamide-based copolymer is amphiphilic.

In some embodiments, the polyacrylamide-based copolymer comprises a non-ionic water-soluble acrylamide monomer and a functional acrylamide dopant monomer selected from the group consisting of a hydrophobic functional acrylamide dopant monomer, an aromatic functional acrylamide dopant monomer, a hydrogen-bonding functional acrylamide dopant monomer, and an ionic functional acrylamide dopant monomer. In some embodiments, the polyacrylamide-based copolymer comprises a non-ionic water-soluble acrylamide monomer and the functional acrylamide dopant monomer is a hydrophobic functional acrylamide dopant monomer. In some embodiments, the copolymer comprises a non-ionic water-soluble acrylamide monomer and the functional acrylamide dopant monomer is an aromatic functional acrylamide dopant monomer. In some embodiments, the copolymer comprises a non-ionic water-soluble acrylamide monomer and the functional acrylamide dopant monomer is a hydrogen-bonding functional acrylamide dopant monomer. In some embodiments, the copolymer comprises a non-ionic water-soluble acrylamide monomer and the functional acrylamide dopant monomer is an ionic functional acrylamide dopant monomer.

The polyacrylamide-based copolymers of the present disclosure contain a water-soluble carrier monomer. In some embodiments, the water-soluble carrier monomer is non-ionic. In some embodiments, the water-soluble carrier monomer is selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM), or combinations thereof. In some embodiments, the water-soluble carrier monomer is selected from the group consisting of MPAM and MORPH. In some embodiments, the water-soluble carrier monomer is N-(3-methoxypropoyl) acrylamide (MPAM). In some embodiments, the water-soluble carrier monomer is 4-acryloylmorpholine (MORPH). In some embodiments, the water-soluble carrier monomer is N,N-dimethylacrylamide (DMA). In some embodiments, the water-soluble carrier monomer is N-hydroxyethyl acrylamide (HEAM). In some embodiments, the water-soluble carrier monomer is acrylamide (AM). In some embodiments, the copolymer comprises a water-soluble carrier monomer selected from the group consisting of N-(3-methoxypropoyl)acrylamide (MPAM) and 4-acryloylmorpholine (MORPH).

The polyacrylamide-based copolymers of the present disclosure also contain a functional dopant monomer. In some embodiments, the functional dopant monomer is selected from the group consisting of a hydrophobic functional acrylamide dopant monomer, an aromatic functional acrylamide dopant monomer, a hydrogen-bonding functional acrylamide dopant monomer, and an ionic functional acrylamide dopant monomer, or mixtures thereof.

In some embodiments, the functional acrylamide dopant monomer is a hydrophobic functional acrylamide dopant monomer. In some embodiments, the hydrophobic functional acrylamide dopant monomer is N-isopropylacrylamide (NIP) or N-tert-butylacrylamide (TBA). In some embodiments, the hydrophobic functional acrylamide dopant monomer is N-isopropylacrylamide (NIP). In some embodiments, the hydrophobic functional acrylamide dopant monomer is N-tert-butylacrylamide (TBA). In some embodiments, the functional acrylamide dopant monomer is an aromatic functional acrylamide dopant monomer. In some embodiments, the aromatic functional acrylamide dopant monomer is N-phenylacrylamide (PHE).

In some embodiments, the functional acrylamide dopant monomer is a hydrogen-bonding functional acrylamide dopant monomer. In some embodiments, the hydrogen-bonding functional acrylamide dopant monomer is N-[tris(hydroxymethyl)-methyl]acrylamide (TRI). In some embodiments, the functional acrylamide dopant monomer is an ionic functional acrylamide dopant monomer. In some embodiments, the ionic functional acrylamide dopant monomer is 2-acrylamido-2-methylpropane sulfonic acid (AMP) or (3-acrylamidopropyl)trimethylammonium chloride (TMA). In some embodiments, the ionic functional acrylamide dopant monomer is 2-acrylamido-2-methylpropane sulfonic acid (AMP). In some embodiments, the ionic functional acrylamide dopant monomer is (3-acrylamidopropyl) trimethylammonium chloride (TMA).

In some embodiments, the functional dopant monomer is selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE), or combinations thereof. In some embodiments, the functional dopant monomer is N-[tris(hydroxymethyl)-methyl]acrylamide (TRI). In some embodiments, the functional dopant monomer is 2-acrylamido-2-methylpropane sulfonic acid (AMP). In some embodiments, the functional dopant monomer is (3-acrylamidopropyl)trimethylammonium chloride (TMA). In some embodiments, the functional dopant monomer is N-isopropylacrylamide (NIP). In some embodiments, the functional dopant monomer is N-tert-butylacrylamide (TBA). In some embodiments, the functional dopant monomer is and N-phenylacrylamide (PHE).

In some embodiments, the polyacrylamide-based copolymer comprises a water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM); and a functional dopant monomer selected from the group consisting of N-[tris (hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE).

In some embodiments, the water-soluble carrier monomer is N-(3-methoxypropoyl)acrylamide (MPAM). In some embodiments, the water-soluble carrier monomer is N-(3-methoxypropoyl)acrylamide (MPAM) and the functional dopant monomer selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the water-soluble carrier monomer is MPAM and the functional dopant monomer is TRI. In some embodiments, the water-soluble carrier monomer is MPAM and the functional dopant monomer is AMP. In some embodiments, the water-soluble carrier monomer is MPAM and the functional dopant monomer is TMA. In some embodiments, the water-soluble carrier monomer is MPAM and the functional dopant monomer is NIP. In some embodiments, the water-soluble carrier monomer is MPAM and the functional dopant monomer is TBA. In some embodiments, the water-soluble carrier monomer is MPAM and the functional dopant monomer is PHE.

In some embodiments, the water-soluble carrier monomer is 4-acryloylmorpholine (MORPH). In some embodiments, the water-soluble carrier monomer is 4-acryloylmorpholine (MORPH) and the functional dopant monomer selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the water-soluble carrier monomer is MORPH and the functional dopant monomer is TRI. In some embodiments, the water-soluble carrier monomer is MORPH and the functional dopant monomer is AMP. In some embodiments, the water-soluble carrier monomer is MORPH and the functional dopant monomer is TMA. In some embodiments, the water-soluble carrier monomer is MORPH and the functional dopant monomer is NIP. In some embodiments, the water-soluble carrier monomer is MORPH and the functional dopant monomer is TBA. In some embodiments, the water-soluble carrier monomer is MORPH and the functional dopant monomer is PHE.

In some embodiments, the water-soluble carrier monomer is N,N-dimethylacrylamide (DMA). In some embodiments, the water-soluble carrier monomer is N,N-dimethylacrylamide (DMA) and the functional dopant monomer selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the water-soluble carrier monomer is DMA and the functional dopant monomer is TRI. In some embodiments, the water-soluble carrier monomer is DMA and the functional dopant monomer is AMP. In some embodiments, the water-soluble carrier monomer is DMA and the functional dopant monomer is TMA. In some embodiments, the water-soluble carrier monomer is DMA and the functional dopant monomer is NIP. In some embodiments, the water-soluble carrier monomer is DMA and the functional dopant monomer is TBA. In some embodiments, the water-soluble carrier monomer is DMA and the functional dopant monomer is PHE.

In some embodiments, the water-soluble carrier monomer is N-hydroxyethyl acrylamide (HEAM). In some embodiments, the water-soluble carrier monomer is N-hydroxyethyl acrylamide (HEAM) and the functional dopant monomer selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the water-soluble carrier monomer is HEAM and the functional dopant monomer is TRI. In some embodiments, the water-soluble carrier monomer is HEAM and the functional dopant monomer is AMP. In some embodiments, the water-soluble carrier monomer is HEAM and the functional dopant monomer is TMA. In some embodiments, the water-soluble carrier monomer is REAM and the functional dopant monomer is NIP. In some embodiments, the water-soluble carrier monomer is REAM and the functional dopant monomer is TBA. In some embodiments, the water-soluble carrier monomer is HEAM and the functional dopant monomer is PHE.

In some embodiments, the water-soluble carrier monomer is acrylamide (AM). In some embodiments, the water-soluble carrier monomer is acrylamide (AM) and the functional dopant monomer selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the water-soluble carrier monomer is AM and the functional dopant monomer is TRI. In some embodiments, the water-soluble carrier monomer is AM and the functional dopant monomer is AMP. In some embodiments, the water-soluble carrier monomer is AM and the functional dopant monomer is TMA. In some embodiments, the water-soluble carrier monomer is AM and the functional dopant monomer is NIP. In some embodiments, the water-soluble carrier monomer is AM and the functional dopant monomer is TBA. In some embodiments, the water-soluble carrier monomer is AM and the functional dopant monomer is PHE.

In some embodiments, the functional dopant monomer is N-[tris(hydroxymethyl)-methyl]acrylamide (TRI). In some embodiments, the functional dopant monomer is N-[tris(hydroxymethyl)-methyl]acrylamide (TRI) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is TRI and the water-soluble carrier monomer is MPAM. In some embodiments, the functional dopant monomer is TRI and the water-soluble carrier monomer is MORPH. In some embodiments, the functional dopant monomer is TRI and the water-soluble carrier monomer is DMA. In some embodiments, the functional dopant monomer is TRI and the water-soluble carrier monomer is REAM. In some embodiments, the functional dopant monomer is TRI and the water-soluble carrier monomer is AM.

In some embodiments, the functional dopant monomer is 2-acrylamido-2-methylpropane sulfonic acid (AMP). In some embodiments, the functional dopant monomer is 2-acrylamido-2-methylpropane sulfonic acid (AMP) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is AMP and the water-soluble carrier monomer is MPAM. In some embodiments, the functional dopant monomer is AMP and the water-soluble carrier monomer is MORPH. In some embodiments, the functional dopant monomer is AMP and the water-soluble carrier monomer is DMA. In some embodiments, the functional dopant monomer is AMP and the water-soluble carrier monomer is HEAM. In some embodiments, the functional dopant monomer is AMP and the water-soluble carrier monomer is AM.

In some embodiments, the functional dopant monomer is (3-acrylamidopropyl)trimethylammonium chloride (TMA). In some embodiments, the functional dopant monomer is (3-acrylamidopropyl)trimethylammonium chloride (TMA) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is TMA and the water-soluble carrier monomer is MPAM. In some embodiments, the functional dopant monomer is TMA and the water-soluble carrier monomer is MORPH. In some embodiments, the functional dopant monomer is TMA and the water-soluble carrier monomer is DMA. In some embodiments, the functional dopant monomer is TMA and the water-soluble carrier monomer is HEAM. In some embodiments, the functional dopant monomer is TMA and the water-soluble carrier monomer is AM.

In some embodiments, the functional dopant monomer is N-isopropylacrylamide (NIP). In some embodiments, the functional dopant monomer is N-isopropylacrylamide (NIP) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is NIP and the water-soluble carrier monomer is MPAM. In some embodiments, the functional dopant monomer is NIP and the water-soluble carrier monomer is MORPH. In some embodiments, the functional dopant monomer is NIP and the water-soluble carrier monomer is DMA. In some embodiments, the functional dopant monomer is NIP and the water-soluble carrier monomer is HEAM. In some embodiments, the functional dopant monomer is NIP and the water-soluble carrier monomer is AM.

In some embodiments, the functional dopant monomer is N-tert-butylacrylamide (TBA). In some embodiments, the functional dopant monomer is N-tert-butylacrylamide (TBA) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is TBA and the water-soluble carrier monomer is MPAM. In some embodiments, the functional dopant monomer is TBA and the water-soluble carrier monomer is MORPH. In some embodiments, the functional dopant monomer is TBA and the water-soluble carrier monomer is DMA. In some embodiments, the functional dopant monomer is TBA and the water-soluble carrier monomer is HEAM. In some embodiments, the functional dopant monomer is TBA and the water-soluble carrier monomer is AM.

In some embodiments, the functional dopant monomer is N-phenylacrylamide (PHE). In some embodiments, the functional dopant monomer is N-phenylacrylamide (PHE) and the water-soluble carrier monomer selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the functional dopant monomer is PHE and the water-soluble carrier monomer is MPAM. In some embodiments, the functional dopant monomer is PHE and the water-soluble carrier monomer is MORPH. In some embodiments, the functional dopant monomer is PHE and the water-soluble carrier monomer is DMA. In some embodiments, the functional dopant monomer is PHE and the water-soluble carrier monomer is HEAM. In some embodiments, the functional dopant monomer is PHE and the water-soluble carrier monomer is AM.

In some embodiments, the polyacrylamide-based copolymer comprises N-(3-methoxypropoyl)acrylamide (MPAM) or 4-acryloylmorpholine (MORPH) as the water-soluble carrier monomer, and N-isopropylacrylamide (NIP) or N-phenylacrylamide (PHE) as the functional dopant monomer. In some embodiments, the polyacrylamide-based copolymer comprises N,N-dimethylacrylamide (DMA), N-hydroxyethyl acrylamide (HEAM), or acrylamide (AM) as the water-soluble carrier monomer, and N-isopropylacrylamide (NIP) or N-phenylacrylamide (PHE) as the functional dopant monomer.

In some embodiments, the polyacrylamide-based copolymer comprises N-(3-methoxypropoyl)acrylamide (MPAM) or 4-acryloylmorpholine (MORPH) as the water-soluble carrier monomer, and N-[tris(hydroxymethyl)-methyl]acrylamide (TRI), 2-acrylamido-2-methylpropane sulfonic acid (AMP), (3-acrylamidopropyl)trimethylammonium chloride (TMA), or N-tert-butylacrylamide (TBA) as the functional dopant monomer.

In some embodiments, the polyacrylamide-based copolymer comprises N,N-dimethylacrylamide (DMA), N-hydroxyethyl acrylamide (HEAM), or acrylamide (AM) as the water-soluble carrier monomer, and the functional dopant monomer is (3-acrylamidopropyl)trimethylammonium chloride (TMA). In some embodiments, the polyacrylamide-based copolymer comprises N,N-dimethylacrylamide (DMA), N-hydroxyethyl acrylamide (HEAM), or acrylamide (AM) as the water-soluble carrier monomer, and the functional dopant monomer is N-tert-butylacrylamide (TBA). In some embodiments, the polyacrylamide-based copolymer comprises N,N-dimethylacrylamide (DMA), N-hydroxyethyl acrylamide (HEAM), or acrylamide (AM) as the water-soluble carrier monomer, and the functional dopant monomer is N-[tris(hydroxymethyl)-methyl]acrylamide (TRI). In some embodiments, the polyacrylamide-based copolymer comprises N,N-dimethylacrylamide (DMA), N-hydroxyethyl acrylamide (HEAM), or acrylamide (AM) as the water-soluble carrier monomer, and the functional dopant monomer is 2-acrylamido-2-methylpropane sulfonic acid (AMP).

In some embodiments, the amount of functional dopant monomer used in the copolymerization reaction is designed to maximize dopant loading while yielding functional copolymers with lower critical solution temperature (LCST) values above 37° C. In some embodiments, this results in copolymers that remain soluble at all relevant temperatures. In some embodiments, the polyacrylamide-based copolymer comprises about 2% to about 30% by weight of a functional dopant monomer, for example, about 5% to about 30%, about 10% to about 30%, about 15% to about 30%, about 20% to about 30%, about 25% to about 30%, about 2% to about 25%, about 5% to about 25%, about 10% to about 25%, about 15% to about 25%, about 20% to about 25%, about 2% to about 20%, about 5% to about 20%, about 10% to about 20%, about 15% to about 20%, about 2% to about 15%, about 5% to about 15%, about 10% to about 15%, about 2% to about 10%, about 5% to about 10%, or about 2% to about 5%, by weight of a functional dopant monomer. In some embodiments, the polyacrylamide-based copolymer comprises about 2%, about 5%, about 8%, about 10%, about 12%, about 15%, about 18%, about 20%, about 22%, about 25%, about 28%, or about 30% by weight of a functional dopant monomer.

In some embodiments, the polyacrylamide-based copolymer comprises about 70% to about 98% by weight of a water-soluble carrier monomer, for example, about 75% to about 98%, about 80% to about 98%, about 85% to about 98%, about 90% to about 98%, about 95% to about 98%, about 70% to about 95%, about 75% to about 95%, about 80% to about 95%, about 85% to about 95%, about 90% to about 95%, about 70% to about 90%, about 75% to about 90%, about 80% to about 90%, about 85% to about 90%, about 70% to about 85%, about 75% to about 85%, about 80% to about 85%, about 70% to about 80%, about 75% to about 80%, or about 70% to about 75%, by weight of a water-soluble carrier monomer. In some embodiments, the polyacrylamide-based copolymer comprises about 70%, about 72%, about 75%, about 78%, about 80%, about 82%, about 85%, about 88%, about 90%, about 92%, about 95%, or about 98% by weight of a water-soluble carrier monomer.

In some embodiments, the polyacrylamide-based copolymer comprises about 70% to about 98% by weight of a water-soluble carrier monomer and about 2% to about 30% by weight of a functional dopant monomer. For example, the polyacrylamide-based copolymer can contain about 70% to about 98%, about 70% to about 95%, about 70% to about 80%, about 80% to about 90%, about 90% to about 98%, about 70%, about 75%, about 80%, about 85%, about 90%, about 95%, or about 98% by weight of a water-soluble carrier monomer and about 2% to about 30%, about 5% to about 25%, about 5% to about 20%, about 2% to about 5%, about 5% to about 10%, about 10% to about 15%, about 15% to about 20%, about 20% to about 25%, or about 25% to about 30%, about 2%, about 5%, about 8%, about 10%, about 12%, about 15%, about 18%, about 20%, about 22%, about 25%, about 28%, or about 30% by weight of a functional dopant monomer.

In some embodiments, the polyacrylamides-based copolymer comprises about 2% to about 30% by weight of the functional dopant monomer NIP. In some embodiments, the polyacrylamides-based copolymer comprises about 5% to about 30% by weight of the functional dopant monomer NIP. In some embodiments, the polyacrylamides-based copolymer comprises about 10% to about 28% by weight of the functional dopant monomer NIP. In some embodiments, the polyacrylamides-based copolymer comprises about 5% to about 26% by weight of the functional dopant monomer NIP. In some embodiments, the polyacrylamides-based copolymer comprises about 5% to about 10% by weight of the functional dopant monomer NIP. In some embodiments, the polyacrylamides-based copolymer comprises about 10% to about 15% by weight of the functional dopant monomer NIP. In some embodiments, the polyacrylamides-based copolymer comprises about 15% to about 20% by weight of the functional dopant monomer NIP. In some embodiments, the polyacrylamides-based copolymer comprises about 20% to about 26% by weight of the functional dopant monomer NIP.

In some embodiments, the polyacrylamides-based copolymer comprises MORPH as the water-soluble carrier monomer and about 2% to about 30% by weight of NIP as the functional dopant monomer. In some embodiments, the copolymer comprises MORPH and from about 5% to about 30% by weight of NIP. In some embodiments, the copolymer comprises MORPH and about 10% to about 28% by weight of NIP. In some embodiments, the copolymer comprises MORPH and about 5% to about 26% by weight of NIP. In some embodiments, the copolymer comprises MORPH and about 5% to about 10% by weight of NIP. In some embodiments, the copolymer comprises MORPH and about 10% to about 15% by weight of NIP. In some embodiments, the copolymer comprises MORPH and about 15% to about 20% by weight of NIP. In some embodiments, the copolymer comprises MORPH and about 20% to about 25% by weight of NIP. In some embodiments, the copolymer comprises MORPH and about 25% to about 30% by weight of NIP. In some embodiments, the copolymer comprises MORPH and about 20% to about 28% by weight of NIP. In some embodiments, the copolymer comprises MORPH and about 21% by weight of NIP. In some embodiments, the copolymer comprises MORPH and about 22% by weight of NIP. In some embodiments, the copolymer comprises MORPH and about 23% by weight of NIP. In some embodiments, the copolymer comprises MORPH and about 24% by weight of NIP. In some embodiments, the copolymer comprises MORPH and about 25% by weight of NIP.

In some embodiments, the polyacrylamide-based copolymer comprises AMP, TMA, TBA, or PHE as the functional dopant monomer. In some embodiments, AMP, TMA, TBA, or PHE functional dopant monomer is present at about 2% to about 16% by weight of the copolymer. In some embodiments, AMP, TMA, TBA, or PHE functional dopant monomer is present at about 5% to about 15% by weight of the copolymer. In some embodiments, AMP, TMA, TBA, or PHE functional dopant monomer is present at about 6% to about 14% by weight of the copolymer. In some embodiments, AMP, TMA, TBA, or PHE functional dopant monomer is present at about 12% to about 15% by weight of the copolymer. In some embodiments, AMP, TMA, TBA, or PHE functional dopant monomer is present at about 2% to about 5% by weight of the copolymer. In some embodiments, AMP, TMA, TBA, or PHE functional dopant monomer is present at about 5% to about 10% by weight of the copolymer.

In some embodiments, the polyacrylamide-based copolymer comprises MORPH as the water-soluble carrier monomer and about 2% to about 16% by weight of PHE as the functional dopant monomer. In some embodiments, the polyacrylamide-based copolymer comprises MORPH as the water-soluble carrier monomer and about 4% to about 16% by weight of PHE as the functional dopant monomer. In some embodiments, the polyacrylamide-based copolymer comprises MORPH as the water-soluble carrier monomer and about 6% to about 14% by weight of PHE as the functional dopant monomer. In some embodiments, the polyacrylamide-based copolymer comprises MORPH as the water-soluble carrier monomer and about 8% to about 14% by weight of PHE as the functional dopant monomer. In some embodiments, the polyacrylamide-based copolymer comprises MORPH as the water-soluble carrier monomer and about 10% to about 14% by weight of PHE as the functional dopant monomer. In some embodiments, the polyacrylamide-based copolymer comprises MORPH as the water-soluble carrier monomer and about 10% to about 12% by weight of PHE as the functional dopant monomer.

In some embodiments, the polyacrylamide-based copolymer comprises MPAM as the water-soluble carrier monomer and about 2% to about 16% by weight of PHE as the functional dopant monomer. In some embodiments, the polyacrylamide-based copolymer comprises MPAM as the water-soluble carrier monomer and about 5% to about 15% by weight of PHE as the functional dopant monomer. In some embodiments, the polyacrylamide-based copolymer comprises MPAM as the water-soluble carrier monomer and about 6% to about 10% by weight of PHE as the functional dopant monomer. In some embodiments, the polyacrylamide-based copolymer comprises MPAM as the water-soluble carrier monomer and about 7% by weight of PHE as the functional dopant monomer. In some embodiments, the polyacrylamide-based copolymer comprises MPAM as the water-soluble carrier monomer and about 8% by weight of PHE as the functional dopant monomer. In some embodiments, the polyacrylamide-based copolymer comprises MPAM as the water-soluble carrier monomer and about 9% by weight of PHE as the functional dopant monomer.

In some embodiments, the polyacrylamide-based copolymer comprises about 3% to about 17% by weight of TRI as the functional dopant monomer. In some embodiments, the polyacrylamide-based copolymer comprises about 7% to about 12% by weight of TRI as the functional dopant monomer. In some embodiments, the polyacrylamide-based copolymer comprises about 4% to about 6% by weight of TRI as the functional dopant monomer. In some embodiments, the polyacrylamide-based copolymer comprises about 13% to about 17% by weight of TRI as the functional dopant monomer.

In some embodiments, the degree of polymerization (DP) of the polyacrylamide-based copolymer is about 10 to about 500, about 20 to about 200, about 50 to about 100, about 100 to about 200, about 200 to about 300, about 300 to about 400, or about 400 to about 500, or about 10, about 50, about 70, about 100, about 120, about 150, about 170, about 200, about 220, about 250, about 270, about 300, about 320, about 350, about 370, about 400, about 420, about 450, about 470, or about 500. In some embodiments, the DP of the copolymer is about 40. In some embodiments, the DP of the copolymer is about 50. In some embodiments, the DP of the copolymer is about 60. In some embodiments, the DP of the copolymer is about 70. In some embodiments, the DP of the copolymer is about 80. In some embodiments, the DP of the copolymer is about 90. In some embodiments, the DP of the copolymer is about 100.

In some embodiments, the molecular weight of the polyacrylamide-based copolymer is about 1,000 g/mol to about 40,000 g/mol, such as about 1,000 g/mol to about 35,000 g/mol, about 1,000 g/mol to about 30,000 g/mol, about 1,000 g/mol to about 25,000 g/mol, about 1,000 g/mol to about 20,000 g/mol, about 1,000 g/mol to about 15,000 g/mol, about 1,000 g/mol to about 10,000 g/mol, about 1,000 g/mol to about 7,000 g/mol, about 1,000 g/mol to about 6,000 g/mol, about 1,000 g/mol to about 5,000 g/mol, about 1,000 g/mol to about 4,000 g/mol, about 1,000 g/mol to about 3,000 g/mol, about 3,000 g/mol to about 40,000 g/mol, about 3,000 g/mol to about 35,000 g/mol, about 3,000 g/mol to about 30,000 g/mol, about 3,000 g/mol to about 25,000 g/mol, about 3,000 g/mol to about 20,000 g/mol, about 3,000 g/mol to about 15,000 g/mol, about 3,000 g/mol to about 10,000 g/mol, about 3,000 g/mol to about 7,000 g/mol, about 3,000 g/mol to about 6,000 g/mol, about 3,000 g/mol to about 5,000 g/mol, about 3,000 g/mol to about 4,000 g/mol, about 4,000 g/mol to about 40,000 g/mol, about 4,000 g/mol to about 35,000 g/mol, about 4,000 g/mol to about 30,000 g/mol, about 4,000 g/mol to about 25,000 g/mol, about 4,000 g/mol to about 20,000 g/mol, about 4,000 g/mol to about 15,000 g/mol, about 4,000 g/mol to about 10,000 g/mol, about 4,000 g/mol to about 7,000 g/mol, about 4,000 g/mol to about 6,000 g/mol, about 4,000 g/mol to about 5,000 g/mol, about 5,000 g/mol to about 40,000 g/mol, about 5,000 g/mol to about 35,000 g/mol, about 5,000 g/mol to about 30,000 g/mol, about 5,000 g/mol to about 25,000 g/mol, about 5,000 g/mol to about 20,000 g/mol, about 5,000 g/mol to about 15,000 g/mol, about 5,000 g/mol to about 10,000 g/mol, about 5,000 g/mol to about 7,000 g/mol, about 5,000 g/mol to about 6,000 g/mol, about 6,000 g/mol to about 40,000 g/mol, about 6,000 g/mol to about 35,000 g/mol, about 6,000 g/mol to about 30,000 g/mol, about 6,000 g/mol to about 25,000 g/mol, about 6,000 g/mol to about 20,000 g/mol, about 6,000 g/mol to about 15,000 g/mol, about 6,000 g/mol to about 10,000 g/mol, about 6,000 g/mol to about 7,000 g/mol, about 7,000 g/mol to about 40,000 g/mol, about 7,000 g/mol to about 35,000 g/mol, about 7000 g/mol to about 30,000 g/mol, about 7,000 g/mol to about 25,000 g/mol, about 7,000 g/mol to about 20,000 g/mol, about 7,000 g/mol to about 15,000 g/mol, about 7,000 g/mol to about 10,000 g/mol, about 10,000 g/mol to about 40,000 g/mol, about 10,000 g/mol to about 35,000 g/mol, about 10,000 g/mol to about 30,000 g/mol, about 10,000 g/mol to about 25,000 g/mol, about 10,000 g/mol to about 20,000 g/mol, about 10,000 g/mol to about 15,000 g/mol, about 15,000 g/mol to about 40,000 g/mol, about 15,000 g/mol to about 35,000 g/mol, about 15,000 g/mol to about 30,000 g/mol, about 15,000 g/mol to about 25,000 g/mol, about 15,000 g/mol to about 20,000 g/mol, about 20,000 g/mol to about 40,000 g/mol, about 20,000 g/mol to about 35,000 g/mol, about 20,000 g/mol to about 30,000 g/mol, about 20,000 g/mol to about 25,000 g/mol, about 25,000 g/mol to about 40,000 g/mol, about 25,000 g/mol to about 35,000 g/mol, about 25,000 g/mol to about 30,000 g/mol, about 30,000 g/mol to about 40,000 g/mol, about 30,000 g/mol to about 35,000 g/mol, or about 35,000 g/mol to about 40,000 g/mol. In some embodiments, the molecular weight of the copolymer is about 1,000 to about 30,000 g/mol. In some embodiments, the molecular weight of the copolymer is about 10,000 to about 20,000 g/mol. In some embodiments, the molecular weight of the copolymer is about 15,000 to about 20,000 g/mol. In some embodiments, the molecular weight of the copolymer is about 20,000 to about 25,000 g/mol. the molecular weight of the copolymer is about 25,000 to about 30,000 g/mol. In some embodiments, the molecular weight of the copolymer is about 30,000 to about 40,000 g/mol. In some embodiments, the molecular weight of the copolymer is about 2,000 to about 10,000 g/mol. In some embodiments, the molecular weight of the copolymer is about 3,000 to about 7,000 g/mol. In some embodiments, the molecular weight of the copolymer is about 4,000 to about 6,000 g/mol.

Also provided in the present disclosure is a polyacrylamide-based copolymer that contains a water-soluble carrier monomer comprising an acrylamide reactive moiety and a functional dopant monomer comprising an acrylamide reactive moiety. In some embodiments, the polyacrylamide-based copolymer comprises about 70% to about 98% of a water-soluble carrier monomer with an acrylamide reactive moiety and about 2% to about 30% of a functional dopant monomer with an acrylamide reactive moiety. In some embodiments, the number-averaged molecular weight ($M_n$) of the copolymer is about 1,000 g/mol to about 30,000 g/mol. In some embodiments, the degree of polymerization is about 10 to about 250. In some embodiments, the water-soluble carrier monomer is non ionic. In some embodiments, the functional dopant monomer is hydrophobic. In some embodiments, the copolymer is amphiphilic.

In some embodiments, the water-soluble carrier monomer is selected from the group consisting of N-(3-methoxypropoyl)acrylamide (MPAM), 4-acryloylmorpholine (MORPH), N,N-dimethylacrylamide (DMA), N-hydroxyethyl acrylamide (HEAM), and acrylamide (AM). In some embodiments, the water-soluble carrier monomer is selected from the group consisting of N-(3-methoxypropoyl)acrylamide (MPAM) and 4-acryloylmorpholine (MORPH). In some embodiments, the water-soluble carrier monomer is N-(3-methoxypropoyl)acrylamide (MPAM). In some embodiments, the water-soluble carrier monomer is 4-acryloylmorpholine (MORPH).

In some embodiments, the functional dopant monomer is selected from the group consisting of N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N-tert-butylacrylamide (TBA), and N-phenylacrylamide (PHE). In some embodiments, the functional dopant monomer is selected from the group consisting of N-isopropylacrylamide (NIP) and N-phenylacrylamide (PHE). In some embodiments, the functional dopant monomer is N-isopropylacrylamide (NIP). In some embodiments, the functional dopant monomer is N-phenylacrylamide (PHE).

In some embodiments, the polyacrylamide-based copolymer comprises about 70% to about 95% by weight of the water-soluble carrier monomer MORPH and about 5% to about 30% by weight of the functional dopant monomer NIP, wherein the number-averaged molecular weight ($M_n$) of the copolymer is about 1,000 g/mol to about 10,000 g/mol and the degree of polymerization is about 10 to about 100. In some embodiments, the polyacrylamide-based copolymer comprises about 74% to about 80% by weight of the water-soluble carrier monomer MORPH and about 20% to about 26% by weight of the functional dopant monomer NIP, wherein the number-averaged molecular weight ($M_n$) of the copolymer is about 1,000 g/mol to about 5,000 g/mol and the degree of polymerization is about 10 to about 50. In some embodiments, the polyacrylamide-based copolymer comprises about 77% by weight of the water-soluble carrier monomer MORPH and about 23% by weight of the functional dopant monomer NIP, wherein the number-averaged molecular weight ($M_n$) of the copolymer is about 3,200 g/mol and the degree of polymerization is about 26.

Compositions Containing a Polyacrylamide-Based Copolymer

Also provided are compositions containing the polyacrylamide-based copolymers described in the present disclosure. In some embodiments, the composition comprises a polyacrylamide-based copolymer of the present disclosure and a pharmaceutically acceptable excipient.

In some embodiments, the composition comprises a polyacrylamide-based copolymer of the present disclosure and a biologic molecule. In some embodiments, the biologic molecule is a protein. In some embodiments, the protein is a protein susceptible to aggregation in an aqueous medium. In some embodiments, the copolymer is uncharged, cationic, or anionic. In some embodiments, the copolymer is amphiphilic. In some embodiments, the carrier monomers are the water-soluble species and are responsible for both maintaining solubility and providing an inert barrier to prevent aggregation of the biological species, for example, to prevent protein-protein interactions. In some embodiments, the water-soluble carrier monomer is the predominant species within the polyacrylamide-based copolymer. In some embodiments, the functional dopant monomers are copolymerized at lower weight percentages and are incorporated statistically throughout the resulting copolymer. In some embodiments, these dopants are selected to promote either polymer-interface interactions or polymer-protein interactions.

In some embodiments, the composition that contains a polyacrylamide-based copolymer of the present disclosure and a biologic molecule or lipid-based vehicle has a copolymer concentration of about 0.0001% to about 5% by weight of the composition, such as about 0.0001% to about 4%, about 0.0001% to about 3%, about 0.0001% to about 2%, about 0.0001% to about 1%, about 0.0001% to about 0.5%, about 0.0001% to about 0.4%, about 0.0001% to about 0.3%, about 0.0001% to about 0.2%, about 0.0001% to about 0.1%, about 0.0001% to about 0.05%, about 0.0001% to about 0.02%, about 0.0001% to about 0.01%, about 0.0001% to about 0.005%, about 0.005% to about 5%, about 0.005% to about 4%, about 0.005% to about 3%, about 0.005% to about 2%, about 0.005% to about 1%, about 0.005% to about 0.5%, about 0.005% to about 0.4%, about 0.005% to about 0.3%, about 0.005% to about 0.2%, about 0.005% to about 0.1%, about 0.005% to about 0.05%, about 0.005% to about 0.02%, about 0.005% to about 0.01%, about 0.01% to about 5%, about 0.01% to about 4%, about 0.01% to about 3%, about 0.01% to about 2%, about 0.01% to about 1%, about 0.01% to about 0.5%, about 0.01% to about 0.4%, about 0.01% to about 0.3%, about 0.01% to about 0.2%, about 0.01% to about 0.1%, about 0.01% to about 0.05%, about 0.01% to about 0.02%, about 0.02% to about 5%, about 0.02% to about 4%, about 0.02% to about 3%, about 0.02% to about 2%, about 0.02% to about 1%, about 0.02% to about 0.5%, about 0.02% to about 0.4%, about 0.02% to about 0.3%, about 0.02% to about 0.2%, about 0.02% to about 0.1%, about 0.02% to about 0.05%, about 0.05% to about 5%, about 0.05% to about 4%, about 0.05% to about 3%, about 0.05% to about 2%, about 0.05% to about 1%, about 0.05% to about 0.5%, about 0.05% to about 0.4%, about 0.05% to about 0.3%, about 0.05% to about 0.2%, about 0.05% to about 0.1%, about 0.1% to about 5%, about 0.1% to about 4%, about 0.1% to about 3%, about 0.1% to about 2%, about 0.1% to about 1%, about 0.1% to about 0.5%, about 0.1% to about 0.4%, about 0.1% to about 0.3%, about 0.1% to about 0.2%, about 0.2% to about 5%, about 0.2% to about 4%, about 0.2% to about 3%, about 0.2% to about 2%, about 0.12% to about 1%, about 0.2% to about 0.5%, about 0.2% to about 0.4%, about 0.2% to about 0.3%, about 0.3% to about 5%, about 0.3% to about 4%, about 0.3% to about 3%, about 0.3% to about 2%, about 0.3% to about 1%, about 0.3% to about 0.5%, about 0.3% to about 0.4%, about 0.4% to about 5%, about 0.4% to about 4%, about 0.4% to about 3%, about 0.4% to about 2%, about 0.4% to about 1%, about 0.4% to about 0.5%, about 0.5% to about 5%, about 0.5% to about 4%, about 0.5% to about 3%, about 0.5% to about 2%, about 0.5% to about 1%, about 1% to about 5%, about 1% to about 4%, about 1% to about 3%, about 1% to about 2%, about 2% to about 5%, about 2% to about 4%, about 2% to about 3%, about 3% to about 5%, about 3% to about 4%, or about 4% to about 5% by weight of the composition. In some embodiments, the copolymer concentration is about 0.0001% to about 5% by weight of the composition. In some embodiments, the copolymer concentration is about 0.001% to about 1% by weight, about 0.005% to about 0.5% by weight, about 0.005% to about 0.02% by weight, about 0.01% to about 0.2% by weight, about 0.1% to about 0.4% by weight, or about 0.2% to about 0.3% by weight of the composition. In some embodiments, the copolymer concentration is about 0.005% by weight of the composition. In some embodiments, the copolymer concentration is about 0.01% by weight of the composition. In some embodiments, the copolymer concentration is about 0.05% by weight of the composition. In some embodiments, the copolymer concentration is about 0.1% by weight of the composition. In some embodiments, the copolymer concentration is about 1% by weight of the composition.

In some embodiments, the protein is selected from the group consisting of antibodies and fragments thereof, cytokines, chemokines, hormones, vaccine antigens, cancer antigens, adjuvants, and combinations thereof. In some embodiments, the protein is an antibody. In some embodiments, the protein is a monoclonal antibody. In some embodiments, the protein is a vaccine. In some embodiments, the protein is a hormone. In some embodiments, the composition exhibits reduced aggregation of the protein as compared to a composition of the same protein without the copolymer. In some embodiments, the composition exhibits reduced precipitation of the protein as compared to a composition of the same protein without the copolymer. In some embodiments, the composition comprises the protein in a concentration at least two times greater, at least three times greater, at least four times greater, or at least five times greater than the concentration of the same protein in the composition without the copolymer.

In some embodiments, the protein is insulin, or an analog thereof. Thus, also provided are compositions that contain a polyacrylamide-based copolymer of the present disclosure and insulin, or an analog thereof.

Non-limiting examples of insulin and insulin analogs include insulin lispro, HUMALOG® (fast-acting insulin lispro), insulin glargine, LANTUS® (insulin glargine), insulin detemir, LEVEMIR® (insulin detemir), ACTRAPID® (fast-acting human insulin), modern insulin, NOVORAPID® (insulin aspart), VELOSULIN® (human insulin), HUMULIN® M3 (a mixture of soluble insulin and isophane insulin called biphasic isophane insulin), HYPURIN® (neutral bovine insulin), INSUMAN® (recombinant human insulin), INSULATARD® (long-acting isophane human insulin), MIXTARD® 30 (a mixture of 30% soluble insulin and 70% isophane insulin), MIXTARD® 40 (a mixture of 40% soluble insulin and 60% isophane insulin), MIXTARD® 50 (a mixture of 50% soluble insulin and 50% isophane insulin), insulin aspart, insulin glulisine, insulin isophane, insulin degludec, insulin icodec, insulin zinc extended, NOVOLIN® R (human insulin), HUMULIN® R (human insulin), HUMULIN® R regular U-500 (concentrated regular insulin), NOVOLIN® N (intermediate-acting human insulin), HUMULIN® N (intermediate-acting human insulin), RELION® (over-the-counter brand of NOVOLIN® R, NOVOLIN® N, and NOVOLIN® 70/30), AFREZZA® (rapid-acting inhaled insulin), HUMULIN® 70/30 (a mixture of 70% human insulin isophane suspension and 30% human insulin injection), NOVOLIN® 70/30 (a mixture of 70% NPH, human insulin isophane suspension and 30% regular, human insulin injection), NOVOLOG® 70/30 (a mixture of 70% insulin aspart protamine suspension and 30% insulin aspart injection), HUMULIN® 50/50 (a mixture of 50% human insulin isophane suspension and 50% human insulin injection), HUMALOG® Mix 75/25 (a mixture of 75% insulin lispro protamine suspension and 25% insulin lispro injection), insulin aspart protamine-insulin aspart, insulin lispro protamine-insulin lispro, insulin lispro protamine-insulin lispro, human insulin NPH-human insulin regular, insulin degludec-insulin aspart, and combinations thereof. In some embodiments, the insulin, or an analog thereof, is a human insulin or a recombinant human insulin. In some embodiments, the insulin, or an analog thereof, is a non-human (e.g., primate, pig, cow, cat, dog, or rodent) insulin or a recombinant non-human insulin. In some embodiments, the insulin, or an analog thereof, is a purified or synthetic insulin. In some embodiments, the insulin, or an analog thereof, is selected from the group consisting of a rapid-acting insulin, a short-acting insulin, an intermediate-acting insulin, a long-acting insulin, and a pre-mixed insulin. In some embodiments, the insulin, or an analog thereof, is insulin lispro. In some embodiments, the insulin, or an analog thereof, is HUMALOG®, a commercially available fast-acting human insulin analog, insulin lispro. In some embodiments, the insulin, or an analog thereof, is insulin aspart. In some embodiments, the insulin, or an analog thereof, is insulin glulisine. In some embodiments, the insulin, or an analog thereof, is recombinant human insulin.

In some embodiments, the insulin, or an analog thereof, is present in the composition in the monomeric form, dimeric form, hexameric form, and combinations thereof. In some embodiments, about 1 mol % to about 5 mol %, about 1 mol % to about 10 mol %, about 1 mol % to about 20 mol %, about 1 mol % to about 30 mol %, about 1 mol % to about 40 mol %, about 1 mol % to about 50 mol %, about 1 mol % to about 60 mol %, about 1 mol % to about 70 mol %, about 1 mol % to about 80 mol %, about 1 mol % to about 90 mol %, or about 10 mol % to about 100 mol % of the insulin, or analog thereof, is present in the composition in monomeric form. For example, about 1 mol %, about 2 mol %, about 3 mol %, about 4 mol %, about 5 mol %, about 6 mol %, about 7 mol %, about 8 mol %, about 9 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 99 mol %, or about 100 mol % of the insulin, or an analog thereof, is present in the composition in monomeric form. In some embodiments, about 3 mol % of the insulin, or an analog thereof, is present in the composition in monomeric form. In some embodiments, insulin, or an analog thereof, is "substantially present" in a composition in the monomeric form, which means greater than about 50 mol % of the insulin, or insulin analog, is present in monomeric form. In some embodiments, the insulin, or an analog thereof, comprises about 50 mol % or greater insulin in monomeric form. In some embodiments, the insulin, or an analog thereof, comprises about 60 mol % or greater insulin in monomeric form. In some embodiments, the insulin, or an analog thereof, comprises about 70 mol % or greater insulin in monomeric form. In some embodiments, the insulin, or an analog thereof, comprises about 80 mol % or greater insulin in monomeric form. In some embodiments, the insulin, or an analog thereof, comprises about 90 mol % or greater insulin in monomeric form. In some embodiments, the insulin, or an analog thereof, comprises about 99 mol % or greater insulin in monomeric form. In some embodiments, the insulin, or an analog thereof, comprises about 100 mol % insulin in monomeric form. In some embodiments, insulin, or an analog thereof, is "substantially absent" in a composition in the monomeric form, which means less than about 10 mol % of the insulin, or insulin analog thereof, is present in monomeric form.

In some embodiments, about 10 mol % to about 100 mol % of the insulin, or analog thereof, is present in the composition in dimeric form. In some embodiments, about 10 mol % to about 100 mol %, about 20 mol % to about 90 mol %, about 30 mol % to about 80 mol %, about 40 mol % to about 70 mol %, about 50 mol % to about 60 mol %, about 60 mol % to about 100 mol %, about 80 mol % to about 100 mol %, about 90 mol % to about 100 mol %, or about 95 mol % to about 100 mol % of the insulin, or analog thereof, is present in the composition in dimeric form. For example, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 97 mol %, about 99 mol %, or about 100 mol % of the insulin, or an analog thereof, is present in the composition in dimeric form. In some embodiments, insulin, or an analog thereof, is "substantially present" in a composition in the dimeric form, which means greater than about 50 mol % of the insulin, or insulin analog, is present in dimeric form. In some embodiments, the insulin, or an analog thereof, comprises about 50 mol % or greater insulin in dimeric form. In some embodiments, the insulin, or an analog thereof, comprises about 60 mol % or greater insulin in dimeric form. In some embodiments, the insulin, or an analog thereof, comprises about 70 mol % or greater insulin in dimeric form. In some embodiments, the insulin, or an analog thereof, comprises about 80 mol % or greater insulin in dimeric form. In some embodiments, the insulin, or an analog thereof, comprises about 90 mol % or greater insulin in dimeric form. In some embodiments, the insulin, or an analog thereof, comprises about 97 mol % or greater insulin in dimeric form. In some embodiments, the insulin, or an analog thereof, comprises about 99 mol % or greater insulin in dimeric form. In some embodiments, the insulin, or an analog thereof, comprises about 100 mol % insulin in dimeric form.

In some embodiments, the insulin is not conjugated to poly(ethylene glycol) (PEG) or a trehalose polymer.

The concentration range of insulin, or analog thereof, can be from about 0.34 mg/mL (10 U/mL) to about 34 mg/mL (1000 U/mL). In some embodiments, the insulin concentration is about 1.7 mg/mL (50 U/mL) to about 17 mg/mL (500 U/mL). In some embodiments, the insulin concentration is about 17 mg/mL (500 U/mL) to about 34 mg/mL (1000 U/mL). In some embodiments, the insulin concentration is about 3.4 mg/mL (100 U/mL). In some embodiments, the insulin concentration is about 6.8 mg/mL (200 U/mL). In some embodiments, the insulin concentration is about 10.2 mg/mL (300 U/mL). In some embodiments, the insulin concentration is about 13.6 mg/mL (400 U/mL). In some embodiments, the insulin concentration is about 17 mg/mL (500 U/mL). In some embodiments, the insulin concentration is about 20.4 mg/mL (600 U/mL). In some embodiments, the insulin concentration is about 23.8 mg/mL (700 U/mL). In some embodiments, the insulin concentration is about 27.2 mg/mL (800 U/mL). In some embodiments, the insulin concentration is about 30.6 mg/mL (900 U/mL). In some embodiments, the insulin concentration is about 34 mg/mL (1000 U/mL).

Thus, also provided are compositions comprising a polyacrylamide-based copolymer of the present disclosure and insulin. In some embodiments, the polyacrylamide-based copolymer contains a MORPH carrier monomer and a NIP dopant monomer. In some embodiments, the composition contains about 0.005 wt % to about 0.2 wt % of a polyacrylamide-based copolymer comprising about 70% to about 95% by weight of a MORPH carrier monomer and about 5% to about 30% by weight of a NIP dopant monomer; and about 100 U/mL insulin, or an analog thereof. In some embodiments, the composition contains about 0.01 wt % of a polyacrylamide-based copolymer comprising about 74% to about 80% by weight of a MORPH carrier monomer and about 20% to about 26% by weight of a NIP dopant monomer; and about 100 U/mL insulin, or an analog thereof. In some embodiments, the composition contains about 0.01 wt % of a polyacrylamide-based copolymer comprising about 77% by weight of a MORPH carrier monomer and about 23% by weight of a NIP dopant monomer; and about 100 U/mL insulin, or an analog thereof.

In some embodiments, the copolymers described in the present disclosure reduce or prevent insulin aggregation. In some embodiments, the copolymers enable the stable formulation of insulin, or an analog thereof, in its monomeric form. In some embodiments, about 10 mol % to about 100 mol % of the insulin molecules, or analog thereof, in the formulation are present as monomeric insulin, or an analog thereof. For example, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 99 mol %, or about 100 mol % of the insulin molecules, or an analog thereof, in the formulation are present as monomeric insulin. In some embodiments, more than about 50 mol % of the insulin molecules, or an analog thereof, in the formulation are present as monomeric insulin, or an analog thereof. In some embodiments, more than about 60 mol % of the insulin molecules, or an analog thereof, in the formulation are present as monomeric insulin, or an analog thereof. In some embodiments, more than about 70 mol % of the insulin molecules, or an analog thereof, in the formulation are present as monomeric insulin, or an analog thereof. In some embodiments, more than about 80 mol % of the insulin molecules, or an analog thereof, in the formulation are present as monomeric insulin, or an analog thereof. In some embodiments, more than about 90 mol % of the insulin molecules, or an analog thereof, in the formulation are present as monomeric insulin, or an analog thereof. In some embodiments, about 100 mol % of the insulin molecules, or an analog thereof, in the formulation are present as monomeric insulin, or an analog thereof. In some embodiments, the formulation contains up to about 100 mol % insulin, or an analog thereof, present as dimeric insulin, or an analog thereof. In some embodiments, less than about 90 mol % of the insulin molecules, or an analog thereof, in the formulation are present as dimeric insulin, or an analog thereof. In some embodiments, less than about 80 mol % of the insulin molecules, or an analog thereof, in the formulation are present as dimeric insulin, or an analog thereof. In some embodiments, less than about 70 mol % of the insulin molecules, or an analog thereof, in the formulation are present as dimeric insulin, or an analog thereof. In some embodiments, less than about 60 mol % of the insulin molecules, or an analog thereof, in the formulation are present as dimeric insulin, or an analog thereof. In some embodiments, less than about 50 mol % of the insulin molecules, or an analog thereof, in the formulation are present as dimeric insulin, or an analog thereof. In some embodiments, less than about 40 mol % of the insulin molecules, or an analog thereof, in the formulation are present as dimeric insulin, or an analog thereof. In some embodiments, less than about 30 mol % of the insulin molecules, or an analog thereof, in the formulation are present as dimeric insulin, or an analog thereof. In some embodiments, less than about 20 mol % of the insulin molecules, or an analog thereof, in the formulation are present as dimeric insulin, or an analog thereof. In some embodiments, less than about 10 mol % of the insulin molecules, or an analog thereof, in the formulation are present as dimeric insulin, or an analog thereof. In some embodiments, the formulation is essentially free of dimeric insulin, or an analog thereof. In some embodiments, about 0 mol % to about 100 mol % of the insulin molecules, or an analog thereof, in the formulation are present as hexameric insulin. In some embodiments, more than about 95 mol % of the insulin molecules, or an analog thereof, in the formulation are present as hexameric insulin, or an analog thereof. In some embodiments, less than about 99 mol % of the insulin molecules, or an analog thereof, in the formulation are present as hexameric insulin, or an analog thereof. In some embodiments, less than about 90 mol % of the insulin molecules, or an analog thereof, in the formulation are present as hexameric insulin, or an analog thereof. In some embodiments, less than about 80 mol % of the insulin molecules, or an analog thereof, in the formulation are present as hexameric insulin, or an analog thereof. In some embodiments, less than about 70 mol % of the insulin molecules, or an analog thereof, in the formulation are present as hexameric insulin, or an analog thereof. In some embodiments, less than about 60 mol % of the insulin molecules, or an analog thereof, in the formulation are present as hexameric insulin, or an analog thereof. In some embodiments, less than about 50 mol % of the insulin molecules, or an analog thereof, in the formulation are present as hexameric insulin, or an analog thereof. In some embodiments, less than about 30 mol % of the insulin molecules, or an analog thereof, in the formulation are present as hexameric insulin, or an analog thereof. In some embodiments, less than about 20 mol % of the insulin molecules, or an analog thereof, in the formulation are present as hexameric insulin, or an analog thereof. In some embodiments, less than about 10 mol % of the insulin molecules, or an analog thereof, in the formulation are present as hexameric insulin, or an analog thereof. In some embodiments, less than about 5 mol % of the insulin molecules, or an analog thereof, in the formulation are present as hexameric insulin, or an analog thereof. In some embodiments, the formulation is essentially free of hexameric insulin, or an analog thereof. In some embodiments, about 0 mol % of the insulin molecules, or an analog thereof, in the formulation are present as hexameric insulin, or an analog thereof. In some embodiments, the formulation does not comprise Zn(II).

In some embodiments, the stable formulation of insulin in its monomeric form results in ultra-fast kinetics in vivo. In some embodiments, the copolymers enable the preparation of an ultrafast-absorbing insulin lispro (UFAL). In some embodiments, more than 50 mol % of the insulin molecules in the UFAL formulation are present as monomeric insulin. In some embodiments, more than 60 mol % of the insulin molecules in the UFAL formulation are present as monomeric insulin. In some embodiments, more than 70 mol % of the insulin molecules in the UFAL formulation are present as monomeric insulin. In some embodiments, more than 80 mol % of the insulin molecules in the UFAL formulation are present as monomeric insulin. In some embodiments, more than 90 mol % of the insulin molecules in the UFAL formulation are present as monomeric insulin. In some embodiments, less than 30 mol % of the insulin molecules in the UFAL formulation are present as dimeric insulin. In some embodiments, less than 20 mol % of the insulin molecules in the UFAL formulation are present as dimeric insulin. In some embodiments, less than 10 mol % of the insulin molecules in the UFAL formulation are present as dimeric insulin. In some embodiments, the UFAL formulation is essentially free of dimeric insulin. In some embodiments, less than 30 mol % of the insulin molecules in the UFAL formulation are present as hexameric insulin. In some embodiments, less than 20 mol % of the insulin molecules in the UFAL formulation are present as hexameric insulin. In some embodiments, less than 10 mol % of the insulin molecules in the UFAL formulation are present as hexameric insulin. In some embodiments, less than 5 mol % of the insulin molecules in the UFAL formulation are present as hexameric insulin. In some embodiments, the UFAL formulation is essentially free of hexameric insulin.

In some embodiments, the composition comprises insulin, or an analog thereof, substantially present in monomeric form, where administration of the composition to a subject results in a shorter duration of action as compared to administration of a composition comprising the same amount of insulin, or an analog thereof, substantially present in dimeric form, hexameric form, or a combination thereof, where the duration of action is the time to depletion of 50% of the maximum concentration observed ($C_{max}$).

In some embodiments, the composition comprises insulin, or an analog thereof, substantially present in monomeric form, where administration of the composition to a subject results in a shorter time to insulin onset as compared to administration of a composition comprising the same amount of insulin, or an analog thereof, substantially present in dimeric form, hexameric form, or a combination thereof, where the time to onset is the time to 50% of the maximum concentration observed ($C_{max}$).

In some embodiments, the composition comprises insulin, or an analog thereof, substantially present in monomeric form, where administration of the composition to a subject results in a greater fraction of total exposure to insulin as compared to administration of a composition comprising the same amount of insulin, or an analog thereof, substantially present in dimeric form, hexameric form, or a combination thereof, where the exposure is the fraction of the area under the curve (AUC) at a given timepoint over the total AUC ($AUC_{time}/AUC_{total}$).

In some embodiments, the composition comprises insulin, or an analog thereof, substantially present in monomeric form, where administration of the composition to a subject results in a shorter time to maximum concentration of insulin observed ($T_{max}$) as compared to administration of a composition comprising the same amount of insulin, or an analog thereof, substantially present in dimeric form, hexameric form, or a combination thereof.

In some embodiments, the composition comprising a copolymer of the present disclosure and a biologic molecule further comprise one or more of a pharmaceutically acceptable carrier, an aqueous buffer, a tonicity modifier, and a preservative. As used herein, pharmaceutically acceptable carriers, tonicity modifiers, and preservatives are nontoxic to recipients at the dosages and concentrations employed. In some embodiments, the composition contains a buffer, such as phosphate, citrate, succinate, other organic acids, and histidine, where the term "buffer" refers to a mixture of a weak acid and its conjugate base, or vice versa, that is used to maintain the pH of a solution at a nearly constant value. In some embodiments, the buffer comprises one or more phosphate salts. In some embodiments, the buffer is sodium phosphate.

In some embodiments, the composition contains a tonicity modifier, such as sodium chloride, potassium chloride, mannitol, dextrose, glycerol, or magnesium chloride. In some embodiments, the tonicity modifier is sodium chloride (NaCl) or glycerol. In some embodiments, the tonicity modifier is glycerol.

In some embodiments, the composition contains one or more preservatives, such as phenoxyethanol, phenol, meta-cresol, methylparaben, propylparaben, and benzyl alcohol. In some embodiments, the one or more preservatives comprise phenoxyethanol and phenol. In some embodiments, the one or more preservatives comprise phenoxyethanol and meta-cresol. In some embodiments, the preservative is phenoxyethanol. In some embodiments, the preservative is phenol or meta-cresol.

In some embodiments, the composition comprising the copolymers of the present disclosure is an aqueous composition. In some embodiments, the composition comprising the copolymers of the present disclosure comprises essentially water.

In some embodiments, the pH of the composition is about 4 to about 9, such as about 4 to about 8, about 4 to about 7, about 4 to about 6, about 4 to about 5, about 5 to about 9, about 5 to about 8, about 5 to about 7, about 5 to about 6, about 6 to about 9, about 6 to about 8, about 6 to about 7, about 7 to about 9, about 7 to about 8, about 8 to about 9, or about 4, about 4.5, about 5, about 5.5, about 6, about 6.5, about 7, about 7.4, about 8, about 8.5, or about 9. In some embodiments, the pH of the composition is about 4 to about 9. In some embodiments, the pH of the composition is about 6 to about 8. In some embodiments, the pH of the composition is about 7 to about 8. In some embodiments, the pH of the composition is about 7.4.

In some embodiments, the UFAL comprising the copolymer MORPH-NIP$_{23\%}$ is stable to stressed aging for over 24 hours. In some embodiments, the UFAL comprising the copolymer MORPH-NIP$_{23\%}$ is stable almost four-fold longer than commercial HUMALOG®.

In some embodiments, the UFAL formulations comprising a copolymer of the present disclosure further comprises one or more of pharmaceutically acceptable carriers, tonicity modifiers, and preservatives. In some embodiments, the UFAL formulation comprises a buffer, a preservative, a tonicity agent, and combinations thereof. In some embodiments, the buffer comprises one or more phosphate salts. In some embodiments, the buffer is sodium phosphate. In some embodiments, the preservative is phenoxyethanol. In some embodiments, the preservative is phenol or meta-cresol. In some embodiments, the tonicity agent is sodium chloride (NaCl) or glycerol. In some embodiments, the tonicity agent is glycerol.

Also provided are compositions containing the polyacrylamide-based copolymers of the present disclosure and a lipid-based vehicle. In some embodiments, the lipid-based vehicle is selected from the group consisting of liposomes, polymerosomes, micelles, and lipid nanoparticles.

In some embodiments, the copolymers of the present disclosure are used as formulation additives in formulations comprising monoclonal antibodies. In some embodiments, the copolymers of the present disclosure are used as formulation additives in formulations comprising antibody-drug conjugates. In some embodiments, the copolymers of the present disclosure are used as formulation additives in formulations comprising protein-based vaccine antigens. In some embodiments, the copolymers of the present disclosure are used as formulation additives in formulations comprising protein-polysaccharide conjugate vaccine antigens. In some embodiments, the copolymers of the present disclosure are used as formulation additives in formulations comprising nucleic acids. In some embodiments, the copolymers of the present disclosure are used as formulation additives in formulations comprising messenger RNA (mRNA). In some embodiments, the copolymers of the present disclosure are used as formulation additives in formulations comprising deoxyribose nucleic acids (DNA). In some embodiments, the copolymers of the present disclosure are used as formulation additives in formulations comprising small-interfering RNA (siRNA). In some embodiments, the copolymers of the present disclosure are used as formulation additives in formulations comprising short hairpin RNA (shRNA). In some embodiments, the copolymers of the present disclosure are used as formulation additives in formulations comprising microRNA (miRNA). In some embodiments, the copolymers of the present disclosure are used as formulation additives in formulations comprising one or more nucleic acids and one or more lipids. In some embodiments, the copolymers of the present disclosure are used as formulation additives in formulations comprising one or more neutral lipids. In some embodiments, the copolymers of the present disclosure are used as formulation additives in formulations comprising one or more cationic lipids. In some embodiments, the copolymers of the present disclosure are used as formulation additives in formulations comprising one or more anionic lipids. In some embodiments, the copolymers of the present disclosure are used as formulation additives in formulations comprising liposomes. In some embodiments, the copolymers of the present disclosure are used as formulation additives in formulations comprising lipid nanoparticles. In some embodiments, the copolymers of the present disclosure are used as formulation additives in formulations comprising micelles. In some embodiments, the copolymers of the present disclosure are used as formulation additives in formulations comprising polymerosomes. In some embodiments, the copolymers of the present disclosure are used as formulation additives in formulations comprising exosomes.

Co-Formulations Containing Insulin

Also provided in the present disclosure is a composition containing a polyacrylamide-based copolymer of the present disclosure, insulin, or an analog thereof, and one or more of a peptide, protein, or hormone.

In some embodiments, the co-formulation contains insulin, or an analog thereof, and glucagon, a glucagon-like peptide-1 (GLP-1) receptor agonist, a glucose-dependent insulinotropic polypeptide (GIP) receptor agonist, or a dual GIP and GLP-1 receptor agonist. In some embodiments, the co-formulation comprising a copolymer of the present disclosure and insulin comprises a GLP-1 receptor agonist. In some embodiments, the GLP-1 receptor agonist is selected from the group consisting of lixisenatide, liraglutide, albiglutide, dulaglutide, exenatide, extended-release exenatide, and semaglutide. In some embodiments, the co-formulation comprising a copolymer of the present disclosure and insulin comprises a GLP-1 receptor agonist and a GIP receptor agonist. In some embodiments, the co-formulation comprising a copolymer of the present disclosure and insulin comprises a dual GIP and GLP-1 receptor agonist. In some embodiments, the dual GIP and GLP-1 receptor agonist is tirzepatide. In some embodiments, the co-formulation comprising a copolymer of the present disclosure and insulin comprises a GIP receptor agonist. In some embodiments, the co-formulation comprising a copolymer of the present disclosure and insulin comprises glucagon.

In some embodiments, the co-formulation comprising a copolymer of the present disclosure and insulin further comprises amylin, or an analog thereof. In some embodiments, the amylin analog is pramlintide. According to embodiments of the disclosure, co-formulation of monomeric insulin, or an analog thereof, and pramlintide in the presence of a copolymer described herein has ultrafast kinetics with a high degree of overlap resulting in improved glucose management after a glucose challenge. In some embodiments, co-formulation of monomeric insulin lispro and pramlintide in the presence of a copolymer described herein is shown to have ultrafast kinetics with a high degree of overlap resulting in improved glucose management after a glucose challenge. As described in Example 3, a formulation containing the amphiphilic copolymer $MoNi_{23\%}$ as a stabilizing agent is physically stable twice as long as commercial HUMALOG® in a stressed aging assay.

In some embodiments, the composition containing a polyacrylamide-based copolymer of the present disclosure, insulin, or an analog thereof, and amylin, or an amylin analog thereof, are present in a ratio of amylin, or an analog thereof to insulin, or an analog thereof of about 1:1 to about 1:20, about 1:1 to about 1:15, about 1:1 to about 1:10, about 1:1 to about 1:6, or about 1:20, about 1:15, about 1:10, about 1:9, about 1:8, about 1:7, about 1:6, about 1:5, about 1:4, about 1:3, about 1:2, or about 1:1.

The copolymers of the present disclosure also enable the formulation of pramlintide at near neutral pH (~pH 7), whereas existing formulations of pramlintide require the pH of the formulation to be at ~pH 4, which is not compatible with insulin. In some embodiments, the pH of the co-formulation comprising a copolymer of the present disclosure, insulin, or an analog thereof, and amylin, or an analog thereof, is at near neutral pH (~pH 7). In some embodiments, the pH of the co-formulation comprising a copolymer of the present disclosure, insulin, or an analog thereof, and amylin, or an analog thereof, is about 6 to about 8. In some embodiments, the pH of the co-formulation comprising a copolymer of the present disclosure, insulin, or an analog thereof, and amylin, or an analog thereof, is about 6.5. In some embodiments, the pH of the co-formulation comprising a copolymer of the present disclosure, insulin, or an analog thereof, and amylin, or an analog thereof, is about 7. In some embodiments, the pH of the co-formulation comprising a copolymer of the present disclosure, insulin, or an analog thereof, and amylin, or an analog thereof, is about 7.4. In some embodiments, the amylin analog is pramlintide.

Thus, also provided are co-formulation comprising a polyacrylamide-based copolymer of the present disclosure, insulin, or an analog thereof, and pramlintide. In some embodiments, the composition comprises about 0.005 wt % to about 0.2 wt % of a polyacrylamide-based copolymer which comprises about 70% to about 95% by weight of a MORPH carrier monomer and about 5% to about 30% by weight of a NIP dopant monomer, about 100 U/mL insulin, or an analog thereof and about 0.01 mg/mL to about 0.1 mg/mL pramlintide. In some embodiments, the composition comprises about 0.01 wt % of a polyacrylamide-based copolymer which comprises about 74% to about 80% by weight of a MORPH carrier monomer and about 20% to about 26% by weight of a NIP dopant monomer, about 100 U/mL insulin, or an analog thereof and about 0.5 mg/mL to about 0.6 mg/mL pramlintide. In some embodiments, the composition comprises about 0.01 wt % of a polyacrylamide-based copolymer which comprises about 77% by weight of a MORPH carrier monomer and about 23% by weight of a NIP dopant monomer, about 100 U/mL insulin, or an analog thereof and about 0.6 mg/mL pramlintide. In some embodiments, the insulin, or an analog thereof, is substantially present in monomeric form. In some embodiments, the composition does not comprise zinc(II).

In some embodiments, administration of the composition to a subject exhibits an insulin $AUC_6/AUC_{120}$ that is at least about 25% greater than the insulin $AUC_6/AUC_{120}$ following administration of HUMALOG® alone or administration of HUMALOG® and pramlintide separately, such as about 30%, 40%, 50%, or greater.

The embodiments of the present disclosure demonstrate that the copolymer present in the co-formulation does not alter the pharmacokinetic (PK) or pharmacodynamic (PD) properties of the active ingredients within the formulation. In some embodiments, the pramlintide in the co-formulation results in delayed gastric emptying similar to separately administered pramlintide. In other embodiments, the combined effects of ultrafast insulin and pramlintide delivery synchronized in the co-formulation of the present disclosure results in reduced glucose depletion below baseline measurements, while maintaining control of the initial glucose spike in our simulated "mealtime" glucose challenge. Thus, in some embodiments, the co-formulation has potential to improve glucose management by reducing the risk of post-prandial hypoglycemia, while reducing patient burden.

In some embodiments, use of the co-formulation results in improved bolus insulin delivery. In some embodiments, insulin with the ultrafast kinetics is delivered synchronously with pramlintide in insulin infusion pumps and "artificial pancreas" closed-loop systems. In some embodiments, a stable insulin-pramlintide co-formulation enables the implementation of dual-hormone treatment in closed-loop systems outside of clinical trials where using two separate infusion pumps is impractical. In some embodiments, the synchronized insulin-pramlintide kinetics and shorter duration of insulin action in the co-formulation of the present results in improved autonomous insulin delivery. Typically, closed-loop systems require patients to input carbohydrates counts at mealtimes and are not fully autonomous, in part because insulin absorption kinetics are not rapid enough to reduce mealtime glucose excursions, and the extended duration of insulin action can result in post-prandial hypoglycemia. Thus, an ultrafast insulin-pramlintide co-formulation can rapidly react to mealtime spikes, as the insulin will have immediate onset and the pramlintide will slow the appearance of glucose (through delayed gastric emptying). Further, with shorter duration of insulin action, the risk of hypoglycemia, as a result of insulin stacking would be reduced.

The present disclosure demonstrates that a stable single administration insulin-pramlintide co-formulation, utilizing monomeric insulin, can have synchronized ultrafast insulin-pramlintide pharmacokinetics that result in better glycemic control in a mealtime simulation. This co-formulation has potential to improve glucose management and reduce patient burden in clinical applications using it for both direct bolus administration as well as in insulin infusion pumps or artificial pancreas closed-loop systems.

Properties of the Copolymer Compositions

The polyacrylamide-based copolymers of the present disclosure have unique properties and, when used in an aqueous formulation with a biologic molecule, can impart beneficial properties to the formulation.

In some embodiments, the copolymers described in the present disclosure reduce or prevent aggregation of a biologic molecule or lipid-based vehicle, such as when formulated in an aqueous formulation containing a biologic molecule or lipid-based vehicle. In some embodiments, the biologic molecule is a protein. Thus, in some embodiments, the copolymers described in the present disclosure reduce or prevent protein aggregation, such as when formulated in an aqueous formulation containing the protein. The copolymers can be used with any protein that is susceptible to aggregation in an aqueous medium. Non-limiting examples include antibodies and fragments thereof, cytokines, chemokines, hormones, vaccine antigens, cancer antigens, adjuvants, and combinations thereof. In some embodiments, the protein is a monoclonal antibody. In some embodiments, the polyacrylamide-based copolymers reduce or prevent aggregation of a protein susceptible to aggregation in an aqueous medium. In some embodiments, the protein is insulin, or an analog thereof. In some embodiments, the protein is a monoclonal antibody. In some embodiments, the protein is a hormone. In some embodiments, the protein is a vaccine.

The copolymers of the present disclosure can also increase the stability of a formulation. According to embodiments of the disclosure, the copolymers described herein can be added to improve the stability of a formulation containing, for example, a biologic molecule or a lipid-based vehicle, for example, peptides, proteins, and conjugates thereof, nucleic acids and oligonucleotides, liposomes, polymerosomes, micelles, and lipid nanoparticles. In some embodiments, addition of a copolymer of the present disclosure increases the stability of a protein formulation. In some embodiments, addition of a copolymer of the present disclosure increases the stability of a liposome formulation. In some embodiments, addition of a copolymer of the present disclosure increases the stability of a micelle formulation. In some embodiments, addition of a copolymer of the present disclosure increases the stability of a lipid nanoparticle formulation. In some embodiments, the addition of a copolymer of the present disclosure increases the stability of a formulation comprising one or more nucleic acids. In some embodiments, the addition of a copolymer of the present disclosure increases the stability of a formulation comprising one or more messenger RNA (mRNA). In some embodiments, the addition of a copolymer of the present disclosure increases the stability of a formulation comprising one or more small interfering RNA (siRNA). In some embodiments, the addition of a copolymer of the present disclosure increases the stability of a formulation comprising one or more deoxyribose nucleic acids (DNA).

In some embodiments, the copolymers of the present disclosure increase the thermal stability of a formulation containing a biologic molecule, which, in some embodiments, is a protein. Protein formulations typically require costly refrigerated transport and storage to prevent loss of protein integrity. Maintaining protein integrity is a challenge for the pharmaceutical industry, health care providers, and patients worldwide, particularly in the developing and low income regions where cold chain required for maintaining protein potency and efficacy is imperfect, overburdened or nonexistent. This results in large amounts of therapeutic protein formulations being wasted and potentially endangering the lives of patients. Thus, interruptions in the cold chain can be costly. The copolymers of the present disclosure can imbue long-term stability and/or cold chain resilience to protein formulations. For example, while commercial protein formulations have good shelf lives when stored properly (i.e., refrigerated), interruptions in the cold chain can decrease protein bioactivity and formulation integrity.

Protein formulations containing the copolymers of the present disclosure are, in some embodiments, stable for extended periods of time at temperatures higher than what is typically required for cold chain storage. For example, protein formulations containing the copolymers of the present disclosure can be stored at room temperature (between about 20° C. to about 22° C.) or at elevated temperatures, such as about 25° C., about 30° C., about 35° C., about 40° C., about 45° C., or higher while maintaining protein integrity. In some embodiments, protein formulations containing the copolymers of the present disclosure can be stored at a higher temperature than typically required, such as at about −20° C., or about 0° C., or about 2° C., or about 4° C., or about 8° C., or about 20° C., instead of at a lower temperature, such as at about −80° C., or about −60° C., or about −40° C. In some embodiments, the copolymers enable protein formulations to be stored at room temperature or higher temperatures rather than requiring cold chain storage. In some embodiments, cold chain storage is not required to maintain protein integrity.

In some embodiments, use of the copolymers of the present disclosure in protein formulations maintains formulation integrity, bioactivity, pharmacokinetics, and pharmacodynamics over a longer period of time when exposed to conditions such as elevated temperatures and agitation as compared to the same formulation without the copolymer. In some embodiments, the formulations maintain protein integrity for about 1 day, about 1 week, about 1 month, about 3 months, about 6 months, about 9 months, about 12 months, about 18 months, about 24 months, or longer at higher temperatures as compared to the same formulation that does not contain the copolymer of the present disclosure.

In some embodiments, the copolymers of the present disclosure reduce the rate of aggregation of a biologic molecule in an aqueous formulation. In some embodiments, the copolymers of the present disclosure reduce the rate of aggregation of a protein in an aqueous protein formulation. In some embodiments, the protein is a protein that tends to aggregate in an aqueous medium. In some embodiments, the protein is an antibody, or fragments thereof, a cytokine, a chemokine, a hormone, a vaccine antigen, a cancer antigen, an adjuvant, and combinations thereof. In some embodiments, this allows for formulation of more concentrated protein solutions, thus reducing the volume of the protein solution that needs to be administered, for example, to a patient. In some embodiments, the composition comprises the protein in a concentration at least two times greater, at least three times greater, at least four times greater, or at least five times greater than the concentration of the same protein in the composition without the copolymer.

Thus, use of the copolymers of the present disclosure can imbue long-term stability and/or cold chain resilience to protein formulations. In some embodiments, a protein in a composition that comprises a copolymer of the present disclosure exhibits increased stability when stored at room temperature as compared to a protein composition that does not contain the copolymer. In some embodiments, the increased stability is at least 10-fold, at least 15-fold, at least 20-fold, at least 25-fold, at least 30-fold, at least 35-fold, at least 40-fold, at least 45-fold, at least 50-fold, or greater as compared to a protein composition that does not contain the copolymer. In some embodiments, the protein is insulin. In some embodiments, the protein is a monoclonal antibody. In some embodiments, the protein is a hormone. In some embodiments, the protein is a vaccine.

Thus, in one particular embodiment, insulin in a composition that comprises a copolymer of the present disclosure exhibits increased stability when stored at room temperature as compared to an insulin composition that does not contain the copolymer. In some embodiments, the increased stability is at least 10-fold, at least 15-fold, at least 20-fold, at least 25-fold, at least 30-fold, at least 35-fold, at least 40-fold, at least 45-fold, at least 50-fold, or greater as compared to an insulin composition that does not contain the copolymer.

In some embodiments, the copolymers of the present disclosure preserve protein activity through 6 months of stressed aging without modifying one or more of formulation pharmacokinetics, protein secondary structure, formulation clarity, and in vivo bioactivity. In some embodiments, the copolymer reduces protein aggregation in the formulation when stored at ambient temperature (about 23° C. to about 27° C.) as compared to a protein formulation that does not contain the copolymer. In some embodiments, the copolymer reduces protein aggregation in the formulation when stored at 37° C. as compared to a protein formulation that does not contain the copolymer. In some embodiments, the copolymer reduces protein aggregation in the formulation when stored at 50° C. as compared to a protein formulation that does not contain the copolymer. In some embodiments, the protein is insulin. In some embodiments, the protein is a monoclonal antibody. In some embodiments, the protein is a hormone. In some embodiments, the protein is a vaccine.

In one particular embodiment, the copolymers of the present disclosure preserve insulin activity through 6 months of stressed aging without modifying one or more of formulation pharmacokinetics, protein secondary structure, formulation clarity, and in vivo bioactivity. In some embodiments, the copolymer reduces insulin aggregation in the formulation when stored at ambient temperature (about 23° C. to about 27° C.) as compared to a human insulin formulation that does not contain the copolymer. In some embodiments, the copolymer reduces insulin aggregation in the formulation when stored at 37° C. as compared to a human insulin formulation that does not contain the copolymer. In some embodiments, the copolymer reduces insulin aggregation in the formulation when stored at 50° C. as compared to a human insulin formulation that does not contain the copolymer. As described in Example 4, when subjected to harsh stressed aging tests in standard packaging, HUMULIN® R formulated with the $MoNi_{23\%}$ copolymer did not aggregate for over 56 days when subject to constant agitation at 37° C., and four days of constant agitation at 50° C., whereas HUMULIN® R alone aggregated within two days at 37° C. and within one day at 50° C. The stress aging conditions used in the studies described herein are designed to mimic typical storage and transportation conditions. Even in hot climates with limited cold chain infrastructure, it is unlikely that shipping containers would remain at 50° C. with continuous agitation with no reprieve for more than a 24-hour period.

In some embodiments, the copolymer increases the time to aggregation of a protein formulation by at least 10-fold, at least 15-fold, at least 20-fold, at least 25-fold, at least 30-fold, at least 35-fold, at least 40-fold, at least 45-fold, or at least 50-fold when stored at 37° C. as compared to a protein formulation that does not contain the copolymer. Time to aggregation can be assessed by any known method, including, for example, by a transmittance assay. In some embodiments, the copolymer increases the time to aggregation of a protein formulation by at least 10-fold when stored at 37° C. as compared to a protein formulation that does not contain the copolymer. In some embodiments, the copolymer increases the time to aggregation of a protein formulation by at least 20-fold when stored at 37° C. as compared to a protein formulation that does not contain the copolymer. In some embodiments, the copolymer increases the time to aggregation of a protein formulation by at least 30-fold when stored at 37° C. as compared to a protein formulation that does not contain the copolymer. In some embodiments, the copolymer increases the time to aggregation of a protein formulation by at least 40-fold when stored at 37° C. as compared to a protein formulation that does not contain the copolymer. In some embodiments, the copolymer increases the time to aggregation of a protein formulation by at least 50-fold when stored at 37° C. as compared to a protein formulation that does not contain the copolymer. In some embodiments, the copolymer increases the time to aggregation of a protein formulation by at least 10-fold, at least 15-fold, at least 20-fold, at least 25-fold, at least 30-fold, at least 35-fold, at least 40-fold, at least 45-fold, or at least 50-fold when stored at 50° C. as compared to a protein formulation that does not contain the copolymer. In some embodiments, the copolymer increases the time to aggregation of a protein formulation by at least 10-fold when stored at 50° C. as compared to a protein formulation that does not contain the copolymer. In some embodiments, the copolymer increases the time to aggregation of a protein formulation by at least 20-fold when stored at 50° C. as compared to a protein formulation that does not contain the copolymer. In some embodiments, the copolymer increases the time to aggregation of a protein formulation by at least 30-fold when stored at 50° C. as compared to a protein formulation that does not contain the copolymer. In some embodiments, the copolymer increases the time to aggregation of a protein formulation by at least 40-fold when stored at 50° C. as compared to a protein formulation that does not contain the copolymer. In some embodiments, the copolymer increases the time to aggregation of a protein formulation by at least 50-fold when stored at 50° C. as compared to a protein formulation that does not contain the copolymer. In some embodiments, the protein is insulin. In some embodiments, the protein is a monoclonal antibody. In some embodiments, the protein is a hormone. In some embodiments, the protein is a vaccine.

In one particular embodiment, the copolymer increases the time to aggregation of the human insulin formulation by at least 10-fold, at least 15-fold, at least 20-fold, at least 25-fold, at least 30-fold, at least 35-fold, at least 40-fold, at least 45-fold, or at least 50-fold when stored at 37° C. as assessed by a transmittance assay as compared to a human insulin formulation that does not contain the copolymer. In some embodiments, the copolymer increases the time to aggregation of the human insulin formulation by at least 10-fold when stored at 37° C. as assessed by a transmittance assay as compared to a human insulin formulation that does not contain the copolymer. In some embodiments, the copolymer increases the time to aggregation of the human insulin formulation by at least 20-fold when stored at 37° C. as assessed by a transmittance assay as compared to a human insulin formulation that does not contain the copolymer. In some embodiments, the copolymer increases the time to aggregation of the human insulin formulation by at least 30-fold when stored at 37° C. as assessed by a transmittance assay as compared to a human insulin formulation that does not contain the copolymer. In some embodiments, the copolymer increases the time to aggregation of the human insulin formulation by at least 40-fold when stored at 37° C. as assessed by a transmittance assay as compared to a human insulin formulation that does not contain the copolymer. In some embodiments, the copolymer increases the time to aggregation of the human insulin formulation by at least 50-fold when stored at 37° C. as assessed by a transmittance assay as compared to a human insulin formulation that does not contain the copolymer. In some embodiments, the copolymer increases the time to aggregation of the human insulin formulation by at least 10-fold, at least 15-fold, at least 20-fold, at least 25-fold, at least 30-fold, at least 35-fold, at least 40-fold, at least 45-fold, or at least 50-fold when stored at 50° C. as assessed by a transmittance assay as compared to a human insulin formulation that does not contain the copolymer. In some embodiments, the copolymer increases the time to aggregation of the human insulin formulation by at least 10-fold when stored at 50° C. as assessed by a transmittance assay as compared to a human insulin formulation that does not contain the copolymer. In some embodiments, the copolymer increases the time to aggregation of the human insulin formulation by at least 20-fold when stored at 50° C. as assessed by a transmittance assay as compared to a human insulin formulation that does not contain the copolymer. In some embodiments, the copolymer increases the time to aggregation of the human insulin formulation by at least 30-fold when stored at 50° C. as assessed by a transmittance assay as compared to a human insulin formulation that does not contain the copolymer. In some embodiments, the copolymer increases the time to aggregation of the human insulin formulation by at least 40-fold when stored at 50° C. as assessed by a transmittance assay as compared to a human insulin formulation that does not contain the copolymer. In some embodiments, the copolymer increases the time to aggregation of the human insulin formulation by at least 50-fold when stored at 50° C. as assessed by a transmittance assay as compared to a human insulin formulation that does not contain the copolymer.

The increased stability observed for HUMULIN® R formulated with the $MoNi_{23\%}$ copolymer compared to HUMULIN® R alone suggests that the $MoNi_{23\%}$ copolymer has utility in stabilizing insulin under various agitation conditions where interfacial turnover may be higher (i.e., horizontal agitation). The conditions evaluated in Example 4 of the present disclosure represent extreme exposure conditions during shipping in uninsulated containers or trucks in the hottest climates in the world where transport can take weeks before reaching patients.

In addition to refrigerated transport in the early stages of the cold chain, maintaining proper transport and storage conditions during local distribution and once in patients' hands presents a challenge in many parts of the world. As described herein, the addition of the polyacrylamide-based copolymers can preserve protein formulation integrity during even severe cold chain interruptions. In some embodiments, this enables a reduction in cold chain requirements for protein transportation and storage that are difficult to maintain in under-resourced environments. As disclosed herein, the polyacrylamide-based copolymers as formulation additives can improve cold chain resilience, thereby expanding global access to critical drugs and vaccines. In some embodiments, addition of the copolymer maintains the in vitro bioactivity of a protein formulation for at least 1 month, at least 2 months, at least 3 months, at least 4 months, at least 5 months, or at least 6 months. In some embodiments, addition of the copolymer maintains the in vitro bioactivity of a protein formulation for at least 1 month. In some embodiments, addition of the copolymer maintains the in vitro bioactivity of a protein formulation for at least 2 months. In some embodiments, addition of the copolymer maintains the in vitro bioactivity of a protein formulation for at least 3 months. In some embodiments, the protein is insulin. In some embodiments, the protein is a monoclonal antibody. In some embodiments, the protein is a hormone. In some embodiments, the protein is a vaccine.

In some embodiments, the copolymer present in a formulation with a protein does not alter the pharmacokinetic (PK) or pharmacodynamic (PD) properties of the active ingredients within the formulation.

Methods of Using the Copolymer Compositions

Provided in the present disclosure are methods of using the compositions and co-formulations described in the present disclosure that contain a polyacrylamide-based copolymer containing a water-soluble carrier monomer and a functional dopant monomer.

Provided in the present disclosure are methods of managing the blood glucose level in a subject in need thereof. In some embodiments, provided is a method of treating elevated blood glucose levels in a subject in need thereof. In some embodiments, the elevated blood glucose level is associated with insulin deficiency. In some embodiments, the elevated blood glucose level is associated with intake of food (e.g., during a mealtime). For example, provided is a method to offset the rise in glucose levels that can accompany ingesting macronutrients that raise glucose, such as carbohydrates (i.e., mealtime insulin). In some embodiments, managing the blood glucose level comprises reducing the glucose level in a subject in need thereof. In some embodiments, managing the blood glucose level comprises regulating the blood glucose level in a subject diagnosed with Type 1 or Type 2 diabetes. In some embodiments, managing the blood glucose level comprises reducing glucose levels during mealtime. The term "insulin deficiency," as used herein, refers to reduced insulin levels and/or reduced insulin sensitivity relative to metabolic demand. A subject with insulin deficiency includes, but is not limited to, a subject with diabetes, including, but not limited to, Type 1 diabetes, Type 1.5 diabetes, Type 2 diabetes, gestational diabetes mellitus, and diabetes post-pancreatectomy, a subject with hyperglycemia, and a subject with transient hyperglycemia, such as transient hyperglycemia from stress in an otherwise non-diabetic subject, for example, during hospitalization. In humans, blood sugar levels less than 100 mg/dL after fasting for at least eight hours and less than 140 mg/dL two hours after eating are deemed normal. A human subject with the normal blood sugar levels described above are considered to be non-diabetic. The methods of the present disclosure include administering to a subject in need thereof a therapeutically effective amount of a composition of the present disclosure comprising a polyacrylamide-based copolymer and insulin, or an analog thereof. In some embodiments, the composition is administered via a pump. In some embodiments, the pump is an infusion pump. In some embodiments, the composition is administered via an artificial pancreas closed-loop system. In some embodiments, the composition is administered via an automated insulin delivery system. In some embodiments, the elevated glucose level is associated with insulin deficiency in the subject. In some embodiments, the subject has been diagnosed with Type 1 diabetes. In some embodiments, the subject has been diagnosed with Type 2 diabetes. In some embodiments, the subject is non-diabetic. In some embodiments, the subject has experienced trauma, surgery, or both.

Also provided is a method for increasing stability of a formulation containing a biologic molecule or lipid-based vehicle. According to embodiments of the disclosure, the copolymers described herein can be added to improve the stability of formulations comprising peptides, proteins, and conjugates thereof, nucleic acids and oligonucleotides, liposomes, polymerosomes, micelles, and lipid nanoparticles. In some embodiments, provided is a method for increasing stability of a protein formulation. In some embodiments, provided is a method of increasing thermal stability of a formulation containing a biologic molecule or lipid-based vehicle. In some embodiments, provided is a method for increasing thermal stability of a protein formulation. Also provided is a method of reducing the rate of aggregation of a biologic molecule or lipid-based vehicle in an aqueous formulation. In some embodiments, the molecule is a molecule that tends to aggregate in an aqueous medium. In some embodiments, the protein is an antibody, or fragments thereof, a cytokine, a chemokine, a hormone, a vaccine antigen, a cancer antigen, an adjuvant, and combinations thereof.

In some embodiments, the methods include adding about 0.001 wt % to about 5 wt % of the polyacrylamide-based copolymer of the present disclosure to the formulation containing a biologic molecule or lipid-based vehicle, such as adding about 0.001 wt % to about 4 wt %, about 0.001 wt % to about 3 wt %, about 0.001 wt % to about 2 wt %, about 0.001 wt % to about 1 wt %, about 0.001 wt % to about 0.5 wt %, about 0.001 wt % to about 0.4 wt %, about 0.001 wt % to about 0.3 wt %, about 0.001 wt % to about 0.2 wt %, about 0.001 wt % to about 0.1 wt %, about 0.001 wt % to about 0.05 wt %, about 0.001 wt % to about 0.02 wt %, about 0.001 wt % to about 0.01 wt %, about 0.001 wt % to about 0.005 wt %, about 0.005 wt % to about 5 wt %, about 0.005 wt % to about 4 wt %, about 0.005 wt % to about 3 wt %, about 0.005 wt % to about 2 wt %, about 0.005 wt % to about 1 wt %, about 0.005 wt % to about 0.5 wt %, about 0.005 wt % to about 0.4 wt %, about 0.005 wt % to about 0.3 wt %, about 0.005 wt % to about 0.2 wt %, about 0.005 wt % to about 0.1 wt %, about 0.005 wt % to about 0.05 wt %, about 0.005 wt % to about 0.02 wt %, about 0.005 wt % to about 0.01 wt %, about 0.01 wt % to about 5 wt %, about 0.01 wt % to about 4 wt %, about 0.01 wt % to about 3 wt %, about 0.01 wt % to about 2 wt %, about 0.01 wt % to about 1 wt %, about 0.01 wt % to about 0.5 wt %, about 0.01 wt % to about 0.4 wt %, about 0.01 wt % to about 0.3 wt %, about 0.01 wt % to about 0.2 wt %, about 0.01 wt % to about 0.1 wt %, about 0.01 wt % to about 0.05 wt %, about 0.01 wt % to about 0.02 wt %, about 0.02 wt % to about 5 wt %, about 0.02 wt % to about 4 wt %, about 0.02 wt % to about 3 wt %, about 0.02 wt % to about 2 wt %, about 0.02 wt % to about 1 wt %, about 0.02 wt % to about 0.5 wt %, about 0.02 wt % to about 0.4 wt %, about 0.02 wt % to about 0.3 wt %, about 0.02 wt % to about 0.2 wt %, about 0.02 wt % to about 0.1 wt %, about 0.02 wt % to about 0.05 wt %, about 0.05 wt % to about 5 wt %, about 0.05 wt % to about 4 wt %, about 0.05 wt % to about 3 wt %, about 0.05 wt % to about 2 wt %, about 0.05 wt % to about 1 wt %, about 0.05 wt % to about 0.5 wt %, about 0.05 wt % to about 0.4 wt %, about 0.05 wt % to about 0.3 wt %, about 0.05 wt % to about 0.2 wt %, about 0.05 wt % to about 0.1 wt %, about 0.1 wt % to about 5 wt %, about 0.1 wt % to about 4 wt %, about 0.1 wt % to about 3 wt %, about 0.1 wt % to about 2 wt %, about 0.1 wt % to about 1 wt %, about 0.1 wt % to about 0.5 wt %, about 0.1 wt % to about 0.4 wt %, about 0.1 wt % to about 0.3 wt %, about 0.1 wt % to about 0.2 wt %, about 0.2 wt % to about 5 wt %, about 0.2 wt % to about 4 wt %, about 0.2 wt % to about 3 wt %, about 0.2 wt % to about 2 wt %, about 0.2 wt % to about 1 wt %, about 0.2 wt % to about 0.5 wt %, about 0.2 wt % to about 0.4 wt %, about 0.2 wt % to about 0.3 wt %, about 0.3 wt % to about 5 wt %, about 0.3 wt % to about 4 wt %, about 0.3 wt % to about 3 wt %, about 0.3 wt % to about 2 wt %, about 0.3 wt % to about 1 wt %, about 0.3 wt % to about 0.5 wt %, about 0.3 wt % to about 0.4 wt %, about 0.4 wt % to about 5 wt %, about 0.4 wt % to about 4 wt %, about 0.4 wt % to about 3 wt %, about 0.4 wt % to about 2 wt %, about 0.4 wt % to about 1 wt %, about 0.4 wt % to about 0.5 wt %, about 0.5 wt % to about 5 wt %, about 0.5 wt % to about 4 wt %, about 0.5 wt % to about 3 wt %, about 0.5 wt % to about 2 wt %, about 0.5 wt % to about 1 wt %, about 1 wt % to about 5 wt %, about 1 wt % to about 4 wt %, about 1 wt % to about 3 wt %, about 1 wt % to about 2 wt %, about 2 wt % to about 5 wt %, about 2 wt % to about 4 wt %, about 2 wt % to about 3 wt %, about 3 wt % to about 5 wt %, about 3 wt % to about 4 wt %, about 4 wt % to about 5 wt %, or about 0.005 wt %, about 0.01 wt %, or about 0.1 wt % of the polyacrylamide-based copolymer of the present disclosure to the formulation. In some embodiments, the method includes adding about 0.0005 wt % to about 5 wt % of the polyacrylamide-based copolymer of the present disclosure to the formulation. In some embodiments, the method includes adding about 0.001 wt % to about 1 wt % of the polyacrylamide-based copolymer of the present disclosure to the formulation. In some embodiments, the formulation comprises a biologic molecule. In some embodiments, the formulation comprises a protein. In some embodiments, the formulation comprises a lipid-based vehicle. In some embodiments, the lipid-based vehicle comprises a liposome, lipid nanoparticle, polymerosome, or micelle.

Other Uses of the Polyacrylamide-Based Copolymers

The polyacrylamide-based copolymers of the present disclosure can be used in any composition or formulation where a surfactant is used. For example, the copolymers of the present disclosure can be used in applications including, but not limited to, cosmetic products, hair products, lotions, food products, nutritional products, pigments, and ink. In some embodiments, copolymers are used to improve food texture or improve mouth-feel. In some embodiments, the copolymers are used in biopharmaceutical compositions for animal or veterinary use. In some embodiments, the presence of the copolymer improves the stability of the formulation.

EXAMPLES

Example 1—Synthesis and Characterization of AD/DC Copolymer Library

Study Design: The pharmacokinetics of an insulin lispro formulation, ultra-fast absorbing insulin lispro (UFAL), were compared to a commercial insulin lispro formulation (HUMALOG®). Blood glucose and plasma lispro concentrations were measured after subcutaneous administration of either (i) HUMALOG® or (ii) UFAL by using a handheld blood glucose monitor or ELISA on collected blood samples. Randomization: 5 pigs were used for this study and each pig received each formulation once. The order in which the formulations were given in was randomized. Blinding: For analysis of pharmacokinetic parameters (t50% up, time to peak, t50% down) pharmacokinetic curves were coded, and were analyzed by a blinded researcher. Replication. 5 pigs were used in this study and each pig acted as its own control receiving each formulation (HUMALOG® and UFAL) once.

Materials: Solvents N,N-dimethylformamide (DMF; HPLC Grade, Alfa Aesar, >99.7%), ethanol (EtOH; Certified ACS, Acros, >99.5%), acetone (Sigma, HPLC Grade, >99.9%), hexanes (Fisher, Certified ACS, >99.9%), ether (Sigma, Certified ACS, Anhydrous, >99%) and $CDCl_3$ (Acros, >99.8%) were used as received. Monomers N,N-dimethylacrylamide (DMA; Sigma, 99%), N-(3-methoxypropyl)acrylamide (MPAM; Sigma, 95%), 4-acryloylmorpholine (MORPH; Sigma, >97%), acrylamide (AM; Sigma, >99%), and N-hydroxyethyl acrylamide (HEAM; Sigma, >97%) were filtered with basic alumina prior to use. Monomers N-phenylacrylamide (PHE; Sigma, 99%), N-tert-butylacrylamide (TBA; Sigma, 97%), N-isopropylacrylamide (NIPAM; Sigma, >99%), and N-[tris(hydroxymethyl)methyl]acrylamide (TRI; Sigma, 93%) were used as received. (3-acrylamidopropyl)trimethylammonium (TMA; Sigma, 75%) was washed with ethyl acetate. 2-acrylamido-2-methylpropane sulfonic acid (AMP; Sigma, 99%) was converted to the sodium salt through equimolar mixing with sodium acetate in methanol and precipitated into acetone. RAFT chain transfer agents 2-cyano-2-propyl dodecyl trithiocarbonate (2-CPDT; Strem Chemicals, >97%) and 4-((((2-carboxyethyl)thio)carbonothioyl)thio)-4-cyanopentanoic acid (BM1433; Boron Molecular, >95%) were used as received. Initiator 2,2'-azobis(2-methyl-propionitrile) (AIBN; Sigma, >98%) was recrystallized from methanol (MeOH; Fisher, HPLC Grade, >99.9%) and dried under vacuum before use. Initiator 4,4-azobis(4-cyanovaleric acid)(ACVA; Sigma, >98%) was used as received. Z group removing agents lauroyl peroxide (LPO; Sigma, 97%) and hydrogen peroxide (H2O2; Sigma, 30%) were used as received.

Synthesis of first copolymer library via automated parallel synthesis: Copolymerizations of carriers and dopants were carried out using RAFT polymerization ([Total Monomer]/[CTA]=50, [CTA]/[AIBN]=0.2). MPAM, MORPH, and DMA carrier monomers copolymerized with AMP, TMA, NIP, TBA, or PHE dopant monomers were polymerized in DMF using 2-CPDT as the CTA and AIBN as the initiator. MPAM, MORPH, and DMA carrier monomers copolymerized with TRI dopant monomer were polymerized in a DMF/water mixture using BM1433 as the CTA and ACVA as the initiator. Total vinyl monomer molarity was held at 2.72M (MPAM copolymerizations), 2.86M (MORPH copolymerizations), and 3.84M (DMA copolymerizations) such that the homopolymerization of the carrier monomer in DMF would be carried at a constant 40 wt. %. HEAM carrier monomer copolymerized with AMP, TMA, NIP, TBA, or PHE dopant monomers were polymerized in DMF/EtOH mixture using 2-CPDT as the CTA and AIBN as the initiator. HEAM carrier monomer copolymerized with AMP, TMA, NIP, TBA, or PHE dopant monomers were polymerized in DMF/EtOH/water mixture using BM1433 as the CTA and ACVA as the initiator. Total vinyl monomer molarity was held at 2.58M (HEAM copolymerizations) such that the homopolymerization of HEAM in DMF would be carried at a constant 30 wt. %. AM carrier monomer copolymerized with AMP, TMA, NIP, TBA, or PHE dopant monomers were polymerized in DMF/water mixture using BM1433 as the CTA and ACVA as the initiator. AM carrier monomer copolymerized with TRI dopant monomer was polymerized in water using BM1433 as the CTA and ACVA as the initiator. Total vinyl monomer molarity was held at 4.05M (AM copolymerizations) such that the homopolymerization of AM in DMF would be carried at a constant 30 wt. %.

Reaction mixtures were prepared by combining stock solutions: (i) carriers, (ii) dopants, and (iii) CTA and initiator. The stock solutions of carrier monomers were HEAM (555 mg/mL in EtOH), AM (462 mg/mL in water), MPAM (818 mg/mL in DMF), DMA (no solvent dilution), and MORPH (no solvent dilution). The stock solutions of dopant monomers were TRI (181 mg/mL in water), PHE (120 mg/mL in DMF), NIP (245 mg/mL in DMF), TBA (122 mg/mL in DMF), AMP (120 mg/mL in DMF), and TMA (124 mg/mL in DMF). Stock solutions of CTA and initiator were prepared such that [CTA]/[initiator]=5 for AM (BM1433 at 310 mg/mL in water), HEAM and MPAM (BM1433 at 198 mg/mL in water, and 2-CPDT at 221 mg/mL in DMF), MORPH (BM1433 at 220 mg/mL in water and 2-CPDT at 247 mg/mL in DMF), and DMA (BM1433 at 220 mg/mL in water and 2-CPDT at 332 mg/mL in DMF). Reaction mixtures of HEAM, DMA, MPAM, and MORPH were diluted with DMF while reaction mixtures of AM were diluted with water to reach the desired vinyl monomer concentration.

Parallel syntheses of polyacrylamide-based copolymer excipients (also referred to as AC/DC excipients) were conducted on a Chemspeed Swing XL automated synthesizer robot equipped with a 4-Needle Head tool and an iSynth reactor. The Reactions were performed in 8 mL disposable ISynth reactor vials. All aspirations and dispensing reagent solutions were performed using a the 4-Needle Head tool equipped with a 2×10 mL and 2×1 mL syringes fitted with septa piercing needles, with both the 1 mL and 10 mL syringes used in this particular experiment. All solvent lines were primed with 60 mL (6 strokes of syringe volume) of degassed DMF. Typical aspiration and dispense rates of the reagents were 10 mL/min for both the 1 mL syringes. An airgap of 50 μL and an extra volume of 50 μL was used for the 1 mL syringes, and an airgap of 50 μL and an extra volume of 100 μL was used for the 10 mL syringes during aspirations using the 4-Needle Head tool. The needles and lines were rinsed after each reagent dispense task with 3 mL inside and outside volume of the priming solvent for the 1 mL syringes and with 20 mL inside and outside volume of the priming solvent for the 10 mL syringes. The DMF reservoir was degassed by continuous nitrogen sparging. All stock solutions were prepared in septa capped reagent vials and degassed by sparging with argon for 15 minutes before transfer into the Chemspeed. The atmosphere within the Chemspeed was reduced to <1% oxygen by purging with nitrogen while exhaust ports were closed. Reactor vials were exposed to nitrogen flow until the start of the reaction. The calculated aliquots of stock solutions and solvent were transferred to the reactors via the automated liquid handling system. Upon dispensing, reactor vials were manually sealed in the inert atmosphere, removed from the Chemspeed, manually shaken to combine reagents, and heated to 65° C. in an oven for 24 hours, after which, reaction vials were cooled to room temperature and exposed to air.

A procedure to remove the CTA Z groups from the AC/DC excipients containing MORPH, DMA, HEAM, and MPAM copolymers was adapted from the literature. The reaction vial was diluted to 6 mL with DMF. LPO (2 eq.) and AIBN (20 eq.) were added to the reaction mixture, which was sealed with a cap utilizing a PTFE seal. The reaction mixture was sparged with nitrogen gas for 10 minutes while heating at 90° C. and subsequently heated for 12 hours at 90° C. A procedure to remove the CTA Z groups from the AC/DC excipients containing AM copolymers was adapted from the literature. The reaction vial was diluted to 5 mL with miliQ water. $H_2O_2$ (20 eq.) was added to the reaction vial, which was sealed and heated to 60° C. for 12 hours. The resulting copolymers were isolated by precipitation as outlined below.

AC/DC excipients synthesized with AM and HEAM carriers were precipitated twice from ace-tone. AC/DC excipients synthesized with DMA and MORPH were precipitated twice from diethyl ether. AC/DC excipients synthesized with MPAM were precipitated twice from diethyl ether and hexane (3:1 ratio) mixtures. The number ($M_n$) and weight ($M_w$) average molecular weights and dispersity for the AC/DC excipients containing MORPH, MPAM, DMA, and HEAM were determined using SEC in DMF with poly(ethyleneglycol) standards. $M_n$, $M_w$, and dispersity for the AC/DC excipients containing AM were determined using aqueous SEC-MALLS.

Synthesis of second polymeric library: A typical procedure to synthesize a MORPH-NIP AC/DC excipient is as follows and is nearly identical for all other carrier/dopant combinations, where only the carrier/dopant selection and concentration are changed. MORPH (645 mg, 4.57 mmol, 41.5 eq.), NIPAM (105 mg, 0.93 mmol, 8.5 eq.), 2CPDT (38 mg, 0.11 mmol, 1 eq.) and AIBN (3.6 mg, 0.02 mmol, 0.2 eq.) were combined and diluted with DMF to a total volume of 2.25 mL (33.3 w/v vinyl monomer concentration) in an 8 mL scintillation vial equipped with a PTFE septa. The reaction mixture was sparged with nitrogen gas for 10 minutes and then heated for 12 hours at 65° C. To remove the Z-terminus of the resulting polymer, AIBN (360 mg, 2.2 mmol, 20 eq.) and LPO (88 mg, 0.22 mmol, 2 eq.) were added to the reaction mixture, which was then sparged with nitrogen gas for 10 minutes and heated for 12 hours at 90° C. Z-group removal was confirmed by the ratio of the refractive index to UV (λ=310 nm) intensity in SEC analysis. Resulting polymers were precipitated three times from ether, and dried under vacuum overnight. Resulting composition and molecular weights were determined via $^1$H NMR spectroscopy and SEC with poly(ethyleneglycol) standards.

Copolymer molecular weight characterization: $M_n$, $M_w$, and dispersity for copolymers with HEAM, DMA, MPAM, and MORPH carrier monomers were determined via SEC implementing poly(ethyleneglycol) standards (American Polymer Standards Corporation) after passing through two size exclusion chromatography columns (Re-solve Mixed Bed Low DVB, ID 7.8 mm, $M_w$ range 200-600,000 g mol$^{-1}$ (Jordi Labs) in a mobile phase of N,N-dimethylformamide (DMF) with 0.1M LiBr at 35° C. and a flow rate of 1.0 ml min$^{-1}$ (Dionex Ultimate 3000 pump, degasser, and autosampler (Thermo Fisher Scientific).

$M_n$, $M_w$, and dispersity for copolymers with AM were determined via SEC-MALLS after passing through a size exclusion chromatography column (Superose 6 Increase 10/300 GL, 5,000-5,000,000 g mol$^{-1}$ (GE Healthcare)) in a mobile phase of phosphate-buffered saline containing 300 ppm sodium azide. Detection consisted of a Optilab T-rEX (Wyatt Technology Corporation) refractive index detector operating at 658 nm and a TREOS II light scattering detector (Wyatt Technology Corporation) operating at 659 nm. The do/dc value for AM copolymers were assumed to be 0.185 in this media.

Method for Determining Experimental VM Wt. % Values

The handling of viscous monomers (HEAM, MPAM, MORPH) by the Chemspeed resulted in monomer loadings that differed from the target monomer loadings for select copolymerizations during the initial AC/DC copolymer library synthesis. Experimental weight percentages were approximated from the peak molecular weights ($M_p$) of the SEC traces. Because only viscous monomers were affected, changes to $M_p$ arose from inadequate addition of carrier monomer (aside from small changes in pervaded volume in the differing weight percentages of the dopant monomer compared to the carrier). Thus, to calculate the experimental weight percentages, $M_{p,max}$ was determined for a given carrier/dopant pair.

Results

Figure 2:
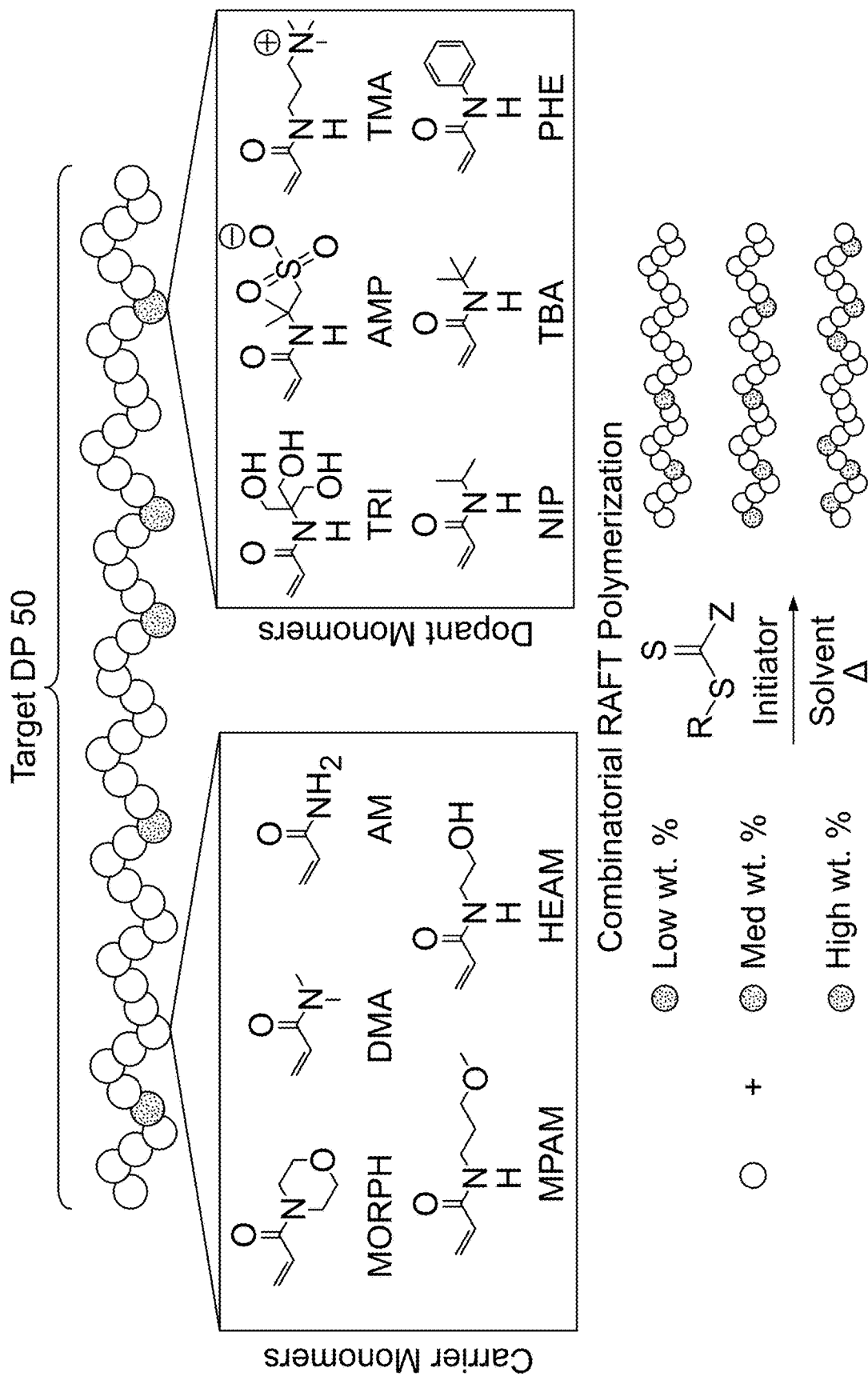
FIG. 2 illustrates a scheme of polymer excipient library design. A library of statistical acrylamide copolymers with a target degree of polymerization (DP) of 50 were synthesized through controlled copolymerization using RAFT. Copolymer combinations consist of one carrier monomer: acryloylmorpholine (MORPH), methoxypropylacrylamide (MPAM), dimethylacrylamide (DMA), hydroxyethylacrylamide (HEAM), or acrylamide (AM). Each copolymer also contains one dopant monomer: tris(hydroxymethyl)-methylacrylamide (TRI), acrylamidomethylpropane sulfonic acid (AMP), acrylamidopropyltrimethylammonium chloride (TMA), n-isopropylacrylamide (NIP), tertbutylacrylamide (TBA), or phenylacrylamide (PHE). Each carrier-dopant combination was repeated at low, medium and high dopant loadings: NIP at 6.7, 13.3, and 20 wt. %, TRI at 5, 10, and 15 wt. %, and AMP, TMA, TBA, PHE at 3.3, 6.7, and 10 wt. %.

High-throughput synthesis of polyacrylamide library: A library of AC/DC excipients was synthesized combinatorially through statistical copolymerizations of water-soluble carrier monomers and functional dopant monomers (FIG. 2). The carrier monomers were the predominant species and responsible for both maintaining solubility and providing an inert barrier to prevent insulin-insulin interactions. The functional dopants copolymerized at lower weight percentages were incorporated statistically throughout the resulting copolymer. These dopants are selected by design to promote either polymer-interface interactions or polymer-insulin interactions. The library targets a degree of polymerization (DP) of 50 for the copolymers, resulting in molecular weights similar to insulin and well below the glomerial filtration threshold for synthetic polymers.

Figure 3:
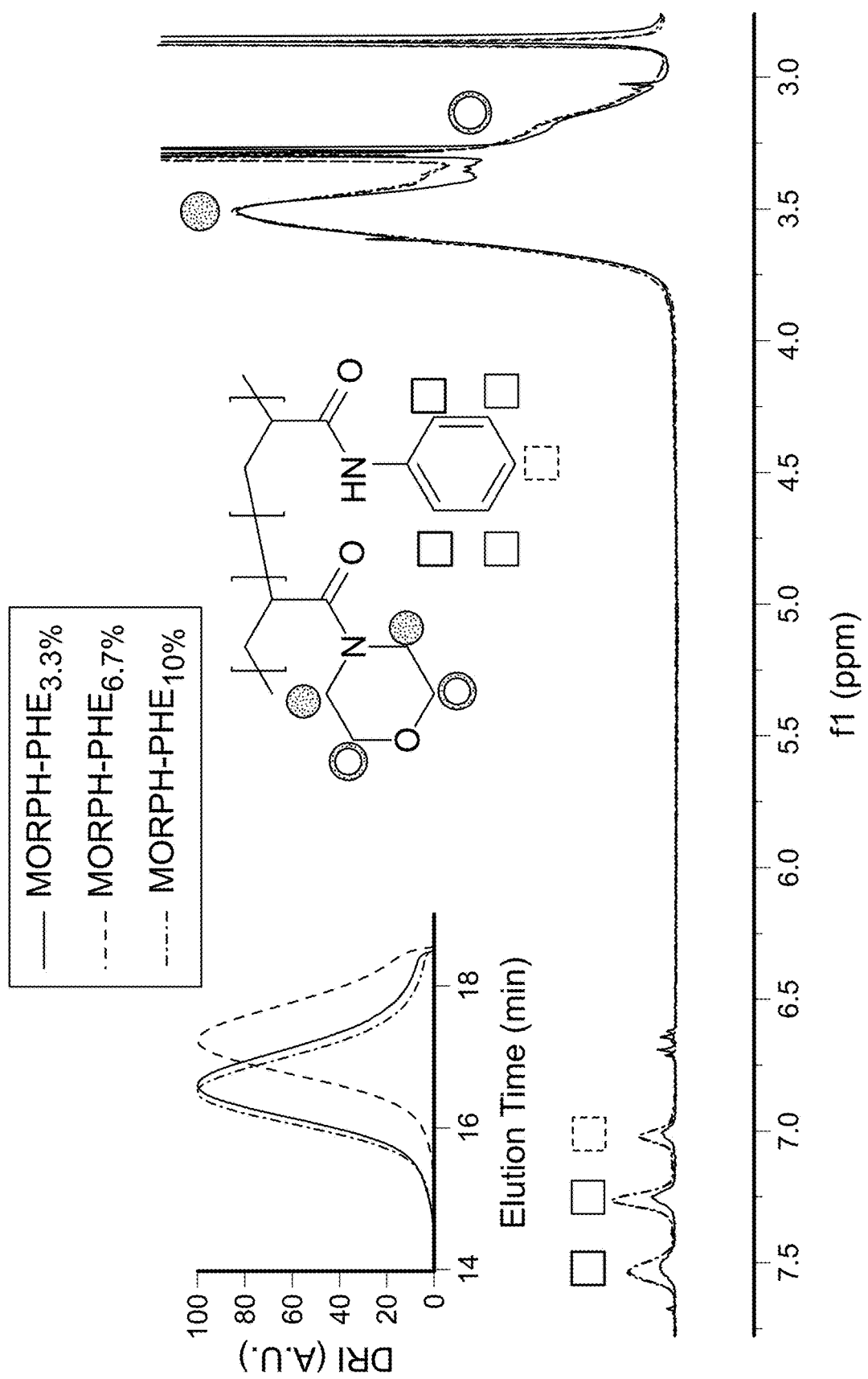
FIG. 3 illustrates the $^1$H NMR spectroscopy and SEC traces to validate SEC wt. % measurement. $^1$H NMR spectroscopy of synthesized copolymers with MORPH as a carrier and PHE as a dopant is shown. MORPH-PHE$_{6.7\%}$ received inadequate MORPH addition on account of the high viscosity of the monomer, yielding a higher than expected loading of PHE in the final copolymer. The experimental loading was confirmed by SEC traces provided in the inset figure, where MORPH-PHE$_{6.7\%}$ was determined to be a lower molecular weight than MORPH-PHE$_{3.3\%}$ and MORPH-PHE$_{10\%}$. This decrease in molecular weight is used to determine experimental loadings of MORPH and PHE in the final copolymers. DRI refers to differential refractive index measured using SEC.

The experimental degree of polymerization (DP) of the carrier monomer was approximated using equation (S1). This value was used to approximate the experimental weight percentages (wt %). Results calculated using this method were corroborated by $^1$H NMR spectroscopy for the copolymerizations of MORPH (carrier) and PHE (dopant) as shown in FIG. 3. The results from this comparison are shown in Table 1. The experimental weight percentage values of the carrier monomer and the functional dopant monomer for each copolymer were determined using $^1$H NMR and SEC and are summarized in Table 2.

$$DP_{carrier, experimental} = \frac{M_p}{M_{p,max}} * DP_{carrier, target} \quad (S1)$$

TABLE 1

Validation of SEC wt. % measurement by $^1$H NMR Spectroscopy

| Carrier | wt. % (Target) | Dopant | wt. % (Target) | wt. %[a] (Experimental, NMR) | wt. %[b] (Experimental, $M_p$) | $M_p$ |
|---|---|---|---|---|---|---|
| MORPH | 96.7 | PHE | 3.3 | 4.5 | 3.6 | 2900 |
| MORPH | 93.3 | PHE | 6.7 | 11.7 | 10.7 | 1850 |
| MORPH | 90 | PHE | 10 | 11.3 | 10 | 3100 |

[a] Experimental wt. % calculated from post precipitated $^1$H NMR (δ = 3.3-3.7, 8 H).
[b] Experimental wt. % calculated from equation 1 using $M_p$ (peak molecular weight) values determined with SEC.

TABLE 2

SEC and MALS characterization and analysis of polymers synthesized in initial AC/DC library

| Carrier | wt. % (Target) | wt. % (Experimental) | Dopant | wt. % (Target) | wt. % (Experimental) | $M_n{}^a$ (Da) | $M_w{}^a$ (Da) | $Ð^a$ |
|---|---|---|---|---|---|---|---|---|
| DMA | 100 | — |  | 0 | — | 2700 | 3000 | 1.1 |
| DMA | 93.34 | — | NIP | 6.66 | — | 2900 | 3500 | 1.2 |
| DMA | 86.67 | — | NIP | 13.33 | — | 3000 | 3500 | 1.15 |
| DMA | 80 | — | NIP | 20 | — | 3000 | 3400 | 1.14 |
| DMA | 96.67 | — | PHE | 3.33 | — | 2800 | 3200 | 1.14 |
| DMA | 93.34 | — | PHE | 6.66 | — | 3000 | 3500 | 1.17 |
| DMA | 90 | — | PHE | 10 | — | 3400 | 3900 | 1.15 |
| DMA | 96.67 | — | AMP | 3.33 | — | 3400 | 4100 | 1.22 |
| DMA | 93.34 | — | AMP | 6.66 | — | 3700 | 4400 | 1.2 |
| DMA | 90 | — | AMP | 10 | — | 3500 | 4100 | 1.16 |
| DMA | 96.67 | — | TMA | 3.33 | — | 3700 | 4300 | 1.15 |
| DMA | 93.34 | — | TMA | 6.66 | — | 3800 | 4600 | 1.2 |
| DMA | 90 | — | TMA | 10 | — | 3800 | 4500 | 1.19 |
| DMA | 96.67 | — | TBA | 3.33 | — | 2900 | 3500 | 1.2 |
| DMA | 93.34 | — | TBA | 6.66 | — | 3000 | 3600 | 1.2 |
| DMA | 90 | — | TBA | 10 | — | 3100 | 3600 | 1.17 |
| DMA | 95 | — | TRI | 5 | — | 2900 | 3500 | 1.2 |
| DMA | 90 | — | TRI | 10 | — | 3500 | 4100 | 1.17 |
| DMA | 85 | — | TRI | 15 | — | 3200 | 3900 | 1.23 |
| MORPH | 100 | — |  | 0 | — | 2300 | 2300 | 1.12 |
| MORPH | 93.34 | 90.2 | NIP | 6.66 | 9.8 | 1600 | 1800 | 1.12 |
| MORPH | 86.67 | 86.7 | NIP | 13.33 | 13.3 | 2300 | 2600 | 1.14 |
| MORPH | 80 | 78.7 | NIP | 20 | 21.3 | 2200 | 2500 | 1.13 |
| MORPH | 96.67 | 96.4 | PHE | 3.33 | 3.6 | 2500 | 2800 | 1.1 |
| MORPH | 93.34 | 89.3 | PHE | 6.66 | 10.7 | 1700 | 2000 | 1.16 |
| MORPH | 90 | 90 | PHE | 10 | 10 | 2700 | 3200 | 1.17 |
| MORPH | 96.67 | 95.6 | AMP | 3.33 | 4.4 | 2900 | 3300 | 1.14 |
| MORPH | 93.34 | 91.8 | AMP | 6.66 | 8.2 | 3000 | 3500 | 1.16 |
| MORPH | 90 | 90 | AMP | 10 | 10 | 3600 | 4200 | 1.17 |
| MORPH | 96.67 | n/a | TMA | 3.33 | n/a | n/a | n/a | n/a |
| MORPH | 93.34 | 78.2 | TMA | 6.66 | 21.8 | 3700 | 4400 | 1.2 |
| MORPH | 90 | 90 | TMA | 10 | 10 | 1700 | 1900 | 1.1 |
| MORPH | 96.67 | 94.5 | TBA | 3.33 | 5.5 | 2400 | 2900 | 1.2 |
| MORPH | 93.34 | 92.8 | TBA | 6.66 | 7.2 | 2700 | 3300 | 1.2 |
| MORPH | 90 | 90 | TBA | 10 | 10 | 2900 | 3300 | 1.14 |
| MORPH | 95 | 92.7 | TRI | 5 | 7.3 | 2200 | 2500 | 1.14 |
| MORPH | 90 | 90 | TRI | 10 | 10 | 3100 | 3900 | 1.25 |
| MORPH | 85 | 84.1 | TRI | 15 | 15.9 | 2900 | 3500 | 1.22 |
| HEAM | 100 | — |  | 0 | — | 4900 | 5500 | 1.13 |
| HEAM | 93.34 | 93 | NIP | 6.66 | 7 | 5300 | 6000 | 1.14 |
| HEAM | 86.67 | 86.7 | NIP | 13.33 | 13.3 | 5600 | 6300 | 1.13 |
| HEAM | 80 | 79.2 | NIP | 20 | 20.8 | 5400 | 6000 | 1.12 |
| HEAM | 96.67 | 96.7 | PHE | 3.33 | 3.3 | 5800 | 6600 | 1.14 |
| HEAM | 93.34 | 93 | PHE | 6.66 | 7 | 5500 | 6300 | 1.13 |
| HEAM | 90 | 89.4 | PHE | 10 | 10.6 | 5200 | 6100 | 1.16 |
| HEAM | 96.67 | 96.2 | AMP | 3.33 | 3.8 | 4900 | 5600 | 1.15 |
| HEAM | 93.34 | 93.3 | AMP | 6.66 | 6.7 | 5800 | 6600 | 1.12 |
| HEAM | 90 | 87.8 | AMP | 10 | 12.2 | 4800 | 5500 | 1.14 |
| HEAM | 96.67 | 96.2 | TMA | 3.33 | 3.8 | 5100 | 5900 | 1.15 |
| HEAM | 93.34 | 93.3 | TMA | 6.66 | 6.7 | 5500 | 6500 | 1.17 |
| HEAM | 90 | 86 | TMA | 10 | 14 | 3900 | 4500 | 1.15 |
| HEAM | 96.67 | 96.6 | TBA | 3.33 | 3.4 | 5300 | 6000 | 1.13 |
| HEAM | 93.34 | 93.3 | TBA | 6.66 | 6.7 | 5300 | 6100 | 1.14 |
| HEAM | 90 | 88.6 | TBA | 10 | 11.4 | 4700 | 5300 | 1.13 |
| HEAM | 95 | 95 | TRI | 5 | 5 | 5100 | 6000 | 1.17 |
| HEAM | 90 | 89.2 | TRI | 10 | 10.8 | 4600 | 5400 | 1.18 |
| HEAM | 85 | 84.3 | TRI | 15 | 15.7 | 4600 | 5400 | 1.18 |
| MPAM | 100 | — |  | 0 | — | 3600 | 4000 | 1.13 |

TABLE 2-continued

SEC and MALS characterization and analysis of polymers synthesized in initial AC/DC library

| Carrier | wt. % (Target) | wt. % (Experimental) | Dopant | wt. % (Target) | wt. % (Experimental) | $M_n^a$ (Da) | $M_w^a$ (Da) | $Đ^a$ |
|---|---|---|---|---|---|---|---|---|
| MPAM | 93.34 | 93.3 | NIP | 6.66 | 6.7 | 4600 | 5100 | 1.12 |
| MPAM | 86.67 | 84.4 | NIP | 13.33 | 15.6 | 3800 | 4300 | 1.14 |
| MPAM | 80 | 72.5 | NIP | 20 | 27.5 | 3000 | 3300 | 1.12 |
| MPAM | 96.67 | 96.5 | PHE | 3.33 | 3.5 | 5000 | 5300 | 1.11 |
| MPAM | 93.34 | 93.3 | PHE | 6.66 | 6.7 | 5000 | 5700 | 1.14 |
| MPAM | 90 | 86.7 | PHE | 10 | 13.3 | 3900 | 4400 | 1.13 |
| MPAM | 96.67 | 96.3 | AMP | 3.33 | 3.7 | 4500 | 5100 | 1.14 |
| MPAM | 93.34 | 93.3 | AMP | 6.66 | 6.7 | 4900 | 5500 | 1.13 |
| MPAM | 90 | 87.9 | AMP | 10 | 12.1 | 4000 | 4500 | 1.13 |
| MPAM | 96.67 | 96.7 | TMA | 3.33 | 3.3 | 4600 | 5200 | 1.14 |
| MPAM | 93.34 | 91.9 | TMA | 6.66 | 8.1 | 3600 | 4100 | 1.13 |
| MPAM | 90 | 89.8 | TMA | 10 | 10.2 | 4400 | 5000 | 1.13 |
| MPAM | 96.67 | 96.6 | TBA | 3.33 | 3.4 | 4500 | 5100 | 1.13 |
| MPAM | 93.34 | 93.3 | TBA | 6.66 | 6.7 | 4800 | 5400 | 1.13 |
| MPAM | 90 | 89.2 | TBA | 10 | 10.8 | 4200 | 4700 | 1.12 |
| MPAM | 95 | 93.9 | TRI | 5 | 6.1 | 4900 | 5700 | 1.17 |
| MPAM | 90 | 90 | TRI | 10 | 10 | 5800 | 6800 | 1.17 |
| MPAM | 85 | 80.3 | TRI | 15 | 19.7 | 4300 | 4800 | 1.13 |
| AM | 100 | — | | 0 | — | 4800 | 5100 | 1.06 |
| AM | 93.34 | — | NIP | 6.66 | — | 4400 | 4600 | 1.05 |
| AM | 86.67 | — | NIP | 13.33 | — | 4500 | 4800 | 1.05 |
| AM | 80 | — | NIP | 20 | — | 4800 | 5100 | 1.07 |
| AM | 96.67 | — | PHE | 3.33 | — | 4300 | 4500 | 1.04 |
| AM | 93.34 | — | PHE | 6.66 | — | 4600 | 4700 | 1.04 |
| AM | 90 | — | PHE | 10 | — | 4500 | 4600 | 1.03 |
| AM | 96.67 | — | AMP | 3.33 | — | 3700 | 4000 | 1.09 |
| AM | 93.34 | — | AMP | 6.66 | — | 4000 | 4300 | 1.07 |
| AM | 90 | — | AMP | 10 | — | 4100 | 4300 | 1.05 |
| AM | 96.67 | — | TMA | 3.33 | — | 4300 | 4500 | 1.04 |
| AM | 93.34 | — | TMA | 6.66 | — | did | not | elute |
| AM | 90 | — | TMA | 10 | — | 4700 | 4900 | 1.06 |
| AM | 96.67 | — | TBA | 3.33 | — | 4300 | 4400 | 1.04 |
| AM | 93.34 | — | TBA | 6.66 | — | 4100 | 4300 | 1.03 |
| AM | 90 | — | TBA | 10 | — | 4400 | 4600 | 1.05 |
| AM | 95 | — | TRI | 5 | — | 4300 | 4500 | 1.05 |
| AM | 90 | — | TRI | 10 | — | 4600 | 4800 | 1.04 |
| AM | 85 | — | TRI | 15 | — | 4600 | 4900 | 1.06 |

$^a M_n$ (number average molecular weight), $M_w$ (weight average molecular weight), and $Đ$ (dispersity) determined via DMF size exclusion chromatography calibrated using polyethylene glycol standards for HEAM, MPAM, MORPH, and DMA. $M_n$ and $M_w$ determined using aqueous SEC-MALS for AM using a dn/dc value of 0.185.
$^b$Experimental wt. % values determined with SEC using equation S1.

The library was generated through parallel synthesis with a Chemspeed Swing XL Auto Synthesizer, a liquid handling robot in an inert environment. RAFT polymerization was implemented because it affords precise copolymerization stoichiometry, low dispersity, and controlled molecular weights for a wide scope of monomers. Polyacrylamide derivatives were used for both the carrier and dopant monomers due to the scope and availability of commercially available water soluble monomers (carriers) and functional monomers (dopants) and polymeric stability. While monomeric acrylamide derivatives often exhibit acute toxicities, polyacrylamide derivatives, when properly purified from their monomeric precursors, demonstrate a high degree of biocompatibility. Moreover, the reactivity ratios between the various acrylamide monomers are close to 1, yielding copolymers with little to no dopant gradient composition. Carrier monomers included acrylamide (AM), hydroxyethylacrylamide (HEAM), dimethylacrylamide (DMA), acryloylmorpholine (MORPH), and methoxypropylacrylamide (MPAM) as they are nonionic and water soluble (ordered in increasing hydrophobicity). Dopant monomers included tris(hydroxymethyl)methylacrylamide (TRI), acrylamidomethylpropane sulfonic acid (AMP), acrylamidopropyltrimethylammonium chloride (TMA), n-isopropylacrylamide (NIP) tertbutylacrylamide (TBA), and phenylacrylamide (PHE). These functional dopants could be further classified into hydrogen bonding (TRI), ionic (AMP, TMA), hydrophobic (NIP, TBA), and aromatic (PHE) monomers based on their chemical composition.

Figure 4:
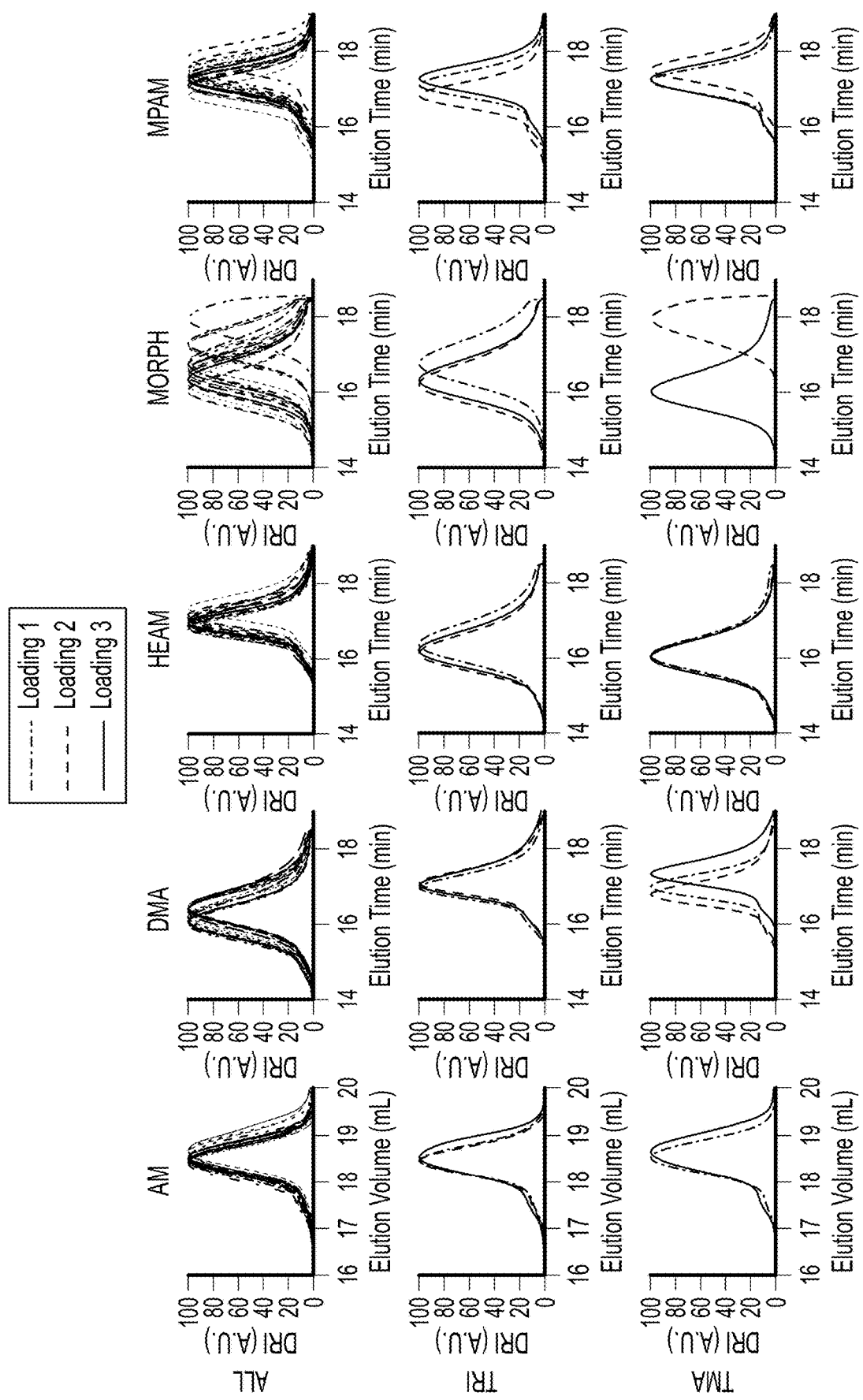
FIG. 4 illustrates SEC traces of polymers from the initial copolymer library synthesis. From left to right, the carrier monomers are: acrylamide (AM), N,N-dimethylacrylamide (DMA), N-hydroxyethyl acrylamide (HEAM), 4-acryloylmorpholine (MORPH), and N-(3-methoxypropyl)acrylamide (MPAM). AM-based copolymers were measured on an aqueous SEC, whereas the others were measured on a DMF SEC. The top row depicts overlays of all synthesized copolymers. Each subsequent row shows the functional dopant loadings for the copolymers. The three copolymerizations for each carrier-dopant pair are low loading, medium loading, and high loading. The functional dopants (abbreviation; low, medium, and high loading) are as follows: N-[tris(hydroxymethyl)methyl]acrylamide (TRI; 5, 10, 15 wt. %), (3-acrylamidopropyl)trimethylammonium chloride solution (TMA; 3.3, 6.7, 10 wt. %), 2-acrylamido-2-methylpropane sulfonic acid (AMP; 3.3, 6.7, 10 wt. %), N-isopropylacrylamide (NIP; 6.7, 13.3, 20 wt. %), N-tert-butylacrylamide (TBA; 3.3, 6.7, 10 wt. %), and N-phenylacrylamide (PHE; 3.3, 6.7, 10 wt. %).
Figure 4:
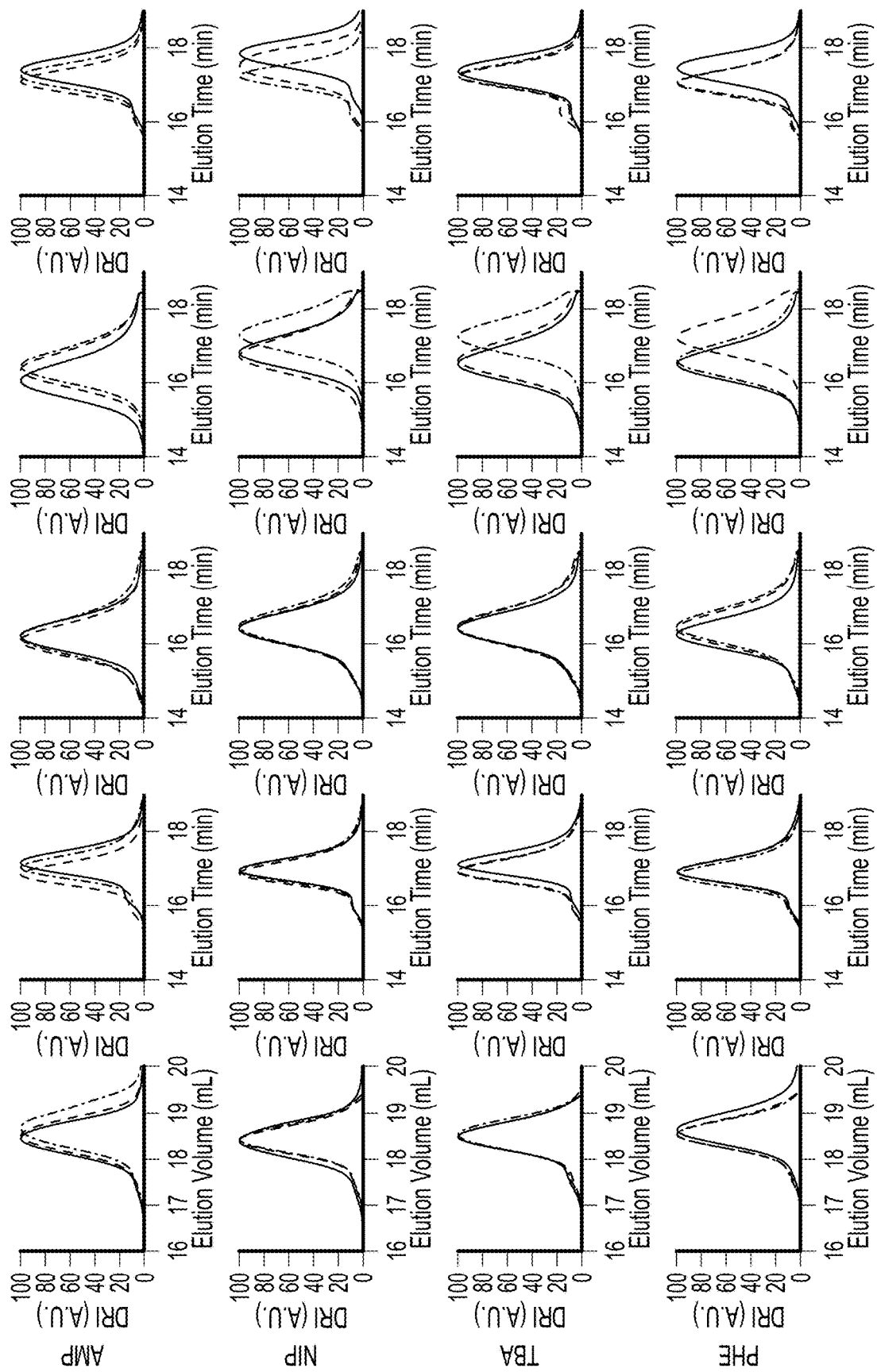

A library of 90 AC/DC excipients were synthesized through the combinatorial copolymerization of carrier and dopant monomers at each of three different compositions for a given carrier-dopant pair. NIP was copolymerized at either 6.7, 13.3, or 20 wt. %. TRI was copolymerized at either 5, 10, or 15 wt. %. AMP, TMA, TBA, and PHE were copolymerized at either 3.3, 6.7, or 10 wt. %. These values were selected to maximize dopant loading while yielding functional copolymers with lower critical solution temperature (LCST) values above 37° C. to ensure they would remain soluble at all relevant temperatures. Polymers were characterized by NMR and SEC (Table 2, FIG. 3 and FIG. 4). While RAFT polymerization affords many synthetic advantages, it yields polymers with a reactive trithiocarbonate Chain Transfer Agent (CTA) attached at the Z-terminus. Accordingly, the CTA moiety on the synthesized AC/DC excipients was removed prior to utilization of the copolymers in subsequent assays to ensure their inertness.

Example 2—Ultra-Fast Absorbing Insulin Lispro (UFAL) Formulation and In Vitro and In Vivo Evaluations Method for Determining Mammalian Cell Viability: NIH/3T3 mouse fibroblasts from ATCC were cultured in DMEM containing 10 wt. % FBS and 1 wt. % Penicillin-Streptomycin in a 37° C., 5% $CO_2$ incubator. 3T3s at passage 9 were seeded at 5000 cells per well in a 96 well plate and cultured for 24 h in 100 μL of media. The media was subsequently replaced with 100 μL of media containing MORPH-NIP$_{23\%}$ at various concentrations and incubated for 24 h. The polymer-containing media was then aspirated from each well. Each well was then washed with 100 μL of PBS and charged with both 100 μL of new media and 10 μL of WST reagent. After 3 hours of incubation in the WST solution, the absorbance was read using a plate reader (λ=450 nm). All experiments were conducted in triplicate. Cell viability was calculated using equation S2, where $A_{well}$, $A_{control}$, and $A_{WST}$ are the absorbance measurements for the cells cultured with polymer, the cells cultured without polymer, and WST in media.

$$\text{Viability} = \frac{A_{well} - A_{WST}}{A_{control} - A_{WST}} \quad (S2)$$

In vitro insulin cellular activity assay: C2C12 mouse muscle myoblasts (ATCC CRL-1772) were cultured to confirm insulin functional activity via the AKT phosphorylation pathway using AlphaLISA SureFire Ultra (Perkin-Elmer) kits for detection of phosphorylated AKT 1/2/3 (pS473) compared to total Akt1. Cells were confirmed to be free of *mycoplasma* contamination prior to use. Dulbecco's Modified Eagle's Medium (DMEM) with 4.5 g/L D-glucose, L-glutamine, and 110 mg/L sodium pyruvate (Gibco) was supplemented with 10% fetal bovine serum (FBS) and 5% penicillin-streptomycin to formulate complete culture media. Cells were seeded at a density of 25,000 cells/well in a volume of 200 μL/well in a 96-well tissue culture plate and grown for 24 hours. Prior to insulin stimulation, the cells were washed twice with 200 μL of unsupplemented DMEM and starved in 100 μL of unsupplemented DMEM overnight. The media was then removed and the cells were stimulated with 100 μL of insulin (i) HUMALOG®, (ii) UFAL, (iii) Aged HUMALOG® (12 h shaking at 37° C.), (iv) Aged UFAL (12 h shaking at 37° C.) diluted in unsupplemented DMEM to the desired concentration, for 30 min while incubating at 37° C. Cells were washed twice with 100 μL of cold 1× Tris-buffered saline before adding 100 μL of lysis buffer to each well and shaking for at least 10 minutes at room temperature to fully lyse cells. 30 μL of lysate was transferred to a 96-well white half-area plate for each assay. Assays were completed according to the manufacturer's protocol. Plates were incubated at room temperature and read 18-20 hours after the addition of the final assay reagents using a Tecan Infinite M1000 PRO plate reader. Results were plotted as a ratio of [pAKT]/[AKT] for each sample (n=3 cellular replicates) and an $EC_{50}$ regression [log(agonist) vs. response (three parameters)] was plotted using GraphPad Prism 8.

In vitro insulin stability: Methods for aggregation assays for recombinant human insulin were adapted from Webber et al. (*Proc. Natl. Acad. Sci. U.S.A* 113, 14189-14194 (2016)). Briefly, formulation samples (3.4 mg/mL) were plated at 150 μL per well (n=3/group) in a clear 96-well plate and sealed with optically clear and thermally stable seal (VWR). The plate was immediately placed into a plate reader and incubated with continuous shaking at 37° C. Absorbance readings were taken every 10 minutes at 540 nm for 100 h (BioTek Syner-gyH1 microplate reader). The aggregation of insulin leads to light scattering, which results in an increase in the measured absorbance. The time-to-aggregation ($t_A$) was defined as the time at which a greater than 10% increase in absorbance from the absorbance at time zero was observed. After 100 h, the plate was removed from the plate reader and transferred to an incubator shaker plate where it was subjected to continued stressed aging. Absorbance readings were taken periodically for up to 30 days.

For the initial high-throughput stability screen, recombinant human insulin (Gibco) was formulated in phosphate buffered saline (0.9 wt. % NaCl) and AC/DC excipients were added at concentrations of 1 mg/mL or 10 mg/mL to the recombinant insulin formulation for a final insulin concentration of 3.4 mg/mL. Each plate contained a recombinant insulin control with no polymer added.

For the secondary stability screen with UFAL formulations, control groups included: (i) commercial HUMALOG® (Eli Lilly), (ii) zinc-free lispro comprising phosphate buffer, glycerol (2.6 wt. %), and phenoxyethanol (0.85 wt. %). Zinc (II) was removed from commercial insulin formulations through competitive binding by addition of ethylenediaminetetraacetic acid (EDTA), which exhibits a dissociation binding constant approaching attomolar concentrations ($K_D \sim 10^{-18}$ M). EDTA was added to formulations (1 eq. with respect to zinc) to sequester zinc from the formulation. Following zinc sequestration, PD MidiTrap G-10 gravity columns (GEHealthcare) were used to remove the zinc/EDTA complexes and other formulation excipients. Lispro was concentrated using Amino Ultra 3K centrifugal units (Millipore), and then reformulated at 100 U/mL with phosphate buffer (10 mM), glycerol (2.6 wt. %), phenoxyethanol (0.85 wt. %), and AC/DC excipient (0.01 wt. %).

NMR DOSY: $^1$H 2D DOSY spectra were recorded at an insulin lispro concentration of 3.4 mg/mL with 40 wt. % D2O for UFAL formulation comprising phosphate buffer, glycerol (2.6 wt. %), phenoxyethanol (0.85 wt. %) and MORPH-NIP$_{23\%}$ copolymer (0.1 wt. %). A Varian Inova 600 MHz NMR instrument was used to acquire the data. Magnetic field strengths ranging from 2 to 57 G cm$^{-1}$. The DOSY time and gradient pulse were set at 132 ms (Δ) and 3 ms (δ) respectively. All NMR data were processed using MestReNova 11.0.4 software.

Streptozotocin-induced model of diabetes in rats: Male Sprague Dawley rats (Charles River) were used for experiments. Animal studies were performed in accordance with the guidelines for the care and use of laboratory animals; all protocols were approved by the Stanford Institutional Animal Care and Use Committee. The protocol used for STZ induction adapted from the protocol by Wu and Huan (*Curr. Protoc. Pharmacol.* (2008) 5:Unit 5.47). Briefly, male Sprague Dawley rats 160-230 g (8-10 weeks) were weighed and fasted 6-8 hours prior to treatment with STZ. STZ was diluted to 10 mg/mL in the sodium citrate buffer immediately before injection. STZ solution was injected intraperitoneally at 65 mg/kg into each rat. Rats were provided with water containing 10% sucrose for 24 hours after injection with STZ. Rat blood glucose levels were tested for hyperglycemia daily after the STZ treatment via a tail vein blood collection using a handheld Bayer Contour Next glucose monitor (Bayer). Diabetes was defined as having 3 consecutive blood glucose measurements >400 mg/dL in non-fasted rats.

In vivo pharmacodynamics in diabetic rats: Diabetic rats were fasted for 4-6 hours. Rats were injected subcutaneously with (i) HUMALOG®, (ii) UFAL, (iii) Aged HUMALOG® (12 h shaking at 37° C.), (iv) Aged UFAL (12 h shaking at 37° C.) at a dose of 1.5 U/kg. To prepare aged samples, 150 uL of each formulation was placed in a 96-well plate under constant agitation. 16 rats were used for this study and they were randomly assigned to two groups (i) HUMALOG® and (ii) UFAL. Within these groups each rat received one dose of the fresh and aged version of the formulation on separate experimental days. The order that the formulations were given was randomized. Insulins were diluted 10-fold in phosphate buffered saline before injection to allow for accurate dosing of small volumes. Before injection, baseline blood glucose was measured After injection, blood was sampled every 30 minutes for 4 hours. Blood glucose was measured using a handheld blood glucose monitor (Bayer Contour Next).

Biocompatibility in diabetic rats: Diabetic rats were treated with either (i) HUMALOG® (n=5) or (ii) UFAL (n=5) for 7 consecutive days. Formulations were administered subcutaneously at a dose of 1.5 U/kg. Blood was collected for blood chemistry tests on day 0 and on Day 7. Chemistry analysis was performed on the Siemens Dimension Xpand analyzer. A medical technologist performed all testing, including dilutions and repeat tests as indicated, and reviewed all data.

In Vivo Pharmacokinetics and Pharmacokinetics Studies of Ultra-Fast Absorbing Insulin Lispro (UFAL) in Swine Model:

Study Design: The pharmacokinetics of an insulin lispro formulation, ultra-fast absorbing insulin lispro (UFAL), were compared to a commercial insulin lispro formulation (HUMALOG®). Blood glucose and plasma lispro concentrations were measured after subcutaneous administration of either (i) HUMALOG® or (ii) UFAL by using a handheld blood glucose monitor or ELISA on collected blood samples. Randomization: 5 pigs were used for this study and each pig received each formulation once. The order in which the formulations were given in was randomized. Blinding: For analysis of pharmacokinetic parameters (t50% up, time to peak, t50% down) pharmacokinetic curves were coded, and were analyzed by a blinded researcher. Replication. 5 pigs were used in this study and each pig acted as its own control receiving each formulation (HUMALOG® and UFAL) once.

Streptozotocin induced diabetes in swine: Five female Yorkshire pigs (Pork Power) were used for our animal studies, which were performed in accordance with the Guidelines for the Care and Use of Laboratory Animals and the Animal Welfare Act Regulations. All protocols were approved by the Stanford Institutional Animal Care and Use Committee. Type-1-like diabetes was induced in pigs (25-30 kg) using streptozotocin (STZ) (MedChemExpress). STZ was infused intravenously at a dose of 125 mg/kg and animals were monitored for 24 hours. Food and administration of 5% dextrose solution was given as needed to prevent hypoglycemia. Diabetes was defined as fasting blood glucose greater than 300 mg/dL.

In vivo pharmacokinetics and pharmacodynamics in diabetic swine: Five diabetic pigs were fasted for 4-6 hours. Pigs were injected subcutaneously with a 2-4 U dose of the following formulations: (i) HUMALOG® (100 U/mL, Eli Lilly) or (ii) ultra-fast absorbing insulin lispro (UFAL) (100 U/mL Zn-free lispro, 2.6 wt. % glycerol, 0.85 wt. % phenoxyethanol, 0.01 wt. % MORPH-NIP$_{23\%}$). Doses were determined based on individual pig insulin sensitivity values with a target of a decrease in blood glucose of approximately 200 mg/dL. Individual pigs received the same dose for each treatment group. Pigs received each formulation once on separate days and the order of the treatment groups were randomized. Before injection, baseline blood was sampled from an intravenous catheter line and measured using a handheld glucose monitor (Bayer Contour Next). After injection, blood was sampled from the intravenous catheter line every 5 minutes for the first 60 minutes, then every 30 minutes up to 4 hours. Blood was collected in K$_2$EDTA plasma tubes (Greiner-BioOne) for analysis with ELISA. Plasma lispro concentrations were quantified using an Insulin Lispro ELISA kit (Mercodia).

Pharmacokinetic Modelling: The pharmacokinetic model used in this analysis was derived from literature reports. Insulin concentrations for injection ($I_{inj}$), equilibrium in the interstitium ($I_{eq}$), and the plasma ($I_p$) were numerically solved using a system of differential equations, outlined below, as a function of time using the SciPy (version 1.2.1) odeint function in Python (version 3.6.8).

$$\frac{d[I]_{inj}}{dt} = -k_1 * I_{inj} \quad (1)$$

$$\frac{d[I]_{eq}}{dt} = k_1 * I_{inj} - k_2 * I_{eq} \quad (2)$$

$$\frac{d[I]_p}{dt} = k_2 * I_{eq} - k_3 * I_p \quad (3)$$

Concentrations were initialized such that at t=0 all insulin was present in $I_{inj}$. Kinetic rate constants were fit for the normalized pig pharmacokinetic curves by minimizing the sum of squared errors (SSE) between the generated, normalized insulin plasma concentrations derived from the model at the experimental time points from 0 to 90 minutes and the normalized pig plasma insulin concentrations for UFAL and HUMALOG®. We assume that $k_2$ and $k_3$ are species dependent, while $k_1$ is both species and formulation dependent. While minimizing the SSE, we observed that there was no upward bound for $k_{1,UFAL,Pig}$; such that higher values of $k_{1,UFAL,Pig}$ resulted in increasingly marginally smaller SSEs for a given $k_2$ and $k_3$. Accordingly, $k_{1,UFAL,Pig}$ was then set at 100,000 min$^{-1}$. The SSE was minimized by first employing a grid search using SciPy's optimize brute function and subsequently refining the rate constants by employing SciPy's optimize minimize function using the L-BFGS-B method. To solve for $k_{1,UFAL,Human}$, we assume the following relationship:

$$\frac{k_{1,UFAL,Pig}}{k_{1,humalog,Pig}} = \frac{k_{1,UFAL,Human}}{k_{1,Humalog,Human}}$$

Values for $k_{1, HUMALOG®,Human}$, $k_{2,Human}$, and $k_{3,Human}$ were used as reported in the literature.

Statistical Analysis: All results are expressed as a mean±standard deviation unless specified otherwise. FIGS. 10D-10F are shown as mean±standard error of the mean. All statistical analyses were performed as general linear models (GLMs) in JMP Pro Version 14. Comparisons between formulations (FIGS. 10D-I and K-M) were conducted using the restricted maximum likelihood (REML) repeated measures mixed model. Suitable transformations applied as needed to meet the assumptions of the methods (i.e. homogeneity of variance, normality of error, and linearity). Time to 50% of peak up, time to peak, and time to 50% peak down were log transformed for analyses to correct for non-homogeneity of variance. Pig was included as a variable in the model as a random effect blocking (control) factor to account for variation in individual pig response. Statistical significance was considered as p<0.05. For FIGS. 10D-I, post-hoc Bonferroni correction was applied to account for multiple comparisons and significance was adjusted to alpha=0.008.

Results

Figure 5A:
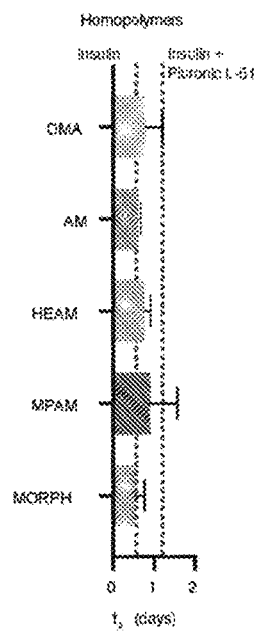
FIGS. 5A-5G illustrate a recombinant insulin stability screen with a polymer excipient library. Time to aggregation of recombinant insulin (100 U/mL) formulated with carrier homopolymers (0.1 wt. %) or a Pluronic L-61 control (0.1 wt. %), which has similar composition to Poloxamer 171 used in commercial insulin formulations is shown in FIG. 5A. Time to aggregation of recombinant insulin (100 U/mL) formulated with carrier-dopant polymers (0.1 wt. %) with DMA (FIG. 5B), AM (FIG. 5C), HEAM (FIG. 5D), MPAM (FIG. 5E), and MORPH (FIG. 5F) carriers is also shown. Dopants and target weight percentages are listed on the x-axis.
Figure 5B:
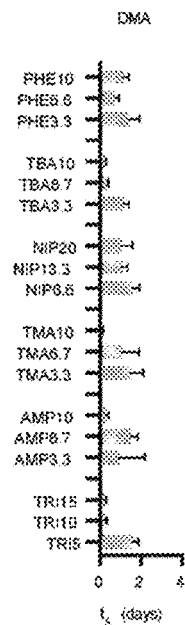
Figure 5C:
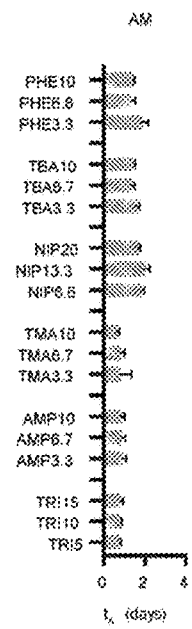
Figure 5D:
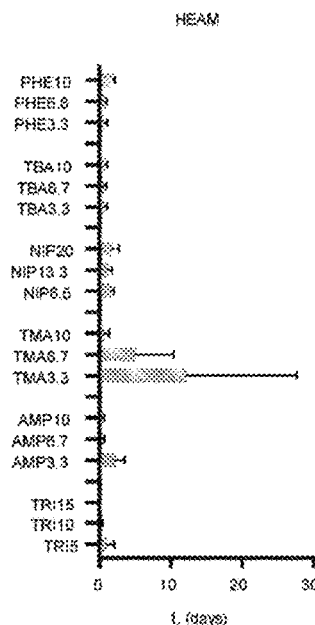
Figure 5E:
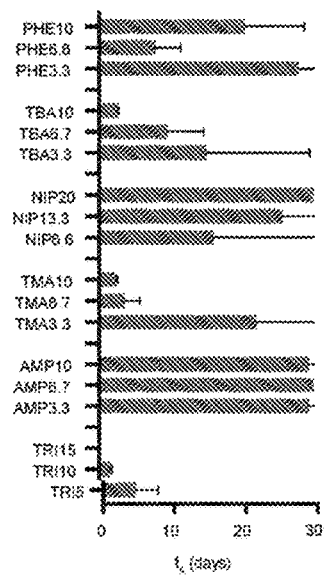
Figure 5F:
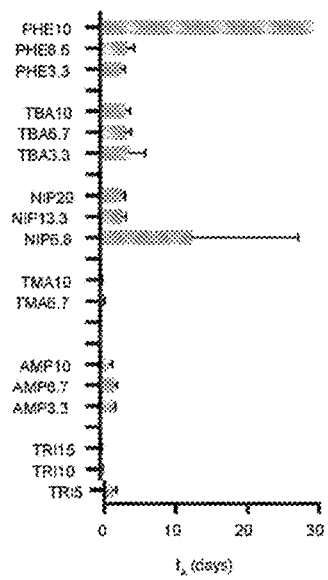
Figure 5G:
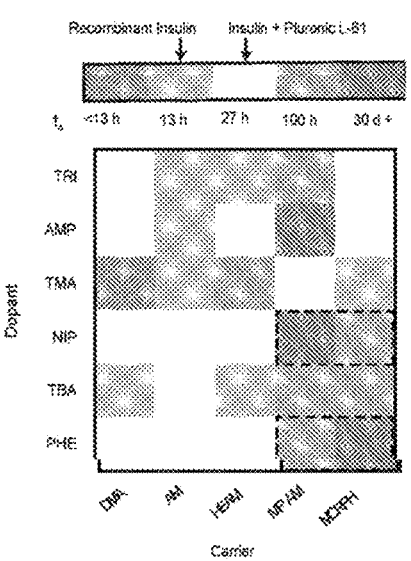

High-throughput screen for insulin stabilizing excipient: The AC/DC excipients prepared as described under Example 1 were evaluated for their potential as a stabilizing excipient for insulin using an absorbance-based stressed aging assay, where destabilized insulin aggregates scatter light and increase the absorbance of the solution. Time to aggregation in these assays is defined as a 10% increase in absorbance of the formulation. Recombinant insulin was formulated in PBS at standard formulation concentrations (100 U/mL; 3.4 mg/mL) and tested with (i) no polymer excipients, (ii) pluronic L-61 (the most similar commercially available polymer both chemically and physically to Poloxamer 171 used in INSUMAN® U400), (iii) 1 mg/mL AC/DC excipients, or (iv) 10 mg/mL AC/DC excipients. Recombinant insulin controls, with no polymer excipient, aggregated in 13±8 hours in this assay. Formulation with pluronic L-61 (1 mg/mL) prolonged aggregation to 27±2 hours, demonstrating efficacy of the commercial polymer as an excipient to prevent insulin aggregation. The use of water-soluble carrier homopolymer excipients (1 mg/mL) had no impact on insulin stability (FIG. 5A), demonstrating that free hydrophilic polymers are not sufficient to prevent insulin aggregation. This finding is supported by previous work showing that other hydrophilic polymers such as poly(ethylene glycol) (PEG) do not improve insulin stability.

Insulin stability when formulated with AC/DC excipients was highly chemistry dependent. Each AC/DC excipient was formulated with insulin and stability was tested for up to one month (FIGS. 5B-G and Table 3). Formulations comprising AC/DC excipients with MPAM and MORPH carrier chemistries demonstrated the overall highest improvement of insulin stabilization, especially when combined with NIP, TBA and PHE dopants. While many carrier-dopant combinations demonstrated long-term stability at 1 wt. % formulation concentrations, we sought to engineer copolymers capable of stabilizing insulin at minimal concentrations in formulation. AC/DC excipients comprising MPAM-PHE, MPAM-TBA, MPAM-TRI, and MORPH-TBA (0.1 wt. %) stabilized insulin for over 100 hours of stressed aging. These formulations are therefore 7-fold more stable than recombinant insulin alone and 3-fold more stable than those containing pluronic L-61. Moreover, AC/DC excipients comprising MPAM-NIP, MPAM-AMP, and MORPH-PHE (0.1 wt. %) stabilized insulin for 30 days of stressed aging, at which point the assay was terminated. These formulations are 50-fold more stable than insulin alone, and 24-fold more stable than formulations containing pluronic L-61. These select carriers and dopants are the most hydrophobic amongst the monomers screened, suggesting that amphiphilic water-soluble copolymers are most effective at preventing insulin aggregation.

TABLE 3

Days until aggregation for recombinant insulin formulated with AC/DC excipients at two excipient concentrations (1 mg/mL and 10 mg/mL)

| Excipient Concentration | | 1 mg/mL | | | 10 mg/mL | |
| --- | --- | --- | --- | --- | --- | --- |
| Dopant Loading | Low | Medium | High | Low | Medium | High |
| Carrier | Dopant | | | | | |
| DMA | NIP | 1.61 | 1.09 | 1.05 | 1.21 | 0.93 | 2.13 |
| DMA | PHE | 1.41 | 0.72 | 1.13 | 1.86 | 2.41 | 3.91 |
| DMA | AMP | 0.9 | 1.49 | 0.29 | 1.42 | n.t. | 0.79 |
| DMA | TMA | 1.46 | 1.07 | 0.15 | 1.7 | n.t. | 0.52 |
| DMA | TBA | 1.13 | 0.36 | 0.29 | 1.5 | 1.66 | 1.29 |
| DMA | TRI | 1.58 | 0.25 | 0.25 | 1.91 | 1.46 | 1.09 |
| MORPH | NIP | 4.39 | 3.25 | 3.53 | 4.79 | 7.14 | 3.4 |
| MORPH | PHE | 3.08 | 3.85 | 30 | 4.82 | 17.55 | 30 |
| MORPH | AMP | 2.09 | 2.03 | 1.33 | 5.15 | 2.27 | 1.59 |
| MORPH | TMA | n.t. | 0.58 | 0.37 | n.t. | 0.6 | 0.71 |
| MORPH | TBA | 4.26 | 3.62 | 3.63 | 21.58 | 9.25 | 14.91 |
| MORPH | TRI | 1.29 | 0.38 | 0.22 | n.t. | n.t. | n.t. |
| HEAM | NIP | 1.7 | 1.19 | 1.79 | 1.82 | 3.26 | 2.59 |
| HEAM | PHE | 0.59 | 0.87 | 1.97 | 1.87 | 11.87 | 30 |
| HEAM | AMP | 2.22 | 0.47 | 0.4 | 4.8 | 2.01 | 2.72 |
| HEAM | TMA | 12.25 | 4.99 | 0.68 | 3.78 | 4.01 | 10.75 |
| HEAM | TBA | 0.7 | 0.56 | 0.87 | 1.96 | 28 | 23.62 |
| HEAM | TRI | 1.07 | 0.37 | 0.17 | 1.34 | 22.68 | 1.34 |
| MPAM | NIP | 17.98 | 25.94 | 30 | 30 | 10.93 | 2.39 |
| MPAM | PHE | 27.91 | 7.89 | 20.37 | 11.72 | 3.61 | 30 |
| MPAM | AMP | 29.32 | 30 | 29.32 | 30 | 29.32 | 28.64 |
| MPAM | TMA | 22.01 | 3.51 | 2.36 | 21.33 | 2.35 | 4.06 |
| MPAM | TBA | 15.04 | 9.55 | 2.63 | 18.26 | 6.35 | 18.25 |
| MPAM | TRI | 4.56 | 1.55 | 0.08 | n.t. | n.t. | n.t. |
| AM | NIP | 1.81 | 1.99 | 1.7 | 1.74 | 1.96 | 1.76 |
| AM | PHE | 1.87 | 1.34 | 1.43 | 2.23 | 3.57 | 2.24 |
| AM | AMP | 0.93 | 0.89 | 0.87 | 1.74 | 3.5 | 1.76 |
| AM | TMA | 0.85 | 0.8 | 0.63 | 1.45 | 2.32 | 4.43 |
| AM | TBA | 1.63 | 1.38 | 1.49 | 5.9 | 3.96 | 2.49 |
| AM | TRI | 0.78 | 0.85 | 0.81 | 1.63 | 3.91 | 4.06 | n.t. indicates not tested.

Figure 6:
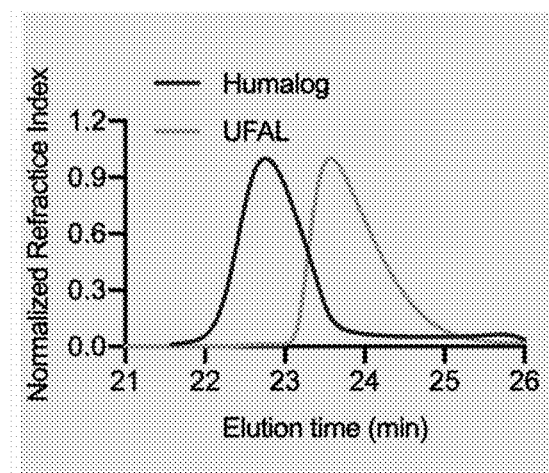
FIG. 6 illustrates aqueous SEC elution profiles for commercial HUMALOG® and UFAL formulations. These traces illustrate the primarily monomeric insulin association state of UFAL by the longer elution time correlating with lower effective molecular weight.
Figure 7A:
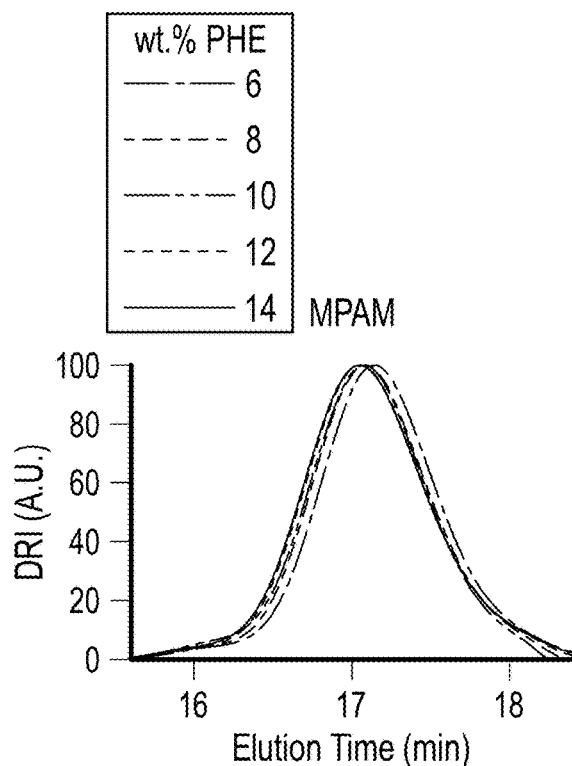
FIGS. 7A-7D illustrate SEC traces of copolymers from the second screen targeting DP 50.
Figure 7C:
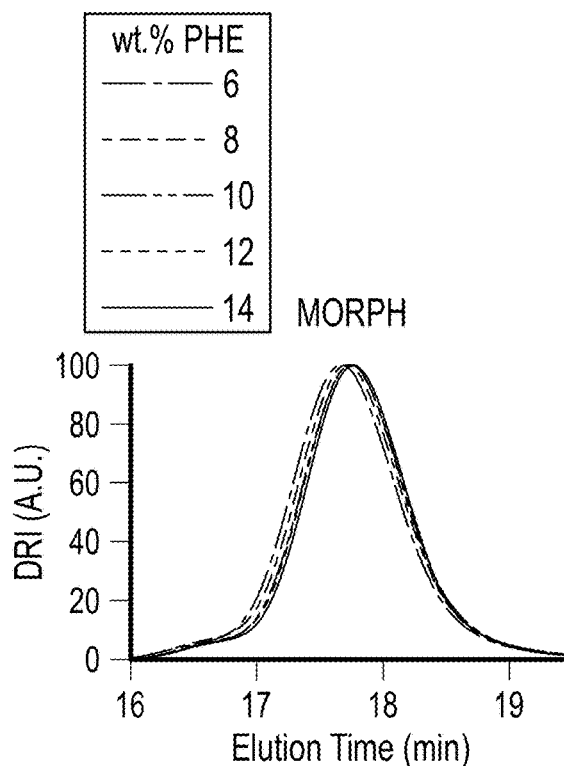
Figure 7B:
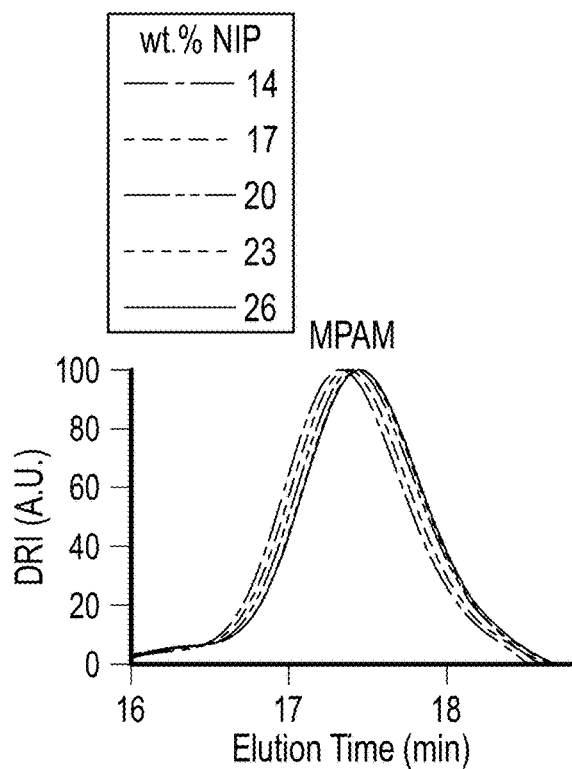
Figure 7D:
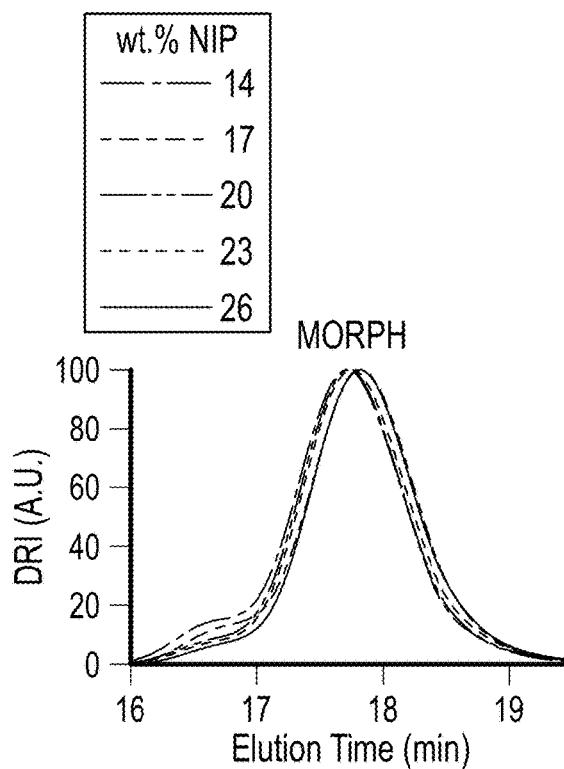

Stabilization of monomeric insulin with refined screen: Based on the initial recombinant insulin stability screen, copolymers comprising MPAM or MORPH carriers with NIP or PHE dopants demonstrated the most promise as candidates for stabilizing monomeric insulin. Previous work by our group demonstrated that the equilibrium between insulin association states can be shifted by altering formulation excipients, where a formulation that is approximately 70% monomers can be achieved with formulation of zinc-free lispro with glycerol and phenoxyethanol. This formulation favors the insulin monomer and completely dissociates the insulin hexamer. Representative SEC traces of predominantly hexameric HUMALOG® and predominantly monomeric zinc free UFAL demonstrate the association states of insulin in formulation (FIG. 6). However, insulin monomers are unstable in formulation and require additional stabilizing excipients to be viable for translation. Further, it will likely be prudent to use the lowest concentration of copolymer excipient possible to reduce chronic exposure to the excipient with frequent insulin use typical of diabetes management.

Figure 9A:
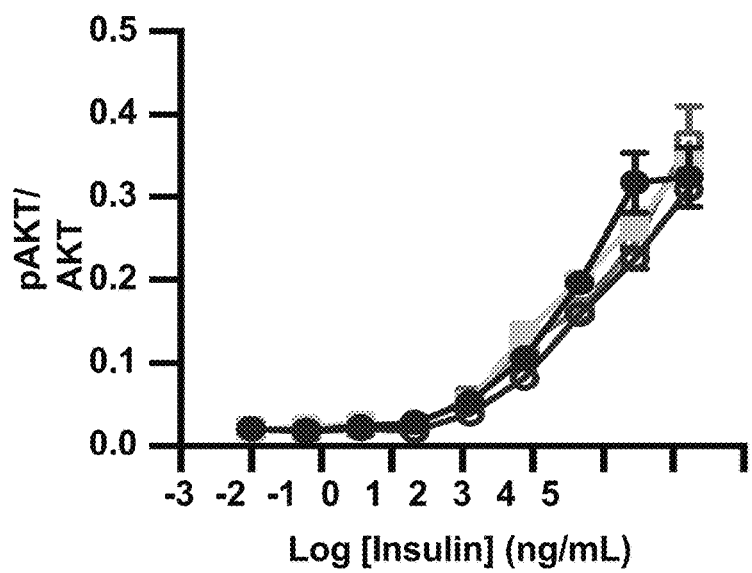
FIGS. 9A-9B illustrate in vitro and in vivo formulation bioactivity of HUMALOG®, UFAL, aged HUMALOG® (12 h shaking at 37° C.), and aged UFAL (12 h shaking at 37° C.).
Figure 9B:
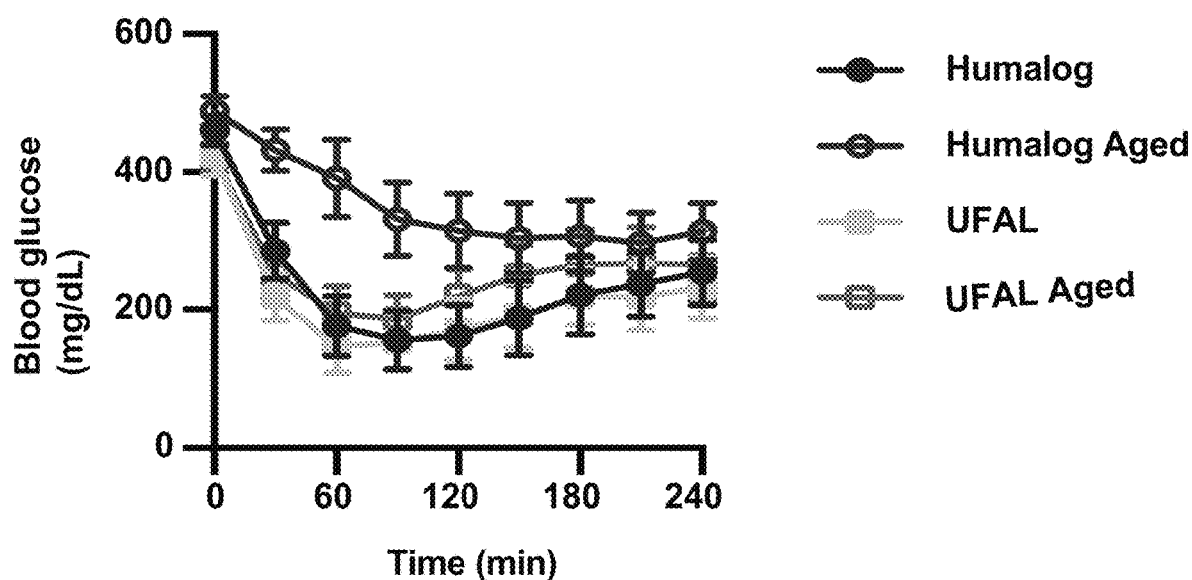

To address this need, a second library of AC/DC excipients was synthesized to evaluate additional carrier-dopant ratios with our top performing candidate monomers: (i) MPAM and MORPH as carriers, and (ii) NIP and PHE as dopants. Standard synthesis practices were implemented to generate this secondary library, which consisted of copolymers at DP 50 with MORPH or MPAM as carriers and either (i) NIP loaded at 14, 17, 20, 23, or 26 wt. %, or (ii) PHE loaded at 6, 8, 10, 12, or 14 wt. %, respectively, via SEC and $^1$H NMR spectroscopy (FIG. 7, Table 4).

assay as the initial screen (Table 5 in Supplemental Attachment A). HUMALOG®, the commercial formulation of insulin lispro, aggregated under these conditions within 6 hours. UFAL without AC/DC excipients aggregated in 1.3±0.3 hours, demonstrating the severe instability of the insulin monomer in solution. All UFAL formulations stabilized with MORPH-PHE or MPAM-PHE AC/DC excipients exhibited stabilities to stressed aging at least equivalent to commercial HUMALOG®. Copolymers comprising MPAM with 14 wt. % PHE (MPAM-PHE$_{14\%}$) and MORPH with 12 wt. % PHE (MORPH-PHE$_{12\%}$) were among the top candidates, extending UFAL formulation stability to 27±2 hours and 25±5 hours, respectively (FIGS. 8B-C). MPAM-NIP copolymers demonstrated limited efficacy in stabilizing the monomeric insulin; however, MORPH-NIP copolymers extended monomeric insulin stability compared to HUMALOG®. Indeed, copolymers comprising MORPH with 23 wt. % NIP (MORPH-NIP$_{23\%}$) extended UFAL formulation stability to over 25±1 hours. The top candidate AC/DC excipients after the second screen were MPAM-PHE$_{14\%}$, MORPH-PHE$_{12\%}$, and MORPH-NIP$_{23\%}$. While these copolymers demonstrated high efficacy, MPAM-PHE$_{14\%}$ and MORPH-PHE$_{12\%}$ also demonstrated decreased solubility and LCST-like phase separation behavior at physiological temperature when present at higher concentrations. Thus, MORPH-NIP$_{23\%}$ was chosen as the top candidate used to stabilize our UFAL formulation in subsequent in vivo studies. In vitro and in vivo bioactivity assays were used to corroborate the transmittance data and confirm UFAL integrity before and after aging. UFAL showed no loss in activity after 12 h of stressed aging in either the cellular assay for phosphorylation of Ser[473] on AKT or in diabetic rats lowering blood glucose levels (FIG. 9).

To verify that formulation with MORPH-NIP$_{23\%}$ did not alter the lispro association state equilibrium away from the

TABLE 4

SEC and $^1$H NMR analysis of polymers synthesized during the second screen targeting DP 50

| Carrier | wt. % (Target) | wt. % by NMR (Experimental) | Dopant | wt. % (Target) | wt. % by NMR (Experimental) | $M_n{}^a$ | $M_w{}^a$ | $Đ^a$ |
|---|---|---|---|---|---|---|---|---|
| MORPH | 94 | 93.68[b] | PHE | 6 | 6.32[b] | 2900 | 3400 | 1.17 |
| MORPH | 92 | 91.83[b] | PHE | 8 | 8.17[b] | 3100 | 3400 | 1.1 |
| MORPH | 90 | 90.12[b] | PHE | 10 | 9.88[b] | 3100 | 3400 | 1.1 |
| MORPH | 88 | 87.93[b] | PHE | 12 | 12.07[b] | 3100 | 3500 | 1.13 |
| MORPH | 86 | 85.51[b] | PHE | 14 | 14.49[b] | 3200 | 3600 | 1.13 |
| MORPH | 86 | 79.75[c] | NIP | 14 | 20.25[c] | 2900 | 3300 | 1.14 |
| MORPH | 83 | 77.9[c] | NIP | 17 | 22.10[c] | 3100 | 3500 | 1.13 |
| MORPH | 80 | 77.73[c] | NIP | 20 | 22.27[c] | 3100 | 3500 | 1.13 |
| MORPH | 77 | 74.46[c] | NIP | 23 | 25.54[c] | 3200 | 3800 | 1.19 |
| MORPH | 74 | 72.23[c] | NIP | 26 | 27.77[c] | 3000 | 3400 | 1.13 |
| MPAM | 94 | 93.54[d] | PHE | 6 | 6.46[d] | 4700 | 5200 | 1.11 |
| MPAM | 92 | 90.94[d] | PHE | 8 | 9.06[d] | 5000 | 5400 | 1.08 |
| MPAM | 90 | 89.05[d] | PHE | 10 | 10.95[d] | 5100 | 5600 | 1.1 |
| MPAM | 88 | 87.61[d] | PHE | 12 | 12.39[d] | 4900 | 5500 | 1.12 |
| MPAM | 86 | 86.15[d] | PHE | 14 | 13.85[d] | 5000 | 5500 | 1.1 |
| MPAM | 86 | 86.33[e] | NIP | 14 | 13.67[e] | 4700 | 5100 | 1.09 |
| MPAM | 83 | 82.35[e] | NIP | 17 | 17.65[e] | 4600 | 5000 | 1.09 |
| MPAM | 80 | 78.91[e] | NIP | 20 | 21.09[e] | 4500 | 4800 | 1.07 |
| MPAM | 77 | 77.95[e] | NIP | 23 | 22.05[e] | 4400 | 4800 | 1.09 |
| MPAM | 74 | 73.11[e] | NIP | 26 | 26.89[e] | 4400 | 4800 | 1.09 |

$^a$$M_n$ (number average molecular weight), $M_w$ (weight average molecular weight), and Đ (dispersity) determined using size exclusion chromatography calibrated using polyethylene glycol standards.
$^b$Weight percentages calculated from post precipitated NMR spectra of MORPH (δ = 3.3-3.7, 8 H) and PHE (δ = 7.6, 2 H).
$^c$Weight percentages difficult to determine due to overlapping spectra. Weight percentages estimated from post precipitated NMR spectra by measuring the more resolved left half of the peak of NIP (δ = 4.0, 0.5 H), doubling it, and subtracting it from the unresolved peaks of MORPH and NIP (δ = 3.2-4.2, 7 H (MORPH) 1 H (NIP)).
$^d$Weight percentages calculated from post precipitated NMR spectra of MPAM (δ = 3.1-3.5, 7 H) and PHE (δ = 7.6, 2 H).
$^e$Weight percentages calculated from post precipitated NMR spectra of MPAM (δ = 3.2, 3 H) and NIP (δ = 3.8, 1 H).

Using the AC/DC excipients synthesized in the second screen, UFAL formulations were prepared with 0.01 wt. % (0.1 mg/mL) copolymer excipient and insulin aggregation were assessed under stressed conditions using the same monomer form, NMR DOSY was used (FIG. 8D). NMR DOSY indicated the diffusion rate of lispro under formulation conditions (100 U/mL lispro, 2.6 wt. % glycerol, 0.85 wt. % phenoxyethanol, and 0.1 wt. % MORPH-NIP$_{23\%}$) had a diffusion rate of $2.0 \times 10^{-10}$ m$^2$ s$^{-1}$, corresponding to a hydrodynamic radius of 1.2 nm, which corresponds to reported literature values of the insulin monomer (28). NMR DOSY also provided insight into the stabilization mechanism of the polymer excipients. MORPH-NIP$_{23\%}$ diffused at a slower rate than insulin, suggesting that the mechanism of stabilization is not related to excipient-insulin complexation and co-diffusion. These data support the hypothesis that copolymer-interface interactions are the primary mechanism driving monomeric insulin stabilization in formulation.

Figure 11A:
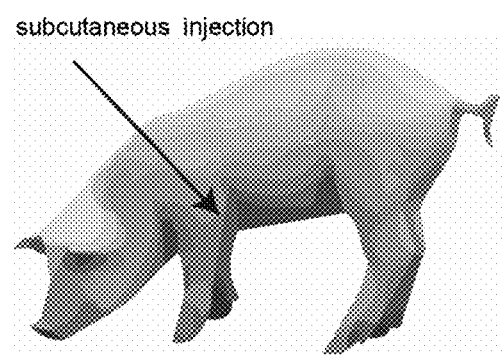
FIGS. 11A-11B illustrate blood glucose of monomeric insulin in diabetic pigs. Diabetic female pigs received subcutaneous administration of therapies comprising either (i) commercial HUMALOG® or (ii) UFAL formulated with polymer.
Figure 11B:
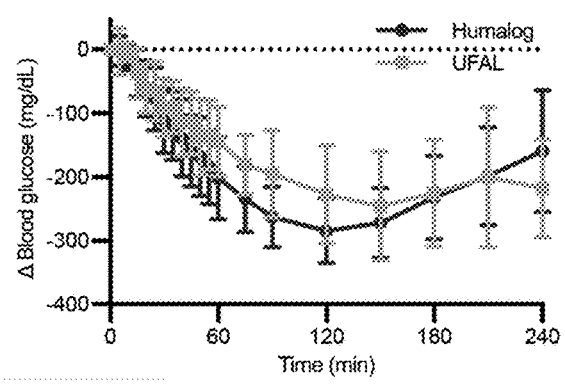
Figure 13:
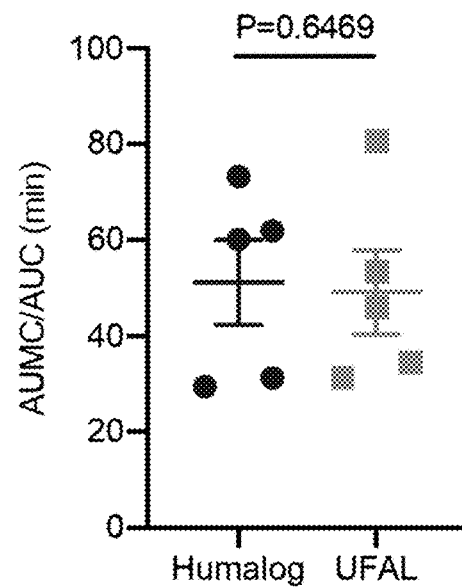
FIG. 13 illustrates AUMC/AUC for UFAL and HUMALOG® in diabetic pigs. Diabetic female pigs received subcutaneous administration of therapies comprising either (i) commercial HUMALOG® or (ii) UFAL formulated with polymer. Pigs were dosed with insulin according to their individual insulin sensitivities to decrease their blood glucose concentrations by about 200 mg/dL. For subcutaneous administration, area under the moment curve (AUMC) divided by area under the curve (AUC) is equal to the mean residence time (MRT)+mean absorption time (MAT). AUMC/AUC=MRT+MAT. Error bars indicate mean±s.e.m. with n=5 for all groups (alpha=0.05). Statistical significance was determined by restricted maximum likelihood (REML) repeated measures mixed model.

Pharmacokinetics and pharmacodynamics of UFAL formulation in diabetic swine: To assess the ultra-fast potential of the monomeric insulin formulations, pharmacokinetic studies were conducted in a swine model of insulin-deficient diabetes. Fasted diabetic swine were treated with either (i) commercial HUMALOG® or (ii) UFAL (100 U/mL lispro, 2.6 wt. % glycerol, 0.85 wt. % phenoxyethanol, and 0.1 wt. % MORPH-NIP$_{23\%}$) at a dose of 2-4 U of insulin lispro, depending on the insulin sensitivity of each pig. Pigs had a starting blood glucose level between 330-430 mg/dL and insulin doses were chosen to reduce blood glucose to approximately 100 mg/dL. The insulin dose given to each pig was consistent between treatment groups and blood glucose depletion was similar in both HUMALOG® and UFAL treatments (FIG. 10A and FIG. 11). Plasma concentrations of lispro were measured over time by enzyme-linked immunosorbent assay (ELISA) to assess pharmacokinetics following subcutaneous injection of each of the treatment groups. No difference in overall exposure (AUC$_{210}$) between groups was observed (FIG. 10C). Percent exposure at various time points was analyzed by looking at the AUC$_t$/AUC$_{210}$. This analysis shows increased exposure for UFAL compared to HUMALOG® at 10 min and 20 min timepoints (FIGS. 10D-10I). Mean residence time (MRT) is commonly reported for formulation pharmacokinetics. MRT is commonly described as area under the moment curve (AUMC) divided by area under the curve (AUC) for intravenous injections; however, when drugs are administered subcutaneously the mean absorption time (MAT) must also be considered. When there is an absorption phase, AUMC/AUC=MAT+MRT. The ratio of the area under the moment curve (AUMC) to the area under the curve for the pharmacokinetic plot (AUMC/AUC) was calculated and plotted, showing no difference between UFAL and HUMALOG® treatment (FIG. 13). This was not surprising, as we would expect the clearance rate from the blood to be similar for both HUMALOG® and UFAL (both are insulin lispro) and the magnitude of MAT in comparison to MRT would be small, thereby masking differences between formulations.

Alternatively, exposure metrics are commonly reported for fast-acting insulin formulations to describe the formulation pharmacokinetics. The "time-to-onset" rate of fast-acting insulins is often determined using two metrics: (i) time-to-50% of the normalized peak height on the way up following administration (denoted "50%-up"), and (ii) time-to-peak insulin plasma concentration. Normalized plasma concentration measurements were used to compare the time-to-peak lispro concentrations between commercial HUMALOG® and UFAL treatment groups (FIGS. 10J-10M). Pigs exhibited almost 2-fold faster HUMALOG® pharmacokinetics compared to humans. UFAL demonstrated faster absorption than HUMALOG®, whereby UFAL time to 50% of peak up (5±2 min) was 2.4-fold faster than HUMALOG® (12±6 min), and UFAL time to peak (9±4 min) was 2.8-fold faster than HUMALOG® (25±10 min). The exposure duration, defined as the time to 50% of the normalized peak height on the way down following peak exposure concentrations (time to 50% peak down), for UFAL (28±8 min) was 1.9-fold shorter than for HUMALOG® (54±21 min).

Modeling UFAL pharmacokinetics in humans: To better understand how the fast onset and short duration demonstrated by UFAL in pigs would translate to humans, a pharmacokinetic model was adapted from Wong et al. (J. Diabetes Sci. Technol. (2008) 2:658-671) to approximate UFAL pharmacokinetics in humans. The model was constructed such that rapid-acting insulin analogues (HUMALOG®) injected into the subcutaneous space (I$_{inj}$) dissociate and diffuse with a rate constant, k$_1$, into the interstitium (I$_{eq}$), absorb with a rate constant, k$_2$, into the plasma (I$_p$), and are subsequently cleared by several mechanisms that can nonetheless be approximated by a single elimination constant, k$_3$ (FIG. 12A). It was assumed that k$_2$ and k$_3$ were species dependent, k$_1$ was formulation and species dependent, and the ratio of k$_1$ between formulations was species independent. Because the UFAL formulation was composed of insulin monomers and dimers, the time necessary to reach equilibrium in the interstitium was expected to be appreciably lower than for HUMALOG®. Indeed, when fitting the experimental pig pharmacokinetics for subcutaneous administration of UFAL, k$_1$ trended towards infinity, meaning that UFAL effectively bypassed the first model compartment and the insulin monomers reached equilibrium in the subcutaneous space immediately (Table 6). The fits for the pig pharmacokinetic data for both UFAL and HUMALOG® are presented in FIG. 12B, and a comparison between the model predictions and experimental data with relevant pharmacokinetic metrics are presented in FIG. 14, Supplemental Attachment A. The infinitely large k$_1$ determined for UFAL in pigs was translated to a human pharmacokinetic model and used to estimate UFAL pharmacokinetics while maintaining k$_2$ and k$_3$ values reported in the literature (FIG. 12C).

TABLE 6

Rate constants used for modeling PK curves in Example 2.

| Species | insulin variant | k$_1$ (min$^{-1}$) | k$_2$ (min$^{-1}$) | k$_3$ (min$^{-1}$) |
|---|---|---|---|---|
| pig | HUMALOG ® | 0.091 | 0.042 | 0.27 |
| pig | UFAL | ∞ | 0.042 | 0.27 |
| human | HUMALOG ® | 0.0104$^a$ | 0.0604$^a$ | 0.16$^a$ |
| human | UFAL | ∞ | 0.0604$^a$ | 0.16$^a$ |

$^a$Human pharmacokinetic rate constants from Wong et al., J. Diabetes Sci. Technol. (2008) 2:658-671.

The model predicts human UFAL time to onset (i.e., 50%-up) of 2.5 minutes, peak exposure at 10 minutes, and duration of exposure (i.e., 50%-down) of 28 minutes (FIG. 12D). In comparison, using parameters reported in the literature, the model predicts "rapid-acting" insulin analogues (RAI), such as HUMALOG®, to exhibit a time to onset of 14 minutes, peak exposure at 43 minutes, and a duration of exposure of 157 minutes (FIG. 12C). While the RAI model underestimates the time to onset of exposure (t50% up), the predicted curve robustly captures published clinical pharmacokinetic data for peak and duration of HUMALOG® exposure. The pharmacokinetic modeling, therefore, predicts UFAL to exhibit kinetics that are more than 4-fold faster than current "rapid-acting" insulin formulations. Further comparison to clinical data for rapid-acting insulin formulations demonstrates that UFAL is predicted to be faster than even second generation rapid-acting insulin formulations such as Fiasp (Novo-Nordisk) and BioChaperone Lispro (Adocia) (FIG. 12E).

In diabetic swine, this UFAL formulation exhibited ultrafast pharmacokinetics, with approximately two-fold faster time to onset and two-fold shorter duration of exposure than HUMALOG®, a commercial "rapid-acting" insulin formulation using the same insulin molecule Lispro. These results suggested that this UFAL formulation more closely mimics endogenous insulin secretion in healthy individuals and highlighted that this formulation is promising for enhancing diabetes management. Even the incremental improvement in pharmacokinetics over current "fast-acting" insulin formulations observed for Fiasp, a faster-acting version of NOVOLOG® (commercial aspart formulation), have shown numerous clinical benefits. While Fiasp shows a modest 10 minute reduction in time to peak action and 15 minute reduction in duration of action over "rapid-acting" insulin formulations, Fiasp use nevertheless reduced post-prandial glucose excursions and reduced HbA1c levels in patients with diabetes. In contrast, in diabetic pigs, where the observed insulin pharmacokinetics were twice as fast as in humans, UFAL reduced time to peak exposure by 16 minutes and reduced duration of exposure by 26 minutes compared to HUMALOG®. The results observed in diabetic pigs, combined with the model predicted human UFAL pharmacokinetics suggested that UFAL may have absorption kinetics that are unprecedented in an injectable insulin formulation. If realized in human clinical studies, these kinetics would be approaching the ultra-fast kinetics of AFREZZA®, the commercially available inhalable insulin. However, unlike AFREZZA®, UFAL is an injectable formulation, which enables more accurate dosing regimens and compatibility with pump and closed-loop systems, providing UFAL the potential to improve post-prandial glycemic control in patients with diabetes.

Figure 14A:
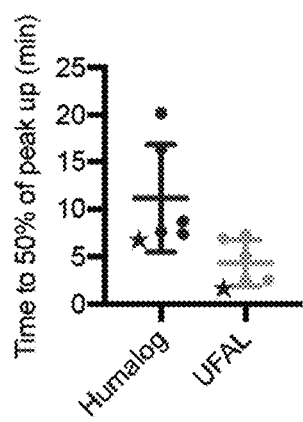
FIGS. 14A-14C illustrate pharmacokinetic outputs from model fitting compared to experimental pharmacokinetic data for HUMALOG® and UFAL in diabetic swine.
Figure 14B:
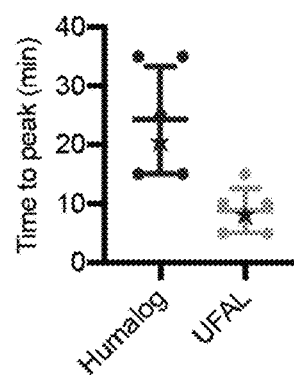
Figure 14C:
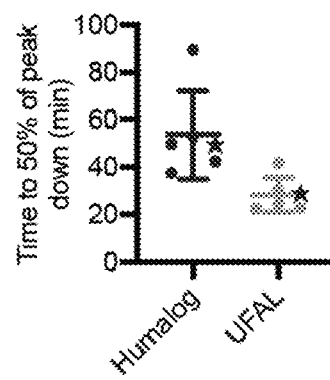

Taken together these studies identified a copolymer excipient for protein stabilization and show its utility in stabilizing an ultra-fast absorbing insulin formulation. Initial cytotoxicity experiments suggested that the copolymer excipient is not toxic at doses an order of magnitude higher than those used in insulin formulations (FIG. 13). Initial biocompatibility studies with UFAL in diabetic rats also corroborated the cytotoxicity results, indicating that UFAL should be well tolerated (FIG. 14).

Example 3: Ultra-Fast Insulin-Pramlintide Co-Formulation

Materials: An amphiphilic acrylamide copolymer excipient acryloylmorpholine$_{77\%}$-N-isopropylacrylamide$_{23\%}$ (MoNi$_{23\%}$) was prepared according to the procedures as set forth above under Example 1, UFAL. HUMALOG® (Eli Lilly) and pramlintide (BioTang) were purchased and used as received. For zinc-free lispro, Zinc(II) was removed from the insulin lispro through competitive binding by addition of ethylenediaminetetraacetic acid (EDTA), which exhibits a dissociation binding constant approaching attomolar concentrations ($K_D \sim 10^{-8}$ M). EDTA was added to formulations (4 eq with respect to zinc) to sequester zinc from the formulation and then lispro was isolated using PD MidiTrap G-10 gravity columns (GE Healthcare) to buffer exchange into water. The solution was then concentrated using Amino Ultra 3K centrifugal units (Millipore) and reformulated with 2.6 wt. % glycerol, 0.85 wt. % phenoxyethanol in 10 mM phosphate buffer (pH=7.4). All other reagents were purchased from Sigma-Aldrich unless otherwise specified.

In-line Size Exclusion Chromatography Multi-Angel Light Scattering (SEC-MALS): Insulin association state composition for monomeric insulin formulation was obtained using SEC-MALS as previously reported (Maikawa et al., *Adv. Ther.* (2019) 75:1900094). Zinc-free insulin lispro was evaluated in a buffer containing glycerol (2.6%) and phenoxyethanol (0.85%). Briefly, number-averaged molecular weight (MW) and dispersity (Đ=Mw/Mn) of formulations were obtained using size exclusion chromatography (SEC) carried out using a Dionex Ultimate 3000 instrument (including pump, autosampler, and column compartment) outfitted with a Dawn Heleos II Multi Angle Light Scattering detector, and a Optilab rEX refractive index detector. The column was a Superose 6 Increase 10/300 GL from GE healthcare. Data was analyzed using Astra 6.0 software. The fraction of each insulin association state was derived by fitting the experimentally derived number-average and weight-average molecular weights to Equation 1 and Equation 2 below. m, d and h, respectively, represent the molar fractions of monomeric, dimeric and hexameric insulin while I represents the molecular weight of monomeric insulin lispro. The solver was constrained so that m+d+h=1 while m, d and h remain between 0 and 1.

$$M_n = m*I + d*2I + h*6I \tag{1}$$

$$M_w = \frac{m*I^2 + d*4I^2 + h*36I^2}{m*I + d*2I + h*6I} \tag{2}$$

In vitro stability evaluation of insulin and pramlintide: Aggregation assays used to evaluate stability were adapted from Webber et al. (*Proc. Natl. Acad. Sci. U.S.A.* (2016) 113:14189-14194). Briefly, formulations were aliquoted 150 μL per well (n=3/group) in a clear 96-well plate and sealed with optically clear and thermally stable seal (VWR). The plate was incubated in a microplate reader (BioTek SynergyH1 microplate reader) at 37° C. with continuous agitation (567 cpm). Absorbance readings were taken every 10 minutes at 540 nm for the duration of the experiment. The formation of insulin or pramlintide aggregates leads to light scattering and a reduction in the transmittance of samples (time to aggregation=time to 10% change in transmittance). Controls included: (i) HUMALOG® (100 U/mL), (ii) HUMALOG® (100 U/mL)+Pramlintide (1:6 lispro:pramlintide), (iii) zinc-free lispro (100 U/mL lispro, 2.6 wt. % glycerol, 0.85 wt. % phenoxyethanol, pH=7.4). The stability of an insulin-pramlintide co-formulation (100 U/mL lispro, 1:6 lispro:pramlintide, 2.6 wt. % glycerol, 0.85 wt. % phenoxyethanol, pH=7.4) mixed with 0.1 mg/mL MoNi$_{23\%}$ was evaluated.

Streptozotocin induced model of diabetes in rats: Male Sprague Dawley rats (Charles River) were used for experiments. Animal studies were performed in accordance with the guidelines for the care and use of laboratory animals; all protocols were approved by the Stanford Institutional Animal Care and Use Committee. The protocol used for streptozotocin (STZ) induction adapted from the protocol by Wu and Huan. Briefly, male Sprague Dawley rats 160-230 g (8-10 weeks) were weighed and fasted in the morning 6-8 hours prior to treatment with STZ. STZ was diluted to 10 mg/mL in the sodium citrate buffer immediately before injection. STZ solution was injected intraperitoneally at 65 mg/kg into each rat. Rats were provided with water containing 10% sucrose for 24 hours after injection with STZ. Rat blood glucose levels were tested for hyperglycemia daily after the STZ treatment via tail vein blood collection using a handheld Bayer Contour Next glucose monitor (Bayer). Diabetes was defined as having 3 consecutive blood glucose measurements >400 mg/dL in non-fasted rats.

In vivo pharmacokinetics and pharmacodynamics in diabetic rats: Diabetic rats were fasted for 4-6 hours before injection. For pharmacokinetic experiments rats were injected with 1 U insulin formulation (~2 U/kg) followed immediately (<30 seconds after injection) by oral gavage with 1 g/kg glucose solution. Formulations tested were: (i) HUMALOG®, (ii) separate injections of HUMALOG® and pramlintide (1:6 pramlintide:lispro, pH=4), (iii) insulin-pramlintide co-formulation (100 U/mL lispro, 1:6 lispro:pramlintide, 2.6 wt. % glycerol, 0.85 wt. % phenoxyethanol, 0.1 mg/mL MoNi$_{23\%}$, pH=7.4). A cohort of 11 rats each received each formulation once, and the order the formulations were given in was randomized. To allow for accurate dosing and to avoid dilution effects (dilution favors the insulin monomer) formulations were diluted two-fold (10 μL formulation+10 μL formulation buffer) immediately before administration. After injection, blood glucose measurements were taken using a handheld glucose monitor (Bayer Contour Next) and additional blood was collected (Sarstedt serum tubes) for analysis with ELISA. Timepoints were taken every 3 minutes for the first 30 minutes, then every 5 minutes for the next 30 minutes, then at 75, 90, and 120 minutes. Serum pramlintide concentrations were quantified using a human amylin ELISA kit (Millipore Sigma). Serum lispro concentrations were quantified using Northern Lights Mercodia Lispro NL-ELISA. A second pharmacodynamics experiment was performed to try to better match insulin dose with oral glucose dose to better simulate meal-time glucose management. The same formulations were tested but doses were changed to 0.75 U/kg insulin delivered subcutaneously immediately before oral gavage with 2 g/kg glucose. A 10 μL Hamilton syringe was used to allow accurate dosing of undiluted (100 U/mL) formulations. A cohort of 10 rats each received each formulation once, and the order the formulations were given in was randomized. Only glucose was measured and timepoints were taken every 5 minutes for the first hour, followed by measurements at 75, 90 and 120 minutes.

Gastric emptying in diabetic rats: Acetaminophen was used as a model compound to evaluate gastric emptying at mealtimes. Diabetic rats were fasted for 4-6 hours before experiment start. Rats were then injected subcutaneously with one of the following formulations (2 U/kg): (i) HUMALOG®, (ii) separate injections of HUMALOG® and pramlintide (1:6 pramlintide:lispro, pH=4), (iii) insulin-pramlintide co-formulation (100 U/mL lispro, 1:6 lispro:pramlintide, 2.6 wt. % glycerol, 0.85 wt. % phenoxyethanol, 0.1 mg/mL MoNi$_{23\%}$, pH=7.4). To allow for accurate dosing and to avoid dilution effects (dilution favors the insulin monomer) formulations were diluted two-fold (10 μL formulation+10 μL formulation buffer) immediately before administration. A cohort of 11 rats each received each formulation once, and the order the formulations were given in was randomized. Acetaminophen was administered via oral gavage as a slurry in phosphate buffer (100 mg/kg) immediately after insulin administration. (Tips of feeding tubes were dipped in glucose solution before oral gavage to reduce stress of administration). Blood samples were collected for ELISA (Neogen) at −30, 0, 15, 30, 60, 90, 120, ands 150 minutes after injection.

Statistics: All results are expressed as mean±standard error (SE) unless specified otherwise. All statistical analyses were performed as general linear models in JMP Pro version 14. Comparisons between formulations were conducted using the restricted maximum likelihood repeated measures mixed model. Post-hoc Tukey HSD tests for multiple comparisons was applied when formulation was a significant fixed effect, and adjusted p-values were reported. Rat was included as a variable in the model as a random effect blocking (control) factor to account for individual variation in rat responses. (Each rat received every formulation and acted as its own control). Statistical significance was considered as $P<0.05$. For FIGS. 18H-18L, post-hoc Bonferroni correction was applied to account for comparison of formulations at multiple exposure timepoints (In addition to Tukey HSD correction) and significance was adjusted to $\alpha=0.01$.

Results

Stabilization of an insulin-pramlintide co-formulation: Characterization of MoNi$_{23\%}$ molecular weight and monomer composition can be found in Table 7. Results shown in Example 2 demonstrated the utility of MoNi$_{23\%}$ as a stabilizing excipient for monomeric insulin. The propensity of insulin and pramlintide to aggregate to form amyloid fibrils, which are primarily initiated at hydrophobic interfaces, makes them strong candidates for stabilization using MoNi$_{23\%}$. Therefore, it was hypothesized that the same MoNi$_{23\%}$ may also be used to physically stabilize an ultrafast mealtime insulin-pramlintide co-formulation to enable a single formulation with increased pharmacokinetic overlap between these two hormones.

TABLE 7

MoNi copolymer excipient characterization.

| Carrier Monomer | wt % (Target) | wt % by NMR (Exp) | Dopant Monomer | wt % (Target) | wt % by NMR (Exp) | $M_n^a$ | $M_w^a$ | $Đ^a$ |
|---|---|---|---|---|---|---|---|---|
| Acryloylmorpholine (Mo) | 77 | 74.5[b] | N-isopropylacrylamide (Ni) | 23 | 25.5[b] | 3200 | 3800 | 1.19 |

[a]Determined using Size Exclusion Chromatography calibrated using polyethylene glycol samples.
[b]Weight percentages difficult to determine due to overlapping spectra. Weight percentages estimated from post- precipitated NMR spectra by measuring the more resolved left half of the peak of N-isopropylacrylamide (δ = 4.0, 0.5 H), doubling it, and subtracting it from the unresolved peaks of Mo and Ni (δ = 3.2-4.2, 7 H (Mo) 1 H (Ni)).

Figure 16:
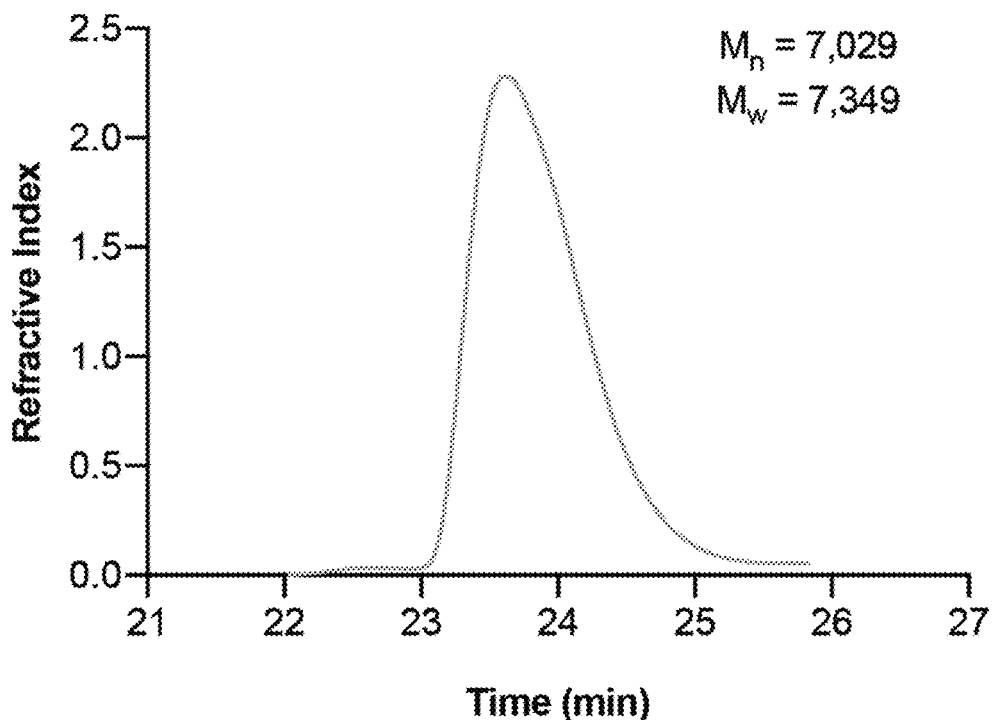
FIG. 16 illustrates SEC-MALS elution profiles of the distribution of insulin lispro aggregation states with number-averaged molecular weight and weight-averaged molecular weight used to calculate percentage of insulin association states.

Zinc-free lispro in the presence of glycerol (2.6 wt. %) and phenoxyethanol (0.85 wt. %) as tonicity and antimicrobial agents, results in a formulation with a high monomer content. This result was confirmed in the current study where 83% monomers, 17% dimers and 0% hexamers in formulation was observed as analyzed by SEC-MALS (FIG. 15E and FIG. 16). In comparison, commercial HUMALOG® is >99% hexameric. For SEC-MALS measurements, insulin association state was tested alone with only small molecule excipients because both pramlintide and the MoNi$_{23\%}$ excipient are of similar molecular weight and would prevent the calculation of monomer content in formulation by SEC-MALS. The addition of MoNi$_{23\%}$ has been shown not to alter the insulin association state by diffusion-ordered nuclear magnetic resonance spectroscopy (DOSY-NMR). It was not anticipated that the presence of pramlintide would alter the insulin association state.

Figure 17:
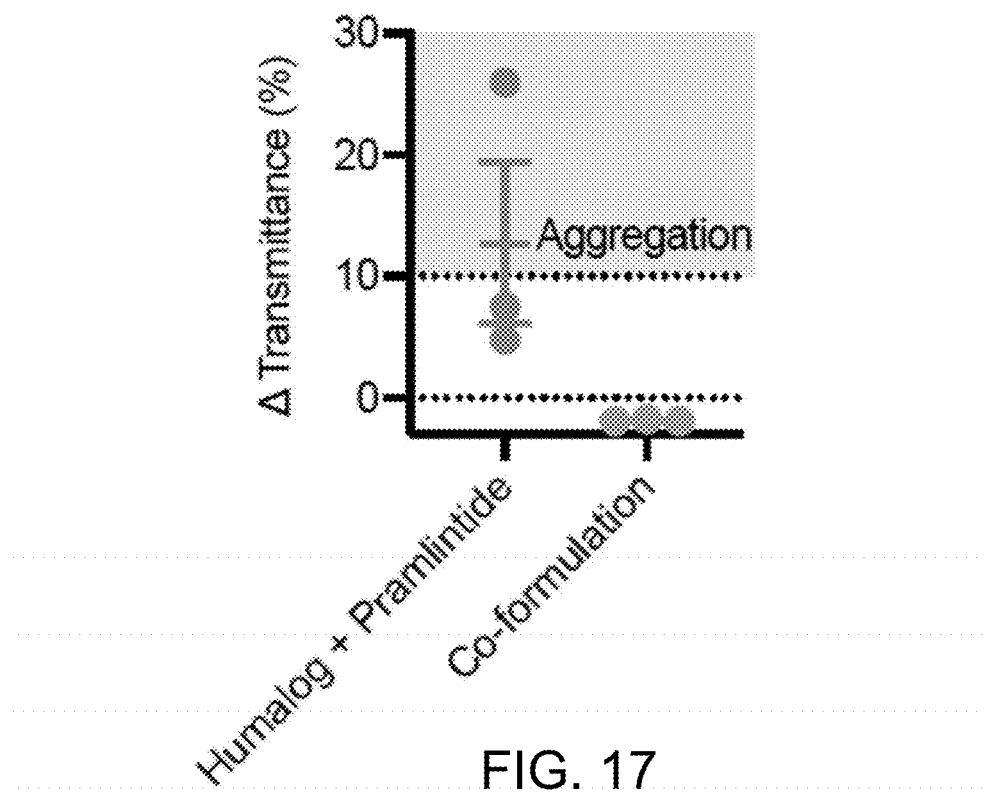
FIG. 17 illustrates initial transmittance for HUMALOG®+pramlintide, and co-formulation (100 U/mL lispro, 1:6 pramlintide:lispro, 0.85 wt. % phenoxyethanol, 2.6 wt. % glycerol, 0.1 mg/mL $MoNi_{23\%}$). Initial transmittance values for (i) HUMALOG®+pramlintide control group and (ii) co-formulation in the stability assay (FIG. 15F) are shown as the change in transmittance of (Average initial HUMALOG® transmittance)−formulation initial transmittance. The decreased transmittance observed for the HUMALOG®+Pramlintide samples before the aging study indicates that there is poor solubility when these two formulations are mixed. In comparison, the initial transmittance for the co-formulation is optically clear to the eye and shows little difference from initial HUMALOG® transmittance.
Figure 27C:
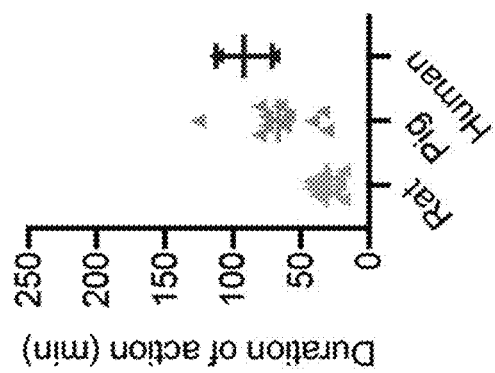
FIGS. 27A-27C illustrate human pharmacokinetics for various insulin formulations and shows normalized pharmacokinetics for pramlintide delivered in rats, pigs and humans (FIG. 27A), time to peak (FIG. 27B), and duration of action (FIG. 27C). The conservation of the ultra-rapid absorbance kinetics from rats to pigs and the similar pramlintide kinetics between pigs and humans corroborates the model predicted kinetics for monomeric lispro in humans. Duration of action is defined here as peak width at 25% peak height (time 25% down–time 25% up). Rat data is taken from the study described in Example 3. Pig data was adapted from previous work (Maikawa et al., *Nat. Biomed. Eng.* (2020) 4:507-517). Human pramlintide data is adapted from two external studies (Kolterman et al., *Diabetologia* (1996) 39:492-499); Riddle et al., *Diabetes Obes. Metab.* (2015) 17:904 907).
Figure 27B:
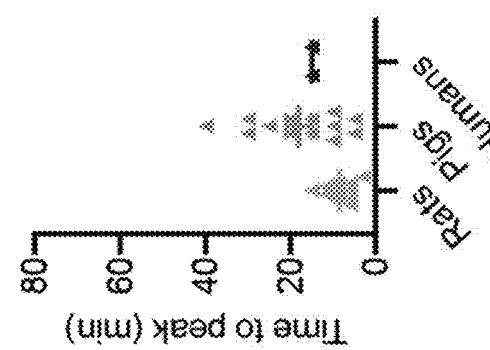
Figure 27A:
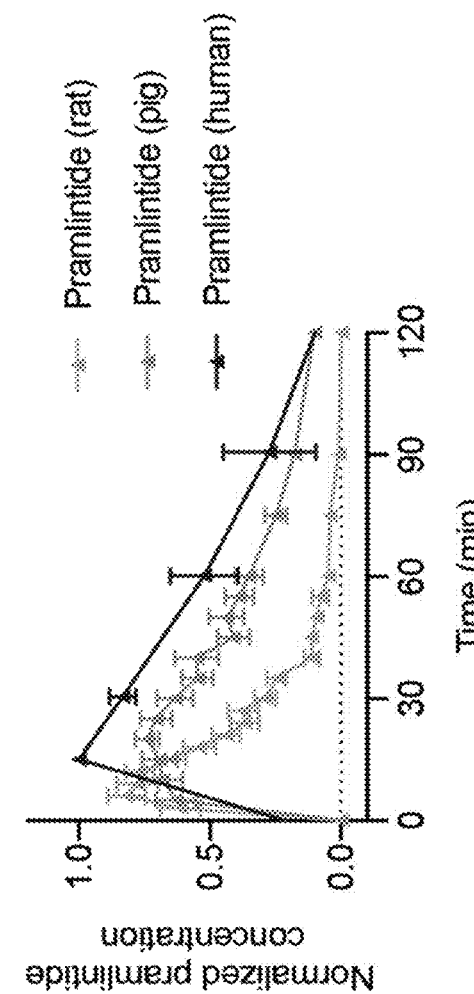
Figure 28A:
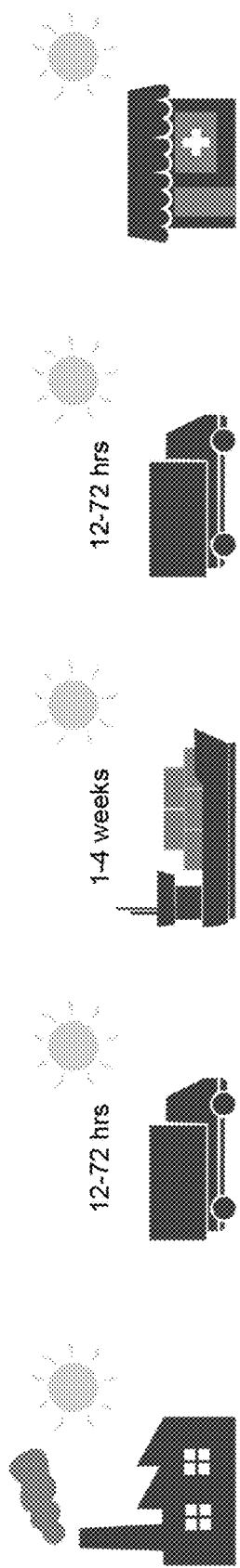
FIGS. 28A-28D illustrate a scheme of cold chain and insulin aggregation mechanism. To maintain integrity, commercial insulin formulations must currently be transported and stored in refrigerated containers for the weeks-long duration of worldwide distribution (FIG. 28A).
Figure 28D:
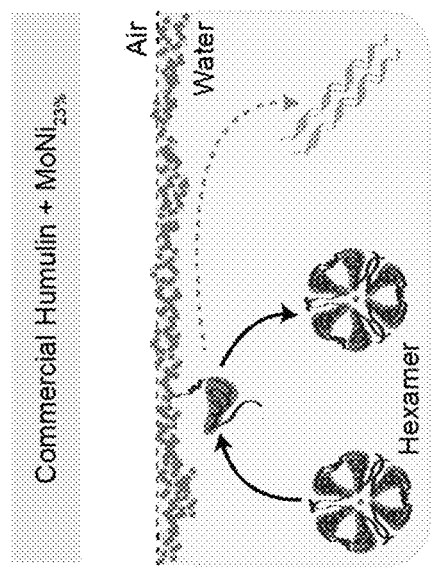
Figure 28C:
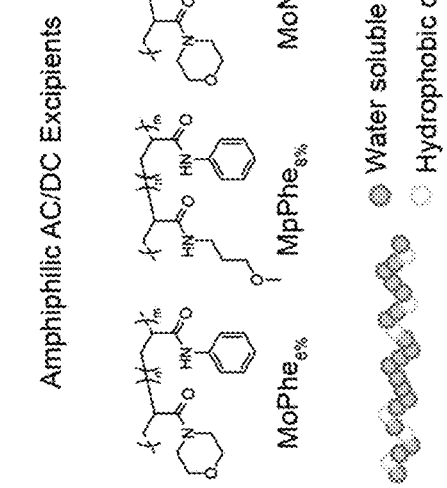
Figure 28B:
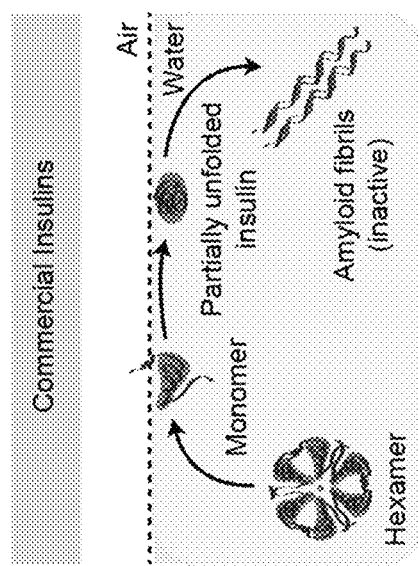

The insulin-pramlintide co-formulation was composed of zinc-free lispro (100 U/mL), pramlintide (1:6 molar ratio pramlintide:lispro), glycerol (2.6 wt. %), phenoxyethanol (0.85 wt. %), and MoNi$_{23\%}$ (0.1 mg/mL) in phosphate buffer at pH-7 (FIG. 15D). A pramlintide ratio of 1:6 was chosen in order to compare with previous work using the CB[7]-PEG stabilized insulin-pramlintide co-formulation in diabetic pigs. Further, a ratio of 1:6 is similar to high endogenous insulin-pramlintide ratios reported in the literature as well as within the range of ratios indicated to be most effective by in silico experiments. Formulation stability was assessed using a stressed aging assay. As insulin and/or pramlintide aggregates form, they scatter light which can be measured by absorbance. As defined herein, formulation aggregation is defined as a 10% or greater change in transmittance. The co-formulation tested was shown to be stable for 16.2±0.1 hours, twice as long as commercial HUMALOG® which aggregated after 8.2±0.5 hours (FIG. 15F). The direct addition of pramlintide to HUMALOG® resulted in a translucent formulation immediately upon mixing which had 5-25% reduced transmittance compared to HUMALOG® alone (FIG. 17). This mixture reached the aggregation threshold after 8±3 hours, which was highly variable due to the variable initial transmittance. Zinc-free lispro alone was mostly monomeric and highly unstable, aggregating rapidly after 5.7±0.1 hours.

Pharmacokinetics and pharmacodynamics in diabetic rats: After establishing the stability of the insulin-pramlintide co-formulation, the pharmacokinetics were evaluated in vivo to determine if the use of monomeric insulin resulted in increased pharmacokinetic overlap for insulin and pramlintide. The co-formulation was tested against controls of HUMALOG® alone and separate injections of insulin and pramlintide (FIG. 18). A high dose of each formulation (2 U/kg) was given to each rat followed by oral gavage with glucose solution (1 g/kg). A similar magnitude in glucose depletion was observed in all three formulations, however glucose depletion for the co-formulation had a trend for more rapid action (faster glucose depletion) and shorter duration of action (faster glucose recovery) compared to HUMALOG® and separate injection controls (FIG. 18A). This trend was mirrored in the insulin lispro pharmacokinetics, where a trend for faster onset and time to peak exposure was observed for the co-formulation (FIGS. 19A-19C). There was a difference in duration of action, defined as 50% of peak down, between formulations (F2, 20=7.07, P=0.0048). The co-formulation had shorter duration of action (22±2 minutes) com-pared to separate injections (34±3 minutes, P=0.0034), and a trend for shorter duration of action compared to HUMALOG® (27±2 minutes, P=0.24) (FIGS. 19A-19D). Faster onset was also corroborated using exposure ratios—the fraction of the area under the curve (AUC) at a given time point over the total (AUC$_t$/AUC$_{120}$). The co-formulation showed a greater fraction of total exposure compared to HUMALOG® and separate injections at 6-, 15- and 30-minute timepoints (FIGS. 19E-19I). There was no difference in insulin lispro or pramlintide area under the exposure curve between formulations (FIG. 20). As expected, there were no differences observed between pramlintide kinetics delivered as separate injections versus in the co-formulation (FIGS. 19J-19M, FIG. 21).

The shift of the co-formulation insulin lispro pharmacokinetic curve to the left was confirmed by overlaying the insulin pramlintide curves for delivery by separate injections or co-formulation and comparing overlap time (FIG. 22). Overlap was defined as the ratio of overlap over total peak width at half peak height (overlap÷(lispro+pramlintide−overlap). As hypothesized, delivery of monomeric insulin with pramlintide in a co-formulation resulted in increased overlap (0.75±0.06) compared to separate injections (0.47±0.07, F1, 10=6.96, P=0.025) (FIG. 10C). The faster insulin kinetics and increased overlap between insulin and pramlintide observed in our co-formulation more closely mimic insulin-pramlintide secretion at mealtimes.

Gastric emptying of acetaminophen in diabetic rats: Once the faster insulin kinetics and increased overlap between insulin and pramlintide were observed for the co-formulation of the present disclosure, the next step was to determine if there were mealtime benefits to this co-formulation compared to standard administrations of HUMALOG® alone or HUMALOG® and pramlintide administered separately. Acetaminophen was used as model cargo to confirm pramlintide function by testing its ability to delay gastric emptying after formulation administration (FIG. 23). It was expected that pramlintide in both separate administrations and in the co-formulation would result in delayed gastric emptying compared to HUMALOG® alone. Indeed, the time to peak acetaminophen concentration was delayed until 76±5 minutes for separate injections and 68±6 minutes for the co-formulation compared to 35±5 minutes for HUMALOG® alone, demonstrating there was no difference in time to peak acetaminophen between separate injections and the co-formulation (FIG. 23C).

Mealtime glucose challenge in diabetic rats: The co-formulation was further tested in a simulated mealtime challenge with a low dose of subcutaneous insulin (0.75 U/kg) and a high dose of glucose (2 g/kg) administered by oral gavage (FIG. 24). In contrast to the glucose measurements in the pharmacokinetic experiments where insulin was dominant, this experiment aimed to reduce the insulin dose and increase the glucose load to better simulate mealtime glucose management. All three formulations had similar control of the glucose peak (FIG. 24C). However, rapid insulin onset combined with delayed gastric emptying and short duration of action was observed for the instant co-formulation of insulin and pramlintide with MoNi$_{23\%}$ copolymer, resulting in tighter control of this mealtime glucose spike while also reducing the magnitude of glucose depletion below baseline levels (FIG. 24B and FIG. 24D). In contrast, while the delayed gastric emptying for the separate injection formulations resulted in rapid glucose depletion and control of the mealtime glucose spike, it also resulted in greater glucose depletion below baseline. The HUMALOG®-only administration resulted in a similar glucose curve to separate administrations of insulin and pramlintide but with delayed glucose depletion since glucose release was not delayed. These results suggested that the co-formulation may enable good prandial glucose control while also reducing post-prandial hypoglycemia.

This study showed that a co-formulation of monomeric insulin lispro and pramlintide had ultrafast kinetics with a high degree of overlap, which resulted in improved glucose management after a glucose challenge. This formulation used amphiphilic acrylamide copolymer excipient MoNi$_{23\%}$ as a stabilizing agent and was physically stable twice as long as commercial HUMALOG® in a stressed aging assay. The pramlintide in the co-formulation resulted in delayed gastric emptying similar to separately administered pramlintide.

Further, the combined effects of ultrafast insulin and pramlintide delivery synchronized in the co-formulation resulted in reduced glucose depletion below baseline measurements while maintaining control of the initial glucose spike in the simulated "mealtime" glucose challenge. These results suggest that the co-formulation has potential to improve glucose management by reducing the risk of post prandial hypoglycemia, while reducing patient burden.

The data in rats showed only trends for increased time to onset (50% of peak up) and time to peak for lispro in the co-formulation compared to HUMALOG® and separate injections. However, AUC ratios representing the fraction of exposure at various timepoints showed that the co-formulation had a greater fraction of early lispro exposure than separate injections and HUMALOG® up until 30 minutes after injection. These observations were surprising, because this study was performed in diabetic rats that have much faster insulin absorption rates on account of their loose skin that result in a larger surface area for subcutaneous absorption compared to humans (FIGS. 25A-25C). Indeed, studies comparing rapid-acting insulin analogues and recombinant human insulin, which have distinct differences in time to onset, do not observe differences when compared in rats. A previous study of monomeric lispro in diabetic pigs showed that time to onset and time to peak were twice as fast for monomeric lispro compared to HUMALOG®. Further, comparison of HUMALOG®, monomeric lispro, and pramlintide kinetics between rats and pigs corroborated previous modeling, suggesting these ultrafast kinetics will be conserved across species (to humans) (FIGS. 26A-26C and FIGS. 27A-27C). Where HUMALOG® time to peak almost doubled from rats (13±1 minutes) to pigs (25±4 minutes), time to peak for monomeric lispro (delivered as part of the co-formulation in rats) was similar in both species (11±1 minutes in rats and 9±2 minutes in pigs) (FIG. 26). The conservation of time to peak exposure from rats to pigs was highly promising for the translation of these ultrafast insulin kinetics to human trials and would result in kinetics faster than current commercial formulations (FIG. 26).

Example 4: Copolymers as "Drop-In" Excipients for Insulin Formulations

Materials: HUMULIN® R (Eli Lilly) was purchased and used as received. Solvents N,N-dimethylformamide (DMF; HPLC Grade, Alfa Aesar, >99.7%), hexanes (Fisher, Certified ACS, >99.9%), ether (Sigma, Certified ACS, Anhydrous, >99%) and $CDCl_3$ (Acros, >99.8%) were used as received. Monomers N-(3-methoxypropyl)acrylamide (MPAM; Sigma, 95%), 4-acryloylmorpholine (MORPH; Sigma, >97%) were filtered with basic alumina prior to use. Monomers N-phenylacrylamide (PHE; Sigma, 99%) and N-isopropylacrylamide (NIPAM; Sigma, >99%) were used as received. RAFT chain transfer agents 2-cyano-2-propyl dodecyl trithiocarbonate (2-CPDT; Strem Chemicals, >97%) and 4-((((2-carboxyethyl)thio)carbonothioyl)thio)-4-cyanopentanoic acid (BM1433; Boron Molecular, >95%) were used as received. Initiator 2,2'-azobis(2-methyl-propionitrile) (AIBN; Sigma, >98%) was recrystallized from methanol (MeOH; Fisher, HPLC Grade, >99.9%) and dried under vacuum before use. Z-group removing agents lauroyl peroxide (LPO; Sigma, 97%) and hydrogen peroxide ($H_2O_2$; Sigma, 30%) were used as received. Streptozotocin (99.58%) was purchased from MedChem Express. All other reagents were purchased from Sigma-Aldrich unless otherwise specified.

Surface Tension: Time resolved surface tension of the air-solution interface was measured with a Platinum/Iridium Wilhelmy plate connected to an electrobalance (KSV Nima, Finland). The Wilhelmy plate was partially immersed in the aqueous solution in a Petri dish, and the surface tension of the interface was recorded for 50 minutes from the formation of a fresh interface. Equilibrium surface tension values (t=50 min) were reported as these values more closely describe the environment in a stored vial before agitation. Two replicates were taken and averaged.

Interfacial Rheology: Interfacial shear rheology was measured using the Discovery HR-3 rheometer (TA Instruments) with an interfacial geometry comprising of a Du Noüy ring made of Platinum/Iridium wire (CSC Scientific, Fairfax, VA, catalog No. 70542000). Before each experiment, the Du Noüy ring was rinsed with ethanol and water and flame treated to remove organic contaminants. The solution chamber consisted of a double-wall Couette flow cell with an internal Teflon cylinder and an external glass beaker. A time-sweep was performed with a strain of 1% (within the linear regime) and a frequency of 0.05 Hz (low enough for instrument inertia to not be significant). Interfacial complex shear viscosity was measured for 30 minutes. The experiment was repeated in triplicate.

Polymer Synthesis: Polymers were synthesized via reversible addition fragmentation transfer as described in Example 1 above. The procedure to synthesize $MoNi_{23\%}$ AC/DC excipient is as follows and was nearly identical for all other carrier/dopant combinations, where only the carrier/dopant selection and concentrations were changed. MORPH (566 mg, 4.02 mmol, 36.5 eq.), NIPAM (168 mg, 1.485 mmol, 13.5 eq.), 2CPDT (38 mg, 0.11 mmol, 1 eq.) and AIBN (3.6 mg, 0.02 mmol, 0.2 eq.) were combined and diluted with DMF to a total volume of 2.25 mL (33.3 w/v vinyl monomer concentration) in an 8 mL scintillation vial equipped with a PTFE septa. The reaction mixture was sparged with nitrogen gas for 10 minutes and then heated for 12 hours at 65° C. To remove the Z-terminus of the resulting copolymer, AIBN (360 mg, 2.2 mmol, 20 eq.) and LPO (88 mg, 0.22 mmol, 2 eq.) were added to the reaction mixture, which was then sparged with nitrogen gas for 10 minutes and heated for 12 hours at 90° C. Z-group removal was confirmed by the ratio of the refractive index to UV ($\lambda$=310 nm) intensity in size exclusion chromatography (SEC) analysis. Resulting copolymers were precipitated three times from ether and dried under vacuum overnight.

In Vitro Insulin Stability Assay (Accelerated Aging): 50 µL of AC/DC excipient ($MoNi_{23\%}$, $MpPhe_{8\%}$, $MoPhe_{6\%}$) in milli-Q water (2.1, 21, or 105 mg/mL) or 50 µL of milli-Q water was added to 1 mL of HUMULIN® R (Eli Lilly 100 U) in a glass autosampler vial (J. G. Finneran, 2.0 mL Clear R.A.M.™ Large Opening Vial, 12×32 mm, 9 mm Thread) and capped, yielding 95 U HUMULIN® either as a control or formulated with 0.01, 0.1, or 0.5 wt. % AC/DC excipient. These vials were incubated at 37° C. and agitated at 150 RPM for 2, 4, and 6 months (in addition, HUMULIN® only control was agitated at 2 weeks and 1 month). The preparation of formulations was staggered so that all samples reached their endpoint age at the same time. Vials were refrigerated until testing upon reaching selected aging timepoint. Following initial transmittance experiments, all further experiments were done with formulations with 0.01 wt. % AC/DC excipient to minimize copolymer concentration. In addition, 500 µL of 2.1 mg/mL $MoNi_{23\%}$ or milli-Q water were added to 10 mL of unadulterated HUMULIN® (Eli Lilly 100 U) in its commercial vial to generate 95 U HUMULIN® control and formulation with 0.01 wt %

AC/DC excipient. These vials were placed in the original individual packaging boxes with the instruction papers. These packages were incubated at either 37° C. or 50° C. until significant opacity change. 300-400 μL aliquots were removed every 24 hours for the first 7 days and refrigerated. Following that, intermittent aliquots were taken to conserve volume. Every 24 hours, the bottoms of the vials were photographed to track the change in opacity. Methods for aggregation assays for recombinant human insulin were adapted from Webber et al. Formulation samples were plated at 150 μL per well in a clear 96-well plate and an absorbance reading was taken at 540 nm (BioTek Synergy H1 microplate reader). The aggregation of insulin leads to light scattering, which results in an increase in the measured absorbance. The time-to-aggregation ($t_A$) was defined as the timepoint when a 10% increase in transmittance from time zero was observed.

Circular dichroism: Circular dichroism was used to validate that aging with AC/DC excipients does not result in changes to the secondary structure of insulin. Aged HUMULIN® (0.5, 1, 2, 4, and 6 months) or HUMULIN® aged with 0.01 wt. % AC/DC excipients (2, 4, and 6 months) were evaluated against an unaged HUMULIN® control or unaged HUMULIN® with 0.01 wt. % AC/DC excipient. Formulation samples were diluted to 0.2 mg/mL in PBS (pH=7.4). Samples were left to equilibrate for 15 minutes at room temperature before measurement. Near-UV circular dichroism spectroscopy was performed at 20° C. with a J-815 CD Spectropolarimeter (Jasco Corporation) over a wavelength range of 200-260 nm using a 0.1 cm pathlength cell.

In vitro insulin cellular activity assay: In vitro insulin activity was tested using the AKT phosphorylation pathway using AlphaLISA SureFire Ultra (Perkin-Elmer) kits for detection of phosphorylated AKT 1/2/3 (pS473) compared to total Akt1. HUMULIN®, Aged HUMULIN® (t=6 months), HUMULIN®+$MoNi_{23\%}$, and Aged HUMULIN®+$MoNi_{23\%}$ (t=6 months) formulations were tested. HUMULIN®+$MoNi_{23\%}$, and Aged HUMULIN®+$MoNi_{23\%}$ (t=6 months) formulations were tested. C2C12 mouse muscle myoblasts (ATCC CRL-1772) were cultured and were confirmed to be *mycoplasma* free prior to use. Dulbecco's Modified Eagle's Medium (DMEM) (Gibco; 4.5 g/L D-glucose, L-glutamine, 110 mg/L sodium pyruvate) was supplemented with 10% fetal bovine serum (FBS) and 5% penicillin-streptomycin. Cells were grown in a 96-well tissue culture plate for 24 hours (Seeding density=25,000 cells/well in 200 μL culture media). Prior to insulin stimulation, the cells were washed twice with 200 μL of unsupplemented DMEM and starved in 100 μL of unsupplemented DMEM overnight. The media was then removed and the cells were stimulated with 100 μL of insulin (i) HUMULIN®, (ii) Aged HUMULIN® (t=6 months), (iii) HUMULIN®+$MoNi_{23\%}$, or (iv) Aged HUMULIN®+$MoNi_{23\%}$ (t=6 months), diluted in unsupplemented DMEM, for 30 min while incubating at 37° C. Cells were washed twice with 100 μL of cold 1× Tris-buffered saline before adding 100 μL of lysis buffer to each well and shaking for at least 10 minutes at room temperature to fully lyse cells. 30 μL of lysate was transferred to a 96-well white half-area plate for each assay. Assays were completed according to the manufacturer's protocol. Plates were incubated at room temperature and read 18-20 hours after the addition of the final assay reagents using a Tecan Infinite M1000 PRO plate reader. Results were plotted as a ratio of [pAKT]/[AKT] for each sample (n=3 cellular replicates) and an $EC_{50}$ regression (log(agonist) vs. response (three parameters)) was plotted using GraphPad Prism 8.

Ethical approval of studies including animal experiments: All animal studies were performed in accordance with the guidelines for the care and use of laboratory animals; all protocols (Protocol No. 32873) were approved by the Stanford Institutional Animal Care and Use Committee prior to the research being conducted.

Streptozotocin (STZ) induced model of diabetes in rats: Male Sprague Dawley rats (Charles River) were used for experiments. Animal studies were performed in accordance with the guidelines for the care and use of laboratory animals; all protocols were approved by the Stanford Institutional Animal Care and Use Committee. The protocol used for STZ induction adapted from the protocol by Wu and Huan, and have been previously described. Male Sprague Dawley rats 180-250 g (8-10 weeks) were weighed and fasted the morning of treatment (6-8 hours) prior to treatment with STZ in the afternoon. Pre-weighed STZ was protected from light and diluted to 10-20 mg/mL in 1 mL sodium citrate buffer (pH=4.5) immediately before injection. Rats were injected with STZ solution (65 mg/kg) intraperitoneally. Rats were given water containing 10% sucrose for 24 hours after administration of STZ. Three days after treatment with STZ, rat blood glucose levels were tested for hyperglycemia via tail vein blood collection using a handheld Bayer Contour Next glucose monitor (Bayer). Subsequent glucose monitoring was performed daily. Diabetes was defined as having 3 consecutive blood glucose measurements >300 mg/dL in non-fasted rats.

In vivo pharmacodynamics in diabetic rats: Diabetic rats were fasted for 4-6 hours. For initial blood glucose studies rats were injected subcutaneously (1.5 U/kg) with the following formulations: (i) HUMULIN®, or (ii) HUMULIN® with 0.01 wt. % AC/DC excipient ($MoNi_{23\%}$, $MpPhe_{8\%}$, $MoPhe_{6\%}$). HUMULIN® formulations were tested at six aging time points of 0, 0.5, 1, 2, 4, and 6 months, and HUMULIN® with AC/DC excipient was tested at 0, 2, 4, and 6 months of aging. The preparation of formulations was staggered so that all samples reached their endpoint age at the same time and all aging timepoints could be compared in the same cohort of rats. 32 rats with fasting glucose levels >300 mg/dL were randomized to a formulation group (8 rats/group) and each rat received that formulation at all levels of aging (the order of the aging timepoints rats received was also randomized). For blood glucose studies after formulation aging at 50° C., rats were injected subcutaneously (1.5 U/kg) with the following formulations: (i) HUMULIN®, (ii) Aged HUMULIN® (t=1 day), (iii) HUMULIN®+$MoNi_{23\%}$, or (iv) Aged HUMULIN®+$MoNi_{23\%}$ (t=4 days). 16 rats with fasting glucose levels >300 mg/dL were randomized to either the HUMULIN® control group or the $MoNi_{23\%}$ group. Within both groups, the order that the aged formulations were given was also randomized and formulations were administered on separate experimental days. Before injection, baseline blood glucose was measured. After injection, blood was sampled every 30 minutes for 5 hours. Blood glucose was measured using a handheld blood glucose monitor. The maximum change in blood glucose measured from baseline was used as a metric of bioactivity of each formulation to assess in vivo bioactivity after aging.

In vivo pharmacokinetics in diabetic rats: Diabetic rats were fasted for 4-6 hours. For pharmacokinetic studies rats were injected subcutaneously (1.5 U/kg) with the following formulations: (i) HUMULIN®, (ii) Aged HUMULIN® (t=6 months), (iii) HUMULIN®+$MoNi_{23\%}$, or (iv) Aged HUMULIN®+$MoNi_{23\%}$ (t=6 months). 16 diabetic rats were randomized to a formulation group: HUMULIN® or HUMULIN®+MoNi$_{23\%}$ (8 rats/group). Within each group, rats received both the fresh (t=0 months) or aged (t=6 months) formulations in a randomized order. After subcutaneous injection, blood was sampled every 15 minutes for 2 hours and blood was collected in serum tubes (Sarstedt) for analysis with ELISA. Serum insulin concentrations were quantified using a Human Insulin ELISA kit (Mercodia).

Statistics: All data is shown as mean±standard error unless specified. For the in vitro activity assay (AKT) EC$_{50}$ regression (log(agonist) vs. response (three parameters)) was plotted using GraphPad Prism 8. GraphPad Prism 8 Extra sum-of-squares F-test was used to test if Log(EC$_{50}$) differed between datasets. Data sets were compared in pairs, and Bonferroni post-hoc tests were used to adjust for multiple comparisons (alpha=0.008). For blood glucose measurements, a REML repeated measures mixed model was used to test for differences at different aging timepoints within a formulation (JMP Pro 14). Rat was included as a random effect and the age of the formulation as a within-subject fixed effect. A post-hoc Tukey HSD test was used on HUMULIN® formulations to determine statistical significance between aging timepoints.

Results

Characterization of copolymers synthesized: The composition and molecular weights of copolymers synthesized were determined via $^1$H NMR spectroscopy and SEC with poly(ethylene glycol) standards (Table 8).

TABLE 8

Characterization of Copolymers

| Carrier | wt. % (Target) | wt. % by NMR (Exp) | Dopant | wt. % (Target) | wt. % by NMR (Exp) | $M_n^a$ (Da) | $M_w^a$ (Da) | $Đ^a$ |
|---|---|---|---|---|---|---|---|---|
| MORPH | 77 | 74.5$^b$ | NIP | 23 | 25.5$^b$ | 3200 | 3800 | 1.19 |
| MORPH | 94 | 93.7$^c$ | PHE | 6 | 6.3$^c$ | 2900 | 3400 | 1.17 |
| MPAM | 92 | 91$^d$ | PHE | 8 | 9$^d$ | 5000 | 5400 | 1.08 |

$^a$Determined using Size Exclusion Chromatography calibrated using polyethylene glycol samples.
$^b$Weight percentages difficult to determine due to overlapping spectra. Weight percentages estimated from post-precipitated NMR spectra by measuring the more resolved left half of the peak of Nipam (δ = 4.0, 0.5 H), doubling it, and subtracting it from the unresolved peaks of MORPH and Nipam (δ = 3.2-4.2, 7 H (MORPH) 1 H (Nipam)).
$^c$Weight percentages calculated from post-precipitated NMR spectra of Morph (δ = 3.3-3.7, 8 H) and Phe (δ = 7.6, 2 H).
$^d$Weight percentages calculated from post-precipitated NMR spectra of Mp (δ = 3.1-3.5, 7 H) and Phe (δ = 7.6, 2 H).

Figure 29A:
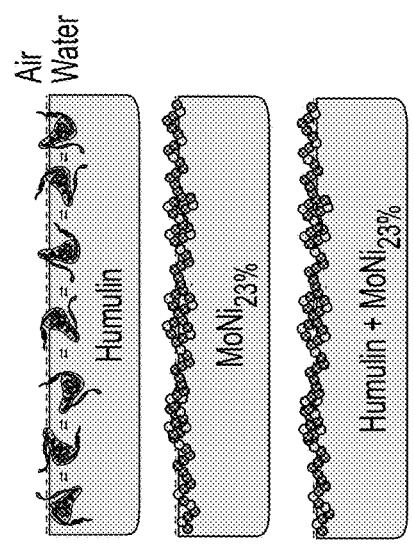
FIGS. 29A-29C illustrate experimental insight into the mechanism of polyacrylamide-based copolymer excipient stabilization.

AC/DC excipient insulin stabilizing mechanism: Three amphiphilic AC/DC excipients that were shown to stabilize monomeric insulin were tested. These excipients were composed of either acryloylmorpholine (MORPH or Mo) or methoxypropylacrylamide (MPAM) as a hydrophilic carrier monomer copolymerized with either N-Isopropylacrylamide (NIP or Ni) or phenylacrylamide (PHE) as a hydrophobic dopant monomer. To test whether these excipients preferentially occupy the air-water interface and consequently inhibit insulin-insulin interactions occurring at these interfaces (FIG. 28), time-resolved surface tension and interfacial rheology experiments were used with a model AC/DC excipient, poly(acryloylmorpholine$_{77\%}$-co-N-Isopropylacrylamide$_{23\%}$) (MoNi$_{23\%}$), co-formulated with commercial HUMULIN® R (Eli Lilly) (FIG. 29).

Figure 29B:
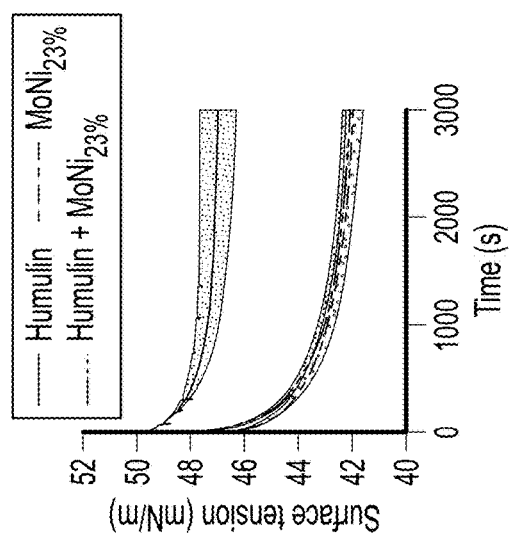
Figure 30:
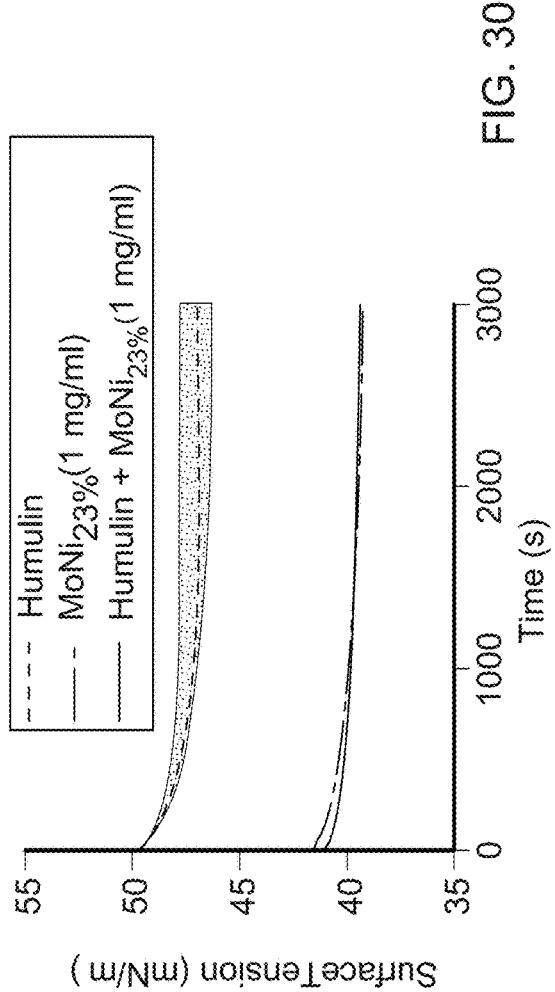
FIG. 30 illustrates surface tension of 1 mg/mL (0.1 wt. %) polymer formulations. Surface tension measurements of HUMULIN® (95 U), MoNi$_{23\%}$ (0.1 wt. %) formulated with glycerol (1.6 wt. %) and metacresol (0.25 wt. %), and HUMULIN® (95 U) formulated with MoNi$_{23\%}$ (0.1 wt. %) are shown.

Equilibrium surface tension measurements of HUMULIN® R, HUMULIN® R containing MoNi$_{23\%}$ (0.01 wt. %), and a solution of MoNi$_{23\%}$ (0.01 wt. %) containing the same formulation excipients (i.e., HUMULIN® R without the insulin) revealed that the presence of MoNi$_{23\%}$ resulted in surface tension values well below HUMULIN® R (approximately 42 vs. 47 mN/m, FIG. 29B). Moreover, a ten-fold increase in the MoNi$_{23\%}$ concentration (0.1 wt. %) further reduced the surface tension of the formulation (FIG. 30). The decrease in surface tension upon addition of MoNi$_{23\%}$ to HUMULIN® indicates that there are more species at the interface when MoNi$_{23\%}$ and HUMULIN® are formulated together, compared to HUMULIN® alone. The decreased surface tension concomitant with the increased concentration of MoNi$_{23\%}$ in the absence of HUMULIN® indicates that the surface is not saturated at 0.01 wt. % MoNi$_{23\%}$. However, the surface tension is identical for formulations of HUMULIN® and MoNi$_{23\%}$ and MoNi$_{23\%}$ with formulation excipients, indicating that there are similar number of molecular species at the interface regardless of the presence of HUMULIN®. Together, these surface tension experiments help demonstrate that MoNi$_{23\%}$ preferentially adsorbs and dominates the air-water interface.

Figure 29C:
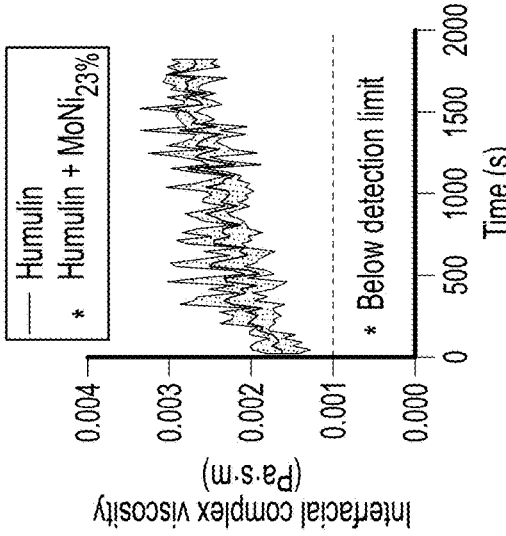

Interfacial shear rheology measurements demonstrated that addition of MoNi$_{23\%}$ (0.01 wt. %) to HUMULIN® R reduced interfacial complex viscosity to below the detection limit of the instrument compared to HUMULIN® R, which exhibited values between 0.002-0.003 Pa·s·m FIG. 29C). The complex viscosity of HUMULIN® is indicative of associative insulin-insulin interactions that can dissipate viscous energy at the interface. While not quantitative, the lowering of the interfacial complex viscosity below instrument detection limits is indicative that the addition of MoNi$_{23\%}$ disrupts insulin-insulin interactions at the interface.

When this complex interface is subjected to interfacial stresses and agitation, it is likely that these insulin-insulin associations can nucleate amyloid fibril formation and lead to aggregation. Together, the surface tension and interfacial rheology experiments suggest a mechanism of AC/DC enhanced insulin stabilization where preferential adsorption of the AC/DC excipient to the air-water interface disrupts insulin-insulin interactions.

AC/DC excipients for long-term stability of insulin: The capacity of the AC/DC excipients MoNi$_{23\%}$, poly(acryloylmorpholine$_{94\%}$-co-phenylacrylamide$_{6\%}$) (MoPhe$_{6\%}$) and poly(methoxypropylacrylamide$_{92\%}$-co-phenylacrylamide$_{8\%}$) (MpPhe$_{8\%}$) to act as simple "drop-in" excipients to stabilize HUMULIN® R through stressed aging was evaluated. Formulations of HUMULIN® alone or HUMULIN® with an AC/DC excipient added were prepared and aged for 0, 2, 4, or 6 months at 37° C. with constant agitation (150 rpm on an orbital shaker plate). The preparation of formulations was staggered so that all samples reached their endpoint age at the same time. Both visual inspection and a transmittance assays were used to determine if the insulin had aggregated (FIG. 31). Insulin aggregates scatter light, and thus aggregation can be defined as a change in transmittance greater than 10%. HUMULIN® alone began to aggregate after 2 weeks of stressed aging. In contrast, all insulin formulations containing AC/DC excipients MoPhe$_{6\%}$, MpPhe$_{8\%}$, and MoNi$_{23\%}$ at concentrations of 0.01, 0.1 or 0.5 wt. % did not show any signs of insulin aggregation over the course of the 6 month study, with the exception of MpPhe$_{8\%}$ at 0.5 wt. % (FIG. 31B and FIG. 32). Thus, to minimize the amount of copolymer excipient in formulation, only the 0.01 wt. % formulations were used for the rest of the studies reported here.

To further validate the transmittance results, which only assessed insulin aggregation, in vitro activity was evaluated by assaying for phosphorylation of Ser$^{473}$ on protein kinase B (AKT) after stimulating C2C12 cells with either HUMULIN® or HUMULIN® containing MoNi$_{23\%}$ (0.01 wt. %) at both the 0 month and 6 month timepoints (FIGS. 31C-31D). Fresh formulations and the aged HUMULIN®+MoNi$_{23\%}$ formulation showed equivalent bioactivity (HUMULIN® t=0 Log(EC$_{50}$)=2.252±0.158; MoNi$_{23\%}$, t=0 Log(EC$_{50}$)=2.448±0.186; MoNi$_{23\%}$, t=6 Log(EC$_{50}$)=2.405±0.158), whereas aged HUMULIN® R exhibited almost complete loss of bioactivity (HUMULIN® t=6 Log(EC$_{50}$)=3.606±0.139) (FIGS. 31C-31D).

While these in vitro AKT assay results supported the transmittance data, insulin formulation integrity was further confirmed using circular dichroism to observe insulin secondary structure for each formulation timepoint (FIGS. 31E-31H). Formulations stabilized with the AC/DC excipients exhibited no changes in secondary structure after stressed aging, whereas HUMULIN® alone had lost all structural features by 1 month. These data corroborate both the transmittance and in vitro activity data.

Figure 33F:
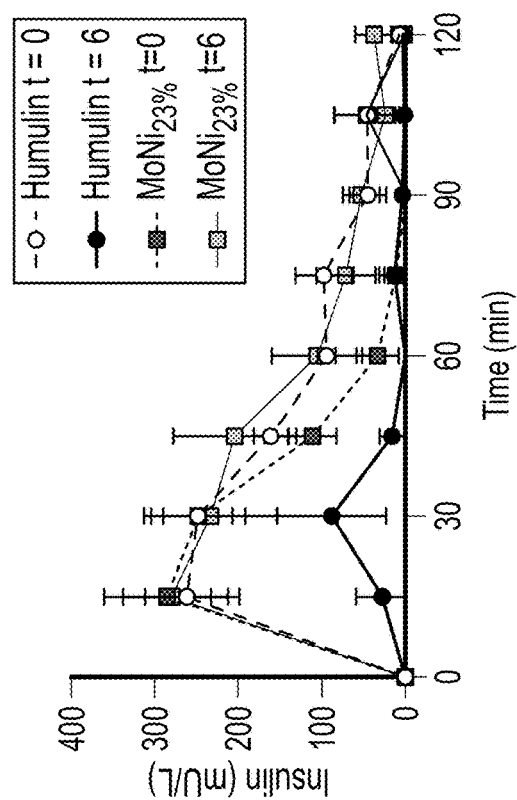
Figure 33E:
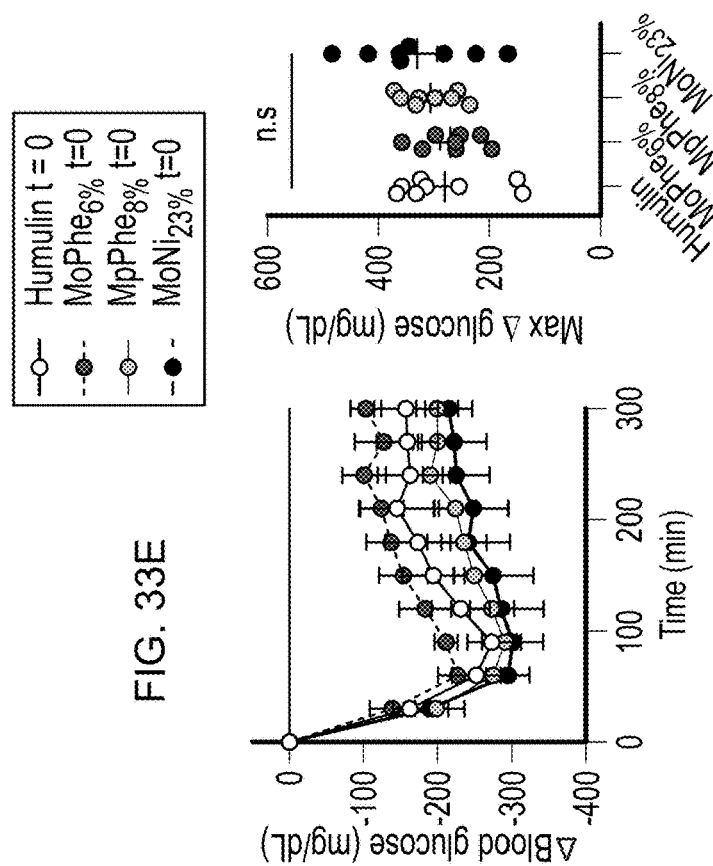
Figure 34A:
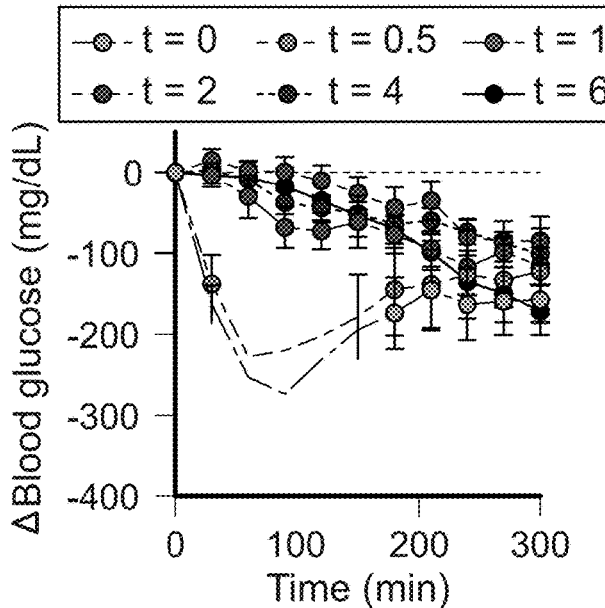
FIGS. 34A-34B illustrate the blood glucose curve for HUMULIN® including t=0.5 and t=1 month time points. Fasted diabetic male rats (n=8) received subcutaneous administration (1.5 U/kg) of HUMULIN®. Eight rats were randomly assigned to the HUMULIN® group. Each rat received one dose of the formulation at each aging timepoint in a random order. Blood glucose levels were measured every 30 minutes using a handheld glucose monitor and the change in blood glucose relative to baseline glucose measurements was plotted. Statistical significance between max Δglucose was assessed using a REML repeated measures mixed model with rat as a random effect and the age of the formulation as a within-subject fixed effect. A post-hoc Tukey HSD test was used on formulations to determine statistical significance between aging timepoints. Groups not connected by the same letter are significantly different.
Figure 34B:
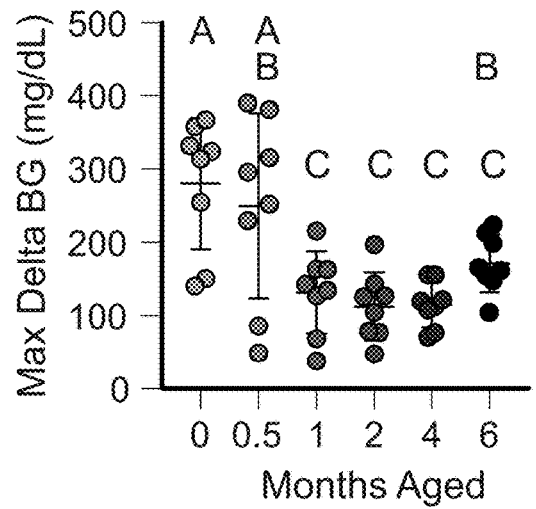
Figure 35:
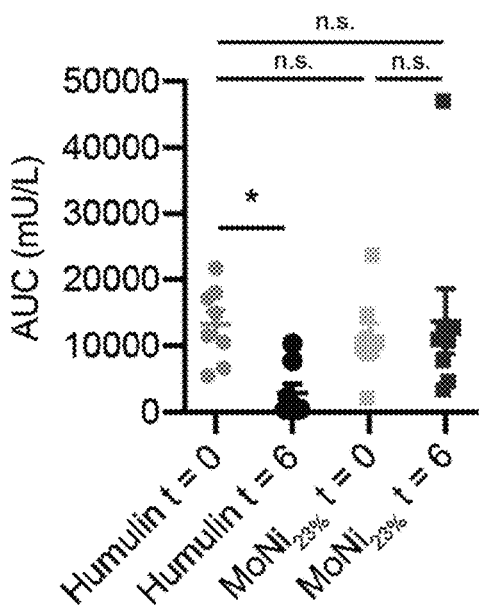
FIG. 35 illustrates area under the curve for pharmacokinetics. Area under the curve was calculated for the pharmacokinetic curves of HUMULIN®, aged HUMULIN® (t=6), HUMULIN®+MoNi$_{23\%}$ and aged MoNi$_{23\%}$ (t=6). No difference was observed between fresh HUMULIN® or polymer stabilized formulations. Aged HUMULIN® showed decreased area under the curve compared to HUMULIN®. All data is shown as mean±s.e. Statistical significance between AUC was assessed using a REML repeated measures mixed model with rat as a random effect and the age of the formulation as a within-subject fixed effect. A post-hoc Tukey HSD test was used on formulations to determine statistical significance between aging timepoints.

Bioactivity of aged insulin in diabetic rats: To evaluate the integrity of the aged insulin formulations in a functional setting in vivo, formulation activity in diabetic rats was assessed. Administration of streptozotocin was used to induce insulin-dependent diabetes in a cohort of 32 male rats. These rats were randomly assigned to one of four formulation groups: (i) HUMULIN®, or HUMULIN® comprising either (ii) MoPhe$_{6\%}$, (iii) MpPhe$_{8\%}$, or (iv) MoNi$_{23\%}$ at 0.01 wt. %, and each rat received that formulation at each aging timepoint (0, 2, 4, 6 months). The preparation of formulations was staggered so that all samples reached their endpoint age at the same time and all aging timepoints could be compared in the same cohort of rats. Insulin was administered subcutaneously in fasted rats (1.5 U/kg) and blood glucose levels were measured every 30 minutes. Active formulations resulted in a distinct initial drop in blood glucose from extreme hyperglycemia that reached a minimum in the range of normoglycemia between 60-100 minutes after administration (FIG. 33 and FIG. 34). After this phase, blood glucose levels began to rise as insulin was cleared. In contrast, formulations that appeared aggregated in the in vitro transmittance assays following aging did not show this distinct reduction in glucose reminiscent of insulin action and instead resulted in a gradual decrease in glucose levels. The gradual decrease in glucose may suggest that some of the insulin is initially trapped in reversible aggregates, and over time these aggregates dissociate and result in a slow-acting insulin effect. The maximum difference in blood glucose from baseline to the minimum glucose levels was plotted for each formulation as a measure of formulation potency. All copolymer-stabilized formulations showed no difference in activity between aging timepoints, but HUMULIN® alone demonstrated a large difference between aging timepoints (F3,21=23.83, P<0.0001), where a post-hoc Tukey HSD test revealed that HUMULIN® after 2, 4, and 6 months of aging had decreased activity compared to fresh HUMULIN® (t=0 months). These observations were corroborated by evaluation of insulin pharmacokinetics, where no differences were observed between fresh HUMULIN® R (t=0 months) and HUMULIN®+MoNi$_{23\%}$ initially (t=0 months) and after 6 months of aging, but a decrease in exposure was observed for the aged HUMULIN® (t=6 months) (FIG. 33F and FIG. 35). These data suggest that AC/DC excipients function as stabilizing ingredients for commercial formulations such as HUMULIN® R without altering the insulin pharmacokinetics or pharmacodynamics.

High temperature aging of insulin formulations: To determine the capacity of AC/DC excipients to improve insulin cold-chain resilience, the extent of stability imbued by MoNi$_{23\%}$ under extreme manufacturing and distribution conditions (37° C. and 50° C. with constant agitation) was evaluated (FIG. 36). Temperatures were selected to represent the temperature on a hot summer day (37° C.), and the upper temperature range that a shipping container or truck without refrigeration or insulation could reach during the peak of summer (50° C.). HUMULIN® R can be purchased in 10 mL glass vials that are packaged and shipped in cardboard boxes (FIG. 36 A and FIG. 37). MoNi$_{23\%}$ (0.01 wt. %) was added to new vials of HUMULIN® R using a syringe (dilution from 100 U/mL to 95 U/mL to allow addition of copolymer; control vial was diluted with water) and the vials were then replaced in the original cardboard packaging with the package insert (FIG. 37A). The cardboard packaging was affixed to a rotary shaker inside a temperature-controlled incubator and agitated at 150 RPM (FIG. 37B).

Visual inspection combined with a transmittance assay were used as the primary measures of insulin integrity (FIG. 36A). These assays were consistent with our earlier experiments that demonstrated that the transmittance readings correlate well with both in vitro and in vivo functional activity assays. At 37° C., HUMULIN® alone began to show visual changes in opacity at day 1 and became fully opaque by day 2. In contrast, when formulated with MoNi$_{23\%}$, the insulin formulation showed no visual changes in opacity until day 56 and remained below a 10% change in transmittance for 56 days. At 50° C., commercial HUMULIN® became fully opaque within one day. In contrast, formulation with MoNi$_{23\%}$ extended stability under these extreme conditions to past 4 days before the formulation became cloudy on day 5. These qualitative observations were consistent with quantitative transmittance readings (FIGS. 36B-36C).

To verify functional insulin activity after aging at 50° C. in vivo, these formulations were evaluated in diabetic rats. The ability of (i) HUMULIN® (t=0 day), (ii) aged HUMULIN® (t=1 day), (iii) HUMULIN® with MoNi$_{23\%}$ (t=0 day), or (iv) aged HUMULIN® with MoNi$_{23\%}$ (t=4 days) to decrease glucose levels was measured in fasted diabetic rats. After subcutaneous administration of formulations (1.5 U/kg), blood glucose levels were measured every 30 minutes (FIG. 36D). HUMULIN® (t=0 day), HUMULIN® with MoNi$_{23\%}$ (t=0 day), and aged HUMULIN® with MoNi$_{23\%}$ (t=4 day) demonstrated an initial blood glucose drop that reached a minimum between 60-100 minutes after injection. These results were consistent with active formulations in earlier experiments. This characteristic glucose drop was absent in rats who received aged HUMULIN® (t=1 day), consistent with inactive formulations in earlier experiments. The maximum difference in glucose from baseline was also plotted for each formulation as a metric of formulation potency (FIG. 36E).

Statistical analysis identified a difference between the potency of these formulations (F3,18.18=10.71, P=0.0003), whereby a post-hoc Tukey HSD test revealed that aged HUMULIN® alone had significantly decreased activity compared to the other formulations. In contrast, there was no statistical difference between unaged HUMULIN®, unaged HUMULIN® with MoNi$_{23\%}$, as well as aged HUMULIN® with MoNi$_{23\%}$ after stressed aging at 50° C. for 4 days.

Various modifications of the invention, in addition to those described herein, will be apparent to those skilled in the art from the foregoing description. Such modifications are also intended to fall within the scope of the appended claims.

The invention claimed is:

1. A polyacrylamide-based copolymer comprising:
   a random copolymer consisting of:
      a water-soluble carrier monomer selected from N-(3 methoxypropyl)acrylamide (MPAM) and 4-acryloylmorpholine (MORPH); and
      a functional dopant monomer that is N-isopropylacrylamide (NIP),
   wherein the random copolymer comprises from 10% to 28% by weight of NIP.

2. The copolymer of claim 1, wherein the water-soluble carrier monomer is MORPH.

3. The copolymer of claim 2, wherein the copolymer comprises from 20% to 26% by weight of NIP.

4. The copolymer of claim 1, wherein the water-soluble carrier monomer is MPAM.

5. The copolymer of claim 1, wherein the degree of polymerization is from 10 to 500.

6. The copolymer of claim 1, wherein the molecular weight of the copolymer is from 1,000 to 50,000 g/mol.

7. The copolymer of claim 1, wherein:
   the degree of polymerization is from 20 to 200; and
   the molecular weight of the copolymer is from 2,000 to 10,000 g/mol.

8. The copolymer of claim 1, wherein
   the average molecular weight (Mn) of the copolymer is from 1,000 g/mol to 30,000 g/mol; and
   the degree of polymerization of the copolymer is from 10 to 250.

9. The copolymer of claim 8, wherein the water-soluble carrier monomer is MORPH.

10. The copolymer of claim 9, wherein the copolymer comprises from 20% to 26% by weight of NIP.

11. The copolymer of claim 9, wherein the copolymer comprises 23% by weight of NIP.

12. The copolymer of claim 9, wherein the copolymer comprises:
   74% to 80% by weight of MORPH; and
   20% to 26% by weight of NIP;
   the average molecular weight (Mn) of the copolymer is from 1,000 g/mol to 5,000 g/mol; and
   the degree of polymerization of the copolymer is 10 to 50.

13. The copolymer of claim 2, wherein the copolymer comprises 77% by weight of MORPH and 23% by weight of NIP.

14. A polyacrylamide-based copolymer comprising:
   a water-soluble carrier monomer selected from MPAM and MORPH; and
   a functional dopant monomer that is N-phenylacrylamide (PHE).

15. The copolymer of claim 14, wherein the water-soluble carrier monomer is MPAM.

16. The copolymer of claim 14, wherein the water-soluble carrier monomer is MORPH.

17. The copolymer of claim 14, wherein the copolymer comprises from 2% to 16% by weight of PHE.

18. The copolymer of claim 14, wherein:
   the degree of polymerization is from 10 to 500; and
   the molecular weight of the copolymer is from 1,000 to 50,000 g/mol.

19. The copolymer of claim 18, wherein:
   the degree of polymerization is from 20 to 200; and
   the molecular weight of the copolymer is from 2,000 to 10,000 g/mol.

20. A polyacrylamide-based copolymer consisting of:
   a water-soluble carrier monomer that is N-(3-methoxypropyl)acrylamide (MPAM); and
   a functional dopant monomer that is N-isopropylacrylamide (NIP).

21. The copolymer of claim 20, wherein the copolymer is a random copolymer that comprises from 2% to 30% by weight of NIP.

22. The copolymer of claim 20, wherein:
   the degree of polymerization is from 10 to 500; and
   the molecular weight of the copolymer is from 1,000 to 50,000 g/mol.

23. The copolymer of claim 22, wherein:
   the degree of polymerization is from 20 to 200; and
   the molecular weight of the copolymer is from 2,000 to 10,000 g/mol.

* * * * *

UNITED STATES PATENT AND TRADEMARK OFFICE
CERTIFICATE OF CORRECTION

| | | |
|---|---|---|
| PATENT NO. | : 11,945,892 B2 | Page 1 of 1 |
| APPLICATION NO. | : 17/962252 | |
| DATED | : April 2, 2024 | |
| INVENTOR(S) | : Eric A. Appel et al. | |

It is certified that error appears in the above-identified patent and that said Letters Patent is hereby corrected as shown below:

In the Specification

In Column 1, Lines 15-18, please replace:
"This invention was made with government support under Grant DK119254 awarded by the National Institutes of Health (NIH). The government has certain rights in the invention."

With:
-- This invention was made with Government support under contracts DK116074 and DK119254 awarded by the National Institutes of Health. The Government has certain rights in the invention. --

Signed and Sealed this
Fourth Day of November, 2025

John A. Squires
*Director of the United States Patent and Trademark Office*